United States Patent
Kubota et al.

(10) Patent No.: US 8,158,640 B2
(45) Date of Patent: Apr. 17, 2012

(54) TETRAHYDROQUINOLINE DERIVATIVES AND A PROCESS FOR PREPARING THE SAME

(75) Inventors: Hitoshi Kubota, Osaka (JP); Masakatsu Sugahara, Osaka (JP); Mariko Furukawa, Osaka (JP); Mayumi Takano, Osaka (JP); Daisuke Motomura, Sagamihara (JP)

(73) Assignee: Mitsubishi Tanabe Pharma Corporation, Osaka-Shi (JP)

( * ) Notice: Subject to any disclaimer, the term of this patent is extended or adjusted under 35 U.S.C. 154(b) by 0 days.

(21) Appl. No.: 12/911,149

(22) Filed: Oct. 25, 2010

(65) Prior Publication Data

US 2011/0039828 A1 Feb. 17, 2011

Related U.S. Application Data

(63) Continuation of application No. 11/527,691, filed on Sep. 27, 2006, now Pat. No. 7,872,126.

(60) Provisional application No. 60/720,447, filed on Sep. 27, 2005.

(51) Int. Cl.
*A61K 31/506* (2006.01)
*C07D 239/24* (2006.01)
*C07D 215/38* (2006.01)

(52) U.S. Cl. .......................... 514/272; 544/298; 546/159

(58) Field of Classification Search .................. 514/272; 544/298; 546/159
See application file for complete search history.

(56) References Cited

U.S. PATENT DOCUMENTS

| | | | |
|---|---|---|---|
| 6,147,089 A | 11/2000 | DeNinno et al. | |
| 6,313,142 B1 | 11/2001 | Damon et al. | |
| 6,489,478 B1* | 12/2002 | DeNinno et al. | 546/159 |
| 2003/0216398 A1 | 11/2003 | Kakihana et al. | |

FOREIGN PATENT DOCUMENTS

| | | |
|---|---|---|
| FR | 2763590 A1 | 11/1998 |
| WO | WO 98/38194 | 9/1998 |
| WO | WO 00/17164 A1 | 3/2000 |
| WO | WO 00/17165 A1 | 3/2000 |
| WO | WO 00/17166 A1 | 3/2000 |
| WO | 0253557 A | 2/2002 |
| WO | WO 02/079165 A1 | 10/2002 |
| WO | WO 03/063868 A1 | 8/2003 |
| WO | WO 2006/012093 A1 | 2/2006 |

OTHER PUBLICATIONS

Kubinyi (3D QSAR in Drug Design: Ligand-Protein Interactions and Molecular Similarity, vol. 2-3, Springer, 1998, 800 pages).*
Rano et al. (Bioorganic & Medicinal Chemistry Letters 19 (2009) 2456-2460).*
Wermuth, The Practice of Medicinal Chemsitry, 2d ed. (2003), 768 pages. Chapters 9-10 provided.*
Park et al. (Toxicology Lett., 120 (2001), 281-91).*
Vergeer et al. (The American Journal of Cardiology, 2009, vol. 104 (10A), 32E-38E).*
Crousse et al., "Synthesis of 2-CF3-Tetrahydroquinoline and Quinoline Derivatives from CF3-N-Aryl-aldimine", J. Org. Chem., vol. 65 (2000) pp. 5009-5013.
Hicks et al., "Differential effects of the novel non-peptidic opioid 4-tyrosylamido-6-benzyl-1,2,3,4 tetrahydroquinoline (CGPM-9) on in vitro rat t lymphocyte and macrophage functions", Life Sciences, vol. 68, No. 24, pp. 2685-2694.
Japanese Office Action issued in Japanese application No. 2006-534487 on Feb. 23, 2010.
Katritzky et al., "Synthesis of Pyrido[4,3,2-de]quinazolines via Nitro-Substituted Tetrahydroquinolines", J. Heterocyclic Chem., vol. 36, No. 3 (1999) pp. 755-759.
Kondo et al., "Formation of Pyrido [3,2,-f]quinoxalines by Reaction of 6-Amino-2, 3-dimethylquinoxaline with Aldehydes", Chem. Pharm. Bull., vol. 45, No. 4, (1997) pp. 722-724.
Kubinyi, H., "3D QSAR in Drug Design: Ligand-Protein Interactions and Molecular Similarity," 1998, Springer, vol. 2-3, 800 pages.
Wang et al., "Design of a High Affinity Peptidomimetic Opioid Agonist from Peptide Pharmacophore Models", Bioorganic & Medicinal Chemistry Letters, vol. 8 (1998) pp. 2685-2688.

* cited by examiner

*Primary Examiner* — Robert Havlin
(74) *Attorney, Agent, or Firm* — Birch, Stewart, Kolasch & Birch, LLP

(57) ABSTRACT

A novel compound of the formula (I):

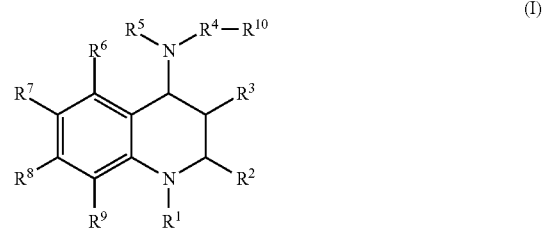

wherein $R^1$ is alkoxycarbonyl or the like, $R^2$ is alkyl or the like; $R^3$ is hydrogen or the like; $R^4$ is alkylene or the like; $R^5$ is optionally substituted heterocyclic group; $R^6$, $R^7$, $R^8$ and $R^9$ are independently hydrogen; alkyl, alkoxy, or the like; $R^{10}$ is optionally substituted aromatic ring, or the like; or a pharmaceutically acceptable salt thereof, which has an inhibitory activity against cholesteryl ester transfer protein (CETP).

11 Claims, No Drawings

TETRAHYDROQUINOLINE DERIVATIVES AND A PROCESS FOR PREPARING THE SAME

This application is a Continuation of application Ser. No. 11/527,691 filed on Sep. 27, 2006, which is now U.S. Pat. No. 7,872,126 B2, which claims priority to Provisional Application No. 60/720,447 filed on Sep. 27, 2005 and Japanese Application No. 2004-109550 filed on Apr. 2, 2004, which claims the benefit of PCT International Application No. PCT/JP2005/006894 filed on Apr. 1, 2005. The entire contents of all of the above applications are hereby incorporated by reference.

TECHNICAL FIELD

The present invention relates to a novel tetrahydroquinoline derivative having an inhibitory activity against cholesteryl ester transfer protein (CETP).

BACKGROUND ART

Hypercholesterolemia, especially high serum level of low-density lipoprotein (LDL) cholesterol, has been revealed to be a risk factor of arteriosclerotic diseases by a number of epidemiological surveys. Actually, drugs capable of decreasing LDL cholesterol level such as 3-hydroxy-3-methylglutaryl-CoA (HMG-CoA) reductase inhibitors have been used with the aim of preventing coronary artery diseases, and demonstrated to have some benefits in many large scale clinical tests. However, their preventive effect on coronary diseases is limited to some extent, and is not satisfactory enough yet.

Recently, low serum level of high density lipoprotein (HDL) cholesterol has been revealed to be a potent risk factor of arteriosclerotic diseases by a number of epidemiological surveys and large scale clinical tests. HDL is known to have various antiarteriosclerotic effects and attnetion is focused on the potentiality of drugs increasing HDL cholesterol level as a means for prevention or treatment of arteriosclerotic diseases. However, there are no drugs that can be used in a satisfactory manner for this purpose. Fibrates and HMG-CoA reductase inhibitors have only low activity of increasing HDL cholesterol; nicotinic acid derivatives can significantly increase HDL, but have serious toleration issues. Accordingly, there has been a demand for a well-tolerated agent which can significantly elevate HDL cholesterol levels, thereby preventing or reversing the progression of atherosclerosis.

It is known that many proteins are involved in the regulation mechanism for catabolism of various lipoproteins. Among them, the role of cholesteryl ester transfer protein (CETP) became to draw attention. CETP is a protein responsible for transfer of cholesteryl ester (CE) and triglyceride between lipoproteins, and mediate the transfer of CE from HDL to LDL or to very low density lipoprotein (VLDL). Accordingly, CETP activity affects greatly the lipid composition in lipoprotein particles. For example, it is known that administration of a neutralizing monoclonal antibody to CETP to rabbit or hamster elevates HDL cholesterol levels and lower LDL cholesterol levels. Furthermore, human being having decreased or eliminated CETP activity due to gene mutation shows raised blood HDL cholesterol level and lowered blood LDL cholesterol level. On the other hand, it is known that transgenic mice and rats made to express CETP show lowered HDL cholesterol level and raised LDL cholesterol level. Thus, it is considered that CETP greatly contribute to the regulation of serum lipids, and thereby affecting the change of serum lipid profile such as decrease of HDL cholesterol level and increase of LDL cholesterol. Accordingly, it is assumed that a high value of CETP activity would induce arteriosclerosis such as atherosclerosis.

In fact, CETP activity varies depending on animal species. It is known that, arteriosclerotic lesions are readily formed by cholesterol loading in animals with high CETP activity such as rabbits, whereas such lesions hardly occur in animals with low CETP activity such as rats. Furthermore, it is confirmed that continuous suppression of CETP activity by administration of antisense oligodeoxynucleotide resulted in effects such as increase of blood HDL cholesterol level and reduction in arteriosclerotic lesions in cholesterol-fed rabbits.

The above findings indicate that CETP activity is in negative correlation with HDL cholesterol, and that inhibition of CETP activity would decrease the degree of risk for arteriosclerotic diseases. It is therefore expected that compounds capable of inhibiting CETP activity can block the transfer of cholesterol from HDL to LDL, and thereby increasing HDL cholesterol that tends to prevent arteriosclerosis such as atherosclerosis while lowering LDL cholesterol that tends to promote arteriosclerosis such as atherosclerosis. In this way, such compounds can serve as a useful preventive or therapeutic agent for arteriosclerotic diseases, hyperlipidemia or dyslipidemia and provide effective medical treatment for the first time.

Examples of compounds having CETP inhibitory activity include tetrahydroquinoline derivatives. See, WO00/17164, WO00/17165, WO00/17166.

However, these compounds have defects. That is, they are poorly soluble in water and cannot be absorbed enough in vivo, a sufficient blood level for taking medicinal effect can hardly be achieved even when administered as an ordinary formulation for oral administration. See, WO03/63868.

Accordingly, novel compounds in which the above-mentioned defects have been solved are highly demanded.

DISCLOSURE OF INVENTION

The present invention provides novel tetrahydroquinoline derivatives having an excellent CETP inhibitory activity wherein defects of existing CETP inhibitory compounds are rectified.

Thus, the present invention provides a compound of the formula (I):

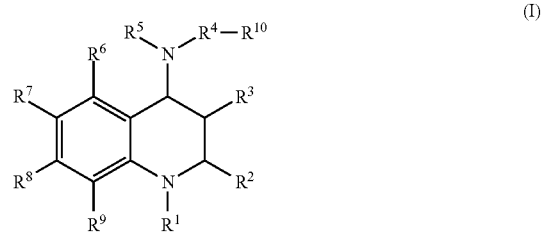

wherein $R^1$ is a hydrogen atom, an optionally substituted alkoxycarbonyl group, an optionally substituted carbamoyl group, an optionally substituted alkyl group, an optionally substituted alkanoyl group, a saturated or unsaturated monocyclic or bicyclic heterocyclic group containing 1 to 4 heteroatoms selected independently from oxygen, sulfur and nitrogen atoms (the heterocyclic group is optionally substituted), or a saturated or unsaturated monocyclic or bicyclic heterocyclic carbonyl group containing 1 to 4 heteroatoms selected independently from oxygen, sulfur and nitrogen atoms (the heterocyclic group is optionally substituted);

$R^2$ is a hydrogen atom or an optionally substituted alkyl group;

$R^3$ is a hydrogen atom or an optionally substituted alkyl group;

$R^4$ is an optionally substituted alkylene group;

$R^5$ is a saturated or unsaturated monocyclic or bicyclic heterocyclic group containing 1 to 4 heteroatoms selected independently from oxygen, sulfur and nitrogen atoms, wherein the heterocyclic group is substituted by 1 to 5 substituents selected from the following groups, or said heterocyclic group is substituted by 1 to 5 substituents selected from the following groups and further by a halogen atom, an oxo and/or hydroxy group:

cyano group, nitro group, carboxyl group, sulfo group, $C_{3-10}$ alkyl group, substituted alkyl group, optionally substituted cycloalkyl group, optionally substituted alkenyl group, $C_{3-10}$ alkoxy group, substituted alkoxy group, optionally substituted cycloalkoxy group, optionally substituted alkoxycarbonyl group, optionally substituted carbamoyl group, optionally substituted carbamimidoyl group, optionally substituted alkylthio group, optionally substituted alkylsulfinyl group, optionally substituted alkylsulfonyl group, optionally substituted amino group, optionally substituted sulfamoyl group, optionally substituted alkanoyl group, a saturated or unsaturated monocyclic or bicyclic heterocyclic group containing 1 to 4 heteroatoms selected independently from oxygen, sulfur and nitrogen atoms (the heterocyclic group is optionally substituted), a saturated or unsaturated monocyclic or bicyclic heterocyclic oxy group containing 1 to 4 heteroatoms selected independently from oxygen, sulfur and nitrogen atoms (the heterocyclic oxy group is optionally substituted), and a saturated or unsaturated monocyclic or bicyclic heterocyclic carbonyl group containing 1 to 4 heteroatoms selected independently from oxygen, sulfur and nitrogen atoms (the heterocyclic carbonyl group is optionally substituted);

$R^6$, $R^7$, $R^8$ and $R^9$ are independently a hydrogen atom, a halogen atom, a hydroxy group, a nitro group, a cyano group, an optionally substituted alkyl group, an optionally substituted alkoxy group, an optionally substituted alkylsulfonyloxy group or an optionally substituted amino group; or $R^6$ and $R^7$, or $R^7$ and $R^8$, or $R^8$ and $R^9$ may combine at the ends to form an alkylene group which alkylene group may contain 1 to 3 heteroatoms selected independently from nitrogen, sulfur and oxygen atoms, and may have a substituent(s); and $R^{10}$ is an aromatic ring optionally containing 1 to 3 heteroatoms selected independently from oxygen, sulfur and nitrogen atoms (the aromatic ring is optionally substituted), or a pharmaceutically acceptable salt thereof.

The compound (I) of the present invention encompasses a mixture of stereoisomers, respective stereoisomers in a purified or substantially purified form. For example, the compounds of the formula (I) may have one or more asymmetric carbon atoms and therefore may occur as individual enantiomers or diastereomers, or a mixture thereof. The present compounds include respective isomers and a mixture thereof. In addition, when the compound (I) has a double bond, geometric isomers may occur (cis- and trans-forms), and when the compound (I) has a group containing an unsaturated bond such as carbonyl, tautomeric forms may occur, and the present compounds include respective isomers and a mixture thereof.

Further, the pharmaceutically acceptable salts of compound (I) of the present invention include an intramolecular salt, a hydrate, solvate, or the like.

As used herein, the term "aromatic ring optionally containing 1 to 3 heteroatoms selected independently from oxygen, sulfur and nitrogen atoms" refers to preferably a "5- to 7-membered monocyclic aromatic ring optionally containing 1 to 3 heteroatoms selected independently from oxygen, sulfur and nitrogen atoms" including specifically phenyl, furyl, thienyl, pyrrolyl, oxazolyl, thiazolyl, imidazolyl, pyrazolyl, isoxazolyl, isothiazolyl, pyridyl, pyridazinyl, pyrimidinyl, pyrazinyl, azepinyl, oxepinyl and thiepinyl groups, and the like.

The term "saturated or unsaturated monocyclic or bicyclic heterocyclic group containing 1 to 4 heteroatoms selected independently from oxygen, sulfur and nitrogen atoms" refers to preferably a "saturated or unsaturated 5- to 8-membered heterocyclic group containing 1 to 4 heteroatoms selected independently from oxygen, sulfur and nitrogen atoms" including specifically the following groups. Examples of 5-membered heterocyclic group include 2H-pyrrolyl, 3H-pyrrolyl, 2-pyrrolyl, 3-pyrrolyl, pyrrolidinyl, 1,3-dioxolanyl, oxazolyl, oxazolinyl, oxazolidinyl, thiazolyl, imidazolyl, imidazolinyl, imidazolidinyl, pyrazolyl, 2-pyrazolinyl, pyrazolidinyl, isoxazolyl, isothiazolyl, tetrazolyl, 1,2-dithiolyl, 1,3-dithiolyl, 3H-1,2-oxathiolyl, 1,2,3-oxadiazolyl, 1,2,4-oxadiazolyl, 1,2,5-oxadiazolyl, 1,3,4-oxadiazolyl, 1,2,3-triazolyl, 1,2,4-triazolyl, 1,3,4-thiadiazolyl, 1,2,3,4-oxatriazolyl, 1,2,3,5-oxatriazolyl, 3H-1,2,3-dioxazolyl, 1,2,4-dioxazolyl, 1,3,2-dioxazolyl, 1,3,4-dioxazolyl, 5H-1,2,5-oxathiazolyl and 1,3-oxathiolyl groups, and the like.

Examples of 6-membered heterocyclic group include 2H-pyranyl, 4H-pyranyl, pyridyl, piperidinyl, 1,2-dioxinyl, 1,3-dioxinyl, 1,4-dioxanyl, morpholinyl, 1,4-dithianyl, thiomorpholinyl, pyridazinyl, pyrimidinyl, pyrazinyl, piperazinyl, 1,3,5-triazinyl, 1,2,4-triazinyl, 1,2,3-triazinyl, 1,3,5-trithianyl, 4H-1,2-oxazinyl, 2H-1,3-oxazinyl, 6H-1,3-oxazinyl, 6H-1,2-oxazinyl, 1,4-oxazinyl, 2H-1,2-oxazinyl, 4H-1,4-oxazinyl, 1,2,5-oxathiazinyl, 1,4-oxazinyl, o-isoxazinyl, p-isoxazinyl, 1,2,5-ozathiazinyl, 1,2,6-oxathiazinyl, 1,4,2-oxadiazinyl and 1,3,5,2-oxadiazinyl groups, and the like.

Examples of 7-membered heterocyclic group include azepinyl, oxepinyl and thiepinyl groups, and the like.

Examples of 8-membered heterocyclic group include azocinyl, oxocinyl and thiocinyl groups, and the like.

As used herein, the heterocyclic moiety of the "saturated or unsaturated monocyclic or bicyclic heterocyclic oxy group containing 1 to 4 heteroatoms selected independently from oxygen, sulfur and nitrogen atoms", "saturated or unsaturated monocyclic or bicyclic heterocyclic carbonyl group containing 1 to 4 heteroatoms selected independently from oxygen, sulfur and nitrogen atoms", and "a saturated or unsaturated monocyclic or bicyclic heterocyclic carbonylamino group containing 1 to 4 heteroatoms selected independently from oxygen, sulfur and nitrogen atoms" refers to the aforementioned "saturated or unsaturated monocyclic or bicyclic heterocyclic group containing 1 to 4 heteroatoms selected independently from oxygen, sulfur and nitrogen atoms".

In such cases where the binding position for these aromatic rings, heterocyclic group, and the like is not specifically defined, the definition is meant to encompass all the possible binding positions. For example, the term "pyridyl group"

means 2-, 3- or 4-pyridyl group, and the term "thienyl group" means 2- or 3-thienyl group. The same is applied to other aromatic rings and heterocyclic groups.

When the saturated or unsaturated monocyclic or bicyclic heterocyclic group, heterocyclic oxy group, heterocyclic carbonyl group and heterocyclic carbonylamino group each containing 1 to 4 heteroatoms selected independently from oxygen, sulfur and nitrogen atoms have a substituent(s), the substitution includes oxidation of heteroatom(s) in the heterocycle in the respective groups. Specifically, compounds having a heteroatom(s) in the heterocycle of said groups as N-oxide, S-oxide (SO) or S,S-dioxide ($SO_2$) also fall within the scope of the present invention.

The term "halogen" refers to fluorine, chlorine, bromine or iodine.

The term "alkyl group" or "alkyl" means a straight or branched saturated hydrocarbon chain having 1 to 10 carbon atoms and a cyclic saturated hydrocarbon chain having 3 to 10 carbon atoms. As a straight or branched hydrocarbon chain, those having 2 to 10 carbon atoms are preferred, those having 3 to 10 carbon atoms are more preferred, those having 2 to 6 carbons are further preferred and those having 3 to 6 carbon atoms are especially preferred. Other preferred examples are straight chain alkyl groups having 1 to 6 carbon atoms, especially those having 1 to 4 carbon atoms. Examples of alkyl group include methyl, ethyl, propyl, isopropyl, butyl, sec-butyl, tert-butyl, pentyl, isopentyl, neopentyl, tert-pentyl, 1-methylbutyl, 2-methylbutyl, 3-methylbutyl, hexyl and isohexyl groups, and the like.

The term "alkoxy group" or "alkoxy" means a straight or branched alkyloxy group having 1 to 10 carbon atoms and a cyclic alkyloxy group having 3 to 10 carbon atoms. As a straight or branched hydrocarbon chain, those having 2 to 10 carbon atoms are preferred and those having 2 to 6 carbons are more preferred. Other preferred examples are straight chain alkoxy groups having 1 to 6 carbon atoms, especially those having 1 to 4 carbon atoms. Examples of alkoxy group include methoxy, ethoxy, propoxy, isopropoxy, butoxy, isobutoxy, tert-butoxy, pentoxy, isopentoxy, neopentoxy, tert-pentoxy, hexoxy and isohexoxy groups, and the like.

The term "alkylene group" or "alkylene" means a saturated hydrocarbon chain wherein a hydrogen atom is removed from each of the terminal carbons of a straight hydrocarbon chain. Preferred examples include an alkylene group having 1 to 6 carbon atoms, specifically, methylene, ethylene, trimethylene and tetramethylene groups, and the like. When an alkylene group herein used contains 1 to 3 heteroatoms selected independently from nitrogen, sulfur and oxygen atoms, the term "alkylene" includes a group of the formula: —O—$(CH_2)_m$—O—, —S—$(CH_2)_m$—S—, —NH—$(CH_2)_m$—NH—, or —O—$(CH_2)_m$—NH— (wherein m is an integer of 1 to 4), or the like.

The term "alkanoyl group" or "alkanoyl" means a straight or branched alkylcarbonyl group having 1 to 10 carbon atoms, preferably an alkylcarbonyl group having 1 to 6 carbon atoms, more preferably an alkylcarbonyl group having 1 to 4 carbon atoms. Examples of alkanoyl group include acetyl, propionyl, butyryl, valeryl and pivaloyl groups, and the like.

The term "alkenyl group" or "alkenyl" means a straight or branched hydrocarbon chain having 2 to 10 carbon atoms and containing at least one double bond, preferably an alkenyl group having 2 to 6 carbon atoms, more preferably an alkenyl group having 2 to 4 carbon atoms Examples of alkenyl group include vinyl, 1-propenyl, allyl, isopropenyl, butenyl, butadienyl and pentenyl groups, and the like.

As herein used throughout the claims and specification, when the term "mono- or di-alkyl" refers to di-alkyl, the alkyl moieties may be independent from each other. In addition, a compound of the formula below means that it takes the configuration (2R*,4S*), wherein (2R*,4S*) refers to a mixture of (2R,4S) and (2S,4R).

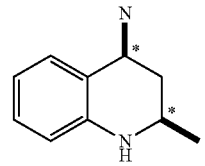

The compounds of the present invention have CETP inhibitory activity and are effective for increasing HDL cholesterol and lowering LDL cholesterol. Accordingly, the said compounds are useful in prevention and/or treatment of diseases such as arteriosclerosis, hyperlipidemia, and the like.

BEST MODE FOR CARRYING OUT THE INVENTION

Preferred compounds of the present invention are those wherein $R^5$ is a saturated or unsaturated monocyclic or bicyclic heterocyclic group containing 1 to 4 heteroatoms selected independently from oxygen, sulfur and nitrogen atoms, wherein the heterocyclic group is substituted by 1 to 5 substituents selected from the following groups, or said heterocyclic group is substituted by 1 to 5 substituents selected from the following groups along with halogen atom, oxo and/or hydroxy group:

cyano group, nitro group, carboxyl group, sulfo group, $C_{3-10}$ alkyl group, substituted alkyl group, optionally substituted cycloalkyl group, optionally substituted alkenyl group, $C_{3-10}$ alkoxy group, substituted alkoxy group, optionally substituted cycloalkoxy group, optionally substituted alkoxycarbonyl group, carbamoyl group, optionally substituted mono- or di-alkylcarbamoyl group, optionally substituted carbamimidoyl group, optionally substituted alkylthio group, optionally substituted alkylsulfinyl group, optionally substituted alkylsulfonyl group, amino group, optionally substituted mono- or di-alkylamino group, optionally substituted alkanoylamino group, optionally substituted alkoxycarbonylamino group, optionally substituted alkylsulfonylamino group, optionally substituted mono- or di-alkylcarbamoylamino group, a saturated or unsaturated monocyclic or bicyclic heterocyclic carbonylamino group containing 1 to 4 heteroatoms selected independently from oxygen, sulfur and nitrogen atoms (the heterocyclic carbonylamino group is optionally substituted), sulfamoyl group, optionally substituted mono- or di-alkyl sulfamoyl group, optionally substituted alkanoyl group, a saturated or unsaturated monocyclic or bicyclic heterocyclic group containing 1 to 4 heteroatoms selected independently from oxygen, sulfur and nitrogen atoms (the heterocyclic group is optionally substituted), a saturated or unsaturated monocyclic or bicyclic heterocyclic oxy group containing 1 to 4 heteroatoms selected independently from oxygen, sulfur and nitrogen atoms (the heterocyclic oxy group is optionally substituted), and a saturated or unsaturated monocyclic or bicyclic heterocyclic carbonyl group containing 1 to 4 heteroatoms selected independently from oxygen, sulfur and nitrogen atoms (the heterocyclic carbonyl group is optionally substituted); and $R^{10}$ is an aromatic ring optionally containing 1 to 3 heteroatoms selected independently from oxygen, sulfur and nitrogen atoms, which aromatic ring is optionally substituted by 1 to 4 substituents selected from the following groups: halogen atom, carboxyl group, optionally substituted alkoxycarbonyl group, carbamoyl group, optionally substituted mono- or di-alkylcarbamoyl group, optionally substituted alkyl group, optionally substituted alkoxy group, hydroxy group, nitro group, cyano group, amino group, optionally substituted mono- or di-alkylamino group, optionally substituted alkanoyl group, optionally substituted alkylthio group, and a saturated or unsaturated monocyclic or bicyclic heterocyclic group containing 1 to 4 heteroatoms selected independently from oxygen, sulfur and nitrogen atoms (the heterocyclic group is optionally substituted).

The substituent(s) for substituted alkyl group, optionally substituted alkyl group, optionally substituted cycloalkyl group, optionally substituted alkenyl group, substituted alkoxy group, optionally substituted alkoxy group, optionally substituted cycloalkoxy group, optionally substituted alkoxycarbonyl group, optionally substituted mono- or di-alkylcarbamoyl group, optionally substituted alkylthio group, optionally substituted alkylsulfinyl group, optionally substituted alkylsulfonyl group, optionally substituted mono- or di-alkylamino group, optionally substituted alkanoylamino group, optionally substituted alkoxycarbonylamino group, optionally substituted alkylsulfonylamino group, optionally substituted mono- or di-alkylcarbamoylamino group, optionally substituted mono- or di-alkylsulfamoyl group, optionally substituted alkanoyl group, optionally substituted alkylene group, a saturated or unsaturated monocyclic or bicyclic heterocyclic carbonylamino group containing 1 to 4 heteroatoms selected independently from oxygen, sulfur and nitrogen atoms (the heterocyclic carbonylamino group is optionally substituted), a saturated or unsaturated monocyclic or bicyclic heterocyclic group containing 1 to 4 heteroatoms selected independently from oxygen, sulfur and nitrogen atoms (the heterocyclic group is optionally substituted), a saturated or unsaturated monocyclic or bicyclic heterocyclic oxy group containing 1 to 4 heteroatoms selected independently from oxygen, sulfur and nitrogen atoms (the heterocyclic oxy group is optionally substituted), and a saturated or unsaturated monocyclic or bicyclic heterocyclic carbonyl group containing 1 to 4 heteroatoms selected independently from oxygen, sulfur and nitrogen atoms (the heterocyclic carbonyl group is optionally substituted) may be 1-5 groups selected from the following groups:

halogen atom; cyano group; hydroxy group; nitro group; carboxyl group; oxo group; thioxo group; sulfo group; cycloalkyl group optionally substituted by hydroxy group, halogen atom, carboxyl group, alkoxycarbonyl group, mono- or di-alkylamino group, phenyl group or morpholinyl group; alkoxycarbonyl group optionally substituted by hydroxy group, halogen atom, carboxyl group, alkoxycarbonyl group, mono- or di-alkylamino group, phenyl group or morpholinyl group; carbamoyl group; mono- or di-alkylcarbamoyl group optionally substituted by hydroxy group, halogen atom, carboxyl group, alkoxycarbonyl group, mono- or di-alkylamino group, phenyl group or morpholinyl group; alkyl group optionally substituted by hydroxy group, halogen atom, carboxyl group, alkoxycarbonyl group, mono- or di-alkylamino group, phenyl group or morpholinyl group; alkanoyl group optionally substituted by hydroxy group, halogen atom, carboxyl group, alkoxycarbonyl group, mono- or di-alkylamino group, phenyl group or morpholinyl group; alkoxy group optionally substituted by hydroxy group, halogen atom, carboxyl group, alkoxycarbonyl group, mono- or di-alkylamino group, phenyl group or morpholinyl group; alkanoyloxy group optionally substituted by hydroxy group, halogen atom, carboxyl group, alkoxycarbonyl group, mono- or di-alkylamino group, phenyl group or morpholinyl group; alkylthio group optionally substituted by hydroxy group, halogen atom, carboxyl group, alkoxycarbonyl group, mono- or di-alkylamino group, phenyl group or morpholinyl group; alkylsulfonyl group optionally substituted by hydroxy group, halogen atom, carboxyl group, alkoxycarbonyl group, mono- or di-alkylamino group, phenyl group or morpholinyl group; alkylsulfinyl group optionally substituted by hydroxy group, halogen atom, carboxyl group, alkoxycarbonyl group, mono- or di-alkylamino group, phenyl group or morpholinyl group; mono- or di-alkylsulfamoyl group optionally substituted by hydroxy group, halogen atom, carboxyl group, alkoxycarbonyl group, mono- or di-alkylamino group, phenyl group or morpholinyl group; amino group; mono- or di-alkylamino group optionally substituted by hydroxy group, halogen atom, carboxyl group, alkoxycarbonyl group, mono- or di-alkylamino group, phenyl group or morpholinyl group; mono- or di-alkylsulfamoylamino group optionally substituted by hydroxy group, halogen atom, carboxyl group, alkoxycarbonyl group, mono- or di-alkylamino group, phenyl group or morpholinyl group; mono- or di-alkylureido group optionally substituted by hydroxy group, halogen atom, carboxyl group, alkoxycarbonyl group, mono- or di-alkylamino group, phenyl group or morpholinyl group; and a group of the formulas:

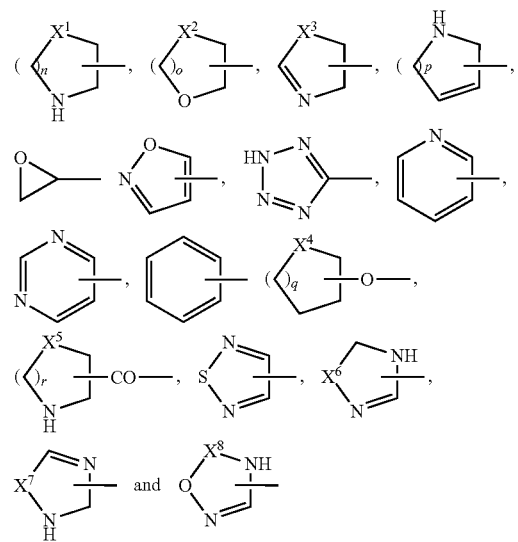

wherein $X^1$ and $X^3$ are independently $CH_2$, NH, O, S, SO or $SO_2$; $X^2$ and $X^5$ are independently $CH_2$, O, S, SO or $SO_2$; $X^4$ is NH, O, S, SO or $SO_2$; $X^6$ and $X^7$ are independently O or S; $X^8$ is S or SO; and n, o, p, q and r are independently an integer of 1 to 4, wherein each group of the above formula is optionally substituted by 1 to 3 substituents selected from the following groups:

halogen atom, carboxyl group, hydroxy group. cyano group, oxo group, thioxo group, alkyl group, hydroxyalkyl group, alkoxycarbonylalkyl group, carboxyalkyl group, morpholinylalkyl group, phenylalkyl group, alkanoyl group, hydroxyalkanoyl group, alkoxyalkanoyl group, alkoxy group, phenylalkoxy group, alkoxycarbonyl group, benzyloxycarbonyl group, mono- or di-alkylamino group, mono- or di-alkylcarbamoyl group, mono- or di-alkylsulfamoyl group, alkylsulfonyl group and tetrazolyl group.

Furthermore, the "aromatic ring optionally containing 1 to 3 heteroatoms selected independently from oxygen, sulfur and nitrogen atoms" is preferably a phenyl, naphthyl, pyridyl, quinolyl, isoquinolyl, furyl, pyrimidinyl, triazolyl or thienyl group;

The "saturated or unsaturated monocyclic or bicyclic heterocyclic group containing 1 to 4 heteroatoms selected independently from oxygen, sulfur and nitrogen atoms" is preferably a morpholinyl, thiomorpholinyl, piperazinyl, pyrrolidinyl, piperidinyl, hexahydroazepinyl, pyrrolinyl, imidazolidinyl, oxazolidinyl, tetrahydropyranyl, tetrahydrofuranyl, dioxolanyl, oxiranyl, pyrimidinyl, pyridyl, triazolyl, tetrazolyl, oxadiazolyl, dihydropyrimidinyl, pyrazinyl, thiazolyl, oxazolinyl, oxazolyl, pyridazinyl, imidazolinyl, imidazolyl, pyrazinyl, thienyl, pyrrolyl, furyl or dihydrooxazinyl group.

The "saturated or unsaturated monocyclic or bicyclic heterocyclic oxy group containing 1 to 4 heteroatoms selected independently from oxygen, sulfur and nitrogen atoms" is preferably a morpholinyloxy, thiomorpholinyloxy piperazinyloxy, pyrrolidinyloxy, piperidinyloxy, hexahydroazepinyloxy, pyrrolinyloxy, imidazolidinyloxy, oxazolidinyloxy, tetrahydropyranyloxy, tetrahydrofuranyloxy, dioxolanyloxy, oxiranyloxy, pyrimidinyloxy, pyridyloxy, triazolyloxy, tetrazolyloxy, oxadiazolyloxy, dihydropyrimidinyloxy, pyrazinyloxy, thiazolyloxy, oxazolinyloxy, oxazolyloxy, pyridazinyloxy, imidazolinyloxy, imidazolyloxy, pyrazinyloxy, thienyloxy, pyrrolyloxy, furyloxy or dihydrooxazinyloxy group.

The "saturated or unsaturated monocyclic or bicyclic heterocyclic carbonyl group containing 1 to 4 heteroatoms selected independently from oxygen, sulfur and nitrogen atoms" is preferably a morpholinylcarbonyl, thiomorpholinylcarbonyl piperazinylcarbonyl, pyrrolidinylcarbonyl, piperidinylcarbonyl, hexahydroazepinylcarbonyl, pyrrolinylcarbonyl, imidazolidinylcarbonyl, oxazolidinylcarbonyl, tetrahydropyranylcarbonyl, tetrahydrofuranylcarbonyl, dioxolanylcarbonyl, oxiranylcarbonyl pyrimidinylcarbonyl, pyridylcarbonyl, triazolylcarbonyl, tetrazolylcarbonyl, oxadiazolylcarbonyl, dihydropyrimidinylcarbonyl, pyrazinylcarbonyl, thiazolylcarbonyl, oxazolinylcarbonyl, oxazolylcarbonyl, pyridazinyl-carbonyl, imidazolinylcarbonyl, imidazolylcarbonyl, pyrazinylcarbonyl, thienylcarbonyl, pyrrolylcarbonyl, furylcarbonyl or dihydrooxazinylcarbonyl group.

The "saturated or unsaturated monocyclic or bicyclic heterocyclic carbonylamino group containing 1 to 4 heteroatoms selected independently from oxygen, sulfur and nitrogen atoms" is preferably a morpholinylcarbonylamino, thiomorpholinylcarbonylamino piperazinyl-carbonylamino, pyrrolidinylcarbonylamino, piperidinylcarbonylamino, hexahydroazepinylcarbonylamino, pyrrolinylcarbonylamino, imidazolidinyl-carbonylamino, oxazolidinylcarbonylamino, tetrahydropyranylcarbonyl-amino, tetrahydrofuranylcarbonylamino, dioxolanylcarbonylamino, oxiranylcarbonylamino, pyrimidinylcarbonylamino, pyridylcarbonylamino, triazolylcarbonylamino, tetrazolylcarbonylamino, oxadiazolylcarbonylamino, dihydropyrimidinylcarbonylamino, pyrazinylcarbonylamino, thiazolyl-carbonylamino, oxazolinylcarbonylamino, oxazolylcarbonylamino, pyridazinylcarbonylamino, imidazolinylcarbonylamino, imidazolyl-carbonylamino, pyrazinylcarbonylamino, thienylcarbonylamino, pyrrolyl-carbonylamino, furylcarbonylamino or dihydrooxazinylcarbonylamino group.

In a preferred embodiment of the present invention, $R^1$ is a hydrogen atom; an alkoxycarbonyl group optionally substituted by 1 to 5 substituents selected independently from cyano group, hydroxy group, carboxyl group, alkoxycarbonyl group, alkoxy group (said alkoxy group is optionally substituted by 1 to 3 substituents selected independently from hydroxy group, amino group, mono- or di-alkylamino group, halogen atom, carboxyl group, alkoxycarbonyl group, carboxyalkoxy group and alkoxycarbonylalkoxy group), alkylthio group, alkylsulfonyl group, alkenyl group, amino group, mono- or di-alkylamino group, tetrazolyl group, carbamoyl group, mono- or di-alkylcarbamoyl group (said mono- or di-alkylcarbamoyl group is optionally substituted by 1 to 3 substituents selected independently from carboxyl group and alkoxycarbonyl group), alkanoylamino group (said alkanoylamino group is optionally substituted by 1 to 3 substituents selected independently from carboxyl group, alkoxycarbonyl group, hydroxy group and halogen atom), halogen atom, cycloalkyl group (said cycloalkyl group is optionally substituted by 1 to 3 substituents selected independently from hydroxy group, amino group, mono- or di-alkylamino group, halogen atom, oxo group, carboxyl group, alkoxycarbonyl group, carboxyalkyl group, alkoxycarbonylalkyl group, carboxyalkoxy group and alkoxycarbonylalkoxy group), phenyl group (said phenyl group is optionally substituted by 1 to 3 substituents selected independently from hydroxy group, amino group, mono- or di-alkylamino group, halogen atom, carboxyl group, alkoxycarbonyl group, carboxyalkyl group, alkoxycarbonylalkyl group, carboxyalkoxy group and alkoxycarbonylalkoxy group), morpholinyl group optionally substituted by oxo group, piperidinyl group (said piperidinyl group is optionally substituted by 1 to 3 substituents selected independently from hydroxy group, amino group, mono- or di-alkylamino group, halogen atom, oxo group, carboxyl group, alkoxycarbonyl group, carboxyalkyl group, alkoxycarbonylalkyl group, carboxyalkoxy group and alkoxycarbonylalkoxy group), pyrrolidinyl group (said pyrrolidinyl group is optionally substituted by 1 to 3 substituents selected independently from hydroxy group, amino group, mono- or di-alkylamino group, halogen atom, oxo group, carboxyl group, alkoxycarbonyl group, carboxyalkyl group, alkoxycarbonylalkyl group, carboxyalkoxy group and alkoxycarbonylalkoxy group), and pyrimidinyl group (said pyrimidinyl group is optionally substituted by 1 to 3 substituents selected independently from carboxyalkyl group, alkoxycarbonylalkyl group, carboxyalkoxy group and alkoxycarbonylalkoxy group); a carbamoyl group optionally substituted by alkoxy group; a dihydrooxazolyl group optionally substituted by 1 to 2 substituents selected independently from carboxyl group, alkoxycarbonyl group, alkyl group, carboxyalkyl group, alkoxycarbonylalkyl group and hydroxyalkyl group; a dihydroimidazolyl group optionally substituted by 1 to 3 substituents selected independently from carboxyl group, alkoxycarbonyl group, alkyl group, carboxyalkyl group, alkoxycarbonylalkyl group and hydroxyalkyl group; a dihydrooxazinyl group optionally substituted by 1 to 3 substituents selected independently from carboxyl group, alkoxycarbonyl group, alkyl group, carboxyalkyl group, alkoxycarbonylalkyl group and hydroxyalkyl group; mono- or di-alkylcarbamoyl group optionally substituted by 1 to 5 substituents selected independently from halogen atom, hydroxy group, carboxyl group, alkoxycarbonyl group, alkoxy group, amino group, mono- or di-alkylamino group, morpholinyl group, pyridyl group, cycloalkyl group (said cycloalkyl group is optionally substituted by 1 to 3 substituents selected independently from carboxyl group, alkoxycarbonyl group, halogen atom, amino group and hydroxy group) and phenyl group (said phenyl group is optionally substituted by 1 to 3 substituents selected independently from carboxyl group, alkoxycarbonyl group, halogen atom, amino group and hydroxy group); an alkyl group optionally substituted by 1 to 5 substituents selected independently from halogen atom, hydroxy group, carboxyl group, alkoxycarbonyl group, alkoxy group, amino group, mono- or di-alkylamino group, morpholinyl group, pyridyl group, cycloalkyl group (said cycloalkyl group is optionally substituted by 1 to 3 substituents selected independently from carboxyl group, alkoxycarbonyl group, halogen atom, amino group and hydroxy group) and phenyl group (said phenyl group is optionally substituted by 1 to 3 substituents selected independently from carboxyl group, alkoxycarbonyl group, halogen atom, amino group and hydroxy group); an alkanoyl group optionally substituted by 1 to 5 substituents selected independently from halogen atom, hydroxy group, carboxyl group, alkoxycarbonyl group, alkoxy group, amino group, mono- or di-alkylamino group, morpholinyl group, pyridyl group, cycloalkyl group (said cycloalkyl group is optionally substituted by 1 to 3 substituents selected independently from carboxyl group, alkoxycarbonyl group, halogen atom, amino group and hydroxy group) and phenyl group (said phenyl group is optionally substituted by 1 to 3 substituents selected independently from carboxyl group, alkoxycarbonyl group, halogen atom, amino group and hydroxy group); a morpholinylcarbonyl group; a piperazinylcarbonyl group optionally substituted by alkyl group, carboxyalkyl group or alkoxycarbonylalkyl group;

a pyrrolidinylcarbonyl group optionally substituted by 1 to 3 substituents selected independently from carboxyl group, alkoxycarbonyl group, carboxyalkyl group and alkoxycarbonylalkyl group; or a piperidinylcarbonyl group optionally substituted by 1 to 3 substituents selected independently from carboxyl group, alkoxycarbonyl group, carboxyalkyl group and alkoxycarbonylalkyl group;

$R^5$ is a saturated or unsaturated 5- to 8-membered heterocyclic group containing 1 to 4 heteroatoms selected independently from oxygen, sulfur and nitrogen atoms;

wherein said heterocyclic group is substituted by 1 to 4 substituents selected from the following groups, or said heterocyclic group is substituted by 1 to 4 substituents selected from the following groups along with a halogen atom, an oxo and/or hydroxy group:

cyano group;
nitro group;
carboxyl group;
sulfo group;
cycloalkyl group optionally substituted by carboxyl or alkoxycarbonyl group;
$C_{3-10}$ alkyl group;
alkyl group substituted by a group selected from halogen atom, cyano group, hydroxy group, carboxyl group, alkoxycarbonyl group, tetrazolyl group, mono- or di-alkylcarbamoyl group, alkoxy group (said alkoxy group is optionally substituted by phenyl, carboxyl or hydroxy group), alkanoyl group, alkanoyloxy group, alkylthio group, alkylsulfonyl group, alkylsulfinyl group, amino group, mono- or di-alkylamino group optionally substituted by carboxyl or alkoxy group, mono- or di-alkylsulfamoylamino group, mono- or di-alkylureido group optionally substituted by morpholinyl group, oxiranyl group, dioxolanyl group optionally substituted by alkyl group, pyrrolidinyl group optionally substituted by alkoxycarbonyl or carboxyl group, pyrrolidinyl group optionally substituted by alkoxycarbonylalkyl or carboxyalkyl group, piperidinyl group optionally substituted by alkoxycarbonyl or carboxyl group, piperidinyl group optionally substituted by alkoxycarbonylalkyl or carboxyalkyl group, piperazinyl group optionally substituted by alkyl group, hexahydroazepinyl group, morpholinyl group, and piperidinyloxy group optionally substituted by alkyl group;

alkenyl group optionally substituted by a group selected from cyano group, hydroxy group, carboxyl group, benzyloxycarbonyl group, and tetrazolyl group;

alkenyloxy group optionally substituted by carboxyl group;

$C_{3-10}$ alkoxy group;

alkoxy group substituted by a group selected from halogen atom, cyano group, hydroxy group, carboxyl group, alkoxycarbonyl group, tetrazolyl group, carbamoyl group, mono- or di-alkylcarbamoyl group (said mono- or di-alkylcarbamoyl group is optionally substituted by carboxyl, alkoxycarbonyl or hydroxy group), alkoxy group (said alkoxy group is optionally substituted by carboxyl, formyl or hydroxy group), alkanoyloxy group, alkylthio group, alkylsulfonyl group, alkylsulfinyl group, aminosulfonyl group, amino group, mono- or di-alkylamino group substituted by carboxyl or alkoxy group, mono- or di-alkylsulfamoylamino group, mono- or di-alkylureido group optionally substituted by morpholinyl group, cycloalkyl group optionally substituted by carboxymethyl group, oxiranyl group, phenyl group optionally substituted by alkoxy or carboxyl group, morpholinyl group, pyrrolidinyl group optionally substituted by alkoxycarbonyl or carboxyl group, pyrrolidinyl group optionally substituted by alkoxycarbonylalkyl or carboxyalkyl group, pyrrolidinyl group substituted by oxo group, piperidinyl group optionally substituted by alkoxycarbonyl or carboxyl group, piperidinyl group optionally substituted by alkoxycarbonylalkyl or carboxyalkyl group, piperazinyl group optionally substituted by alkyl group, hexahydroazepinyl group, pyrimidinyl group, pyridyl group, dioxolanyl group optionally substituted by alkyl group, oxadiazolyl group optionally substituted by oxo group, oxathiadiazolyl group optionally substituted by oxo group, pyrrolidinylcarbonyl group optionally substituted by carboxyl group, piperidinyloxy group optionally substituted by alkyl group, and morpholinylcarbonyl group; alkoxycarbonyl group optionally substituted by phenyl group; carbamoyl group;

mono- or di-alkylcarbamoyl group optionally substituted by a group selected from carboxyl group, morpholinyl group and alkoxy group; hydroxycarbamimidoyl group;

alkylthio group optionally substituted by a group selected from hydroxy group, carboxyl group and mono- or di-alkylcarbamoyl group; alkylsulfinyl group;

alkylsulfonyl group optionally substituted by a group selected from hydroxy group, carboxyl group, alkoxycarbonyl group and mono- or di-alkylcarbamoyl group;

amino group;

mono- or di-alkylamino group optionally substituted by a group selected from hydroxy group, carboxyl group, alkoxycarbonyl group, alkoxy group, mono- or di-alkylamino group and morpholinyl group;

mono- or di-alkanoylamino group optionally substituted by a group selected from hydroxy group, alkoxy group, carboxyl group and amino group;

mono- or di-alkylcarbamoylamino group optionally substituted by alkoxy group;
morpholinylcarbonylamino group;
sulfamoyl group;
mono- or di-alkylsulfamoyl group;
alkanoyl group optionally substituted by a group selected from hydroxy group, carboxyl group, alkoxycarbonyl group, alkoxy group, mono- or di-alkylamino group and morpholinyl group; or
a group selected from the following groups:

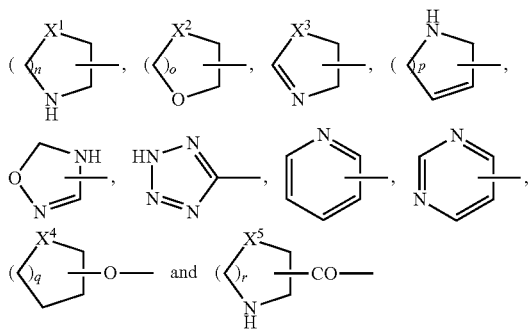

wherein $X^1$ and $X^3$ are independently $CH_2$, NH, O, S, SO or $SO_2$; $X^2$ and $X^5$ are independently $CH_2$, O, S, SO or $SO_2$; $X^4$ is NH, O, S, SO or $SO_2$; and n, o, p, q and r are independently an integer of 1 to 4, wherein each group of the above formula is optionally substituted by a substituent(s) selected from the following groups:
carboxyl group, hydroxy group, cyano group, oxo group, alkyl group, hydroxyalkyl group, alkoxycarbonylalkyl group, carboxyalkyl group, morpholinylalkyl group, phenylalkyl group, alkanoyl group, hydroxyalkanoyl group, alkoxyalkanoyl group, alkoxy group, phenylalkoxy group, alkoxycarbonyl group, benzyloxycarbonyl group, mono- or di-alkylamino group, mono- or di-alkylcarbamoyl group, mono- or di-alkylsulfamoyl group, alkylsulfonyl group and tetrazolyl group;
$R^6$, $R^7$, $R^8$ and $R^9$ are independently a hydrogen atom, a halogen atom, a hydroxy group, a nitro group, a cyano group, an alkyl group, an alkoxy group, or a mono- or di-alkylamino group, wherein said alkyl, alkoxy and mono- or di-alkylamino groups are optionally substituted by 1 to 6 substituents selected independently from halogen atom, hydroxy group, alkoxy group, alkylthio group, amino group, nitro group, cyano group, oxo group, carboxyl group, alkoxycarbonyl group and mono- or di-alkylamino group; or
$R^6$ and $R^7$, or $R^7$ and $R^8$, or $R^8$ and $R^9$ may combine at the ends to form an alkylene group which alkylene group may contain 1 to 3 heteroatoms selected independently from nitrogen, sulfur and oxygen atoms;
$R^{10}$ is an aromatic monocyclic ring optionally containing 1 to 3 heteroatoms selected independently from oxygen, sulfur and nitrogen atoms;
wherein the monocyclic aromatic ring is optionally substituted by 1 to 4 substituents selected independently from halogen atom, carboxyl group, alkoxycarbonyl group, carbamoyl group, mono- or di-alkylcarbamoyl group, alkyl group, alkoxy group, hydroxy group, nitro group, cyano group, amino group, mono- or di-alkylamino group, alkanoyl group, alkylthio group, tetrazolyl group and dihydrooxazolyl group, wherein the alkyl, alkoxy, mono- or di-alkylamino, mono- or di-alkylcarbamoyl, alkanoyl and alkylthio groups are optionally substituted by a substituent(s) selected independently from halogen atom, and hydroxy, alkoxy, amino, morpholinyl, piperidinyl, pyrrolidinyl, piperazinyl, alkylpiperazinyl and alkanoylpiperazinyl groups.

Furthermore, in the preferred compounds, the "aromatic monocyclic ring optionally containing 1 to 3 heteroatoms selected independently from oxygen, sulfur and nitrogen atoms" is a phenyl group, a pyridyl group, a pyrimidinyl group, a furyl group or a thienyl group; and the "saturated or unsaturated 5- to 8-membered heterocyclic group containing 1 to 4 heteroatoms selected independently from oxygen, sulfur and nitrogen atoms" is a pyrimidinyl group, a pyridyl group, a triazolyl group, a tetrazolyl group, a oxadiazolyl group, a dihydropyrimidinyl group, a pyrazinyl group, a thiazolyl group, an oxazolyl group, an imidazolyl group, a dihydrooxazinyl group, a dihydropyrazinyl group or a pyrazolyl group.

In more preferred compounds, $R^1$ is a hydrogen atom; an alkoxycarbonyl group optionally substituted by 1 to 5 substituents selected independently from cyano group, hydroxy group, carboxyl group, alkoxycarbonyl group, alkoxy group (said alkoxy group is optionally substituted by 1 to 3 substituents selected independently from hydroxy group, amino group, mono- or di-alkylamino group, halogen atom, carboxyl group, alkoxycarbonyl group, carboxyalkoxy group and alkoxycarbonylalkoxy group), alkylthio group, alkylsulfonyl group, alkenyl group, amino group, mono- or di-alkylamino group, tetrazolyl group, carbamoyl group, mono- or di-alkylcarbamoyl group (said mono- or di-alkylcarbamoyl group is optionally substituted by 1 to 3 substituents selected independently from carboxyl group and alkoxycarbonyl group), alkanoylamino group (said alkanoylamino group is optionally substituted by 1 to 3 substituents selected independently from carboxyl group, alkoxycarbonyl group, hydroxy group and halogen atom), halogen atom, cycloalkyl group (said cycloalkyl group is optionally substituted by 1 to 3 substituents selected independently from hydroxy group, amino group, mono- or di-alkylamino group, halogen atom, oxo group, carboxyl group, alkoxycarbonyl group, carboxyalkyl group, alkoxycarbonylalkyl group, carboxyalkoxy group and alkoxycarbonylalkoxy group), phenyl group (said phenyl group is optionally substituted by 1 to 3 substituents selected independently from hydroxy group, amino group, mono- or di-alkylamino group, halogen atom, carboxyl group, alkoxycarbonyl group, carboxyalkyl group, alkoxycarbonylalkyl group, carboxyalkoxy group and alkoxycarbonylalkoxy group), morpholinyl group optionally substituted by oxo group, piperidinyl group (said piperidinyl group is optionally substituted by 1 to 3 substituents selected independently from hydroxy group, amino group, mono- or di-alkylamino group, halogen atom, oxo group, carboxyl group, alkoxycarbonyl group, carboxyalkyl group, alkoxycarbonylalkyl group and carboxyalkoxy group, alkoxycarbonylalkoxy group), pyrrolidinyl group (said pyrrolidinyl group is optionally substituted by 1 to 3 substituents selected independently from hydroxy group, amino group, mono- or di-alkylamino group, halogen atom, oxo group, carboxyl group, alkoxycarbonyl group, carboxyalkyl group, alkoxycarbonylalkyl group, carboxyalkoxy group and alkoxycarbonylalkoxy group), and pyrimidinyl group (said pyrimidinyl group is optionally substituted by 1 to 3 substituents selected independently from carboxyalkyl group, alkoxycarbonylalkyl group and carboxyalkoxy group, alkoxycarbonylalkoxy group); dihydrooxazolyl group optionally substituted by 1 to 2 substituents selected independently from carboxyl group, alkoxycarbonyl group, alkyl group, carboxyalkyl group, alkoxycarbonylalkyl group and hydroxyalkyl group; or a mono- or di-alkylcarbamoyl group optionally substituted by 1 to 5 substituents selected independently from halogen atom, hydroxy group, carboxyl group, alkoxycarbonyl group, alkoxy group, amino group, mono- or di-alkylamino group, morpholinyl group, pyridyl group, cycloalkyl group (said cycloalkyl group is optionally substituted by 1 to 3 substituents selected independently from carboxyl group, alkoxycarbonyl group, halogen atom, amino group and hydroxy group) and phenyl group (said phenyl group is optionally substituted by 1 to 3 substituents selected independently from carboxyl group, alkoxycarbonyl group, halogen atom, amino group and hydroxy group);

$R^2$ is an alkyl group;

$R^3$ is a hydrogen atom;

$R^4$ is an alkylene group;

$R^5$ is a heterocyclic group selected from pyrimidinyl group, pyridyl group, triazolyl group, tetrazolyl group, oxadiazolyl group, dihydropyrimidinyl group, pyrazinyl group, thiazolyl group, oxazolyl group, imidazolyl group, dihydrooxazinyl group, pyrazolyl group and dihydropyrazinyl group, wherein said heterocyclic group is substituted by 1 to 4 substituents selected from the following groups, or 1 to 4 substituents selected from the following groups and oxo group:

cyano group;

nitro group;

carboxyl group;

sulfo group;

$C_{3-10}$ alkyl group;

alkyl group substituted by a group selected from halogen atom, cyano group, hydroxy group, carboxyl group, alkoxycarbonyl group, tetrazolyl group, mono- or di-alkylcarbamoyl group, alkoxy group (said alkoxy group is optionally substituted by phenyl, carboxyl or hydroxy group), alkanoyloxy group, alkylthio group, alkylsulfonyl group, alkylsulfinyl group, amino group, mono- or di-alkylamino group optionally substituted by carboxyl or alkoxy group, mono- or di-alkylsulfamoylamino group, mono- or di-alkylureido group optionally substituted by morpholinyl group, oxiranyl group, dioxolanyl group optionally substituted by alkyl group, pyrrolidinyl group optionally substituted by alkoxycarbonyl or carboxyl group, pyrrolidinyl group optionally substituted by alkoxycarbonylalkyl or carboxyalkyl group, piperidinyl group optionally substituted by alkoxycarbonyl or carboxyl group, piperidinyl group optionally substituted by alkoxycarbonylalkyl or carboxyalkyl group, piperazinyl group optionally substituted by alkyl group, hexahydroazepinyl group, morpholinyl group, and piperidinyloxy group optionally substituted by alkyl group;

alkenyl group optionally substituted by a group selected from cyano group, hydroxy group, carboxyl group, benzyloxycarbonyl group, and tetrazolyl group;

alkenyloxy group optionally substituted by carboxyl group;

$C_{3-10}$ alkoxy group;

alkoxy group substituted by a group selected from halogen atom, cyano group, hydroxy group, carboxyl group, alkoxycarbonyl group, tetrazolyl group, carbamoyl group, mono- or di-alkylcarbamoyl group optionally substituted by hydroxy group, alkoxy group optionally substituted by carboxyl or hydroxy group, alkanoyloxy group, alkylthio group, alkylsulfonyl group, alkylsulfinyl group, aminosulfonyl group, amino group, mono- or di-alkylamino group substituted by carboxyl or alkoxy group, mono- or di-alkylsulfamoylamino group, mono- or di-alkylureido group optionally substituted by morpholinyl group, cycloalkyl group optionally substituted by carboxymethyl group, oxiranyl group, phenyl group optionally substituted by alkoxy or carboxyl group, morpholinyl group, pyrrolidinyl group optionally substituted by alkoxycarbonyl or carboxyl group, pyrrolidinyl group optionally substituted by alkoxycarbonylalkyl or carboxyalkyl group, pyrrolidinyl group optionally substituted by oxo group, piperidinyl group optionally substituted by alkoxycarbonyl or carboxyl group, piperidinyl group optionally substituted by alkoxycarbonylalkyl or carboxyalkyl group, piperazinyl group optionally substituted by alkyl group, hexahydroazepinyl group, pyrimidinyl group, pyridyl group, dioxolanyl group optionally substituted by alkyl group, oxadiazolyl group optionally substituted by oxo group, oxathiadiazolyl group optionally substituted by oxo group, pyrrolidinylcarbonyl group optionally substituted by carboxyl group, piperidinyloxy group optionally substituted by alkyl group, and morpholinylcarbonyl group;

alkoxycarbonyl group optionally substituted by phenyl group; carbamoyl group;

mono- or di-alkylcarbamoyl group optionally substituted by a group selected from carboxyl group, morpholinyl group and alkoxy group; hydroxycarbamimidoyl group;

alkylthio group optionally substituted by a group selected from hydroxy group, carboxyl group and mono- or di-alkylcarbamoyl group; alkylsulfinyl group;

alkylsulfonyl group optionally substituted by a group selected from hydroxy group, carboxyl group and mono- or di-alkylcarbamoyl group;

amino group;

mono- or di-alkylamino group optionally substituted by a group selected from hydroxy group, carboxyl group, alkoxycarbonyl group, alkoxy group, mono- or di-alkylamino group and morpholinyl group; alkanoylamino group optionally substituted by a group selected from hydroxy group, alkoxy group, carboxyl group and amino group;

mono- or di-alkylureido group optionally substituted by alkoxy group; morpholinylcarbonylamino group;

sulfamoyl group;

mono- or di-alkylsulfamoyl group;

morpholinyl group optionally substituted by a group selected from oxo group and carboxyl group;

optionally oxidized thiomorpholinyl group;

piperazinyl group optionally substituted by a group selected from cyano group, alkyl group, hydroxyalkyl group, alkoxycarbonylalkyl group, carboxyalkyl group, alkanoyl group, hydroxyalkanoyl group, alkoxyalkanoyl group, benzyloxycarbonyl group, mono- or di-alkyl-carbamoyl group, mono- or di-alkylsulfamoyl group, alkylsulfonyl group and tetrazolyl group;

piperidinyl group optionally substituted by a group selected from carboxyl group, hydroxy group, oxo group, alkyl group, hydroxyalkyl group, carboxyalkyl group, alkanoyl group, alkoxy group, phenylalkoxy group, alkoxycarbonyl group and alkoxycarbonylalkyl group;

pyrrolidinyl group optionally substituted by a group selected from oxo group, carboxyl group, alkanoyl group and mono- or di-alkylamino group;

pyrrolinyl group optionally substituted by oxo group;

hexahydrodiazepinyl group optionally substituted by alkanoyl group;

diazolidinyl group optionally substituted by oxo group;

dioxolanyl group optionally substituted by alkyl group;

pyridyl group optionally substituted by carboxyl group, hydroxy group
or hydroxyalkyl group (said pyridyl group is optionally further oxidized);
tetrazolyl group substituted by hydroxy group or alkyl group that is optionally substituted by morpholinyl group;
dihydrooxadiazolyl group optionally substituted by oxo group;
dihydroimidazolyl group;
dihydrooxazolyl group;
oxazolidinyl group optionally substituted by oxo group;
tetrahydropyridyl group optionally substituted by benzyl group;
pyrimidinyl group;
tetrahydropyranyl group;
piperidinyloxy group optionally substituted by a group selected from alkyl group, carboxyl group, carboxyalkyl group and alkanoyl group;
pyrrolidinyloxy group optionally substituted by a group selected from alkyl group, carboxyl group, carboxyalkyl group and alkanoyl group;
tetrahydropyranyloxy group;
tetrahydrofuranyloxy group;
optionally oxidized thianyloxy group;
morpholinylcarbonyl group;
piperazinylcarbonyl group optionally substituted by a group selected from alkanoyl group and alkyl group; and
pyrrolidinylcarbonyl group;
$R^6$ and $R^9$ each are a hydrogen atom;
$R^7$ and $R^8$ are independently a hydrogen atom, an alkyl group optionally substituted by halogen atom, an alkoxy group, a mono- or di-alkylamino group or halogen atom; or
$R^7$ and $R^8$ combine at the ends to form an alkylenedioxy group; and
$R^{10}$ is a phenyl or pyridyl group, which phenyl or pyridyl group is optionally substituted by 1 to 4 substituents selected from alkyl group optionally substituted by halogen atom, alkoxy group, hydroxy group, halogen atom, cyano group, amino group and mono- or di-alkylamino group.

In further preferred compounds, $R^1$ is an alkoxycarbonyl group optionally substituted by 1 to 5 substituents selected independently from hydroxy group, carboxyl group, alkoxycarbonyl group, alkoxy group (said alkoxy group is optionally substituted by 1 to 3 substituents selected independently from hydroxy group, halogen atom, carboxyl group and alkoxycarbonyl group), alkenyl group, halogen atom, cycloalkyl group (said cycloalkyl group is optionally substituted by 1 to 3 substituents selected independently from hydroxy group, halogen atom, carboxyl group, alkoxycarbonyl group, carboxyalkyl group and alkoxycarbonylalkyl group), phenyl group (said phenyl group is optionally substituted by 1 to 3 substituents selected independently from hydroxy group, halogen atom, carboxyl group, alkoxycarbonyl group, carboxyalkyl group and alkoxycarbonylalkyl group), piperidinyl group (said piperidinyl group is optionally substituted by 1 to 3 substituents selected independently from hydroxy group, halogen atom, carboxyl group, alkoxycarbonyl group, carboxyalkyl group and alkoxycarbonylalkyl group), and pyrrolidinyl group (said pyrrolidinyl group is optionally substituted by 1 to 3 substituents selected independently from hydroxy group, halogen atom, carboxyl group, alkoxycarbonyl group, carboxyalkyl group and alkoxycarbonylalkyl group); or a dihydrooxazolyl group optionally substituted by 1 or 2 substituents selected independently from carboxyl group, alkoxycarbonyl group, carboxyalkyl group, alkoxycarbonylalkyl group and hydroxyalkyl group;

$R^5$ is a pyrimidinyl group, a pyridyl group, a triazolyl group, a tetrazolyl group, an oxadiazolyl group, a dihydropyrimidinyl group, a pyrazinyl group, a thiazolyl group, an oxazolyl group, a dihydrooxazinyl group, a pyrazolyl group or a dihydropyrazinyl group, said group being substituted by 1 to 4 substituents selected from the following groups: cyano group;
nitro group;
carboxyl group;
sulfo group;
alkyl group substituted by a group selected from halogen atom, cyano group, hydroxy group, carboxyl group, alkoxycarbonyl group, alkoxy group optionally substituted by carboxyl or hydroxy group, alkanoyloxy group, alkylthio group, alkylsulfonyl group, alkylsulfinyl group, amino group, mono- or di-alkylamino group, mono- or di-alkylsulfamoylamino group, mono- or di-alkylureido group optionally substituted by morpholinyl group, oxiranyl group, di-alkyldioxolanyl group, pyrrolidinyl group optionally substituted by alkoxycarbonyl or carboxyl group, piperidinyl group optionally substituted by alkoxycarbonyl or carboxyl group, piperazinyl group optionally substituted by alkyl group, hexahydroazepinyl group and morpholinyl group;
alkenyl group optionally substituted by carboxyl group, cyano group or benzyloxycarbonyl group;
alkoxy group substituted by a group selected from halogen atom, cyano group, hydroxy group, carboxyl group, alkoxycarbonyl group, alkoxy group optionally substituted by carboxyl or hydroxy group, alkanoyloxy group, alkylthio group, alkylsulfonyl group, alkylsulfinyl group, amino group, mono- or di-alkylamino group, mono- or di-alkylsulfamoylamino group, mono- or di-alkylureido group optionally substituted by morpholinyl group, oxiranyl group, di-alkyldioxolanyl group, pyrrolidinyl group optionally substituted by alkoxycarbonyl or carboxyl group, piperidinyl group optionally substituted by alkoxycarbonyl or carboxyl group, piperazinyl group optionally substituted by alkyl group, hexahydroazepinyl group and morpholinyl group;
alkoxycarbonyl group optionally substituted by phenyl group;
mono- or di-alkylcarbamoyl group optionally substituted by carboxyl group;
hydroxycarbamimidoyl group;
alkylthio group;
alkylsulfinyl group;
alkylsulfonyl group optionally substituted by carboxyl group;
mono- or di-alkylamino group optionally substituted by hydroxy group, carboxyl group, alkoxycarbonyl group, alkoxy group, mono- or di-alkylamino group or morpholinyl group;
mono- or di-alkylsulfamoyl group;
morpholinyl group;
optionally oxidized thiomorpholinyl group;
piperazinyl group optionally substituted by a group selected from alkyl
group, alkanoyl group and hydroxyalkanoyl group;
piperidinyl group optionally substituted by a group selected from carboxyl group, alkyl group and alkoxycarbonyl group;
dioxolanyl group optionally substituted by alkyl group;
tetrazolyl group optionally substituted by alkyl group, hydroxyalkyl group or morpholinylalkyl group;

dihydrooxadiazolyl group optionally substituted by oxo group;
pyrimidinyl group; or
tetrahydropyranyl group; and
$R^{10}$ is a phenyl or pyridyl group, which phenyl or pyridyl group is optionally substituted by 1 to 4 substituents selected from alkyl group optionally substituted by halogen atom, alkoxy group, hydroxy group, halogen atom, cyano group, amino group and mono- or di-alkylamino group.

Another embodiment of the present invention includes compounds of the formula (I) wherein $R^5$ is a group of the formula:

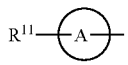

wherein Ring A is a saturated or unsaturated 5- to 8-membered heterocyclic group containing 1 to 4 heteroatoms selected independently from oxygen, sulfur and nitrogen atoms, and $R^{11}$ is a group selected from the following groups:
cyano group;
nitro group;
carboxyl group;
sulfo group;
alkyl group substituted by a group selected from halogen atom, cyano group, hydroxy group, carboxyl group, alkoxycarbonyl group, alkoxy group (said alkoxy group is optionally substituted by phenyl, hydroxy or carboxyl group), alkanoyloxy group, alkylthio group, alkylsulfonyl group, alkylsulfinyl group, amino group, mono- or di-alkylamino group, mono- or di-alkylsulfamoylamino group, mono- or di-alkylureido group optionally substituted by morpholinyl group, oxiranyl group, di-alkyldioxolanyl group, pyrrolidinyl group optionally substituted by alkoxycarbonyl or carboxyl group, piperidinyl group optionally substituted by alkoxycarbonyl or carboxyl group, piperazinyl group optionally substituted by alkyl group, hexahydroazepinyl group and morpholinyl group;
alkenyl group optionally substituted by carboxyl group, cyano group or benzyloxycarbonyl group;
alkoxy group substituted by a group selected from halogen atom, cyano group, hydroxy group, carboxyl group, alkoxycarbonyl group, alkoxy group (said alkoxy group is optionally substituted by phenyl, hydroxy or carboxyl group), alkanoyloxy group, alkylthio group, alkylsulfonyl group, alkylsulfinyl group, amino group, mono- or di-alkylamino group, mono- or di-alkylsulfamoylamino group, mono- or di-alkylureido group optionally substituted by morpholinyl group, oxiranyl group, di-alkyldioxolanyl group, pyrrolidinyl group optionally substituted by alkoxycarbonyl or carboxyl group, piperidinyl group optionally substituted by alkoxycarbonyl or carboxyl group, piperazinyl group optionally substituted by alkyl group, hexahydroazepinyl group and morpholinyl group;
alkoxycarbonyl group optionally substituted by phenyl group;
mono- or di-alkylcarbamoyl group optionally substituted by carboxyl group;
hydroxycarbamimidoyl group;
alkylthio group;
alkylsulfinyl group;
alkylsulfonyl group optionally substituted by carboxyl group;
mono- or di-alkylamino group optionally substituted by hydroxy group, carboxyl group, alkoxycarbonyl group, alkoxy group, mono- or di-alkylamino group or morpholinyl group;
mono- or di-alkylsulfamoyl group;
morpholinyl group;
optionally oxidized thiomorpholinyl group;
piperazinyl group optionally substituted by a group selected from alkyl group, alkanoyl group and hydroxyalkanoyl group;
pyrrolidinyl group optionally substituted by carboxyl group, carboxyalkyl group, alkyl group, alkoxycarbonyl group or alkoxycarbonylalkyl group;
piperidinyl group optionally substituted by carboxyl group, carboxyalkyl group, alkyl group, alkoxycarbonyl group or alkoxycarbonylalkyl group;
dioxolanyl group optionally substituted by alkyl group;
tetrazolyl group optionally substituted by alkyl group, hydroxyalkyl group or morpholinylalkyl group;
dihydrooxadiazolyl group optionally substituted by oxo group; pyrimidinyl group; or
tetrahydropyranyl group;
which compound is shown by the formula (I-A):

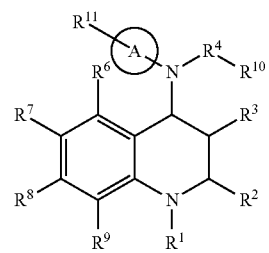

(I-A)

wherein each symbol has the same meaning as defined above.

More preferred embodiment includes compounds of the formula (I) wherein $R^1$ is a hydrogen atom; an alkoxycarbonyl group optionally substituted by 1 to 5 substituents selected independently from cyano group, hydroxy group, carboxyl group, alkoxycarbonyl group, alkoxy group (said alkoxy group is optionally substituted by 1 to 3 substituents selected independently from hydroxy group, amino group, mono- or di-alkylamino group, halogen atom, carboxyl group, alkoxycarbonyl group, carboxyalkoxy group and alkoxycarbonylalkoxy group), alkylthio group, alkylsulfonyl group, alkenyl group, amino group, mono- or di-alkylamino group, tetrazolyl group, carbamoyl group, mono- or di-alkylcarbamoyl group (said mono- or di-alkylcarbamoyl group is optionally substituted by 1 to 3 substituents selected independently from carboxyl group and alkoxycarbonyl group), alkanoylamino group (said alkanoylamino group is optionally substituted by 1 to 3 substituents selected independently from carboxyl group, alkoxycarbonyl group, hydroxy group and halogen atom), halogen atom, cycloalkyl group (said cycloalkyl group is optionally substituted by 1 to 3 substituents selected independently from hydroxy group, amino group, mono- or di-alkylamino group, halogen atom, oxo group, carboxyl group, alkoxycarbonyl group, carboxyalkyl group, alkoxycarbonylalkyl group, carboxyalkoxy group and alkoxycarbonylalkoxy group), phenyl group (said phenyl group is optionally substituted by 1 to 3 substituents selected independently from hydroxy group, amino group, mono- or di-alkylamino group, halogen atom, carboxyl group, alkoxycarbonyl group, carboxyalkyl group, alkoxycarbonylalkyl group, carboxyalkoxy group and alkoxycarbonylalkoxy group), morpholinyl group optionally substituted by oxo group, piperidinyl group (said piperidinyl group is optionally substituted by 1 to 3 substituents selected independently from hydroxy group, amino group, mono- or di-alkylamino group, halogen atom, oxo group, carboxyl group, alkoxycarbonyl group, carboxyalkyl group, alkoxycarbonylalkyl group and carboxyalkoxy group, alkoxycarbonylalkoxy group), pyrrolidinyl group (said pyrrolidinyl group is optionally substituted by 1 to 3 substituents selected independently from hydroxy group, amino group, mono- or di-alkylamino group, halogen atom, oxo group, carboxyl group, alkoxycarbonyl group, carboxyalkyl group, alkoxycarbonylalkyl group, carboxyalkoxy group and alkoxycarbonylalkoxy group), and pyrimidinyl group (said pyrimidinyl group is optionally substituted by 1 to 3 substituents selected independently from carboxyalkyl group, alkoxycarbonylalkyl group and carboxyalkoxy group, alkoxycarbonylalkoxy group); dihydrooxazolyl group optionally substituted by 1 to 2 substituents selected independently from carboxyl group, alkoxycarbonyl group, alkyl group, carboxyalkyl group, alkoxycarbonylalkyl group and hydroxyalkyl group; or a mono- or di-alkylcarbamoyl group optionally substituted by 1 to 5 substituents selected independently from halogen atom, hydroxy group, carboxyl group, alkoxycarbonyl group, alkoxy group, amino group, mono- or di-alkylamino group, morpholinyl group, pyridyl group, cycloalkyl group (said cycloalkyl group is optionally substituted by 1 to 3 substituents selected independently from carboxyl group, alkoxycarbonyl group, halogen atom, amino group and hydroxy group) and phenyl group (said phenyl group is optionally substituted by 1 to 3 substituents selected independently from carboxyl group, alkoxycarbonyl group, halogen atom, amino group and hydroxy group);

$R^2$ is an alkyl group;
$R^3$ is a hydrogen atom;
$R^4$ is an alkylene group;
Ring A and R" are the same groups as defined above;
$R^6$ and $R^9$ each are a hydrogen atom;
$R^7$ and $R^8$ are independently a hydrogen atom, an alkyl group optionally substituted by halogen atom, alkoxy group, or mono- or di-alkylamino group; or combine at the ends to form an alkylenedioxy group; and
$R^{10}$ is a phenyl or pyridyl group, which phenyl or pyridyl group is optionally substituted by 1 to 4 substituents selected from alkyl group optionally substituted by halogen atom, alkoxy group, hydroxy group, halogen atom, cyano group, amino group and mono- or di-alkylamino group.

Another preferred embodiment includes compounds of the formula (I) wherein Ring A is a saturated or unsaturated 5- to 8-membered heterocyclic group containing 1 to 4 heteroatoms selected independently from oxygen, sulfur and nitrogen atoms, and $R^{11}$ is a group selected from the followings groups:
cyano group; nitro group; carboxyl group; sulfo group; alkyl group substituted by a group selected from halogen atom, hydroxy group, carboxyl group, alkoxycarbonyl group, alkoxy group optionally substituted by phenyl or hydroxy group, alkanoyloxy group, alkylthio group, alkylsulfonyl group, alkylsulfinyl group, amino group, mono- or di-alkylamino group, mono- or di-alkylsulfamoylamino group, mono- or di-alkylureido group optionally substituted by morpholinyl group, oxiranyl group, di-alkyldioxolanyl group, pyrrolidinyl group optionally substituted by alkoxycarbonyl or carboxyl group, piperazinyl group optionally substituted by alkyl group, hexahydroazepinyl group and morpholinyl group; alkenyl group optionally substituted by carboxyl group or benzyloxycarbonyl group; alkoxy group substituted by carboxyl group, hydroxy group, alkoxy group, alkylthio group, alkylsulfonyl group or alkoxyphenyl group; alkoxycarbonyl group optionally substituted by phenyl group; mono- or di-alkylcarbamoyl group optionally substituted by carboxyl group; hydroxycarbamimidoyl group; alkylthio group; alkylsulfinyl group; alkylsulfonyl group optionally substituted by alkoxycarbonyl group; mono- or di-alkylamino group optionally substituted by hydroxy group, carboxyl group, alkoxycarbonyl group, alkoxy group, mono- or di-alkylamino group or morpholinyl group; mono- or di-alkylsulfamoyl group; morpholinyl group; optionally oxidized thiomorpholinyl group; piperazinyl group optionally substituted by a group selected from alkyl group, alkanoyl group and hydroxyalkanoyl group; piperidinyl group optionally substituted by carboxyl group, alkyl group or alkoxycarbonyl group; dioxolanyl group optionally substituted by alkyl group; tetrazolyl group substituted by alkyl group, hydroxyalkyl group or morpholinylalkyl group; dihydrooxadiazolyl group optionally substituted by oxo group; pyrimidinyl group; or tetrahydropyranyl group.

More preferred embodiment herein includes compounds of the formula (I) wherein $R^1$ is an alkoxycarbonyl group optionally substituted by a group selected from hydroxy group and alkoxy group; or a dihydrooxazolyl group optionally substituted by hydroxyalkyl group;

$R^2$ is an alkyl group;
$R^3$ is a hydrogen atom;
$R^4$ is an alkylene group;
Ring A and $R^{11}$ are the same groups as defined above;
$R^6$ and $R^9$ each are a hydrogen atom; and
$R^7$ and $R^8$ are independently a hydrogen atom, an alkyl group optionally substituted by 1 to 9 halogen atoms, an alkoxy group, or a mono- or di-alkylamino group; or combine at the ends to form an alkylenedioxy group;
$R^{10}$ is a phenyl or pyridyl group, which phenyl or pyridyl group is optionally substituted by 1 to 4 substituents selected from alkyl group optionally substituted by 1 to 9 halogen atoms, alkoxy group, hydroxy group, halogen atom, cyano group, amino group and mono- or di-alkylamino group.

Examples of Ring A include a pyrimidinyl group, a pyridyl group, a triazolyl group, a tetrazolyl group, an oxadiazolyl group, a dihydropyrimidinyl group, a pyrazinyl group, a thiazolyl group, an oxazolyl group, a dihydrooxazinyl group, an imidazolyl group, a pyrazolyl group, a dihydropyrazinyl group, and the like.

More preferred compounds include those wherein Ring A is a pyrimidinyl group, a pyridyl group, a tetrazolyl group, an oxadiazolyl group, a pyrazinyl group, a thiazolyl group or an oxazolyl group; and $R^{11}$ is a carboxyl group; a cyano group; a nitro group; an alkyl group substituted by a group selected from hydroxy group, cyano group, carboxyl group, alkoxycarbonyl group, alkoxy group, phenylalkoxy group, hydroxyalkoxy group, carboxyalkoxy group, alkylthio group, alkylsulfonyl group, alkylsulfinyl group, amino group, mono- or di-alkylamino group, mono- or di-alkylsulfamoylamino group, mono- or di-alkylureido group optionally substituted by morpholinyl group, oxiranyl group, di-alkyldioxolanyl group, pyrrolidinyl group optionally substituted by carboxyl group, piperidinyl group optionally substituted by carboxyl group, piperazinyl group optionally substituted by alkyl group and morpholinyl group; an alkenyl group optionally substituted by carboxyl group; an alkoxy group substituted by a group selected from hydroxy group, cyano group, carboxyl group, alkoxycarbonyl group, alkoxy group, phenylalkoxy group, hydroxyalkoxy group, carboxyalkoxy group, alkylthio group, alkylsulfonyl group, alkylsulfinyl group, amino group, mono- or di-alkylamino group, mono- or di-alkylsulfamoylamino group, mono- or di-alkylureido group optionally substituted by morpholinyl group, oxiranyl group, di-alkyldioxolanyl group, pyrrolidinyl group optionally substituted by carboxyl group, piperidinyl group optionally substituted by carboxyl group, piperazinyl group optionally substituted by alkyl group and morpholinyl group; an alkoxycarbonyl group; a hydroxycarbamimidoyl group; alkylthio group; an alkylsulfonyl group optionally substituted by carboxyl group; a mono- or di-alkylamino group optionally substituted by hydroxy group, carboxyl group, alkoxy group or mono- or di-alkylamino group; a morpholinyl group; an optionally oxidized thiomorpholinyl group; a piperazinyl group optionally substituted by a group selected from alkyl group, alkanoyl group and hydroxyalkanoyl group; a pyrrolidinyl group optionally substituted by carboxyl group, alkyl group carboxyalkyl group or alkoxycarbonyl group; a piperidinyl group optionally substituted by carboxyl group, alkyl group, carboxyalkyl group or alkoxycarbonyl group; a tetrazolyl group optionally substituted by alkyl group, hydroxyalkyl group, or morpholinylalkyl group; an oxodihydrooxadiazolyl group; a pyrimidinyl group; or a tetrahydropyranyl group.

Still more preferred compounds include those wherein $R^1$ is an alkoxycarbonyl group optionally substituted by 1 to 5 substituents selected independently from hydroxy group, carboxyl group, alkoxycarbonyl group, alkoxy group (said alkoxy group is optionally substituted by 1 to 3 substituents selected independently from hydroxy group, halogen atom, carboxyl group and alkoxycarbonyl group), alkenyl group, halogen atom, cycloalkyl group (said cycloalkyl group is optionally substituted by 1 to 3 substituents selected independently from hydroxy group, halogen atom, carboxyl group, alkoxycarbonyl group, carboxyalkyl group and alkoxycarbonylalkyl group), phenyl group (said phenyl group is optionally substituted by 1 to 3 substituents selected independently from hydroxy group, halogen atom, carboxyl group, alkoxycarbonyl group, carboxyalkyl group and alkoxycarbonylalkyl group), piperidinyl group (said piperidinyl group is optionally substituted by 1 to 3 substituents selected independently from hydroxy group, halogen atom, carboxyl group, alkoxycarbonyl group, carboxyalkyl group and alkoxycarbonylalkyl group), and pyrrolidinyl group (said pyrrolidinyl group is optionally substituted by 1 to 3 substituents selected independently from hydroxy group, halogen atom, carboxyl group, alkoxycarbonyl group, carboxyalkyl group and alkoxycarbonylalkyl group); or a dihydrooxazolyl group optionally substituted by 1 or 2 substituents selected independently from carboxyl group, alkoxycarbonyl group, carboxyalkyl group, alkoxycarbonylalkyl group and hydroxyalkyl group;

$R^{10}$ is a phenyl group substituted by 1 to 3 substituents selected from alkyl group optionally substituted by halogen atom, alkoxy group, halogen atom and cyano group;

Ring A is a pyrimidinyl group, a pyridyl group, a tetrazolyl group, an oxadiazolyl group or a thiazolyl group; and $R^{11}$ is a carboxyl group; a cyano group; a nitro group; an alkyl group substituted by a group selected from hydroxy group, carboxyl group, alkoxycarbonyl group, alkoxy group, phenylalkoxy group, carboxyalkoxy group, alkylthio group, alkylsulfonyl group, alkylsulfinyl group, amino group, mono- or di-alkylamino group, mono- or di-alkylsulfamoylamino group, mono- or di-alkylureido group optionally substituted by morpholinyl group, oxiranyl group, di-alkyldioxolanyl group, piperazinyl group optionally substituted by alkyl group and morpholinyl group; an alkenyl group optionally substituted by carboxyl group; an alkoxy group substituted by a group selected from cyano group, hydroxy group, carboxyl group, alkoxycarbonyl group, alkoxy group, phenylalkoxy group, carboxyalkoxy group, alkylthio group, alkylsulfonyl group, alkylsulfinyl group, amino group, mono- or di-alkylamino group, mono- or di-alkylsulfamoylamino group, mono- or di-alkylureido group optionally substituted by morpholinyl group, oxiranyl group, di-alkyldioxolanyl group, piperazinyl group optionally substituted by alkyl group and morpholinyl group; a hydroxycarbamimidoyl group; an alkylthio group; an alkylsulfonyl group optionally substituted by alkoxycarbonyl group; a mono- or di-alkylamino group optionally substituted by hydroxy group, carboxyl group or alkoxy group; a morpholinyl group; optionally oxidized thiomorpholinyl group; a piperazinyl group optionally substituted by a group selected from alkyl group, alkanoyl group and hydroxyalkanoyl group; a pyrrolidinyl group optionally substituted by carboxyl group, alkyl group carboxyalkyl group or alkoxycarbonyl group; a piperidinyl group optionally substituted by carboxyl group, alkyl group, carboxyalkyl group or alkoxycarbonyl group; a tetrazolyl group optionally substituted by alkyl group, hydroxyalkyl group, or morpholinylalkyl group; an oxodihydrooxadiazolyl group; a pyrimidinyl group; or a tetrahydropyranyl group.

Still furthermore preferred compounds include those wherein $R^1$ is an alkoxycarbonyl group optionally substituted by 1 or 5 substituents selected independently from carboxyl group, alkoxycarbonyl group, halogen atom, hydroxy group and cycloalkyl group;

$R^{10}$ is a phenyl group substituted by 1 to 3 substituents selected from cyano group, alkyl group optionally substituted by halogen atom and alkoxy group;

Ring A is a pyrimidinyl group, a pyridyl group, a tetrazolyl group or an oxadiazolyl group;

$R^{11}$ is a carboxyl group; an alkyl group substituted by hydroxy group, carboxyl group, alkoxy group or alkylsulfonyl group; an alkenyl group optionally substituted by carboxyl group; an alkoxy group substituted by cyano group, carboxyl group, hydroxy group, alkoxy group, alkylthio group or alkylsulfonyl group; a mono- or di-alkylamino group optionally substituted by carboxyl group or alkoxy group; a morpholinyl group; a piperidinyl group substituted by carboxyl group; or a tetrazolyl group substituted by hydroxyalkyl group;

$R^7$ is an alkyl group optionally substituted by halogen atom, alkoxy group, or mono- or di-alkylamino group; and $R^8$ is a hydrogen atom.

Especially preferred compounds include those wherein $R^1$ is an ethoxycarbonyl group, a hydroxyethoxycarbonyl group, a 2-fluoroethoxycarbonyl group, a 2,2-difluoroethoxycarbonyl group or a 2,2,2-trifluoroethoxycarbonyl group; $R^2$ is an ethyl group; $R^{10}$ is a phenyl group substituted by 1 to 2 substituents selected from cyano group, trifluoromethyl group and methoxy group; $R^7$ is a trifluoromethyl group or a methoxy group. In this regard, other examples of especially preferred compounds include those wherein $R^1$ is a carboxy ($C_{2-10}$alkoxy)carbonyl group or an alkoxycarbonyl($C_{2-10}$alkoxy)carbonyl group, and $R^2$, $R^{10}$ and $R^7$ are the same above.

Especially more preferred compounds include those wherein $R^1$ is an ethoxycarbonyl group or a hydroxyethoxycarbonyl group; $R^2$ is an ethyl group; $R^{10}$ is a phenyl group substituted by 1 to 2 substituents selected from cyano group, trifluoromethyl group and methoxy group; $R^7$ is a trifluoromethyl group or a methoxy group.

Most preferred compounds include those listed below.

(2R,4S)-4-{[3,5-Bis(trifluoromethyl)benzyl]-[5-(morpholin-4-yl)pyrimidin-2-yl]}amino-2-ethyl-6-trifluoromethyl-3,4-dihydro-2H-quinoline-1-carboxylic acid ethyl ester;

(2R,4S)-4-[[3,5-Bis(trifluoromethyl)benzyl]-(5-{[methyl-(2-methoxyethyl)]-amino}pyrimidin-2-yl)]amino-2-ethyl-6-trifluoromethyl-3,4-dihydro-2H-quinoline-1-carboxylic acid ethyl ester;

(2R,4S)-4-{[3,5-Bis(trifluoromethyl)benzyl]-[5-(2-methoxyethoxy)pyrimidin-2-yl]}amino-2-ethyl-6-trifluoromethyl-3,4-dihydro-2H-quinoline-1-carboxylic acid ethyl ester;

(2R,4S)-4-{[3,5-Bis(trifluoromethyl)benzyl]-(5-carboxypyrimidin-2-yl)}amino-2-ethyl-6-trifluoromethyl-3,4-dihydro-2H-quinoline-1-carboxylic acid ethyl ester;

(2R,4S)-4-{[3,5-Bis(trifluoromethyl)benzyl]-[5-(2-carboxyethyl)pyrimidin-2-yl]}amino-2-ethyl-6-trifluoromethyl-3,4-dihydro-2H-quinoline-1-carboxylic acid ethyl ester;

(2R,4S)-4-([3,5-Bis(trifluoromethyl)benzyl]-{5-[2-(2-hydroxyethyl)-2H-tetrazol-5-yl]pyrimidin-2-yl})amino-2-ethyl-6-trifluoromethyl-3,4-dihydro-2H-quinoline-1-carboxylic acid ethyl ester;

(2R,4S)-4-{[3,5-Bis(trifluoromethyl)benzyl]-[5-(morpholin-4-yl)pyrimidin-2-yl]}amino-2-ethyl-6-methoxy-3,4-dihydro-2H-quinoline-1-carboxylic acid ethyl ester;

(2R,4S)-4-{(3,5-Dimethoxybenzyl)-[5-(morpholin-4-yl)pyrimidin-2-yl]}amino-2-ethyl-6-trifluoromethyl-3,4-dihydro-2H-quinoline-1-carboxylic acid ethyl ester;

(2R,4S)-4-{(3,5-Dicyanobenzyl)-[5-(morpholin-4-yl)pyrimidin-2-yl]}amino-2-ethyl-6-trifluoromethyl-3,4-dihydro-2H-quinoline-1-carboxylic acid ethyl ester;

(2R,4S)-4-{(3-Cyanobenzyl)-[5-(morpholin-4-yl)pyrimidin-2-yl]}amino-2-ethyl-6-trifluoromethyl-3,4-dihydro-2H-quinoline-1-carboxylic acid ethyl ester;

(2R*,4S*)-4-([3,5-Bis(trifluoromethyl)benzyl]-{5-[2-(2-hydroxyethyl)-2H-tetrazol-5-yl]pyrimidin-2-yl})amino-2-ethyl-6-methoxy-3,4-dihydro-2H-quinoline-1-carboxylic acid ethyl ester;

(2R,4S)-4-{[3,5-Bis(trifluoromethyl)benzyl]-[2-(2-hydroxyethyl)-2H-tetrazol-5-yl]}amino-2-ethyl-6-trifluoromethyl-3,4-dihydro-2H-quinoline-1-carboxylic acid ethyl ester;

(2R,4S)-4-{[3,5-Bis(trifluoromethyl)benzyl]-[2-(2-methanesulphonylethyl)-2H-tetrazol-5-yl]}amino-2-ethyl-6-trifluoromethyl-3,4-dihydro-2H-quinoline-1-carboxylic acid ethyl ester;

(2R,4S)-4-{(3-Cyano-5-trifluoromethylbenzyl)-[5-(morpholin-4-yl)pyrimidin-2-yl]}amino-2-ethyl-6-trifluoromethyl-3,4-dihydro-2H-quinoline-1-carboxylic acid ethyl ester;

(2R*,4S*)-4-{[3,5-Bis(trifluoromethyl)benzyl]-[5-(morpholin-4-yl)pyrimidin-2-yl]}amino-2-ethyl-6-trifluoromethyl-3,4-dihydro-2H-quinoline-1-carboxylic acid 2-hydroxyethyl ester;

(2R,4S)-4-{[3,5-Bis(trifluoromethyl)benzyl]-[5-(4-carboxypyperidin-1-yl)pyrimidin-2-yl]}amino-2-ethyl-6-methoxy-3,4-dihydro-2H-quinoline-1-carboxylic acid ethyl ester;

(2R,4S)-4-{(3-Cyano-5-trifluoromethylbenzyl)-[5-(2-carboxyethyl)pyrimidin-2-yl]}amino-2-ethyl-6-trifluoromethyl-3,4-dihydro-2H-quinoline-1-carboxylic acid ethyl ester;

(2R,4S)-4-[[3,5-Bis(trifluoromethyl)benzyl]-(5-{[methyl-(2-carboxyethyl)]amino}pyrimidin-2-yl)]amino-2-ethyl-6-trifluoromethyl-3,4-dihydro-2H-quinoline-1-carboxylic acid ethyl ester;

(2R,4S)-4-{[3,5-Bis(trifluoromethyl)benzyl]-[5-(3-carboxypropoxy)pyrimidin-2-yl]}amino-2-ethyl-6-trifluoromethyl-3,4-dihydro-2H-quinoline-1-carboxylic acid ethyl ester;

(2R,4S)-4-([3,5-Bis(trifluoromethyl)benzyl]-{5-[3-(tetrazol-5-yl)-propoxy]pyrimidin-2-yl})amino-2-ethyl-6-trifluoromethyl-3,4-dihydro-2H-quinoline-1-carboxylic acid ethyl ester;

(2R,4S)-4-{[3,5-Bis(trifluoromethyl)benzyl]-[5-(4-carboxybutoxy)pyrimidin-2-yl]}amino-2-ethyl-6-trifluoromethyl-3,4-dihydro-2H-quinoline-1-carboxylic acid ethyl ester;

(2R,4S)-4-{[3,5-Bis(trifluoromethyl)benzyl]-[5-(5-carboxypentyloxy)-pyrimidin-2-yl]}amino-2-ethyl-6-trifluoromethyl-3,4-dihydro-2H-quinoline-1-carboxylic acid ethyl ester;

(2R,4S)-4-{[3,5-Bis(trifluoromethyl)benzyl]-[5-(2-carboxyethoxy)pyrimidin-2-yl]}amino-2-ethyl-6-trifluoromethyl-3,4-dihydro-2H-quinoline-1-carboxylic acid ethyl ester;

(2R,4S)-4-{[3,5-Bis(trifluoromethyl)benzyl]-[5-(4-carboxymethylpyperidin-1-yl)pyrimidin-2-yl]}amino-2-ethyl-6-trifluoromethyl-3,4-dihydro-2H-quinoline-1-carboxylic acid ethyl ester;

(2R,4S)-4-{[3,5-Bis(trifluoromethyl)benzyl]-[5-(3-carboxypropoxy)pyridin-2-yl]}amino-2-ethyl-6-trifluoromethyl-3,4-dihydro-2H-quinoline-1-carboxylic acid ethyl ester;

(2R,4S)-4-{[3,5-Bis(trifluoromethyl)benzyl]-[5-(4-carboxybutoxy)pyridin-2-yl]}amino-2-ethyl-6-trifluoromethyl-3,4-dihydro-2H-quinoline-1-carboxylic acid ethyl ester;

(2R,4S)-4-{(3-Cyano-5-trifluoromethylbenzyl)-[5-(4-carboxybutoxy)-pyrimidin-2-yl]}amino-2-ethyl-6-trifluoromethyl-3,4-dihydro-2H-quinoline-1-carboxylic acid ethyl ester;

(2R,4S)-4-{[3,5-Bis(trifluoromethyl)benzyl]-[5-(3-carboxypropoxy)pyrimidin-2-yl]}amino-2-ethyl-6-methoxy-3,4-dihydro-2H-quinoline-1-carboxylic acid ethyl ester;

(2R,4S)-4-{[3,5-Bis(trifluoromethyl)benzyl]-[5-(3-carboxypropoxy)pyrimidin-2-yl]}amino-2-ethyl-6-dimethylamino-3,4-dihydro-2H-quinoline-1-carboxylic acid ethyl ester;

(2R,4S)-4-{[3,5-Bis(trifluoromethyl)benzyl]-[5-(4-carboxypyperidin-1-yl)pyrimidin-2-yl]}amino-2-ethyl-6-trifluoromethyl-3,4-dihydro-2H-quinoline-1-carboxylic acid 2,2,2-trifluoroethyl ester;

(2R,4S)-4-{[3,5-Bis(trifluoromethyl)benzyl]-[5-(4-carboxypyperidin-1-yl)pyrimidin-2-yl]}amino-2-ethyl-6-trifluoromethyl-3,4-dihydro-2H-quinoline-1-carboxylic acid ethyl ester;

(2R,4S)-4-{[3,5-Bis(trifluoromethyl)benzyl]-[5-(3-carboxypropoxy)pyrimidin-2-yl]}amino-2-ethyl-6-trifluoromethyl-3,4-dihydro-2H-quinoline-1-carboxylic acid 2,2,2-trifluoroethyl ester;

(2R,4S)-4-{(3-Cyano-5-trifluoromethylbenzyl)-[5-(3-carboxypropoxy)-pyrimidin-2-yl]}amino-2-ethyl-6-trifluoromethyl-3,4-dihydro-2H-quinoline-1-carboxylic acid 2,2,2-trifluoroethyl ester;

(2R,4S)-4-{[3,5-Bis(trifluoromethyl)benzyl]-[5-(4-carboxypyperidin-1-yl)pyrimidin-2-yl]}amino-2-ethyl-6-trifluoromethyl-3,4-dihydro-2H-quinoline-1-carboxylic acid 2-hydroxyethyl ester;

(2R,4S)-4-{[3,5-Bis(trifluoromethyl)benzyl]-[5-(morpholin-4-yl)pyrimidin-2-yl]}amino-2-ethyl-6-trifluoromethyl-3,4-dihydro-2H-quinoline-1-carboxylic acid 2-carboxyethyl ester;

(2R,4S)-4-{[3,5-Bis(trifluoromethyl)benzyl]-[5-(morpholin-4-yl)pyrimidin-2-yl]}amino-2-ethyl-6-trifluoromethyl-3,4-dihydro-2H-quinoline-1-carboxylic acid 3-carboxypropyl ester;

(2R,4S)-4-{[3,5-Bis(trifluoromethyl)benzyl]-[5-(morpholin-4-yl)pyrimidin-2-yl]}amino-2-ethyl-6-trifluoromethyl-3,4-dihydro-2H-quinoline-1-carboxylic acid 4-carboxybutyl ester;

(2R,4S)-4-{[3,5-Bis(trifluoromethyl)benzyl]-[5-(morpholin-4-yl)pyrimidin-2-yl]}amino-2-ethyl-6-trifluoromethyl-3,4-dihydro-2H-quinoline-1-carboxylic acid 2-carboxy-2-methylpropyl ester;

(2R,4S)-4-{[3,5-Bis(trifluoromethyl)benzyl]-[5-(morpholin-4-yl)pyrimidin-2-yl]}amino-2-ethyl-6-trifluoromethyl-3,4-dihydro-2H-quinoline-1-carboxylic acid 5-carboxypentyl ester;

(2R,4S)-4-{[3,5-Bis(trifluoromethyl)benzyl]-[5-(2-hydroxyethoxy)pyrimidin-2-yl]}amino-2-ethyl-6-trifluoromethyl-3,4-dihydro-2H-quinoline-1-carboxylic acid 2-carboxyethyl ester;

(2R,4S)-4-{[3,5-Bis(trifluoromethyl)benzyl]-[5-(2-hydroxyethoxy)pyrimidin-2-yl]}amino-2-ethyl-6-trifluoromethyl-3,4-dihydro-2H-quinoline-1-carboxylic acid 5-carboxypentyl ester;

(2R,4S)-4-{[3,5-Bis(trifluoromethyl)benzyl]-[5-(2-methoxyethoxy)pyrimidin-2-yl]}amino-2-ethyl-6-trifluoromethyl-3,4-dihydro-2H-quinoline-1-carboxylic acid 2-carboxyethyl ester;

(2R,4S)-4-{[3,5-Bis(trifluoromethyl)benzyl]-[5-(2-methoxyethoxy)pyrimidin-2-yl]}amino-2-ethyl-6-trifluoromethyl-3,4-dihydro-2H-quinoline-1-carboxylic acid 3-carboxypropyl ester;

(2R,4S)-4-{[3,5-Bis(trifluoromethyl)benzyl]-[5-(2-methoxyethoxy)pyrimidin-2-yl]}amino-2-ethyl-6-trifluoromethyl-3,4-dihydro-2H-quinoline-1-carboxylic acid 4-carboxybutyl ester;

(2R,4S)-4-{[3,5-Bis(trifluoromethyl)benzyl]-5-(3-cyanopropoxy)pyrimidin-2-yl)}amino-2-ethyl-6-trifluoromethyl-3,4-dihydro-2H-quinoline-1-carboxylic acid 2-carboxyethyl ester; or (2R,4S)-4-{[3,5-Bis(trifluoromethyl)benzyl]-(5-dimethylaminopyrimidin-2-yl)}amino-2-ethyl-6-trifluoromethyl-3,4-dihydro-2H-quinoline-1-carboxylic acid 2-carboxyethyl ester; or a pharmaceutically acceptable salt thereof.

Further examples of most preferred compounds include:

(2R,4S)-4-{[3,5-Bis(trifluoromethyl)benzyl]-[5-(2-hydroxyethoxy)pyrimidin-2-yl]}amino-2-ethyl-6-trifluoromethyl-3,4-dihydro-2H-quinoline-1-carboxylic acid 3-carboxypropyl ester;

(2R,4S)-4-{[3,5-Bis(trifluoromethyl)benzyl]-[5-(2-hydroxyethoxy)pyrimidin-2-yl]}amino-2-ethyl-6-trifluoromethyl-3,4-dihydro-2H-quinoline-1-carboxylic acid 4-carboxybutyl ester;

(2R,4S)-4-{[3,5-Bis(trifluoromethyl)benzyl]-[5-(2-hydroxyethoxy)pyrimidin-2-yl]}amino-2-ethyl-6-trifluoromethyl-3,4-dihydro-2H-quinoline-1-carboxylic acid 2-carboxy-2-methylpropyl ester;

(2R,4S)-4-{[3,5-Bis(trifluoromethyl)benzyl]-[5-(2-methoxyethoxy)pyrimidin-2-yl]}amino-2-ethyl-6-trifluoromethyl-3,4-dihydro-2H-quinoline-1-carboxylic acid 2-carboxy-2-methylpropyl ester;

(2R,4S)-4-{[3,5-Bis(trifluoromethyl)benzyl]-[5-(2-methoxyethoxy)pyrimidin-2-yl]}amino-2-ethyl-6-trifluoromethyl-3,4-dihydro-2H-quinoline-1-carboxylic acid 5-carboxypentyl ester;

(2R,4S)-4-{[3,5-Bis(trifluoromethyl)benzyl]-[5-(3-cyanopropoxy)pyrimidin-2-yl]}amino-2-ethyl-6-trifluoromethyl-3,4-dihydro-2H-quinoline-1-carboxylic acid 3-carboxypropyl ester;

(2R,4S)-4-{[3,5-Bis(trifluoromethyl)benzyl]-[5-(3-cyanopropoxy)pyrimidin-2-yl]}amino-2-ethyl-6-trifluoromethyl-3,4-dihydro-2H-quinoline-1-carboxylic acid 4-carboxybutyl ester;

(2R,4S)-4-{[3,5-Bis(trifluoromethyl)benzyl]-[5-(3-cyanopropoxy)pyrimidin-2-yl]}amino-2-ethyl-6-trifluoromethyl-3,4-dihydro-2H-quinoline-1-carboxylic acid 2-carboxy-2-methylpropyl ester;

(2R,4S)-4-{[3,5-Bis(trifluoromethyl)benzyl]-[5-(3-cyanopropoxy)pyrimidin-2-yl]}amino-2-ethyl-6-trifluoromethyl-3,4-dihydro-2H-quinoline-1-carboxylic acid 5-carboxypentyl ester;

(2R,4S)-4-{[3,5-Bis(trifluoromethyl)benzyl]-[5-dimethylaminopyrimidin-2-yl]}amino-2-ethyl-6-trifluoromethyl-3,4-dihydro-2H-quinoline-1-carboxylic acid 3-carboxypropyl ester;

(2R,4S)-4-{[3,5-Bis(trifluoromethyl)benzyl]-(5-dimethylaminopyrimidin-2-yl)}amino-2-ethyl-6-trifluoromethyl-3,4-dihydro-2H-quinoline-1-carboxylic acid 4-carboxybutyl ester;

(2R,4S)-4-{[3,5-Bis(trifluoromethyl)benzyl]-(5-dimethylaminopyrimidin-2-yl)}amino-2-ethyl-6-trifluoromethyl-3,4-dihydro-2H-quinoline-1-carboxylic acid 2-carboxy-2-methylpropyl ester;

(2R,4S)-4-{[3,5-Bis(trifluoromethyl)benzyl]-(5-dimethylaminopyrimidin-2-yl)}amino-2-ethyl-6-trifluoromethyl-3,4-dihydro-2H-quinoline-1-carboxylic acid 5-carboxypentyl ester;

(2R,4S)-4-{(3-Cyano-5-trifluoromethylbenzyl)-[5-(morpholin-4-yl)pyrimidin-2-yl]}amino-2-ethyl-6-trifluoromethyl-3,4-dihydro-2H-quinoline-1-carboxylic acid 2-carboxyethyl ester;

(2R,4S)-4-{(3-Cyano-5-trifluoromethylbenzyl)-[5-(morpholin-4-yl)pyrimidin-2-yl]}amino-2-ethyl-6-trifluoromethyl-3,4-dihydro-2H-quinoline-1-carboxylic acid 3-carboxypropyl ester;

(2R,4S)-4-{(3-Cyano-5-trifluoromethylbenzyl)-[5-(morpholin-4-yl)pyrimidin-2-yl]}amino-2-ethyl-6-trifluoromethyl-3,4-dihydro-2H-quinoline-1-carboxylic acid 4-carboxybutyl ester;

(2R,4S)-4-{(3-Cyano-5-trifluoromethylbenzyl)-[5-(morpholin-4-yl)pyrimidin-2-yl]}amino-2-ethyl-6-trifluoromethyl-3,4-dihydro-2H-quinoline-1-carboxylic acid 2-carboxy-2-methylpropyl ester;

(2R,4S)-4-{(3-Cyano-5-trifluoromethylbenzyl)-[5-(2-methoxyethoxy)pyrimidin-2-yl]}amino-2-ethyl-6-trifluoromethyl-3,4-dihydro-2H-quinoline-1-carboxylic acid 2-carboxyethyl ester;

(2R,4S)-4-{(3-Cyano-5-trifluoromethylbenzyl)-[5-(2-methoxyethoxy)pyrimidin-2-yl]}amino-2-ethyl-6-trifluoromethyl-3,4-dihydro-2H-quinoline-1-carboxylic acid 3-carboxypropyl ester;

(2R,4S)-4-{(3-Cyano-5-trifluoromethylbenzyl)-[5-(2-methoxyethoxy)pyrimidin-2-yl]}amino-2-ethyl-6-trifluoromethyl-3,4-dihydro-2H-quinoline-1-carboxylic acid 4-carboxybutyl ester;

(2R,4S)-4-{(3-Cyano-5-trifluoromethylbenzyl)-[5-(2-methoxyethoxy)pyrimidin-2-yl]}amino-2-ethyl-6-trifluoromethyl-3,4-dihydro-2H-quinoline-1-carboxylic acid 2-carboxy-2-methylpropyl ester;

(2R,4S)-4-{[3,5-Bis(trifluoromethyl)benzyl]-[5-(morpholin-4-yl)pyridin-2-yl]}amino-2-ethyl-6-trifluoromethyl-3,4-dihydro-2H-quinoline-1-carboxylic acid 2-carboxyethyl ester;

(2R,4S)-4-{[3,5-Bis(trifluoromethyl)benzyl]-[5-(morpholin-4-yl)pyridin-2-yl]}amino-2-ethyl-6-trifluoromethyl-3,4-dihydro-2H-quinoline-1-carboxylic acid 3-carboxypropyl ester;

(2R,4S)-4-{[3,5-Bis(trifluoromethyl)benzyl]-[5-(morpholin-4-yl)pyridin-2-yl]}amino-2-ethyl-6-trifluoromethyl-3,4-dihydro-2H-quinoline-1-carboxylic acid 4-carboxybutyl ester;

(2R,4S)-4-{[3,5-Bis(trifluoromethyl)benzyl]-[5-(morpholin-4-yl)pyridin-2-yl]}amino-2-ethyl-6-trifluoromethyl-3,4-dihydro-2H-quinoline-1-carboxylic acid 2-carboxy-2-methylpropyl ester;

(2R,4S)-4-{[3,5-Bis(trifluoromethyl)benzyl]-[5-(2-hydroxyethoxy)pyridin-2-yl]}amino-2-ethyl-6-trifluoromethyl-3,4-dihydro-2H-quinoline-1-carboxylic acid 2-carboxy-2-methylpropyl ester;

(2R,4S)-4-{[3,5-Bis(trifluoromethyl)benzyl]-[5-(2-methoxyethoxy)pyridin-2-yl]}amino-2-ethyl-6-trifluoromethyl-3,4-dihydro-2H-quinoline-1-carboxylic acid 2-carboxyethyl ester;

(2R,4S)-4-{[3,5-Bis(trifluoromethyl)benzyl]-[5-(2-methoxyethoxy)pyridin-2-yl]}amino-2-ethyl-6-trifluoromethyl-3,4-dihydro-2H-quinoline-1-carboxylic acid 3-carboxypropyl ester;

(2R,4S)-4-{[3,5-Bis(trifluoromethyl)benzyl]-[5-(2-methoxyethoxy)pyridin-2-yl]}amino-2-ethyl-6-trifluoromethyl-3,4-dihydro-2H-quinoline-1-carboxylic acid 4-carboxybutyl ester;

(2R,4S)-4-{[3,5-Bis(trifluoromethyl)benzyl]-[5-(2-methoxyethoxy)pyridin-2-yl]}amino-2-ethyl-6-trifluoromethyl-3,4-dihydro-2H-quinoline-1-carboxylic acid 2-carboxy-2-methylpropyl ester;

(2R,4S)-4-{[3,5-Bis(trifluoromethyl)benzyl]-[5-(3-cyanopropoxy)pyridin-2-yl]}amino-2-ethyl-6-trifluoromethyl-3,4-dihydro-2H-quinoline-1-carboxylic acid 2-carboxyethyl ester;

(2R,4S)-4-{[3,5-Bis(trifluoromethyl)benzyl]-(5-dimethylaminopyridin-2-yl)}amino-2-ethyl-6-trifluoromethyl-3,4-dihydro-2H-quinoline-1-carboxylic acid 2-carboxyethyl ester;

(2R,4S)-4-{[3,5-Bis(trifluoromethyl)benzyl]-(5-dimethylaminopyridin-2-yl)}amino-2-ethyl-6-trifluoro methyl-3,4-dihydro-2H-quinoline-1-carboxylic acid 3-carboxypropyl ester;

(2R,4S)-4-{[3,5-Bis(trifluoromethyl)benzyl]-(5-dimethylaminopyridin-2-yl)}amino-2-ethyl-6-trifluoro methyl-3,4-dihydro-2H-quinoline-1-carboxylic acid 4-carboxybutyl ester;

(2R,4S)-4-{[3,5-Bis(trifluoromethyl)benzyl]-(5-dimethylaminopyridin-2-yl)}amino-2-ethyl-6-trifluoromethyl-3,4-dihydro-2H-quinoline-1-carboxylic acid 2-carboxy-2-methylpropyl ester;

(2R,4S)-4-{(3-Cyano-5-trifluoromethylbenzyl)-[5-(morpholin-4-yl)pyridin-2-yl]}amino-2-ethyl-6-trifluoromethyl-3,4-dihydro-2H-quinoline-1-carboxylic acid 2-carboxyethyl ester;

(2R,4S)-4-{(3-Cyano-5-trifluoromethylbenzyl)-[5-(morpholin-4-yl)pyridin-2-yl]}amino-2-ethyl-6-trifluoromethyl-3,4-dihydro-2H-quinoline-1-carboxylic acid 3-carboxypropyl ester;

(2R,4S)-4-{(3-Cyano-5-trifluoromethylbenzyl)-[5-(morpholin-4-yl)pyridin-2-yl]}amino-2-ethyl-6-trifluoromethyl-3,4-dihydro-2H-quinoline-1-carboxylic acid 4-carboxybutyl ester;

(2R,4S)-4-{(3-Cyano-5-trifluoromethylbenzyl)-[5-(morpholin-4-yl)pyridin-2-yl]}amino-2-ethyl-6-trifluoromethyl-3,4-dihydro-2H-quinoline-1-carboxylic acid 2-carboxy-2-methylpropyl ester;

(2R,4S)-4-{(3-Cyano-5-trifluoromethylbenzyl)-[5-(2-methoxyethoxy)pyridin-2-yl]}amino-2-ethyl-6-trifluoromethyl-3,4-dihydro-2H-quinoline-1-carboxylic acid 2-carboxyethyl ester;

(2R,4S)-4-{[3,5-Bis(trifluoromethyl)benzyl]-[5-(morpholin-4-yl)pyrimidin-2-yl]}amino-2-ethyl-6-methoxy-3,4-dihydro-2H-quinoline-1-carboxylic acid 2-carboxyethyl ester;

(2R,4S)-4-{[3,5-Bis(trifluoromethyl)benzyl]-[5-(morpholin-4-yl)pyrimidin-2-yl]}amino-2-ethyl-6-methoxy-3,4-dihydro-2H-quinoline-1-carboxylic acid 3-carboxypropyl ester;

(2R,4S)-4-{[3,5-Bis(trifluoromethyl)benzyl]-[5-(morpholin-4-yl)pyrimidin-2-yl]}amino-2-ethyl-6-methoxy-3,4-dihydro-2H-quinoline-1-carboxylic acid 4-carboxybutyl ester;

(2R,4S)-4-{[3,5-Bis(trifluoromethyl)benzyl]-[5-(morpholin-4-yl)pyrimidin-2-yl]}amino-2-ethyl-6-methoxy-3,4-dihydro-2H-quinoline-1-carboxylic acid 2-carboxy-2-methylpropyl ester;

(2R,4S)-4-{(3-Cyano-5-trifluoromethylbenzyl)-[5-(morpholin-4-yl)pyrimidin-2-yl]}amino-2-ethyl-6-methoxy-3,4-dihydro-2H-quinoline-1-carboxylic acid 4-carboxybutyl ester;

(2R,4S)-4-{(3-Cyano-5-trifluoromethylbenzyl)-[5-(morpholin-4-yl)pyrimidin-2-yl]}amino-2-ethyl-6-methoxy-3,4-dihydro-2H-quinoline-1-carboxylic acid 2-carboxy-2-methylpropyl ester;

(2R,4S)-4-{[3,5-Bis(trifluoromethyl)benzyl]-[5-(morpholin-4-yl)pyridin-2-yl]}amino-2-ethyl-6-methoxy-3,4-dihydro-2H-quinoline-1-carboxylic acid 2-carboxyethyl ester;

(2R,4S)-4-{[3,5-Bis(trifluoromethyl)benzyl]-[5-(morpholin-4-yl)pyridin-2-yl]}amino-2-ethyl-6-methoxy-3,4-dihydro-2H-quinoline-1-carboxylic acid 3-carboxypropyl ester;

(2R,4S)-4-{[3,5-Bis(trifluoromethyl)benzyl]-[5-(morpholin-4-yl)pyridin-2-yl]}amino-2-ethyl-6-methoxy-3,4-dihydro-2H-quinoline-1-carboxylic acid 4-carboxybutyl ester;

(2R,4S)-4-{[3,5-Bis(trifluoromethyl)benzyl]-[5-(morpholin-4-yl)pyridin-2-yl]}amino-2-ethyl-6-methoxy-3,4-dihydro-2H-quinoline-1-carboxylic acid 2-carboxy-2-methylpropyl ester;

(2R,4S)-4-{(3-Cyano-5-trifluoromethylbenzyl)-[5-(morpholin-4-yl)pyridin-2-yl]}amino-2-ethyl-6-methoxy-3,4-dihydro-2H-quinoline-1-carboxylic acid 4-carboxybutyl ester;

(2R,4S)-4-{(3-Cyano-5-trifluoromethylbenzyl)-[5-(morpholin-4-yl)pyridin-2-yl]}amino-2-ethyl-6-methoxy-3,4-dihydro-2H-quinoline-1-carboxylic acid 2-carboxy-2-methylpropyl ester;

(2R,4S)-4-{[3,5-Bis(trifluoromethyl)benzyl]-[5-(morpholin-4-yl)pyrimidin-2-yl]}amino-2-ethyl-6,7-ethylenedioxy-3,4-dihydro-2H-quinoline-1-carboxylic acid 2-carboxyethyl ester; or (2R,4S)-4-{(3-Cyano-5-trifluoromethylbenzyl)-[5-(2-methoxyethoxy)pyrimidin-2-yl]}amino-2-ethyl-6,7-ethylenedioxy-3,4-dihydro-2H-quinoline-1-carboxylic acid 2-carboxyethyl ester;

or a pharmaceutically acceptable salt thereof.

Additionally, in another preferable embodiment of the present invention, $R^1$ is a hydrogen atom; an alkoxycarbonyl group optionally substituted by 1 to 5 substituents selected independently from cyano group, hydroxy group, carboxyl group, alkoxycarbonyl group, alkoxy group (said alkoxy group is optionally substituted by 1 to 3 substituents selected independently from hydroxy group, amino group, mono- or di-alkylamino group, halogen atom, carboxyl group, alkoxycarbonyl group, carboxyalkoxy group and alkoxycarbonylalkoxy group), alkylthio group, alkylsulfonyl group, alkenyl group, amino group, mono- or di-alkylamino group, tetrazolyl group, carbamoyl group, mono- or di-alkylcarbamoyl group (said mono- or di-alkylcarbamoyl group is optionally substituted by 1 to 3 substituents selected independently from carboxyl group and alkoxycarbonyl group), alkanoylamino group (said alkanoylamino group is optionally substituted by 1 to 3 substituents selected independently from carboxyl group, alkoxycarbonyl group, hydroxy group and halogen atom), halogen atom, cycloalkyl group (said cycloalkyl group is optionally substituted by 1 to 3 substituents selected independently from hydroxy group, amino group, mono- or di-alkylamino group, halogen atom, oxo group, carboxyl group, alkoxycarbonyl group, carboxyalkyl group, alkoxycarbonylalkyl group, carboxyalkoxy group and alkoxycarbonylalkoxy group), phenyl group (said phenyl group is optionally substituted by 1 to 3 substituents selected independently from hydroxy group, amino group, mono- or di-alkylamino group, halogen atom, carboxyl group, alkoxycarbonyl group, carboxyalkyl group, alkoxycarbonylalkyl group, carboxyalkoxy group and alkoxycarbonylalkoxy group), morpholinyl group optionally substituted by oxo group, piperidinyl group (said piperidinyl group is optionally substituted by 1 to 3 substituents selected independently from hydroxy group, amino group, mono- or di-alkylamino group, halogen atom, oxo group, carboxyl group, alkoxycarbonyl group, carboxyalkyl group, alkoxycarbonylalkyl group and carboxyalkoxy group, alkoxycarbonylalkoxy group), pyrrolidinyl group (said pyrrolidinyl group is optionally substituted by 1 to 3 substituents selected independently from hydroxy group, amino group, mono- or di-alkylamino group, halogen atom, oxo group, carboxyl group, alkoxycarbonyl group, carboxyalkyl group, alkoxycarbonylalkyl group, carboxyalkoxy group and alkoxycarbonylalkoxy group), and pyrimidinyl group (said pyrimidinyl group is optionally substituted by 1 to 3 substituents selected independently from carboxyalkyl group, alkoxycarbonylalkyl group and carboxyalkoxy group, alkoxycarbonylalkoxy group); dihydrooxazolyl group optionally substituted by 1 to 2 substituents selected independently from carboxyl group, alkoxycarbonyl group, alkyl group, carboxyalkyl group, alkoxycarbonylalkyl group and hydroxyalkyl group; or a mono- or di-alkylcarbamoyl group optionally substituted by 1 to 5 substituents selected independently from halogen atom, hydroxy group, carboxyl group, alkoxycarbonyl group, alkoxy group, amino group, mono- or di-alkylamino group, morpholinyl group, pyridyl group, cycloalkyl group (said cycloalkyl group is optionally substituted by 1 to 3 substituents selected independently from carboxyl group, alkoxycarbonyl group, halogen atom, amino group and hydroxy group) and phenyl group (said phenyl group is optionally substituted by 1 to 3 substituents selected independently from carboxyl group, alkoxycarbonyl group, halogen atom, amino group and hydroxy group);

$R^2$ is an alkyl group;
$R^3$ is a hydrogen atom;
$R^4$ is an alkylene group;
$R^5$ is a group of the formula:

wherein Ring A is a saturated or unsaturated 5- to 8-membered heterocyclic group containing 1 to 4 heteroatoms selected independently from oxygen, sulfur and nitrogen atoms, $R^{11}$ is a group selected from the following groups:
cyano group;
nitro group;
carboxyl group;
sulfo group;
cycloalkyl group optionally substituted by carboxyl or alkoxycarbonyl group;
alkyl group substituted by 1 to 3 substitutents selected independently from halogen atom, cyano group, hydroxy group, carboxyl group, alkoxycarbonyl group, alkoxy group (said alkoxy group is optionally substituted by phenyl, hydroxy or carboxyl group), alkanoyloxy group, alkylthio group, alkylsulfonyl group, alkylsulfinyl group, amino group, mono- or di-alkylamino group, mono- or di-alkylsulfamoylamino group, mono- or di-alkylureido group optionally substituted by morpholinyl group, oxiranyl group, di-alkyldioxolanyl group, pyrrolidinyl group optionally substituted by alkoxycarbonyl or carboxyl group, piperidinyl group optionally substituted by alkoxycarbonyl or carboxyl group, piperazinyl group optionally substituted by alkyl group, hexahydroazepinyl group and morpholinyl group;
alkenyl group optionally substituted by carboxyl group, cyano group or benzyloxycarbonyl group;
alkoxy group substituted by 1 to 3 substituents selected independently from halogen atom, cyano group, hydroxy group, carboxyl group, alkoxycarbonyl group, alkoxy group (said alkoxy group is optionally substituted by phenyl, hydroxy or carboxyl group), alkanoyloxy group, alkylthio group, alkylsulfonyl group, alkylsulfinyl group, amino group, mono- or di-alkylamino group, mono- or di-alkylsulfamoylamino group, mono- or di-alkylureido group optionally substituted by morpholinyl group, oxiranyl group, di-alkyldioxolanyl group, pyrrolidinyl group optionally substituted by alkoxycarbonyl or carboxyl group, piperidinyl group optionally substituted by alkoxycarbonyl or carboxyl group, piperazinyl group optionally substituted by alkyl group, hexahydroazepinyl group and morpholinyl group;

alkoxycarbonyl group optionally substituted by phenyl group;
mono- or di-alkylcarbamoyl group optionally substituted by carboxyl group;
hydroxycarbamimidoyl group;
alkylthio group;
alkylsulfinyl group;
alkylsulfonyl group optionally substituted by carboxyl group;
mono- or di-alkylamino group optionally substituted by hydroxy group, carboxyl group, alkoxycarbonyl group, alkoxy group, mono- or di-alkylamino group or morpholinyl group;
mono- or di-alkylsulfamoyl group;
morpholinyl group;
optionally oxidized thiomorpholinyl group;
piperazinyl group optionally substituted by a group selected from alkyl group, alkanoyl group and hydroxyalkanoyl group;
pyrrolidinyl group optionally substituted by carboxyl group, carboxyalkyl group, alkyl group, alkoxycarbonyl group or alkoxycarbonylalkyl group;
piperidinyl group optionally substituted by carboxyl group, carboxyalkyl group, alkyl group, alkoxycarbonyl group or alkoxycarbonylalkyl group;
dioxolanyl group optionally substituted by alkyl group;
tetrazolyl group optionally substituted by alkyl group, hydroxyalkyl group or morpholinylalkyl group;
dihydrooxadiazolyl group optionally substituted by oxo group;
pyrimidinyl group; or
tetrahydropyranyl group;

$R^6$ and $R^9$ each are a hydrogen atom;

$R^7$ and $R^8$ are independently a hydrogen atom, an alkyl group optionally substituted by halogen atom, alkoxy group, or mono- or di-alkylamino group; or combine at the ends to form an alkylenedioxy group; and $R^{10}$ is a phenyl or pyridyl group, which phenyl or pyridyl group is optionally substituted by 1 to 4 substituents selected from alkyl group optionally substituted by halogen atom, alkoxy group, hydroxy group, halogen atom, cyano group, amino group and mono- or di-alkylamino group.

In still another preferable embodiment of the present invention, Ring A is a pyrimidinyl group, a pyridyl group, a triazolyl group, a tetrazolyl group, an oxadiazolyl group, a dihydropyrimidinyl group, a pyrazinyl group, a thiazolyl group, an oxazolyl group, a dihydrooxazinyl group, an imidazolyl group, a pyrazolyl group, or a dihydropyrazinyl group.

In still another preferable embodiment of the present invention, Ring A is a pyrimidinyl group, a pyridyl group, a tetrazolyl group, an oxadiazolyl group, a pyrazinyl group, a thiazolyl group or an oxazolyl group; and $R^{11}$ is a carboxyl group; a cyano group; a nitro group; a cycloalkyl group optionally substituted by carboxyl or alkoxycarbonyl group; an alkyl group substituted by 1 to 3 substituents selected independently from hydroxy group, cyano group, carboxyl group, alkoxycarbonyl group, alkoxy group, phenylalkoxy group, hydroxyalkoxy group, carboxyalkoxy group, alkylthio group, alkylsulfonyl group, alkylsulfinyl group, amino group, mono- or di-alkylamino group, mono- or di-alkylsulfamoylamino group, mono- or di-alkylureido group optionally substituted by morpholinyl group, oxiranyl group, di-alkyldioxolanyl group, pyrrolidinyl group optionally substituted by carboxyl group, piperidinyl group optionally substituted by carboxyl group, piperazinyl group optionally substituted by alkyl group and morpholinyl group; an alkenyl group optionally substituted by carboxyl group; an alkoxy group substituted by 1 to 3 substituents selected independently from hydroxy group, cyano group, carboxyl group, alkoxycarbonyl group, alkoxy group, phenylalkoxy group, hydroxyalkoxy group, carboxyalkoxy group, alkylthio group, alkylsulfonyl group, alkylsulfinyl group, amino group, mono- or di-alkylamino group, mono- or di-alkylsulfamoylamino group, mono- or di-alkylureido group optionally substituted by morpholinyl group, oxiranyl group, di-alkyldioxolanyl group, pyrrolidinyl group optionally substituted by carboxyl group, piperidinyl group optionally substituted by carboxyl group, piperazinyl group optionally substituted by alkyl group and morpholinyl group; an alkoxycarbonyl group; a hydroxycarbamimidoyl group; alkylthio group; an alkylsulfonyl group optionally substituted by carboxyl group; a mono- or di-alkylamino group optionally substituted by hydroxy group, carboxyl group, alkoxy group or mono- or di-alkylamino group; a morpholinyl group; an optionally oxidized thiomorpholinyl group; a piperazinyl group optionally substituted by a group selected from alkyl group, alkanoyl group and hydroxyalkanoyl group; a pyrrolidinyl group optionally substituted by carboxyl group, alkyl group carboxyalkyl group or alkoxycarbonyl group; a piperidinyl group optionally substituted by carboxyl group, alkyl group, carboxyalkyl group or alkoxycarbonyl group; a tetrazolyl group optionally substituted by alkyl group, hydroxyalkyl group, or morpholinylalkyl group; an oxodihydrooxadiazolyl group; a pyrimidinyl group; or a tetrahydropyranyl group.

In still another preferable embodiment of the present invention, $R^1$ is an alkoxycarbonyl group optionally substituted by 1 to 5 substituents selected independently from hydroxy group, carboxyl group, alkoxycarbonyl group, alkoxy group (said alkoxy group is optionally substituted by 1 to 3 substituents selected independently from hydroxy group, halogen atom, carboxyl group and alkoxycarbonyl group), alkenyl group, halogen atom, cycloalkyl group (said cycloalkyl group is optionally substituted by 1 to 3 substituents selected independently from hydroxy group, halogen atom, carboxyl group, alkoxycarbonyl group, carboxyalkyl group and alkoxycarbonylalkyl group), phenyl group (said phenyl group is optionally substituted by 1 to 3 substituents selected independently from hydroxy group, halogen atom, carboxyl group, alkoxycarbonyl group, carboxyalkyl group and alkoxycarbonylalkyl group), piperidinyl group (said piperidinyl group is optionally substituted by 1 to 3 substituents selected independently from hydroxy group, halogen atom, carboxyl group, alkoxycarbonyl group, carboxyalkyl group and alkoxycarbonylalkyl group), and pyrrolidinyl group (said pyrrolidinyl group is optionally substituted by 1 to 3 substituents selected independently from hydroxy group, halogen atom, carboxyl group, alkoxycarbonyl group, carboxyalkyl group and alkoxycarbonylalkyl group); or a dihydrooxazolyl group optionally substituted by 1 or 2 substituents selected independently from carboxyl group, alkoxycarbonyl group, carboxyalkyl group, alkoxycarbonylalkyl group and hydroxyalkyl group;

$R^{10}$ is a phenyl group substituted by 1 to 3 substituents selected from alkyl group optionally substituted by halogen atom, alkoxy group, halogen atom and cyano group;

Ring A is a pyrimidinyl group, a pyridyl group, a tetrazolyl group, an oxadiazolyl group or a thiazolyl group; and $R^{11}$ is a carboxyl group; a cyano group; a nitro group; a cycloalkyl group optionally substituted by carboxyl or alkoxycarbonyl group; an alkyl group substituted by 1 to 3 substituents selected independently from hydroxy group, carboxyl group, alkoxycarbonyl group, alkoxy group, phenylalkoxy group, carboxyalkoxy group, alkylthio group, alkylsulfonyl group, alkylsulfinyl group, amino group, mono- or di-alkylamino group, mono- or di-alkylsulfamoylamino group, mono- or di-alkylureido group optionally substituted by morpholinyl group, oxiranyl group, di-alkyldioxolanyl group, piperazinyl group optionally substituted by alkyl group and morpholinyl group; an alkenyl group optionally substituted by carboxyl group; an alkoxy group substituted by 1 to 3 substituents selected independently from cyano group, hydroxy group, carboxyl group, alkoxycarbonyl group, alkoxy group, phenylalkoxy group, carboxyalkoxy group, alkylthio group, alkylsulfonyl group, alkylsulfinyl group, amino group, mono- or di-alkylamino group, mono- or di-alkylsulfamoylamino group, mono- or di-alkylureido group optionally substituted by morpholinyl group, oxiranyl group, di-alkyldioxolanyl group, piperazinyl group optionally substituted by alkyl group and morpholinyl group; a hydroxycarbamimidoyl group; an alkylthio group; an alkylsulfonyl group optionally substituted by alkoxycarbonyl group; a mono- or di-alkylamino group optionally substituted by hydroxy group, carboxyl group or alkoxy group; a morpholinyl group; optionally oxidized thiomorpholinyl group; a piperazinyl group optionally substituted by a group selected from alkyl group, alkanoyl group and hydroxyalkanoyl group; a pyrrolidinyl group optionally substituted by carboxyl group, alkyl group carboxyalkyl group or alkoxycarbonyl group; a piperidinyl group optionally substituted by carboxyl group, alkyl group, carboxyalkyl group or alkoxycarbonyl group; a tetrazolyl group optionally substituted by alkyl group, hydroxyalkyl group, or morpholinylalkyl group; an oxodihydrooxadiazolyl group; a pyrimidinyl group; or a tetrahydropyranyl group.

In still another preferable embodiment of the present invention, $R^1$ is an alkoxycarbonyl group optionally substituted by 1 or 5 substituents selected independently from carboxyl group, alkoxycarbonyl group, halogen atom, hydroxy group and cycloalkyl group;
$R^{10}$ is a phenyl group substituted by 1 to 3 substituents selected from cyano group, alkyl group optionally substituted by halogen atom and alkoxy group;
Ring A is a pyrimidinyl group, a pyridyl group, a tetrazolyl group or an oxadiazolyl group;
$R^{11}$ is a carboxyl group; an alkyl group substituted by 1 to 3 substituents selected independently from hydroxy group, carboxyl group, alkoxy group and alkylsulfonyl group; an alkenyl group optionally substituted by carboxyl group; an alkoxy group substituted by 1 to 3 substituents selected independently from carboxyl group, cyano group, hydroxy group, alkoxy group, alkylthio group and alkylsulfonyl group; a mono- or di-alkylamino group optionally substituted by carboxyl group or alkoxy group; a morpholinyl group; a piperidinyl group substituted by carboxyl group; or a tetrazolyl group substituted by hydroxyalkyl group;
$R^7$ is an alkyl group optionally substituted by halogen atom, alkoxy group, or mono- or di-alkylamino group; and
$R^8$ is a hydrogen atom.

In still another preferable embodiment of the present invention, $R^1$ is an ethoxycarbonyl group, a hydroxyethoxycarbonyl group, a 2-fluoroethoxycarbonyl group, a 2,2-difluoroethoxycarbonyl group or a 2,2,2-trifluoroethoxycarbonyl group; $R^2$ is an ethyl group; $R^{10}$ is a phenyl group substituted by 1 to 2 substituents selected from cyano group, trifluoromethyl group and methoxy group; and $R^7$ is a trifluoromethyl group or a methoxy group.

In still another preferable embodiment of the present invention, $R^1$ is a carboxy($C_{2-10}$alkoxy)carbonyl group or an alkoxycarbonyl($C_{2-10}$alkoxy)carbonyl group; $R^2$ is an ethyl group; $R^{10}$ is a phenyl group substituted by 1 to 2 substituents selected from cyano group, trifluoromethyl group and methoxy group; and $R^7$ is a trifluoromethyl group or a methoxy group.

A compound selected from the following compounds or a pharmaceutically acceptable salt thereof is further preferable.

(2R,4S)-4-{[3,5-Bis(trifluoromethyl)benzyl]-[5-(3-hydroxypropoxy)pyrimidin-2-yl]}amino-2-ethyl-6-trifluoromethyl-3,4-dihydro-2H-quinoline-1-carboxylic acid 2-carboxy-2-methylpropyl ester;

(2R,4S)-4-([3,5-Bis(trifluoromethyl)benzyl]-{5-[2-(2-hydroxyethoxy)ethoxy]pyrimidin-2-yl})amino-2-ethyl-6-trifluoromethyl-3,4-dihydro-2H-quinoline-1-carboxylic acid 2-carboxy-2-methylpropyl ester;

(2R,4S)-4-{[3,5-Bis(trifluoromethyl)benzyl]-[5-(2,3-dihydroxypropoxy)pyrimidin-2-yl]}amino-2-ethyl-6-trifluoromethyl-3,4-dihydro-2H-quinoline-1-carboxylic acid 2-carboxy-2-methylpropyl ester;

(2R,4S)-4-{[3,5-Bis(trifluoromethyl)benzyl]-[5-(3-hydroxypropoxy)pyrimidin-2-yl]}amino-2-ethyl-6-trifluoromethyl-3,4-dihydro-2H-quinoline-1-carboxylic acid 2-carboxyethyl ester;

(2R,4S)-4-([3,5-Bis(trifluoromethyl)benzyl]-{5-[2-(2-hydroxyethoxy)ethoxy]pyrimidin-2-yl})amino-2-ethyl-6-trifluoromethyl-3,4-dihydro-2H-quinoline-1-carboxylic acid 2-carboxyethyl ester;

(2R,4S)-4-{[3,5-Bis(trifluoromethyl)benzyl]-[5-(2,3-dihydroxypropoxy)pyrimidin-2-yl]}amino-2-ethyl-6-trifluoromethyl-3,4-dihydro-2H-quinoline-1-carboxylic acid 2-carboxyethyl ester;

(2R,4S)-4-{(3-Cyano-5-trifluoromethylbenzyl)-[5-(2-hydroxyethoxy)pyrimidin-2-yl]}amino-2-ethyl-6-trifluoromethyl-3,4-dihydro-2H-quinoline-1-carboxylic acid 2-carboxy-2-methylpropyl ester;

(2R,4S)-4-{(3-Cyano-5-trifluoromethylbenzyl)-[5-(2-methoxyethoxy)pyrimidin-2-yl]}amino-2-ethyl-6-trifluoromethyl-3,4-dihydro-2H-quinoline-1-carboxylic acid 2-carboxy-2-methylpropyl ester;

(2R,4S)-4-{[5-(3-Cyanopropoxy)pyrimidin-2-yl]-(3-Cyano-5-trifluoromethylbenzyl)}amino-2-ethyl-6-trifluoromethyl-3,4-dihydro-2H-quinoline-1-carboxylic acid 2-carboxy-2-methylpropyl ester;

(2R,4S)-4-{(3-Cyano-5-trifluoromethylbenzyl)-[5-(2-hydroxyethoxy)pyrimidin-2-yl]}amino-2-ethyl-6-trifluoromethyl-3,4-dihydro-2H-quinoline-1-carboxylic acid 2-carboxyethyl ester;

(2R,4S)-4-{(3-Cyano-5-trifluoromethylbenzyl)-[5-(2-methoxyethoxy)pyrimidin-2-yl]}amino-2-ethyl-6-trifluoromethyl-3,4-dihydro-2H-quinoline-1-carboxylic acid 2-carboxyethyl ester;

(2R,4S)-4-{[5-(3-Cyanopropoxy)pyrimidin-2-yl]-(3-Cyano-5-trifluoromethylbenzyl)}amino-2-ethyl-6-trifluoromethyl-3,4-dihydro-2H-quinoline-1-carboxylic acid 2-carboxyethyl ester;

(2R,4S)-4-[(3-Cyano-5-trifluoromethylbenzyl)-(5-dimethylaminopyrimidin-2-yl)]amino-2-ethyl-6-trifluoromethyl-3,4-dihydro-2H-quinoline-1-carboxylic acid 2-carboxyethyl ester;

(2R,4S)-4-([3,5-Bis(trifluoromethyl)benzyl]-{5-[(ethyl-methyl)amino]pyrimidin-2-yl})amino-2-ethyl-6-trifluoromethyl-3,4-dihydro-2H-quinoline-1-carboxylic acid 2-carboxyethyl ester;

(2R,4S)-4-{[3,5-Bis(trifluoromethyl)benzyl]-(5-diethylaminopyrimidin-2-yl)}amino-2-ethyl-6-trifluoromethyl-3,4-dihydro-2H-quinoline-1-carboxylic acid 2-carboxyethyl ester;

(2R,4S)-4-([3,5-Bis(trifluoromethyl)benzyl]-{5-[(ethyl-methyl)amino]pyrimidin-2-yl})amino-2-ethyl-6-trifluoromethyl-3,4-dihydro-2H-quinoline-1-carboxylic acid 2-carboxy-2-methylpropyl ester; and (2R,4S)-4-{[3,5-Bis(trifluoromethyl)benzyl]-(5-diethylaminopyrimidin-2-yl)}amino-2-ethyl-6-trifluoromethyl-3,4-dihydro-2H-quinoline-1-carboxylic acid 2-carboxy-2-methylpropyl ester.

A particularly preferred sub-class of the compound of formula (I) is a compound of formula (I-1) or a pharmaceutically acceptable derivative thereof:

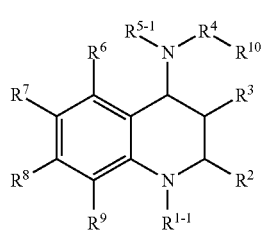

(I-1)

wherein $R^{1-1}$ is an alkoxycarbonyl group optionally substituted by 1 to 3 substituents selected independently from alkoxycarbonyl group, halogen atom and cycloalkyl group;

$R^2$ is a hydrogen atom or an optionally substituted alkyl group;

$R^3$ is a hydrogen atom or an optionally substituted alkyl group;

$R^4$ is an optionally substituted alkylene group;

$R^{5-1}$ is a saturated or unsaturated 5- to 8-membered heterocyclic group containing 1 to 4 heteroatoms selected independently from oxygen, sulfur and nitrogen atoms;

wherein said heterocyclic group is substituted by 1 to 4 substituents selected from the following groups, or said heterocyclic group is substituted by 1 to 4 substituents selected from the following groups along with a halogen atom, an oxo and/or hydroxy group:

alkoxy group substituted by a group selected from cyano group, hydroxy group, carboxyl group, alkoxycarbonyl group, tetrazolyl group, carbamoyl group, mono- or di-alkylcarbamoyl group (said mono- or di-alkylcarbamoyl group is optionally substituted by carboxyl, alkoxycarbonyl or hydroxy group), alkoxy group (said alkoxy group is optionally substituted by carboxyl, formyl or hydroxy group), alkanoyloxy group, alkylsulfonyl group, alkylsulfinyl group, aminosulfonyl group, amino group, mono- or di-alkylamino group substituted by carboxyl or alkoxy group, mono- or di-alkylsulfamoylamino group, mono- or di-alkylureido group optionally substituted by morpholinyl group, cycloalkyl group optionally substituted by carboxymethyl group, oxiranyl group, phenyl group optionally substituted by alkoxy or carboxyl group, morpholinyl group, pyrrolidinyl group optionally substituted by alkoxycarbonyl or carboxyl group, pyrrolidinyl group optionally substituted by alkoxycarbonylalkyl or carboxyalkyl group, pyrrolidinyl group substituted by oxo group, piperidinyl group optionally substituted by alkoxycarbonyl or carboxyl group, piperidinyl group optionally substituted by alkoxycarbonylalkyl or carboxyalkyl group, piperazinyl group optionally substituted by alkyl group, hexahydroazepinyl group, pyrimidinyl group, pyridyl group, dioxolanyl group optionally substituted by alkyl group, oxadiazolyl group optionally substituted by oxo group, oxathiadiazolyl group optionally substituted by oxo group, pyrrolidinylcarbonyl group optionally substituted by carboxyl group, piperidinyloxy group optionally substituted by alkyl group, and morpholinylcarbonyl group;

$R^6$, $R^7$, $R^8$ and $R^9$ are independently a hydrogen atom, a halogen atom, a hydroxy group, a nitro group, a cyano group, an optionally substituted alkyl group, an optionally substituted alkoxy group, an optionally substituted alkylsulfonyloxy group or an optionally substituted amino group; or $R^6$ and $R^7$, or $R^7$ and $R^8$, or $R^8$ and $R^9$ may combine at the ends to form an alkylene group which alkylene group may contain 1 to 3 heteroatoms selected independently from nitrogen, sulfur and oxygen atoms, and may have a substituent(s); and $R^{10}$ is an aromatic ring optionally containing 1 to 3 heteroatoms selected independently from oxygen, sulfur and nitrogen atoms (the aromatic ring is optionally substituted), or a pharmaceutically acceptable salt thereof.

In still another preferable embodiment of the present invention, $R^{5-1}$ is a group of the formula:

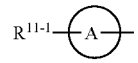

wherein Ring A is a saturated or unsaturated 5- to 8-membered heterocyclic group containing 1 to 4 heteroatoms selected independently from oxygen, sulfur and nitrogen atoms, $R^{11-1}$ is a group selected from the following groups:

alkoxy group substituted by a group selected from cyano group, hydroxy group, carboxyl group, alkoxycarbonyl group, alkoxy group (said alkoxy group is optionally substituted by phenyl, hydroxy or carboxyl group), alkanoyloxy group, alkylsulfonyl group, alkylsulfinyl group, amino group, mono- or di-alkylamino group, mono- or di-alkylsulfamoylamino group, mono- or di-alkylureido group optionally substituted by morpholinyl group, oxiranyl group, di-alkyldioxolanyl group, pyrrolidinyl group optionally substituted by alkoxycarbonyl or carboxyl group, piperidinyl group optionally substituted by alkoxycarbonyl or carboxyl group, piperazinyl group optionally substituted by alkyl group, hexahydroazepinyl group, and morpholinyl group;

Another particularly preferred sub-class of the compound of formula (I) is a compound of formula (I-2) or a pharmaceutically acceptable derivative thereof:

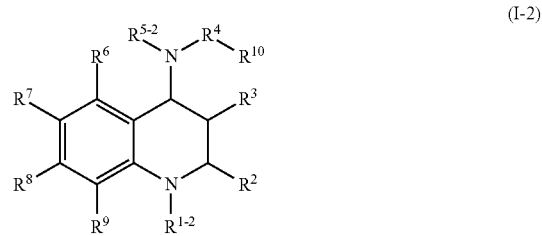

(I-2)

wherein $R^{1-2}$ is an alkoxycarbonyl group optionally substituted by 1 to 3 substituents selected independently from carboxyl group and hydroxy group;

$R^2$ is a hydrogen atom or an optionally substituted alkyl group;

$R^3$ is a hydrogen atom or an optionally substituted alkyl group;

$R^4$ is an optionally substituted alkylene group;

$R^{5-2}$ is a saturated or unsaturated monocyclic or bicyclic heterocyclic group containing 1 to 4 heteroatoms selected independently from oxygen, sulfur and nitrogen atoms, wherein the heterocyclic group is substituted by 1 to 5 substituents selected from the following groups, or said heterocyclic group is substituted by 1 to 5 substituents selected from the following groups and further by a halogen atom, an oxo and/or hydroxy group:

cyano group, nitro group, carboxyl group, sulfo group, $C_{3-10}$ alkyl group, substituted $C_{3-10}$ alkyl group, optionally substituted cycloalkyl group, optionally substituted alkenyl group, $C_{3-10}$ alkoxy group, substituted alkoxy group, optionally substituted cycloalkoxy group, optionally substituted alkoxycarbonyl group, optionally substituted carbamoyl group, optionally substituted carbamimidoyl group, optionally substituted alkylthio group, optionally substituted alkylsulfinyl group, optionally substituted alkylsulfonyl group, optionally substituted amino group, optionally substituted sulfamoyl group, optionally substituted alkanoyl group, a saturated or unsaturated monocyclic or bicyclic heterocyclic group containing 1 to 4 heteroatoms selected independently from oxygen, sulfur and nitrogen atoms (the heterocyclic group is optionally substituted), a saturated or unsaturated monocyclic or bicyclic heterocyclic oxy group containing 1 to 4 heteroatoms selected independently from oxygen, sulfur and nitrogen atoms (the heterocyclic oxy group is optionally substituted), and a saturated or unsaturated monocyclic or bicyclic heterocyclic carbonyl group containing 1 to 4 heteroatoms selected independently from oxygen, sulfur and nitrogen atoms (the heterocyclic carbonyl group is optionally substituted);

$R^6$, $R^7$, $R^8$ and $R^9$ are independently a hydrogen atom, a halogen atom, a hydroxy group, a nitro group, a cyano group, an optionally substituted alkyl group, an optionally substituted alkoxy group, an optionally substituted alkylsulfonyloxy group or an optionally substituted amino group; or $R^6$ and $R^7$, or $R^7$ and $R^8$, or $R^8$ and $R^9$ may combine at the ends to form an alkylene group which alkylene group may contain 1 to 3 heteroatoms selected independently from nitrogen, sulfur and oxygen atoms, and may have a substituent(s); and $R^{10}$ is an aromatic ring optionally containing 1 to 3 heteroatoms selected independently from oxygen, sulfur and nitrogen atoms (the aromatic ring is optionally substituted), or a pharmaceutically acceptable salt thereof.

The present compound (I) or a pharmaceutically acceptable salt thereof can be administered either orally or parenterally, and can be formulated into pharmaceutical preparations with a conventional pharmaceutically acceptable carriers used therefor.

The pharmaceutically acceptable salts of the compound (I) may include, for example, alkali metal salts such as lithium, sodium or potassium salt; alkali earth metal salts such as calcium or magnesium salt; salts with zinc or aluminum; salts with organic bases such as ammonium, choline, diethanolamine, lysine, ethylenediamine, tert-butylamine, tert-octylamine, tris(hydroxymethyl)aminomethane, N-methylglucosamie, triethanolamine or dehydroabiethylamine; salts with inorganic acids such as hydrochloric acid, hydrobromic acid, hydroiodic acid, sulfuric acid, nitric acid or phosphoric acid; salts with organic acids such as formic acid, acetic acid, propionic acid, oxalic acid, malonic acid, succinic acid, fumaric acid, maleic acid, lactic acid, malic acid, tartaric acid, citric acid, methanesulfonic acid, ethanesulfonic acid, benzenesulfonic acid or toluenesulfonic acid; or salts derived from acidic amino acids such as aspartic acid or glutamic acid.

Additionally, the pharmaceutically acceptable salts of the compound (I) may include, for example, quaternary salts formed between a compound of the formula (I) and an alkyl halide or phenylalkyl halide.

Preferred pharmaceutical preparations for oral administration of the present compound (I) or a pharmaceutically acceptable salt thereof include solid formulations such as tablets, granules, capsules or powders; and liquid formulations such as solutions, suspensions or emulsions. Preferred pharmaceutical preparations for parenteral administration include injections or infusions formulated with injectable distilled-water, physiological saline or aqueous glucose solution; suppository; or inhalation preparation.

These pharmaceutical preparations comprise a compound (I) of the present invention or a pharmaceutically acceptable salt thereof and a pharmaceutically acceptable carrier which is usually used for oral or parenteral administration. The pharmaceutically acceptable carriers for oral administration include, for example, a binder (syrup, gum acacia, gelatin, sorbit, tragacanth, polyvinylpyrrolidone, and the like), an excipient (lactose, sugar, cornstarch, potassium phosphate, sorbit, glycine, and the like), a lubricant (magnesium stearate, talc, polyethylene glycol, silica, and the like), a disintegrant (potato starch, and the like), and a wetting agent (anhydrous sodium lauryl sulfate, and the like). The pharmaceutically acceptable carriers for parenteral administration include, for example, injectable distilled-water, physiological saline and aqueous glucose solution.

The dose of a compound (I) of the present invention or a pharmaceutically acceptable salt thereof varies depending on the administration route, age, body weight, disease, and condition/severity, of the patient. It however can usually be in the range of about 0.001-1,000 mg/kg/day, preferably in the range of about 0.01-100 mg/kg/day, more preferably in the range of about 0.1-10 mg/kg/day.

The compounds of the present invention have an inhibitory activity against CETP and show effects of increasing HDL cholesterol and lowering LDL cholesterol. Accordingly, they are useful in the prophylaxis or treatment of a subject (particularly, mammal including human) suffering from arteriosclerosis such as atherosclerosis, peripheral vascular disease, dyslipidemia, hyperbetalipoproteinemia, hypoalphalipoproteinemia, hypercholesterolemia, hypertriglyceridemia, familial-hypercholesterolemia, cardiovascular diseases, angina, ischemia, cardiac ischemia, stroke, myocardial infarction, reperfusion injury, restenosis after angioplasty, hypertension, cerebral infarction, cerebral stroke, diabetes, vascular complication of diabetes, thrombotic diseases, obesity, endotoxemia, metabolic syndrome, cerebrovascular disease, coronary artery disease, ventricular dysfunction, cardiac arrhythmia, pulmonary vascular disease, reno-vascular disease, renal disease, splanchnic vascular disease, vascular hemostatic disease, fatty liver disease, steatohepatitis, inflammatory disease, autoimmune disorders and other systemic disease indications, immune function modulation, pulmonary disease, antioxidant disease, sexual dysfunction, cognitive dysfunction, schistosomiasis, cancer, regression of xanthoma, Alzheimer's disease, or the like.

In addition, the compounds of the present invention may be used in combination with other drugs useful for treatment of these diseases. For example, a compound of the present invention may be used in combination with an inhibitor of cholesterol synthesis such as HMG-CoA reductase inhibitor; an inhibitor of cholesterol absorption such as anion exchange resin; a triglyceride lowering agent such as fibrates, niacin and fish oil; an antihypertensive such as ACE inhibitor, angiotensin receptor blocker, calcium antagonist and beta blocker; an antiobesity agent such as central anorectic, lipase inhibitor and CB1 antagonist; an antidiabetic, agent such as insulin sensitizer, D2 agonist, sulfonylurea, biguanide, α-glucosidase inhibitor, SGLT inhibitor and DPPIV inhibitor; or other cholesterol reducer such as ACAT inhibitor.

The compounds of the present invention are characterized by that an amino group substituted by a heterocycle having a substituent(s) as defined above is introduced into the 4-position of tetrahydroquinoline skeleton, whereby they can exhibit an excellent inhibitory activity against CETP and have an improved bioavailability. Above all, compounds having a carboxyl group at the terminal position of respective substituents $R^1$-$R^{11}$, especially those having a carboxyl group at the terminal position of $R^1$ and/or $R^5$, or $R^1$ and/or $R^{11}$ are preferred. Additionally, compounds having a hydrophilic group at the terminal position of respective substituents $R^1$ or $R^5$ are preferred.

The compound (I) of the present invention can be prepared by the following methods.

Process 1

The compound (I) of the present invention can be prepared by condensing a compound of the formula (II):

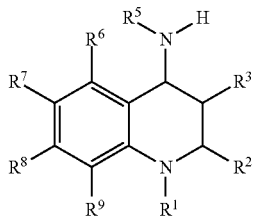

(II)

wherein the symbols have the same meaning as defined above with a compound of the formula (III):

$R^{10}$—$R^4$—$Z^1$     (III)

wherein $Z^1$ is a leaving group and the other symbols have the same meaning as defined above.

The condensation can be carried out in the presence of a base in a suitable solvent.

The leaving group includes a halogen atom including chlorine atom, bromine atom, iodine atom, and a substituted sulfonyloxy group including methanesulfonyloxy group, p-toluenesulfonyloxy group, trifluoro-methanesulfonyloxy group.

A conventional base can be used as the base, and for example, alkaline metal hydride including sodium hydride, potassium hydride; alkaline metal hydroxide including sodium hydroxide, potassium hydroxide; alkaline earth metal hydroxide including barium hydroxide; alkaline metal alkoxide including sodium methoxide, sodium ethoxide, potassium ethoxide, potassium tert-butoxide; alkaline metal carbonate including sodium carbonate, potassium carbonate, cesium carbonate; alkaline metal bicarbonate including sodium bicarbonate, potassium bicarbonate; amines including triethylamine, diisopropylethylamine, methylpiperidine, dimethylaniline, 1,8-diazabicyclo[5.4.0]undecene, 1,4-diazabicyclo[2.2.2]octane, 1,5-diazabicyclo[4.3.0]nonene; pyridines including pyridine, dimethylaminopyridine can be preferably used.

Any solvent which dose not disturb the reaction can be preferably used, and such a solvent includes, for example, hydrocarbons including pentane, hexane; aromatic hydrocarbons including benzene, toluene, nitrobenzene; halogenated hydrocarbons including dichloromethane, chloroform; ethers including diethylether, tetrahydrofuran; amides including dimethylformamide, N-methylpyrrolidone, 1,3-dimethylimidazolidin-2-one; sulfoxides including dimethylsulfoxide; alcohols including methanol, ethanol; esters including ethyl acetate, butyl acetate; ketones including acetone, methyl ethyl ketone; nitriles including acetonitrile; water, or a mixed solvent thereof.

The reaction is carried out from under cooling to under heating, preferably from −78° C. to 200° C., more preferably from −30° C. to 100° C.

Process 2

Among the compound of the formula (I-A), a compound of the formula (I-b):

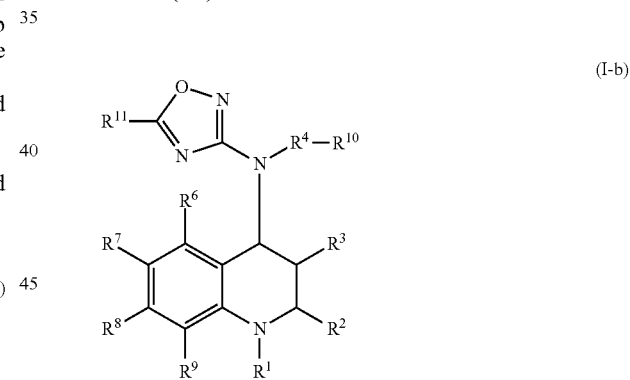

(I-b)

wherein the symbols have the same meaning as defined above can be prepared by (a) cyanating a compound of the formula (IV):

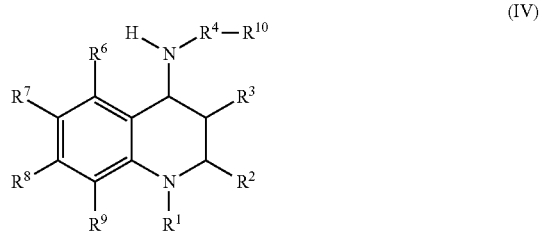

(IV)

wherein the symbols have the same meaning as defined above to provide a compound of the formula (V):

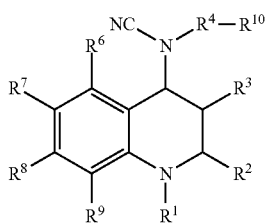

(V)

wherein the symbols have the same meaning as defined above, (b) reacting the compound (V) with hydroxylamine or a salt thereof to provide a compound of the formula (VI):

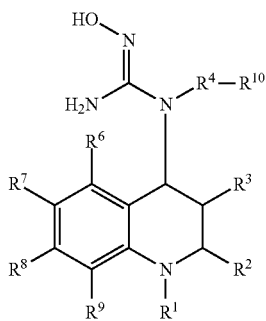

(VI)

wherein the symbols have the same meaning as defined above, (c) alkanoylating the compound (VI) to provide a compound of the formula (VII):

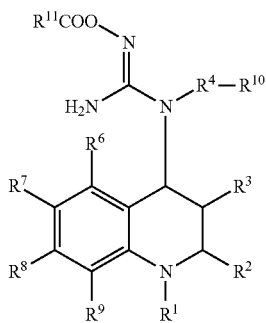

(VII)

wherein the symbols have the same meaning as defined above, and further (d) cyclizing the compound (VII) with a base.

The cyanation in the process (a) can be carried out by reacting a halogenated cyanogen in the presence of a base in a suitable solvent.

Cyanogen bromide is preferable as the halogenated cyanogen.

A conventional base can be preferably used as the base, and alkaline metal carbonate including potassium carbonate, or alkaline metal bicarbonate including sodium bicarbonate can be preferably used.

Any solvent which dose not disturb the reaction can be used and the solvent referred to in the PROCESS 1 can be preferably used.

The reaction with hydroxylamine in the process (b) can be carried out in the presence of a base in a suitable solvent.

Tertiary alkylamines including triethylamine, diisopropylethylamine, and the like can be preferably used as the base.

Any solvent which dose not disturb the reaction can be used and the solvent referred to in the PROCESS 1 can be preferably used.

The alkanoylation in the process (c) can be carried out with an alkanoyl halide in the presence of a base in a suitable solvent.

A conventional base can be used as the base, and amines including triethylamine or diisopropylethylamine, or pyridines including pyridine, 4-dimethylaminopyridine can be preferably used.

Any solvent which dose not disturb the reaction can be used and the solvent referred to in the PROCESS 1 can be preferably used.

In the cyclization in the process (d), a conventional base can be used as the base, and amines including triethylamine or diisopropylethylamine; pyridines including pyridine, 4-dimethylaminopyridine; or alkaline metal alkoxide including sodium methoxide can be preferably used.

Any solvent which dose not disturb the reaction can be used and the solvent referred to in the PROCESS 1 can be preferably used.

Additionally, the cyclization following the alkanoylating can also be carried out in situ.

The reaction is carried out from under cooling to under heating, preferably from −50° C. to 100° C., more preferably from 0° C. to 50° C.

Process 3

Among the compound of the formula (I-A), a compound of the formula (I-c):

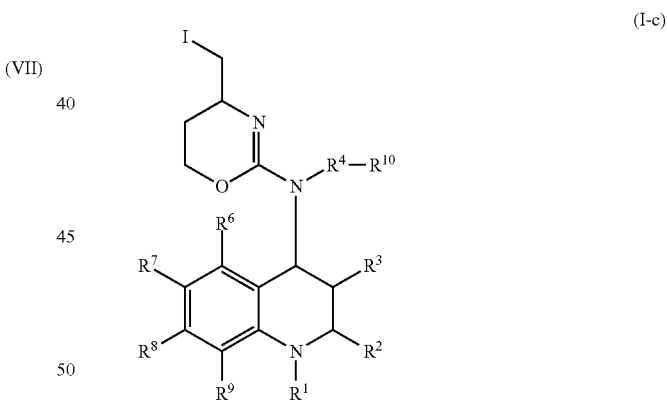

(I-c)

wherein the symbols have the same meaning as defined above can be prepared by reacting a compound of the formula (V):

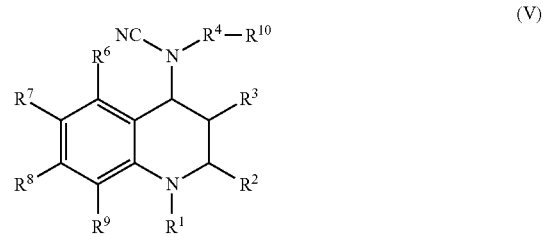

(V)

wherein the symbols have the same meaning as defined above with 3-buten-1-ol to provide a compound of the formula (VIII):

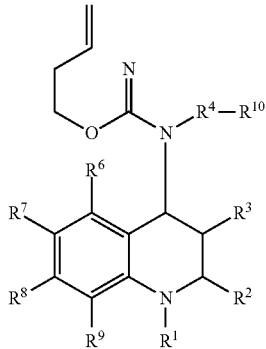

wherein the symbols have the same meaning as defined above, followed by cyclizing the resulting compound in the presence of iodine, N-iodosuccinimide, or the like.

The reaction with 3-buten-1-ol can be carried out in the presence of a base in a suitable solvent.

Any base which dose not disturb the reaction can be used and the base referred to in the PROCESS 1 can be preferably used.

Any solvent which dose not disturb the reaction can be used and the solvent referred to in the PROCESS 1 can be preferably used.

In the cyclization any solvent which dose not disturb the reaction can be used and the solvent referred to in the PROCESS 1 can be preferably used.

The reaction is carried out from under cooling to under heating, preferably from −50° C. to 100° C., more preferably from 0° C. to 50° C.

Process 4

The compound of the formula (I-A) can also be prepared by the following methods with a compound of the formula (IX):

wherein $X^{10}$ is a hydrogen atom, a halogen atom or a hydroxy group and the other symbols have the same meaning as defined above.

In each process of following (A) to (K), unless otherwise specified, the base referred to in the PROCESS 1 can be preferably used as the base.

Additionally, in each process of following (A) to (K) a conventional acid can be used as an acid, and unless otherwise specified, a mineral acid including hydrochloric acid, nitric acid, sulfuric acid; an organic acid represented by sulfonic acids (e.g., methanesulfonic acid, p-toluenesulfonic acid, trifluoromethanesulfonic acid, and the like) can be preferably used.

Additionally, in each process of following (A) to (K), any solvent which dose not disturb the reaction can be used as the solvent, and specifically, the solvent referred to in the PROCESS 1 can be preferably used.

The leaving group includes a halogen atom including chlorine atom, bromine atom, iodine atom, and a substituted sulfonyloxy group including methanesulfonyloxy group, and trifluoromethanesulfonyloxy group, toluenesulfonyloxy group.

(A) The compound wherein Ring A is a tetrazolyl group and $R^{11}$ is an alkyl group having 3 to 10 carbon atoms or a substituted alkyl group can be prepared by alkylating a compound of the formula (IX) wherein Ring A is a tetrazolyl group and $X^{10}$ is a hydrogen atom.

The alkylation can be carried out by reacting a starting compound with a compound of the formula:

$$R^{11A}\text{—}Z^2$$

wherein $R^{11A}$ is an alkyl group having 3 to 10 carbon atoms or a substituted alkyl group and $Z^2$ refers to a leaving group in a suitable solvent in the presence or absence of a base, or reacting with a compound of the formula:

$$R^{11A}\text{—OH}$$

wherein the symbol has the same meaning as defined above in a suitable solvent in the presence of phosphines and azodicarboxylic esters.

The reaction proceeds more preferably when a catalytic amount of an alkaline metal iodide (e.g., potassium iodide, and the like) is added.

Both phosphines and azodicarboxylic esters which usually employed in Mitsunobu reaction can be preferably used. Phosphines include, for example, triphenylphosphine, tributylphosphine, and the like, and azodicarboxylic esters include diethyl azodicarboxylate, diisopropyl azodiformate, and the like.

(B) The compound wherein Ring A is 2-oxodihydropyrimidinyl group and $R^{11}$ is an alkyl group having 3 to 10 carbon atoms or a substituted alkyl group can be prepared by alkylating a compound of the formula (IX) wherein Ring A is 2-hydroxypyrimidinyl group and $X^{10}$ is a hydrogen atom with a compound of the formula:

$$R^{11A}\text{—}Z^2$$

wherein the symbols have the same meaning as defined above.

The reaction can be carried out in the same manner as (A).

(C) The compound wherein $R^{11}$ is an optionally substituted amino group or a group of the formula:

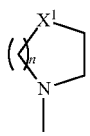

wherein the symbols have the same meaning as defined above can be prepared by reacting a compound of the formula (IX) wherein $X^{10}$ is a halogen atom with a corresponding amine or a compound of the formula:

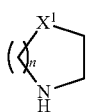

wherein the symbols have the same meaning as defined above.

The reaction can be carried out in the presence or absence of a base, and in the presence or absence of a palladium catalyst in a suitable solvent.

As the palladium catalyst, a conventional palladium catalyst including palladium acetate, tetrakis(triphenylphosphine)palladium, tris(dibenzylideneacetone) dipalladium, dichlorobis(triphenylphosphine)-palladium, dichlorobis(tri-o-tolylphosphine)palladium, bis-(triphenylphosphine)palladium acetate, or the like can be used.

As the base, alkaline metal hydroxide including sodium hydroxide, potassium hydroxide; alkaline earth metal hydroxide including barium hydroxide; alkaline metal alkoxide including sodium methoxide, sodium ethoxide, potassium ethoxide, potassium tert-butoxide; alkaline metal carbonate including sodium carbonate, potassium carbonate, cesium carbonate; alkaline metal bicarbonate including sodium bicarbonate, potassium bicarbonate; alkaline metal phosphate including potassium phosphate; amines including triethylamine, diisopropylethylamine, methylpiperidine, dicyclohexylmethylamine; and pyridines including pyridine, 4-dimethylaminopyridine can be preferably used.

Additionally, phosphines may be added in the present reaction. As the phosphines, triphenylphosphine, tributylphosphine, tri-tert-butylphosphonium tetrafluoroborate, 1,3-bis(diphenylphosphino)propane, 2,2'-bis(diphenylphosphino)-1,1'-binaphthyl, 1,1'-bis(diphenylphosphino)-ferrocene, 2-(di-tert-butylphosphino)biphenyl, 2-dicyclohexylphosphino-2'-(N,N-dimethylamino)biphenyl, 2-(dicyclohexylphosphino)biphenyl, and the like can be preferably used as the phosphines.

(D) The compound wherein $R^{11}$ is an optionally substituted amino group can be prepared by coupling a compound of the formula (IX) wherein $X^{10}$ is a halogen atom with a compound of the formula:

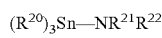

$$(R^{20})_3Sn\text{---}NR^{21}R^{22}$$

wherein $R^{20}$ is an alkyl group and $NR^{21}R^{22}$ is an optionally substituted amino group.

The coupling reaction can be carried out in the presence of a palladium catalyst in the presence or absence of a base in a suitable solvent.

The palladium catalysts, bases, and phosphines referred to in (C) can be used in the same manner as (C) above.

(E) The compound wherein $R^{11}$ is a cyano group can be prepared by cyanating a compound of the formula (IX) wherein $X^{10}$ is a halogen atom.

The cyanation can be carried out by reacting a starting compound with a metal cyanide including sodium cyanide, potassium cyanide, or zinc cyanide in the presence of a palladium catalyst in a suitable solvent.

The same palladium catalyst as that described in (C) can be preferably used.

(F) The compound wherein $R^{11}$ is an optionally substituted alkoxycarbonyl group can be prepared by reacting a compound of the formula (IX) wherein $X^{10}$ is a halogen atom with a corresponding alkylalcohol under carbon monoxide using a palladium catalyst in the presence of a base in a suitable solvent.

The same palladium catalyst and base as those described in (C) can be preferably used.

Additionally, the reaction can be more preferably carried out by adding a ligand, and phosphines referred to in (C) can be preferably used as the ligand.

(G) The compound wherein $R^{11}$ is an optionally substituted alkenyl group can be prepared by coupling a compound of the formula (IX) wherein $X^{10}$ is a halogen atom with a corresponding alkene.

The coupling reaction can be carried out in the presence of a palladium catalyst in the presence or absence of a base in a suitable solvent.

The same palladium catalyst as that described in (C) can be preferably used.

The same base as referred to in (C) can be preferably used and silver carbonate can also be used.

Additionally, the reaction can be more preferably carried out by adding a ligand, and phosphines referred to in (C) can be preferably used as the ligand.

(H) The compound wherein $R^{11}$ is an alkoxy group having 3 to 10 carbon atoms or a substituted alkoxy group can be prepared by alkoxylating a compound of the formula (IX) wherein $X^{10}$ is a halogen atom.

The alkoxylation can be carried out by optionally adding a copper catalyst to react a starting compound with a corresponding alcohol in a suitable solvent or neat in the presence of a base.

The same base as referred to in (C), in particular, cesium carbonate can be preferably used.

The copper catalyst including copper iodide, copper bromide, copper chloride, copper acetate, copper trifluoromethanesulfonate, and the like can be preferably used.

Additionally, the reaction proceeds more preferably when 1,10-phenanthroline, 2-aminopyridine, or the like is added.

(I) The compound wherein $R^{11}$ is an optionally substituted heterocyclic group can be prepared by coupling a compound of the formula (IX) wherein $X^{10}$ is a halogen atom with a corresponding heterocyclic boronic acids or a corresponding heterocyclic boronic ester.

The coupling can be carried out in the presence of a palladium catalyst, and in the presence or absence of a base in a suitable solvent.

The reaction can be carried out in the same manner as (C).

(J) The compound wherein $R^{11}$ is an alkoxycarbonylalkylsulfonyl group can be prepared by reacting a compound of the formula (IX) wherein $X^{10}$ is a halogen atom with an alkoxycarbonylalkylsulfinic acid alkaline metal salt.

The alkoxycarbonylalkylsulfinic acid alkaline metal salt can be prepared according to the method described, for example, in Baskin et al., Tetrahedron Lett., 43, 8479 (2002).

Additionally, the reaction can be carried out in the presence of a copper catalyst in a suitable solvent according to the method described in the said literature.

The same copper catalyst as described in (H) can be used, and in particular, copper iodide can be preferably used.

(K) The compound wherein $R^{11}$ is a group of the formula:

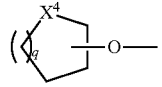

wherein the symbols have the same meaning as defined above can be prepared by condensing a compound wherein $R^{11}$ is a hydroxy group with a compound of the formula:

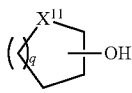

wherein $X^{11}$ is O, SO, $SO_2$ or $NR^p$ ($R^p$ is a protecting group) and q is an integer from 1 to 4, and if needed, removing a protecting group for amino group.

As a protecting group, a conventional protecting group including benzyloxycarbonyl group, tert-butoxycarbonyl group, and the like can be used.

The reaction can be carried out in a suitable solvent in the presence of phosphines and azodicarboxylic esters. The reaction can be carried out in the same manner as the PROCESS 4-(A).

The removal of a protecting group can be carried out in a conventional manner including catalytic reduction, acid-treatment, and the like, depending on the type of a protecting group.

The reactions (A) to (K) for conversions of $R^{11}$ can also be applied for conversion in the same manner of an other substituent ($R^1$, $R^2$, $R^3$, $R^4$, $R^5$, $R^6$, $R^7$, $R^8$, $R^9$ or $R^{10}$) as appropriate.

Additionally, a substituent(s) of a compound (I) of the present invention can be converted into different one(s) within the scope of the compound (I) according to the following methods as appropriate.

In the following each process, a conventional base can be used as a base, and unless otherwise specified, the base referred to in the PROCESS 1 can be preferably used.

Additionally, in the following each process, a conventional acid can be used as an acid, and unless otherwise specified, a mineral acid including hydrochloric acid, nitric acid, sulfuric acid, or an organic acid represented by sulfonic acids (e.g., methanesulfonic acid, p-toluenesulfonic acid, trifluoromethanesulfonic acid) or carboxylic acids (e.g., acetic acid, trifluoroacetic acid) can be preferably used.

Further additionally, in the following each process, any solvent which dose not disturb the reaction can be used, and as such, the solvent referred to in the PROCESS 1 can be preferably used.

The leaving group includes a halogen atom including chlorine atom, bromine atom, iodine atom, and a substituted sulfonyloxy group including methanesulfonyloxy group, trifluoromethanesulfonyloxy group, and toluenesulfonyloxy group.

In addition, in the following each process, "a saturated or unsaturated monocyclic or bicyclic heterocyclic group having one to four heteroatoms independently selected from oxygen atom, sulfur atom and nitrogen atom" in $R^5$ is simply referred to as "a heterocyclic group".

(1) The compound wherein $R^5$ is a heterocyclic group substituted by an optionally substituted amino group or a group of the formula:

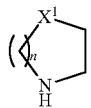

wherein the symbols have the same meaning as defined above can be prepared by reacting a compound (I) wherein $R^5$ is a heterocyclic group substituted by an optionally substituted alkylsulfonyloxy group with a corresponding amine or a compound of the formula:

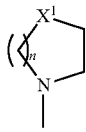

wherein the symbols have the same meaning as defined above in the presence of a palladium catalyst, and in the presence or absence of a base in a suitable solvent or neat.

The reaction can be carried out in the same manner as the PROCESS 4-(C).

(2) The compound wherein $R^5$ is a heterocyclic group substituted by an optionally substituted amino group or a group of the formula:

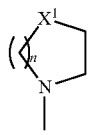

wherein the symbols have the same meaning as defined above can also be prepared by reacting a compound wherein $R^5$ is a heterocyclic group substituted by a halogen atom or an optionally substituted alkylsulfonyloxy group with a corresponding amine or a compound of the formula:

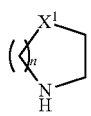

wherein the symbols have the same meaning as defined above.

The reaction can be carried out by optionally adding a copper catalyst in the presence or absence of a base in a suitable solvent.

Copper iodide, copper bromide, copper chloride, copper acetate, copper trifluoromethanesulfonate, and the like can be preferably used as the copper catalyst.

The same base as referred to in the PROCESS 4-(C) can be preferably used.

Additionally, the reaction proceeds more preferably when N,N'-dimethylethylenediamine, 1,10-phenanthroline, ethylene glycol, phenylphenol, and the like is added.

(3) The compound wherein $R^5$ is a heterocyclic group substituted by an optionally substituted alkylthio group can be prepared by reacting a compound wherein $R^5$ is a heterocyclic group substituted by a halogen atom or an optionally substituted alkylsulfonyloxy group with a corresponding alkylthiol.

The reaction can be carried out in the same manner as previously described in the PROCESS 4-(H) and facilitated by adding 1,10-phenanthroline or ethylene glycol.

(4) The compound wherein $R^5$ is a heterocyclic group substituted by an optionally substituted heterocyclic group can be prepared by coupling a compound wherein $R^5$ is a heterocyclic group substituted by a halogen atom or an optionally substituted alkylsulfonyloxy group with a corresponding heterocyclic alkyl tin compound.

The reaction can be carried out in the same manner as the PROCESS 4-(D).

(5) The compound wherein $R^5$ is a heterocyclic group substituted by an alkoxy group or an alkoxyphenylalkoxy group can be prepared by reacting a compound wherein $R^5$ is a heterocyclic group substituted by an alkylsulfonyl group with a corresponding alkaline metal alkoxide in a suitable solvent. The corresponding alkaline metal alkoxide can be obtained by treating a corresponding alkylalcohol with alkaline metal hydride or alkaline metal in the said solvent.

(6) The compound having an aminoalkyl group as a substituent on $R^5$ can be prepared by catalytically reducing a compound having a cyano group or a cyanoalkyl group as a substituent on $R^5$.

The catalytic reduction can be carried out by using a catalyst under hydrogen in a suitable solvent according to a conventional manner. The catalyst includes a palladium catalyst including palladium-carbon, a nickel catalyst including Raney nickel, a platinum catalyst including platinum-carbon, and the like.

(7) The compound having an optionally substituted mono- or di-alkylsulfamoylaminoalkyl group as a substituent on $R^5$ can be prepared by reacting a compound having an aminoalkyl group as a substituent on $R^5$ with a corresponding halogenated mono- or di-alkylsulfamoyl.

The reaction can be carried out in a suitable solvent in the presence of a base.

(8) The compound having an optionally substituted monoalkylcarbamoylaminoalkyl group as a substituent on $R^5$ can be prepared by reacting a compound having an aminoalkyl group as a substituent on $R^5$ with a corresponding alkyl isocyanate in a suitable solvent.

(9) The compound having a group of the formula:

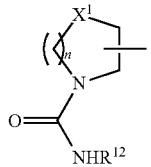

wherein $R^{12}$ is an alkyl group and the other symbol has the same meaning as defined above as a substituent on $R^5$ can be prepared by reacting a compound having a group of the formula:

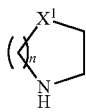

wherein the symbols have the same meaning as defined above as a substituent on $R^5$ with a corresponding alkyl isocyanate ($R^{12}$NCO). The reaction can be carried out in the same manner as (8).

(10) The compound having an optionally substituted mono- or di-alkylcarbamoylaminoalkyl group as a substituent on $R^5$ can be prepared by condensing a compound having an aminoalkyl group as a substituent on $R^5$ with an optionally substituted mono- or di-alkylamine using a carbonylating agent in a suitable solvent in the presence or absence of a base.

A conventional carbonylating agent such as carbonyldiimidazole, phosgene, triphosgene, and the like can be used.

(11) The compound having a morpholinylcarbonylamino group as a substituent on $R^5$ can be prepared by condensing a compound having an amino group as a substituent on $R^5$ with morpholine using a carbonylating agent in a suitable solvent. The reaction can be carried out in the same manner as (10).

(12) The compound having a group of the formula:

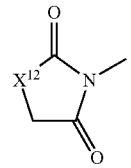

wherein $X^{12}$ is O or NH as a substituent on $R^5$ can be prepared by treating a compound having a group of the formula

wherein the symbols have the same meaning as defined above as a substituent on $R^5$ with a carbonylating agent in a suitable solvent.

The reaction can be carried out in the same manner as (10).

(13) The compound having an optionally substituted carbamoyl group as a substituent on $R^5$ can be prepared by condensing a compound having a carboxyl group as a substituent on $R^5$ with a desirable amine.

The condensation can be carried out using a condensing agent in a suitable solvent. A conventional condensing agent such as dicyclohexylcarbodiimide, 1-ethyl-3-(3-dimethylaminopropyl)carbodiimide, carbonyldiimidazole, and the like can be preferably used.

Additionally, the condensation can be more preferably carried out by adding an activating agent including 1-hydroxybenzotriazole, 1-hydroxysuccinimide, and the like.

(14) The compound having a group of the formula:

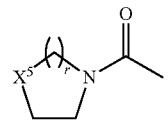

wherein the symbols have the same meaning as defined above as a substituent on $R^5$ can be prepared by condensing a compound having a carboxyl group as a substituent on $R^5$ with a compound of the formula:

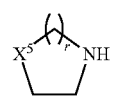

wherein the symbols have the same meaning as defined above.

The reaction can be carried out in the same manner as (13).

(15) The compound having a tetrazolyl group as a substituent on $R^5$ can be prepared by reacting a compound having a cyano group as a substituent on $R^5$ with an alkaline metal azide in the presence of an acid in a suitable solvent.

The alkaline metal azide includes sodium azide, lithium azide, and the like.

An ammonium salt of a halogenated hydrogen including ammonium chloride can be preferably used as the acid.

(16) The compound having an optionally substituted alkyl tetrazolyl group as a substituent on $R^5$ can be prepared by alkylating a compound having a tetrazolyl group as a substituent on $R^5$.

The alkylation can be carried out in the same manner as the PROCESS 4-(A).

(17) The compound having an optionally substituted amino group or a group of the formula:

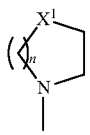

wherein the symbols have the same meaning as defined above as a substituent on $R^5$ can be prepared by reacting a compound having a halogen atom or an optionally substituted alkylsulfonyloxy group as a substituent on $R^5$ with a corresponding amine or a compound of the formula:

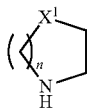

wherein the symbols have the same meaning as defined above.

The reaction can be preferably carried out in the presence or absence of a base in a suitable solvent.

(18) The compound having an optionally substituted alkylamino group or a group of the formula:

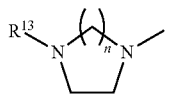

wherein $R^{13}$ is an alkyl group optionally substituted by a hydroxy group, an alkoxycarbonyl group, a morpholinyl group or a phenyl group, and n has the same meaning as defined above as a substituent on $R^5$ can be obtained by reacting a compound having an amino group or a group of the formula:

wherein the symbols have the same meaning as defined above as a substituent on $R^5$ with a corresponding alkyl halide or a corresponding sulfonic alkyl ester.

The sulfonic alkyl ester including methanesulfonic ester, toluenesulfonic ester, trifluoromethanesulfonic ester, and the like can be preferably used.

The reaction can be preferably carried out in the presence or absence of a base in a suitable solvent.

(19) The compound having a group of the formula:

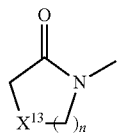

wherein $X^{13}$ is O or NH, and the other symbols have the same meaning as defined above as a substituent on $R^5$ can be prepared by ring-closing a compound having a group of the formula:

$$Z^3-(CH_2)_n-X^{13}-CH_2-CONH-$$

wherein $Z^3$ is a leaving group and the other symbols have the same meaning as defined above as a substituent on $R^5$.

The reaction can be preferably carried out in the presence or absence of a base in a suitable solvent.

(20) The compound having a carboxyl group as a substituent on $R^5$ can be prepared by hydrolyzing a compound having an alkoxycarbonyl group as a substituent on $R^5$.

The hydrolysis can be carried out by treating a starting compound with a base or an acid in a suitable solvent according to a conventional manner. An alkaline metal hydroxide can be preferably used as the base.

(21) The compound containing a carboxyl group as a substituent on $R^5$ can be prepared by hydrolyzing a compound containing a cyano group as a substituent on $R^5$.

The hydrolysis can be carried out by treating a starting compound with an acid in a suitable solvent.

(22) The compound containing a carbamoyl group as a substituent on $R^5$ can be prepared by hydrolyzing a compound containing a cyano group as a substituent on $R^5$.

The hydrolysis can be carried out by treating a starting compound with an acid in a suitable solvent.

(23) The compound having a carboxyalkyl group as a substituent on $R^5$ can also be prepared by catalytically reducing a compound having a carboxyalkenyl group, a benzyloxycarbonylalkenyl group or a benzyloxycarbonylalkyl group as a substituent on $R^5$.

The catalytic reduction can be carried out in the same manner as (6).

(24) The compound having a hydroxy group as a substituent on $R^5$ can be prepared by hydrolyzing a compound wherein $R^5$ has an alkanoyloxy group.

The hydrolysis can be carried out in the same manner as (20).

(25) The compound containing sulfin (SO) or sulfoxide ($SO_2$) in a substituent on $R^5$ can be prepared by oxidizing a compound having S in a substituent on $R^5$ (e.g., a compound having a thiomorpholinyl group or an alkylthioalkyl group as a substituent on $R^5$).

The oxidation can be carried out by treating a starting compound with an oxidizing agent in a suitable solvent.

Peroxides such as hydrogen peroxide, m-chloroperbenzoic acid, acetyl hydroperoxide, and the like can be preferably used as the oxidizing agent.

(26) The compound containing N-oxide in a substituent on $R^5$ can be prepared by oxidizing a compound having N in a substituent on $R^5$ (e.g., a compound having a pyridyl group as a substituent on $R^5$).

The oxidation can be carried out in the same manner as (25).

(27) The compound having a 1,2-dihydroxyalkyl group as a substituent on $R^5$ can be prepared by treating a compound having an alkyl group substituted by mono- or di-alkyldioxolanyl group as a substituent on $R^5$ with an acid in a suitable solvent.

A strongly acidic resin can also be preferably used as the acid, in addition to those previously described.

(28) The compound having an alkyl group substituted by a hydroxy group and an optionally substituted alkoxy group as substituents on $R^5$ can be prepared by reacting a compound having an oxiranylalkyl group as a substituent on $R^5$ with an alkaline metal salt of the corresponding alcohol in a suitable solvent.

The alkaline metal salt of alcohol includes a lithium salt, a sodium salt, a potassium salt, and the like.

(29) The compound having an alkyl group substituted by a hydroxy group and an amino group, or an alkyl group substituted by a hydroxy group and an optionally substituted mono- or di-alkylamino group as substituents on $R^5$ can be prepared by reacting a compound having an oxiranylalkyl group as a substituent on $R^5$ with ammonia or a corresponding mono- or di-alkylamines in a suitable solvent.

(30) The compound having a hydroxycarbamimidoyl group as a substituent on $R^5$ can be prepared by reacting a compound having a cyano group as a substituent on $R^5$ with hydroxylamine or a salt thereof in a suitable solvent. This process can be carried out in the same manner as the PROCESS 2-(b) previously described.

(31) The compound having an oxodihydrooxadiazolyl group as a substituent on $R^5$ can be prepared by reacting a compound having a hydroxycarbamimidoyl group as a substituent on $R^5$ with a carbonylating agent in a suitable solvent in the presence or absence of a base.

The same carbonylating agent as that described in (10) can be used.

(32) The compound having a sulfo group as a substituent on $R^5$ can be prepared by hydrolyzing a compound having an alkoxycarbonylalkylsulfonyl group as a substituent on $R^5$.

The hydrolysis can be carried out in the same manner as (20).

(33) The compound having a sulfamoyl group as a substituent on $R^5$ can be prepared by condensing a compound having a sulfo group as a substituent on $R^5$ with a desirable amine.

The condensation can be carried out by treating a compound having a sulfo group as a substituent on $R^5$ with a halogenating agent in a suitable solvent, followed by reacting the resulting compound with a desirable amine in the presence or absence of a base.

A conventional halogenating agent including thionyl halide, phosphorus oxyhalide, or the like can be used.

(34) The compound having a hydroxyalkyl group as a substituent on $R^5$ can be prepared by reducing a compound having a carboxyalkyl group as a substituent on $R^5$, or by converting the carboxyl group into an acid anhydride or an ester and reducing the resulting compound.

A process for conversion into an acid anhydride can be carried out by reacting a starting compound with a halogenated alkyl formate in a suitable solvent in the presence of a base.

A process for conversion into an ester can be carried out by reacting a starting compound with an alcohol in the presence of a condensing agent in a suitable solvent. This process can be carried out in the same manner as (33) except that a desirable alcohol is used in place of amine.

The reduction can be carried out by treating the resulting compound with a reducing agent in a suitable solvent.

Boron hydrides (sodium borohydride, and the like), aluminum hydrides (lithium aluminum hydride, diisobutylaluminum hydride, and the like) can be preferably used as the reducing agent.

(35) The compound wherein $R^{10}$ is an aromatic group substituted by a cyano group, optionally having one to three heteroatoms independently selected from oxygen atom, sulfur atom and nitrogen atom (hereinafter, referred to as "an aromatic group"), can be prepared by cyanating a compound wherein $R^{10}$ is an aromatic group substituted by a halogen atom.

The cyanation can be carried out in the same manner as the PROCESS 4-(E).

(36) The compound wherein $R^1$ is a hydrogen atom can be prepared by acid-treatment or reduction of a compound wherein $R^1$ is a tert-butoxycarbonyl group or a benzyloxycarbonyl group.

The acid-treatment can be carried out in the same manner as (27) and the reduction can be carried out in the same manner as (23).

(37) The compound wherein $R^1$ is an optionally substituted alkoxycarbonyl group, or an optionally substituted carbamoyl group can be prepared by reacting a compound wherein $R^1$ is a hydrogen atom with a carbonylating agent, or a desirable alcohol or a desirable amine in a suitable solvent.

The reaction can be carried out in the same manner as (10).

(38) The compound having an amino group as a substituent on $R^5$ can be prepared by reacting a compound having a carboxyl group as a substituent on $R^5$ under Curtius rearrangement reaction condition.

Curtius rearrangement reaction can be carried out using a conventional azidating agent (e.g., diphenylphosphorylazide) in a suitable solvent in the presence or absence of a base.

The reaction may also be carried out by adding an alcohol to provide a compound having an optionally substituted alkoxycarbonylamino group as a substituent on $R^5$, followed by removing the alkoxycarbonyl group.

The removal of the alkoxycarbonyl group can be carried out in a conventional manner such as an acid-treatment or a reduction depending on the type of alkoxycarbonyl group to be removed. The acid-treatment can be carried out in the same manner as (27) and the reduction can be carried out in the same manner as (23).

(39) The compound having a hydroxy group as a substituent on $R^5$ can be prepared by catalytically reducing a compound having a benzyloxy group as a substituent on $R^5$. The reduction can be carried out in the same manner as (23).

(40) The compound having an oxo group as a substituent on $R^5$ can be prepared by oxidizing a compound having a hydroxy group as a substituent on $R^5$.

The oxidation can be carried out by using an oxidizing agent in a suitable solvent.

A conventional oxidizing agent can be used as the oxidizing agent, such as chromate-pyridine complex, pyridinium chlorochromate, pyridinium dichromate, Dess-Martin reagent (1,1,1-tris(acetoxy)-1,1-dihydro-1,2-benziodoxol-3-(1H)-one), dimethylsulfoxide, and the like.

(41) The compound containing an optionally substituted alkoxy group as a substituent on $R^5$ can be prepared by alkylating a compound containing a hydroxy group as a substituent on $R^5$.

The alkylation can be carried out by using a corresponding compound in the same manner as the PROCESS 4-(A).

(42) The compound having an optionally substituted alkanoylamino group as a substituent on $R^5$ can be prepared by condensing a compound having an amino group as a substituent on $R^5$ with a corresponding carboxylic acid or a reactive derivative thereof.

The condensation with the corresponding carboxylic acid can be preferably carried out in a suitable solvent in the presence of a condensing agent. The reaction can be carried out in the same manner as (13).

Additionally, the condensation with the reactive derivative of the corresponding carboxylic acid can be carried out in a suitable solvent or neat in the presence or absence of a base.

The reactive derivative includes an acid halide, an acid anhydride, an activated ester, an activated amide, and the like.

(43) The compound having a group of the formula:

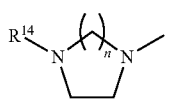

wherein $R^{14}$ is an alkanoyl group optionally substituted by a hydroxy group or an alkoxy group, and n has the same meaning as defined above as a substituent on $R^5$ can be prepared by condensing a compound of a group of the formula:

wherein the symbols have the same meaning as defined above as a substituent on $R^5$ with a corresponding carboxylic acid or a reactive derivative thereof.

The reaction can be carried out in the same manner as (42).

(44) The compound having a maleimide group as a substituent on $R^5$ can be prepared by reacting a compound having an amino group as a substituent on $R^5$ with a maleic anhydride. The reaction can be carried out in a suitable solvent.

(45) The compound having an alkyl group substituted by a pyridyl group and a hydroxy group as substituents on $R^5$ can be prepared by reacting a compound having an alkyl group substituted by a pyridyl group of which nitrogen atom is oxidized as a substituent on $R^5$ with a trifluoroacetic anhydride. The reaction can be carried out in a suitable solvent.

(46) The compound having a halogen atom as a substituent on $R^5$ can be prepared by treating a compound having a hydroxy group as a substituent on $R^5$ with a halogenating agent.

As the halogenating agent, a conventional halogenating agent including thionyl chloride, phosphorus oxychloride, as well as carbon tetrahalide (e.g., carbon tetrachloride, carbon tetrabromide, and the like) and phosphines (e.g., triphenylphosphine, tritolylphosphine, triethylphosphine, and the like) can be preferably used.

(47) The compound having a cyanoalkyl group as a substituent on $R^5$ can be prepared by reducing a compound having a cyanoalkenyl group as a substituent on $R^5$.

The reduction can be carried out by treating a starting compound with a reducing agent or by catalytically reducing in a suitable solvent.

Any reducing agent can be used subject that it reduces only a double bond without affecting a cyano group. For example, sodium bis(2-methoxyethoxy)aluminum hydride in the presence of a copper bromide can be preferably used.

The catalytic reduction can be carried out in the same manner as (23).

(48) The compound having a hydroxyalkyl group as a substituent on $R^5$ can be prepared by reducing a compound having a formyl group as a substituent on $R^5$.

The reduction can be carried out by treating a starting compound with a reducing agent in a suitable solvent.

The reaction can be carried out in the same manner as the process for reducing in (34).

(49) The compound wherein $R^7$ is a hydroxy group can be prepared by demethylating a compound wherein $R^7$ is a methoxy group.

The demethylation can be carried out by treating a starting compound with a demethylating agent in a suitable solvent.

A conventional agent including trimethylsilyl iodide, hydrogen bromide/acetic acid, boron tribromide, concentrated sulfuric acid, and the like can be used as the demethylating agent.

(50) The compound wherein $R^7$ is an optionally substituted alkoxy group can be prepared by alkylating a compound wherein $R^7$ is a hydroxy group.

The alkylation can be carried out in the same manner as the PROCESS 4-(A).

(51) The compound wherein $R^7$ is an optionally substituted alkylsulfonyloxy group can be prepared by alkylsulfonylating a compound wherein $R^7$ is a hydroxy group.

The alkylsulfonylation can be carried out by reacting a corresponding alkylsulfonyl halide or a corresponding alkylsulfonic anhydride in a suitable solvent in the presence or absence of a base.

(52) The compound wherein $R^7$ is a cyano group can be prepared by cyanating a compound wherein $R^7$ is an optionally substituted alkylsulfonyloxy group.

The cyanation can be carried out in the same manner as the PROCESS 4-(E).

(53) The compound wherein $R^7$ is an aminoalkyl group can be prepared by reducing a compound wherein $R^7$ is a cyano group.

The reduction can be carried out in the same manner as (6).

(54) The compound wherein $R^7$ is an alkyl group can be prepared by alkylating a compound wherein $R^7$ is an optionally substituted alkylsulfonyloxy group.

The alkylation can be carried out by reacting alkyl aluminums in the presence of a palladium catalyst, a silver catalyst and a copper catalyst in a suitable solvent.

Tetrakis(triphenylphosphine)palladium as the palladium catalyst, silver carbonate as the silver catalyst, copper (I) chloride as the copper catalyst can be preferably used.

(55) The compound having an imidazolinyl group or an oxazolinyl group as a substituent on $R^5$ can be prepared by (i) reacting a compound containing a cyano group as a substituent on $R^5$ with a desirable alcohol in the presence of an acid in a suitable solvent or neat to provide a compound containing an alkoxycarbonimidoyl group as a substituent on $R^5$, and (ii) reacting the compound containing an alkoxycarbonimidoyl group as a substituent on $R^5$ with 2-aminoethanol or ethylene diamine in a suitable solvent or neat.

(56) The compound having a carboxyl group as a substituent on $R^1$ can be prepared by (i) oxidizing a compound containing a hydroxyalkyl group as a substituent on $R^1$ in the same manner as (40) to provide a compound containing an oxo group as a substituent on $R^1$, and (ii) oxidizing the compound containing an oxo group as a substituent on $R^1$.

The oxidization for the second step can be carried out by using an oxidizing agent in a suitable solvent. Sodium chlorite, Silver(I) oxide, Sodium periodate and the like can be preferably used as the oxidizing agent.

(57) The compound having a carboxyl group as a substituent on $R^1$ can be directly prepared by oxidizing a compound containing a hydroxyalkyl group as a substituent on $R^1$.

The oxidization can be carried out by using Jones reagent, potassium permanganate, and the like as the oxidizing agent.

(58) The compound wherein $R^1$ is hydrogen atom can be prepared by treating a compound wherein $R^1$ is ethoxycarbonyl group with a silyl halides or a base. Trimethylsilyl iodide can be preferably used as the silyl halides. Sodium hydroxide can be preferably used as the base.

In each process for preparing a compound of the formula (I) described above, when protection of a functional group contained in any compound is needed, the protection can be carried out in a conventional manner ad libitum. General statement related to protecting groups and their use is provided by Greene, Protective Groups in Organic Synthesis, John Wiley and Sons, New York, 1991.

When an amino group is protected by a benzyloxycarbonyl group, the protecting group can be removed by a catalytic reduction under hydrogen in a suitable solvent.

When a hydroxy group is protected by a benzyl group, the protecting group can also be removed by a catalytic reduction in a similar manner as above.

When an amino group is protected by a t-butoxycarbonyl group, the protecting group can be removed by treating a starting compound with an acid (e.g., hydrochloric acid, trifluoroacetic acid, toluenesulfonic acid, and the like) in a suitable solvent.

When a hydroxy group is protected by a tetrahydropyranyl group, the protecting group can also be removed by treating a starting compound with an acid in a similar manner as above.

The reactions (1) to (58) for conversion of $R^1$, $R^5$, $R^7$ or $R^{10}$ can also be applied for conversion in the same manner of other substituent of the present compound (I) as appropriate.

The starting compound (II) is a novel compound, and can be prepared by condensing a compound of the formula (X):

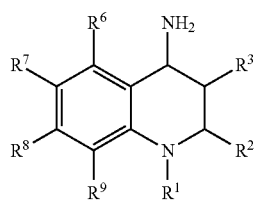

wherein the symbols have the same meaning as defined above with a compound of the formula (XI):

$R^5-Z^4$ (XI)

wherein $Z^4$ is a leaving group and $R^5$ has the same meaning as defined above.

As the leaving group, a halogen atom including chlorine atom, bromine atom, iodine atom, and a substituted sulfonyloxy group including methanesulfonyloxy group, p-toluenesulfonyloxy group, trifluoro-methanesulfonyloxy group are preferably used.

The reaction can be carried out in a suitable solvent (e.g., 1,4-dioxane, dimethylformamide, 1,3-dimethylimidazolidinone, and the like) in the presence or absence of a base (e.g., diisopropylethylamine, and the like) from room temperature to under heating.

The reaction can also be carried out by adding a palladium catalyst (e.g., tris(dibenzylideneacetone)dipalladium) and a phosphine [for example, triphenylphosphine, tributylphosphine, or 2-(di-tert-butyl-phosphino)biphenyl] at room temperature in the presence of a base (e.g., sodium tert-butoxide), if desired.

A compound of the formula (X) can be prepared according to the method described in WO00/17165 or U.S. Pat. No. 6,313,142.

Alternatively, the compound (X) can be prepared according to the following scheme:

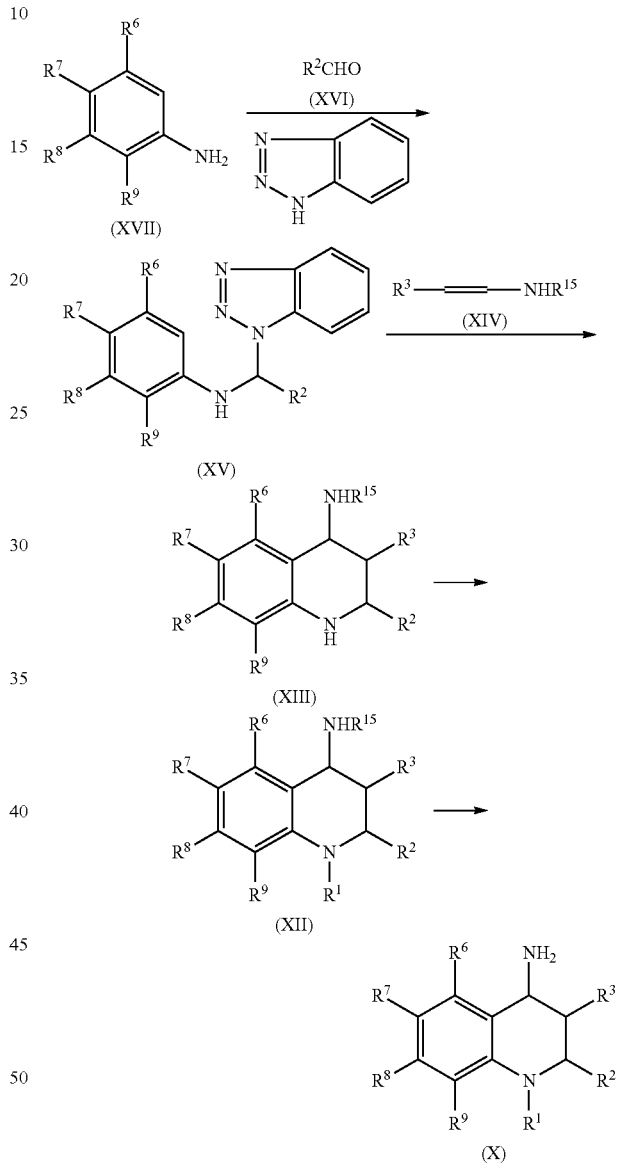

wherein $R^{15}$ is a protecting group for amino group or an asymmetric group and the other symbols have the same meaning as defined as above.

A conventional protecting group including a benzyloxycarbonyl group can be used as the protecting group for amino group. Additionally, an optically-active compound (X) can be prepared by substituting an asymmetric group (e.g., an optically-active α-substituted benzyloxycarbonyl group having a chiral center at the benzyl position, such as α-methylbenzyloxycarbonyl group) for a protecting group for amino group, resolving diastereomers in the process for preparation of compound (XII) or compound (XIII), and removing the asymmetric group.

A compound of the formula (XV) can be prepared by reacting benzotriazole, a compound of the formula (XVI) and a compound of the formula (XVII) in a suitable solvent (e.g., toluene) at room temperature.

A compound of the formula (XIII) can be prepared by reacting a compound of the formula (XIV) with a compound of the formula (XV) in the presence of an acidic catalyst (e.g., an organic acid including p-toluenesulfonic acid, acetic acid, methanesulfonic acid, or Lewis acid including boron trifluoride-diethylether complex, titanium tetrachloride, aluminum chloride) in a suitable solvent (e.g., toluene, tetrahydrofuran, methylene chloride, and the like) under heating or at room temperature (e.g., 0° C. to 150° C., preferably 25° C. to 120° C.).

A compound of the formula (XII) can be prepared by alkanoylation, alkoxycarbonylation, alkylation, and the like of a compound of the formula (XIII) as appropriate.

A compound of the formula (X) can be prepared by removing a protecting group for amino group or an asymmetric group of a compound of the formula (XII). The removal can be carried out in a conventional manner including acid-treatment, base-treatment, reduction, and the like depending on the type of the group. When a benzyloxycarbonyl group or an α-substituted benzyloxycarbonyl group is used, they can be removed by a catalytic reduction in a suitable solvent (e.g., ethanol, methanol, tetrahydrofuran, acetic acid, and the like) under hydrogen. The removal of a protecting group for amino group or an asymmetric group of a compound of the formula (XIII) can be carried out in the same manner as the removal of the groups of a compound of the formula (XII).

When an asymmetric group such as α-substituted benzyloxycarbonyl group is substituted for a protecting group for amino group, resolution of a diastereomer can be carried out in a conventional manner such as recrystallization or column chromatography.

A compound of the formula (XIII) can also be prepared by reacting a compound of the formula (XIV) with a compound of the formula (XVIII).

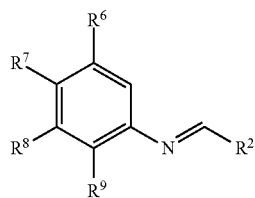

(XVIII)

This reaction can be carried out in the same manner as the reaction of a compound of the formula (XIV) with a compound of the formula (XV).

Additionally, respective substituents $R^1$, $R^5$, $R^6$, $R^7$, $R^8$ and $R^9$ can be converted into a desirable substituent in accordance with any one of processes from the PROCESS 4-(A) to (K) and from (1) to (58).

A compound of the formula (IV) can be prepared by condensing a compound of the formula (X) with a compound of the formula (III)

$$R^{10}-R^4-Z^1$$ (III)

wherein the symbols have the same meaning as defined above.

The condensation can be carried out in the same manner as described in WO00/17165 or the PROCESS 1 above.

A compound of the formula (IX) can be prepared by condensing a compound of the formula (IV) with a compound of the formula:

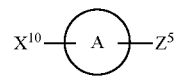

wherein $Z^5$ is a leaving group and the other symbols have the same meaning as defined above.

As the leaving group, a halogen atom including chlorine atom, bromine atom, iodine atom; a substituted sulfonyloxy group including methanesulfonyloxy group, p-toluenesulfonyloxy group, trifluoro-methanesulfonyloxy group can be preferably used.

The condensation can be carried out in the same manner as the one of the said compound (X) with the compound (XI).

Additionally, the compound of the formula (IX) wherein Ring A is a tetrazolyl group and $X^{10}$ is a hydrogen atom can be prepared by reacting a compound of the formula (V) with an alkyl metal azide. The reaction can be carried out in the same manner as (15) described above.

Further, the compound of the formula (IX) wherein $X^{10}$ is a hydroxyl group can be prepared by (i) reacting a compound wherein $X^{10}$ is a halogen atom with diboron or borane to provide a compound wherein $X^{10}$ is a boronic ester, and (ii) reacting the compound wherein $X^{10}$ is a boronic ester with peroxides.

Hydrogen peroxide solution, m-chloroperbenzoic acid or OXONE™ (Manufactured by DuPont) can be preferably used as the peroxides.

Many of starting materials and reagents for preparation of the aforementioned compound of the formula I are either commercially available or disclosed in literatures, or can be readily prepared by a method that is disclosed in literatures or used generally in the organic synthesis.

As used herein, "3,4-dihydro-2H-quinoline" represents the same structure as "1,2,3,4-tetrahydroquinoline".

Experiment

The inhibitory activity of the compounds of the present invention against CETP was tested in this experiment.

Preparation of Acceptor Microemulsion

A solution of 1-Palmitoyl-2-oleoyl-sn-glycero-3-phosphocholine (3.5 mg), cholesteryl oleate (3 mg) and triolein (0.7 mg) in chloroform was mixed and lipid was air-dried under nitrogen gas to remove solvent. 1,4-Dioxane (0.25 ml) was then added and the mixture was stirred for dissolution. The resultant lipid solution (0.2 ml) was slowly injected under the surface of Tris-saline-EDTA(TSE) buffer solution [10 mM Tris/HCl (pH 7.4), 0.15M NaCl, 2 mM EDTA] (10 ml) with Hamilton syringe, while sonicating in ice-bath. After 1-hour-sonication in ice-bath, the solution was stored at 4° C.

Preparation of Donor Microemulsion

A solution of egg PC (phosphatidylcholine) (0.33 mg) and BODIPY-CE (0.62 mg) in chloroform was mixed. After removing solvent by air-drying lipid under nitrogen gas, TSE buffer solution (3 ml) was added and the solution was sonicated in ice-bath. This solution was filtered to sterilize through 0.22 μm filter and stored at 4° C.

Inhibitory Activity Against CETP In Vitro

A test solution was prepared using dimethyl sulfoxide as a solvent. Plasma from a healthy volunteer was diluted to 0.64% with TSE buffer, and to the resultant plasma solution (187 μl) was added a test solution (3 μl) or the solvent alone followed by incubation at 37° C. for 24 hours. After addition of TSE buffer solution (10 µl) containing 5% donor microemulsion and 5% acceptor microemulsion, the mixture was incubated at 37° C. for 3 hours. Before and after the incubation, the fluorescence intensity was measured at Ex.550 nm/Em.600 nm. CETP activity was defined as the difference between the measurements obtained before incubation and after incubation. The decreasing rate of the difference in the sample was defined as the inhibition rate of CETP activity. $IC_{50}$ for each sample was calculated from the inhibition rate of CETP activity.

Results

| Example No. | $IC_{50}$ (nM) |
|---|---|
| 1 | 0.17 |
| 16 | 4.2 |
| 127 | 0.89 |
| 174 | 0.23 |
| 198 | 0.66 |
| 231 | 0.53 |
| 235 | 2.7 |
| 275 | 0.18 |
| 291 | 0.32 |

EXAMPLES

The present invention is illustrated in more detail by Examples and Reference Examples, but the present invention should not be construed to be limited thereto.

In Examples, the compounds having a structure of the formula:

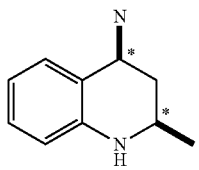

indicate that the configuration thereof is (2R*,4S*). Besides, Me means a methyl group.

Example 1

(1) (2R,4S)-4-Amino-2-ethyl-6-trifluoromethyl-3,4-dihydro-2H-quinoline-1-carboxylic acid ethyl ester (3 g) and 5-bromo-2-chloro-pyrimidine (3.7 g) are dissolved in N,N-dimethylformamide (30 ml), and the mixture is stirred at 150° C. for 5 hours. The reaction solution is cooled to room temperature, and thereto are added a saturated aqueous sodium hydrogen carbonate solution and ethyl acetate. The organic layer is washed with a saturated brine, dried over sodium sulfate, and concentrated under reduced pressure. The resulting residue is purified by column chromatography (silica gel; hexane:ethyl acetate=8:1→4:1) to give (2R,4S)-4-(5-bromopyrimidin-2-yl)amino-2-ethyl-6-trifluoromethyl-3,4-dihydro-2H-quinoline-1-carboxylic acid ethyl ester (2.2 g). MS (m/z): 473/475 [M+H]$^+$ (2) (2R,4S)-4-(5-Bromopyrimidin-2-yl)amino-2-ethyl-6-trifluoromethyl-3,4-dihydro-2H-quinoline-1-carboxylic acid ethyl ester (2.2 g) is dissolved in N,N-dimethylformamide (20 ml), and thereto is added sodium hydride (62.7%, 223 mg) under ice-cooling, and the mixture is stirred at room temperature for 30 minutes. To the mixture is added 3,5-bis(trifluoro-methyl)benzyl bromide (1.3 ml) under ice-cooling, and the mixture is stirred at room temperature for one hour. A saturated brine and ethyl acetate are added to the mixture, and the organic layer is dried over sodium sulfate, and concentrated under reduced pressure. The resulting residue is purified by column chromatography (silica gel; hexane:ethyl acetate=10:1) to give (2R,4S)-4-{[3,5-bis(trifluoromethyl)benzyl]-(5-bromo-pyrimidin-2-yl)}amino-2-ethyl-6-trifluoromethyl-3,4-dihydro-2H-quinoline-1-carboxylic acid ethyl ester (2.75 g). MS (m/z): 699/701 [M+H]$^+$ (3) (2R,4S)-4-{[3,5-Bis(trifluoromethyl)benzyl]-(5-bromopyrimidin-2-yl)}-amino-2-ethyl-6-trifluoromethyl-3,4-dihydro-2H-quinoline-1-carboxylic acid ethyl ester (94 mg), tris(dibenzylideneacetone)dipalladium (2.5 mg), sodium tert-butoxide (19 mg), 2-(di-tert-butylphosphino)biphenyl (3 mg), morpholine (18 µl) are dissolved in toluene (1 ml), and the mixture is stirred at room temperature under nitrogen atmosphere for 60 hours. To the reaction solution is added acetic acid, and thereto are added water and ethyl acetate. The organic layer is dried over magnesium sulfate, and concentrated under reduced pressure. The resulting residue is purified by column chromatography (silica gel; hexane:ethyl acetate=19:1→3:2) to give (2R,4S)-4-{[3,5-bis(trifluoromethyl)benzyl]-[5-(morpholin-4-yl)-pyrimidin-2-yl]}amino-2-ethyl-6-trifluoromethyl-3,4-dihydro-2H-quinoline-1-carboxylic acid ethyl ester (40 mg). MS (m/z): 706 [M+H]$^+$ Examples 2-6

The corresponding starting compounds are treated in a similar manner to Example 1-(3) to give the compounds as listed in Table 1.

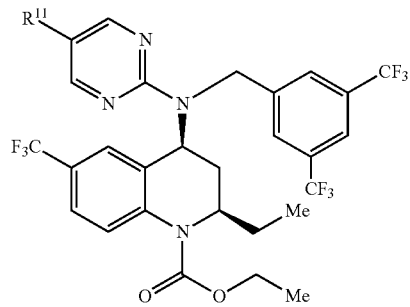

TABLE 1

| Example | $R^{11}$ | Physical properties, etc. |
|---|---|---|
| 2 | S-morpholine (thiomorpholine) | MS (m/z): 722 [M + H]$^+$ |
| 3 | Me—N(piperazine)N— | MS (m/z): 719 [M + H]$^+$ |
| 4 | Me-O-CH$_2$CH$_2$-NH- | MS (m/z): 694 [M + H]$^+$ |

TABLE 1-continued

| Example | R¹¹ | Physical properties, etc. |
|---------|-----|---------------------------|
| 5 | 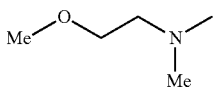 | MS (m/z): 708 [M + H]⁺ |
| 6 | 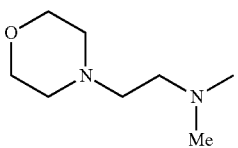 | MS (m/z): 763 [M + H]⁺ |

Example 7

(2R,4S)-4-{[3,5-Bis(trifluoromethyl)benzyl]-[5-(thiomorpholin-4-yl)pyrimidin-2-yl]}amino-2-ethyl-6-trifluoromethyl-3,4-dihydro-2H-quinoline-1-carboxylic acid ethyl ester (75 mg) is dissolved in chloroform (3 ml), and thereto is added m-chloroperbenzoic acid (25 mg), and the mixture is stirred at room temperature overnight. To the reaction solution are added water and chloroform, and the organic layer is washed with a saturated brine, dried over magnesium sulfate, and concentrated under reduced pressure. The resulting residue is purified by column chromatography (silica gel; chloroform:acetone=10:1) to give (2R,4S)-4-{[3,5-bis(trifluoromethyl)benzyl]-[5-(1-oxothiomorpholin-4-yl)pyrimidin-2-yl]}amino-2-ethyl-6-trifluoromethyl-3,4-dihydro-2H-quinoline-1-carboxylic acid ethyl ester (34 mg). MS (m/z): 738 [M+H]⁺

Example 8

(2R,4S)-4-{[3,5-Bis(trifluoromethyl)benzyl]-(5-bromopyrimidin-2-yl)}amino-2-ethyl-6-trifluoro methyl-3,4-dihydro-2H-quinoline-1-carboxylic acid ethyl ester (250 mg) and dichlorobis(tri-o-tolylphosphine)palladium (5.9 mg) are dissolved in toluene (2 ml), and the mixture is heated at 100° C. under nitrogen atmosphere. To the reaction solution is added (dimethyl-amino)trimethyltin (118 mg), and the mixture is stirred for 2 hours. The mixture is allowed to cool to room temperature, and the reaction solution is concentrated under reduced pressure. The resulting residue is purified by column chromatography (NH-silica gel; hexane:ethyl acetate=5:1) to give (2R,4S)-4-{[3,5-bis(trifluoromethyl)benzyl]-(5-dimethylaminopyrimidin-2-yl)}amino-2-ethyl-6-trifluoromethyl-3,4-dihydro-2H-quinoline-1-carboxylic acid ethyl ester (18 mg). MS (m/z): 664 [M+H]⁺

Example 9

(1) (2R,4S)-2-Ethyl-4-amino-6-trifluoromethyl-3,4-dihydro-2H-quinoline-1-carboxylic acid ethyl ester (600 mg) and 2-chloro-5-propylpyrimidine (1.5 g) are dissolved in 1,3-dimethylimidazolidinone (10 ml), and the mixture is stirred at 135° C. for 72 hours. The reaction solution is cooled to room temperature, and thereto are added water and ethyl acetate. The organic layer is washed with a saturated brine, dried over magnesium sulfate, and concentrated under reduced pressure. The resulting residue is purified by column chromatography (silica gel; hexane:ethyl acetate=6:1→4:1) to give (2R,4S)-2-ethyl-4-(5-propylpyrimidin-2-yl)amino-6-trifluoromethyl-3,4-dihydro-2H-quinoline-1-carboxylic acid ethyl ester (250 mg). MS (m/z): 437 [M+H]⁺

(2) (2R,4S)-2-Ethyl-4-(5-propylpyrimidin-2-yl)amino-6-trifluoromethyl-3,4-dihydro-2H-quinoline-1-carboxylic acid ethyl ester (240 mg) and 3,5-bis(trifluoromethyl)benzyl bromide (337 mg) are dissolved in N,N-dimethyl-formamide (3 ml), and thereto is added sodium hydride (62.7%, 32 mg) at room temperature, and the mixture is stirred at the same temperature for 2 hours. To the reaction solution is added acetic acid, and water and ethyl acetate are added thereto. The organic layer is dried over magnesium sulfate, and concentrated under reduced pressure. The resulting residue is purified by column chromatography (silica gel; hexane:ethyl acetate=49:1→7:3) to give (2R,4S)-4-{[3,5-bis(trifluoromethyl)benzyl]-(5-propylpyrimidin-2-yl)}amino-2-ethyl-6-trifluoromethyl-3,4-dihydro-2H-quinoline-1-carboxylic acid ethyl ester (130 mg). MS (m/z): 663 [M+H]⁺

Example 10

To (2R,4S)-4-{[3,5-bis(trifluoromethyl)benzyl]-(5-bromopyrimidin-2-yl)}amino-2-ethyl-6-trifluoromethyl-3,4-dihydro-2H-quinoline-1-carboxylic acid ethyl ester (1 g) are added N,N-dimethylformamide (10 ml), tetrakis-(triphenylphosphine)palladium (a catalytic amount), and zinc cyanide (176 mg), and the mixture is stirred at 110° C. under nitrogen atmosphere for 4 hours. The reaction solution is cooled to room temperature, and thereto are added a saturated aqueous sodium hydrogen carbonate solution and ethyl acetate. The organic layer is washed with a saturated brine, dried over sodium sulfate, and concentrated under reduced pressure. The resulting residue is purified by column chromatography (silica gel; hexane:ethyl acetate=10:1→4:1) to give (2R,4S)-4-{[3,5-bis(trifluoro-methyl)benzyl]-(5-cyanopyrimidin-2-yl)}amino-2-ethyl-6-trifluoromethyl-3,4-dihydro-2H-quinoline-1-carboxylic acid ethyl ester (760 mg). MS (m/z): 646 [M+H]⁺

Example 11

(2R,4S)-4-{[3,5-Bis(trifluoromethyl)benzyl]-(5-cyanopyrimidin-2-yl)}amino-2-ethyl-6-trifluoromethyl-3,4-dihydro-2H-quinoline-1-carboxylic acid ethyl ester (200 mg) is dissolved in ethanol (3 ml), and thereto is added a catalytic amount of Raney nickel, and the mixture is stirred at room temperature overnight under hydrogen atmosphere. The catalyst is removed by filtration, and the filtrate is concentrated under reduced pressure. The residue is purified by column chromatography (silica gel; hexane:ethyl acetate=1:1) to give (2R,4S)-4-{(5-aminomethylpyrimidin-2-yl)-[3,5-bis(trifluoromethyl)benzyl]}amino-2-ethyl-6-trifluoromethyl-3,4-dihydro-2H-quinoline-1-boxylic acid ethyl ester (142 mg). MS (m/z): 650 [M+H]⁺

Example 12

(2R,4S)-4-{[3,5-Bis(trifluoromethyl)benzyl]-(5-aminomethyl-pyrimidin-2-yl)}amino-2-ethyl-6-trifluoromethyl-3,4-dihydro-2H-quinoline-1-carboxylic acid ethyl ester (92 mg) and an excess amount of triethyl-amine are dissolved in methylene chloride (2 ml), and thereto is added an excess amount of N,N-dimethylsulfamoyl chloride under ice-cooling. The mixture is stirred at room temperature for 2 hours, and to the reaction solution are added a saturated brine and ethyl acetate. The organic layer is dried over sodium sulfate, and concentrated under reduced pressure. The resulting residue is purified by column chromatography (silica gel; hexane:ethyl acetate=4:1→67:33) to give (2R,4S)-4-{[3,5-bis(trifluoromethyl)benzyl]-[5-(N,N-dimethylsulfamoyl)aminomethylpyrimidin-2-yl]}-amino-2-ethyl-6-trifluoromethyl-3,4-dihydro-2H-quinoline-1-carboxylic acid ethyl ester (54 mg). MS (m/z): 757 [M+H]$^+$ Example 13

Acetic acid (88 μl) is dissolved in toluene (3 ml), and thereto are added triethylamine (236 μl) and diphenylphosphoryl azide (466 μl). The mixture is stirred at 70° C. for 1.5 hour. To the reaction solution is added (2R,4S)-4-{(5-aminomethylpyrimidin-2-yl)-[3,5-bis(trifluoromethyl)-benzyl]}amino-2-ethyl-6-trifluoromethyl-3,4-dihydro-2H-quinoline-1-carboxylic acid ethyl ester (100 mg), and the mixture is stirred at the same temperature for 4 hours. The mixture is allowed to cool to room temperature, and to the reaction solution are added a saturated aqueous sodium hydrogen carbonate solution and ethyl acetate. The organic layer is washed with a saturated brine, dried over magnesium sulfate, and concentrated under reduced pressure. The resulting residue is purified by column chromatography (NH-silica gel; hexane:ethyl acetate=1:2) to give (2R,4S)-4-([3,5-bis(trifluoromethyl)benzyl]-{5-[(3-methylureido)methyl]-pyrimidin-2-yl})amino-2-ethyl-6-trifluoromethyl-3,4-dihydro-2H-quinoline-1-carboxylic acid ethyl ester (63 mg). MS (m/z): 707 [M+H]$^+$ Example 14

4-(2-Aminoethyl)morpholine (100 mg) is dissolved in tetrahydrofuran (3 ml), and thereto is added N,N'-carbonyldiimidazole (125 mg), and the mixture is stirred at 70° C. for one hour. To the reaction solution is added (2R,4S)-4-{[3,5-bis(trifluoromethyl)benzyl]-(5-aminomethylpyrimidin-2-yl)}amino-2-ethyl-6-trifluoromethyl-3,4-dihydro-2H-quinoline-1-carboxylic acid ethyl ester (100 mg), and the mixture is stirred at the same temperature for 4 hours. The mixture is allowed to cool to room temperature, and thereto are added a saturated aqueous sodium hydrogen carbonate solution and ethyl acetate. The organic layer is washed with a saturated brine, dried over magnesium sulfate, and concentrated under reduced pressure. The resulting residue is purified by column chromatography (NH-silica gel; ethyl acetate) to give (2R,4S)-4-{[3,5-bis(trifluoro-methyl)benzyl]-[5-[3-(2-morpholin-4-ylethyl)ureidomethyl]pyrimidin-2-yl)}amino-2-ethyl-6-trifluoromethyl-3,4-dihydro-2H-quinoline-1-carboxylic acid ethyl ester (118 mg). MS (m/z): 806 [M+H]$^+$ Example 15

(2R,4S)-4-{[3,5-Bis(trifluoromethyl)benzyl]-(5-bromopyrimidin-2-1)}amino-2-ethyl-6-trifluoromethyl-3,4-dihydro-2H-quinoline-1-carboxylic acid ethyl ester (300 mg), palladium acetate (12 mg), 1,1'-bis(diphenyl-phosphino)ferrocene (55 mg), benzyl alcohol (970 mg) and triethylamine (625 μl) are dissolved in N,N-dimethylformamide (1 ml), and the mixture is stirred at room temperature under carbon monoxide atmosphere for 3 minutes. Subsequently, the mixture is heated at 90° C. and stirred overnight. The reaction solution is cooled to at room temperature, and thereto are added a saturated aqueous sodium hydrogen carbonate solution and ethyl acetate. The organic layer is washed with a saturated brine, dried over magnesium sulfate, and concentrated under reduced pressure. The resulting residue is purified by column chromatography (silica gel; hexane:ethyl acetate=24:1→3:1) to give (2R,4S)-4-{(5-benzyl-oxycarbonylpyrimidin-2-yl)-[3,5-bis(trifluoromethyl)benzyl]}amino-2-ethyl-6-trifluoromethyl-3,4-dihydro-2H-quinoline-1-carboxylic acid ethyl ester (250 mg). MS (m/z): 755 [M+H]$^+$ Example 16

(2R,4S)-4-{(5-Benzyloxycarbonylpyrimidin-2-yl)-[3,5-bis(trifluoro-methyl)benzyl]}amino-2-ethyl-6-trifluoromethyl-3,4-dihydro-2H-quinoline-1-carboxylic acid ethyl ester (220 mg) is dissolved in a mixture of methanol (2 ml) and tetrahydrofuran (6 ml), and thereto is added 10% palladium-carbon (100 mg), and the mixture is stirred at room temperature under hydrogen atmosphere for 30 minutes. The catalyst (10% palladium-carbon) is removed by filtration, and the filtrate is concentrated under reduced pressure. The resulting residue is purified by column chromatography (silica gel; ethyl acetate) to give (2R,4S)-4-{[3,5-bis(trifluoromethyl)-benzyl]-(5-carboxypyrimidin-2-yl)}amino-2-ethyl-6-trifluoromethyl-3,4-dihydro-2H-quinoline-1-carboxylic acid ethyl ester (178 mg). MS (m/z): 665 [M+H]$^+$ Example 17

(2R,4S)-4-{[3,5-Bis(trifluoromethyl)benzyl]-(5-carboxypyrimidin-2-yl)}amino-2-ethyl-6-trifluoromethyl-3,4-dihydro-2H-quinoline-1-carboxylic acid ethyl ester (100 mg) and an excess amount of 1-hydroxybenzotriazole hydrate are dissolved in N,N-dimethylformamide (5 ml), and thereto is added an excess amount of 1-ethyl-3-(3-dimethylaminopropyl)carbodiimide hydrochloride, and the mixture is stirred at room temperature for 10 minutes. To the reaction solution are added glycine tert-butyl ester hydrochloride (50 mg) and an excess amount of triethylamine, and the mixture is stirred at room temperature for 10 minutes. To the reaction solution are added an aqueous citric acid solution and ethyl acetate, and the organic layer is washed with a saturated aqueous sodium hydrogen carbonate solution, dried over magnesium sulfate, and concentrated under reduced pressure. The resulting residue is purified by column chromatography (silica gel; hexane:ethyl acetate=9:1→1:1) to give (2R,4S)-4-{[3,5-bis(trifluoromethyl)benzyl]-(5-tert-butoxycarbonylmethylcarbamoyl-pyrimidin-2-yl)}amino-2-ethyl-6-trifluoromethyl-3,4-dihydro-2H-quinoline-1-carboxylic acid ethyl ester. Then, to the mixture is added a 4N hydrochloric acid in 1,4-dioxane (2 ml) at room temperature, and the mixture is stirred overnight. The reaction solution is concentrated under reduced pressure, and the concentrated residue is purified by column chromatography (silica gel; hexane:ethyl acetate=1:1→chloro-form:methanol=19:1) to give (2R,4S)-4-{[3,5-bis(trifluoromethyl)benzyl]-(5-carboxymethylcarbamoylpyrimidin-2-yl)}amino-2-ethyl-6-trifluoromethyl-3,4-dihydro-2H-quinoline-1-carboxylic acid ethyl ester (13 mg). MS (m/z): 722 [M+H]$^+$ Example 18

(1) (2R,4S)-4-{[3,5-Bis(trifluoromethyl)benzyl]-(5-bromopyrimidin-2-yl)}amino-2-ethyl-6-trifluoromethyl-3,4-dihydro-2H-quinoline-1-carboxylic acid ethyl ester (300 mg), acrylic acid benzyl ester (125 mg), tris(di-benzylideneacetone)dipalladium (12 mg), diisopropylethylamine (90 μl), tri-tert-butylphosphonium tetrafluoroborate (7.5 mg) are dissolved in 1,4-dioxane (3.5 ml), and the mixture is stirred under nitrogen atmosphere at room temperature for 3 days. To the reaction solution are added an aqueous citric acid solution and ethyl acetate, and the organic layer is dried over magnesium sulfate, and concentrated under reduced pressure. The resulting residue is purified by column chromatography (silica gel; hexane:ethyl acetate=97:3→13:7) to give (2R,4S)-4-{[5-(2-benzyloxy-carbonylvinyl)pyrimidin-2-yl]-[3,5-bis(trifluoromethyl)benzyl]}amino-2-ethyl-6-trifluoromethyl-3,4-dihydro-2H-quinoline-1-carboxylic acid ethyl ester (186 mg). MS (m/z): 781 [M+H]+

(2) (2R,4S)-4-{[5-(2-Benzyloxycarbonylvinyl)pyrimidin-2-yl]-[3,5-bis-(trifluoromethyl)benzyl]}amino-2-ethyl-6-trifluoromethyl-3,4-dihydro-2H-quinoline-1-carboxylic acid ethyl ester (180 mg) is dissolved in a mixture of methanol (5 ml) and tetrahydrofuran (10 ml), and thereto is added 10% palladium-carbon (300 mg). The mixture is stirred at room temperature under hydrogen atmosphere for 3 hours. The catalyst is removed by filtration, and the filtrate is concentrated under reduced pressure to give (2R,4S)-4-{[3,5-bis(trifluoromethyl)benzyl]-[5-(2-carboxyethyl)pyrimidin-2-yl]}amino-2-ethyl-6-trifluoromethyl-3,4-dihydro-2H-quinoline-1-carboxylic acid ethyl ester (40 mg). MS (m/z): 693 [M+H]+

Example 19

(2R,4S)-4-{[3,5-bis(trifluoromethyl)benzyl]-(5-cyanopyrimidin-2-yl)}amino-2-ethyl-6-trifluoromethyl-3,4-dihydro-2H-quinoline-1-carboxylic acid ethyl ester (880 mg), sodium azide (886 mg) and ammonium chloride (729 mg) are dissolved in N,N-dimethylformamide (5 ml), and the mixture is stirred at 100° C. for 4 hours. The mixture is allowed to cool to room temperature, and thereto are added water and ethyl acetate. The organic layer is washed with a saturated brine, dried over magnesium sulfate, and concentrated under reduced pressure to give (2R,4S)-4-{[3,5-bis(trifluoro-methyl)benzyl]-[5-(tetrazol-5-yl)pyrimidin-2-yl]}amino-2-ethyl-6-trifluoro-methyl-3,4-dihydro-2H-quinoline-1-carboxylic acid ethyl ester (920 mg). MS (m/z): 689 [M+H]+

Example 20

(2R,4S)-4-{[3,5-Bis(trifluoromethyl)benzyl]-[5-(tetrazol-5-yl)pyrimidin-2-yl]}amino-2-ethyl-6-trifluoromethyl-3,4-dihydro-2H-quinoline-1-carboxylic acid ethyl ester (150 mg), potassium carbonate (60 mg), and an excess amount of methyl iodide are dissolved in N,N-dimethylformamide (2 ml), and the mixture is stirred at 50° C. for 4 hours. The mixture is allowed to cool to room temperature, and thereto are added water and ethyl acetate. The organic layer is washed with a saturated brine, dried over magnesium sulfate, and concentrated under reduced pressure. The resulting residue is purified by column chromatography (silica gel; hexane:ethyl acetate=9:1→4:1) to give (2R,4S)-4-{[3,5-bis(trifluoromethyl)benzyl]-[5-(2-methyl-2H-tetrazol-5-yl)pyrimidin-2-yl]}amino-2-ethyl-6-trifluoromethyl-3,4-dihydro-2H-quinoline-1-carboxylic acid ethyl ester (107 mg). MS (m/z): 703 [M+H]+

Examples 21-22

The corresponding starting compounds are treated in a similar manner to Example 20 to give the compounds as listed in Table 2.

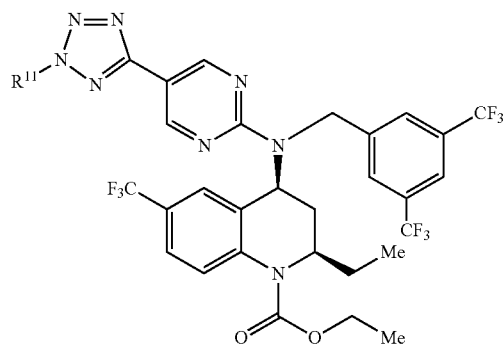

TABLE 2

| Example | R[11] | Physical properties, etc. |
|---|---|---|
| 21 | HO~~~ | MS (m/z): 733 [M + H]+ |
| 22 | HO~~~~ | MS (m/z): 747 [M + H]+ |

Example 23

(2R,4S)-4-{[3,5-Bis(trifluoromethyl)benzyl]-[5-(tetrazol-5-yl)pyrimidin-2-yl]}amino-2-ethyl-6-trifluoromethyl-3,4-dihydro-2H-quinoline-1-carboxylic acid ethyl ester (127 mg), 4-(2-hydroxyethyl)morpholine (35 μl), and triphenylphosphine (76 mg) are dissolved in tetrahydrofuran (3 ml), and thereto is added dropwise 40% solution of azodicarboxylic acid diethyl ester in toluene (113 μl) under ice-cooling, and the mixture is stirred at room temperature for 4 hours. To the reaction solution are added water and ethyl acetate, and the organic layer is washed with a saturated brine, dried over sodium sulfate, and concentrated under reduced pressure. The resulting residue is purified by column chromatography (NH-silica gel; hexane:ethyl acetate=9:1→67:33) to give (2R,4S)-4-([3,5-bis(trifluoromethyl)benzyl]-{5-[2-(2-morpholin-4-ylethyl)-2H-tetrazol-5-yl]pyrimidin-2-yl}) amino-2-ethyl-6-trifluoromethyl-3,4-dihydro-2H-quinoline-1-carboxylic acid ethyl ester (136 mg). MS (m/z): 802 [M+H]+

Example 24

(1) (2R,4S)-4-{[3,5-Bis(trifluoromethyl)benzyl]-(5-bromopyrimidin-2-yl)}amino-2-ethyl-6-trifluoromethyl-3,4-dihydro-2H-quinoline-1-carboxylic acid ethyl ester (1.00 g) is dissolved in 1,4-dioxane (4.0 ml), and thereto are added sodium iodide (857 mg), copper iodide (27 mg) and trans-N,N'-dimethylcyclohexane-1,2-diamine (43 mg), and the mixture is stirred at 110° C. under nitrogen atmosphere overnight. The mixture is allowed to cool to room temperature, and thereto is added a diluted aqueous ammonia, and the mixture is extracted with ethyl acetate. The organic layer is washed with a saturated brine, dried over magnesium sulfate, and concentrated under reduced pressure. The resulting residue is purified by column chromatography (silica gel; hexane:ethyl acetate=97:3→70:30) to give (2R,4S)-4-{[3,5-bis(trifluoromethyl)benzyl]-(5-iodopyrimidin-2-yl)}-amino-2-ethyl-6-trifluoromethyl-3,4-dihydro-2H-quinoline-1-carboxylic acid ethyl ester (969 mg). MS (m/z): 747 [M+H]+

(2) To (2R,4S)-4-{[3,5-bis(trifluoromethyl)benzyl]-(5-iodopyrimidin-2-yl)}amino-2-ethyl-6-trifluoromethyl-3,4-dihydro-2H-quinoline-1-carboxylic acid ethyl ester (200 mg) are added 2-methoxyethanol (1.0 ml), cesium carbonate (350 mg), copper iodide (23 mg) and 1,10-phenanthroline (44 mg), and the mixture is stirred at 110° C. for 4 days. The mixture is allowed to cool to room temperature, and thereto is added water, and the mixture is extracted with ethyl acetate. The organic layer is washed with a saturated brine, dried over magnesium sulfate, and concentrated under reduced pressure. The resulting residue is purified by column chromatography (silica gel; hexane:ethyl acetate=10:1, and NH-silica gel; hexane:ethyl acetate=10:1) to give (2R,4S)-4-{[3,5-bis(trifluoromethyl)-benzyl]-[5-(2-methoxyethoxy)pyrimidin-2-yl]}amino-2-ethyl-6-trifluoro-methyl-3,4-dihydro-2H-quinoline-1-carboxylic acid ethyl ester (90 mg, MS (m/z): 695 [M+H]$^+$) and (2R,4S)-4-{[3,5-bis(trifluoromethyl)benzyl]-[5-(2-methoxyethoxy)primidin-2-yl]}amino-2-ethyl-6-trifluoromethyl-3,4-dihydro-2H-quinoline-1-carboxylic acid 2-methoxyethyl ester (28 mg, MS (m/z): 725 [M+H]$^+$).

Example 25

(1) (2R,4S)-4-Amino-2-ethyl-6-trifluoromethyl-3,4-dihydro-2H-quinoline-1-carboxylic acid ethyl ester (1 g), 6-chloronicotinonitrile (1.76 g), diisopropylethylamine (804 µl) are dissolved in N,N-dimethylformamide (15 ml), and the mixture is stirred at 100° C. overnight. The reaction solution is cooled to room temperature, and thereto are added an aqueous citric acid solution and ethyl acetate. The organic layer is washed with a saturated brine, dried over magnesium sulfate, and concentrated under reduced pressure. The resulting residue is purified by column chromatography (silica gel; chloroform:hexane:ethyl acetate=5:5:1) to give (2R,4S)-4-(5-cyanopyridin-2-yl)amino-2-ethyl-6-trifluoromethyl-3,4-dihydro-2H-quinoline-1-carboxylic acid ethyl ester (800 mg). MS (m/z): 419 [M+H]$^+$ (2) (2R,4S)-4-(5-Cyanopyridin-2-yl)amino-2-ethyl-6-trifluoromethyl-3,4-dihydro-2H-quinoline-1-carboxylic acid ethyl ester (790 mg) and 3,5-bis-(trifluoromethyl)benzyl bromide (1.159 g) are dissolved in N,N-dimethyl-formamide (9 ml), and thereto is added sodium hydride (62.7%, 108 mg) at room temperature, and the mixture is further stirred for 15 minutes. To the reaction solution is added acetic acid, and thereto are added a saturated brine and ether. The organic layer is washed with a saturated brine, dried over magnesium sulfate, and concentrated under reduced pressure. The resulting residue is purified by column chromatography (silica gel; hexane:ethyl acetate=19:1→17:8) to give (2R,4S)-4-{[3,5-bis-(trifluoromethyl)benzyl]-(5-cyanopyridin-2-yl)}amino-2-ethyl-6-trifluoromethyl-3,4-dihydro-2H-quinoline-1-carboxylic acid ethyl ester (700 mg). MS (m/z): 645 [M+H]$^+$ Example 26

(2R,4S)-4-{[3,5-Bis(trifluoromethyl)benzyl]-(5-cyanopyridin-2-yl)}-amino-2-ethyl-6-trifluoromethyl-3,4-dihydro-2H-quinoline-1-carboxylic acid ethyl ester (127 mg), sodium azide (300 mg) and ammonium chloride (300 mg) are dissolved in N,N-dimethylformamide (5 ml), and the mixture is stirred at 95° C. overnight. The mixture is allowed to cool to room temperature, and thereto are added water and ethyl acetate. The organic layer is washed with a saturated brine, dried over magnesium sulfate, and concentrated under reduced pressure to give (2R,4S)-4-{[3,5-bis(trifluoro-methyl)benzyl]-[5-(tetrazol-5-yl)pyridin-2-yl]}amino-2-ethyl-6-trifluoro-methyl-3,4-dihydro-2H-quinoline-1-carboxylic acid ethyl ester (128 mg). MS (m/z): 688 [M+H]$^+$ Example 27

(1) (2R,4S)-4-Amino-2-ethyl-6-trifluoromethyl-3,4-dihydro-2H-quinoline-1-carboxylic acid ethyl ester (1.5 g) and 2-chloro-5-nitropyridine (3.795 g) are dissolved in 1,3-dimethylimidazolidinone (25 ml), and the mixture is stirred at 140° C. for 74 hours. The reaction solution is cooled to room temperature, and thereto are added water and ethyl acetate. The organic layer is washed with a saturated brine, dried over magnesium sulfate, and concentrated under reduced pressure. The resulting residue is purified by column chromatography (silica gel; chloroform→hexane:ethyl acetate=3:1) to give (2R,4S)-2-ethyl-4-(5-nitropyridin-2-yl)amino-6-trifluoromethyl-3,4-dihydro-2H-quinoline-1-carboxylic acid ethyl ester (991 mg). MS (m/z): 439 [M+H]$^+$ (2) (2R,4S)-2-Ethyl-4-(5-nitropyridin-2-yl)amino-6-trifluoromethyl-3,4-dihydro-2H-quinoline-1-carboxylic acid ethyl ester (980 mg) and 3,5-bis(trifluoromethyl)benzyl bromide (1.372 g) are dissolved in N,N-dimethyl-formamide (10 ml), and thereto is added sodium hydride (62.7%, 171 mg) at room temperature, and the mixture is stirred for 15 minutes. To the reaction solution is added acetic acid, and thereto are added water and ethyl acetate. The organic layer is washed again with water, and the organic layer is dried over magnesium sulfate, and concentrated under reduced pressure. The resulting residue is purified by column chromatography (silica gel; hexane:ethyl acetate=49:1→13:7) to give (2R,4S)-4-{[3,5-bis(trifluoromethyl)benzyl]-(5-nitropyridin-2-yl)}amino-2-ethyl-6-trifluoromethyl-3,4-dihydro-2H-quinoline-1-carboxylic acid ethyl ester (650 mg). MS (m/z): 665 [M+H]$^+$ Example 28

(1) (2R,4S)-4-[3,5-Bis(trifluoromethyl)benzyl]amino-2-ethyl-6-trifluoro-methyl-3,4-dihydro-2H-quinoline-1-carboxylic acid ethyl ester (600 mg) is dissolved in ethanol (5.0 ml), and thereto are added cyanogen bromide (129 mg) and sodium hydrogen carbonate (283 mg), and the mixture is stirred at room temperature for 23 hours and 15 minutes. Distilled water is added to the mixture, and the mixture is extracted with ether. The organic layer is dried over magnesium sulfate, and concentrated under reduced pressure. The resulting residue is purified by column chromatography (silica gel; hexane:ethyl acetate=4:1→3:2) to give (2R,4S)-4-{[3,5-bis(trifluoromethyl)benzyl]-cyano}amino-2-ethyl-6-trifluoromethyl-3,4-dihydro-2H-quinoline-1-carboxylic acid ethyl ester (581 mg). MS (m/z): 585 [M+H$_2$O]$^+$ (2) (2R,4S)-4-{[3,5-Bis(trifluoromethyl)benzyl]-cyano}amino-2-ethyl-6-trifluoromethyl-3,4-dihydro-2H-quinoline-1-carboxylic acid ethyl ester (50 mg) is dissolved in N,N-dimethylformamide (1 ml), and thereto are added sodium azide (57.2 mg) and ammonium chloride (47.1 mg), and the mixture is stirred at 100° C. for 16.5 hours. The mixture is allowed to cool to room temperature, and thereto is added distilled water, and the mixture is extracted with ethyl acetate. The organic layer is dried over magnesium sulfate, and concentrated under reduced pressure. The resulting residue is purified by column chromatography (silica gel; chloroform:methanol=9:1) to give (2R,4S)-4-{[3,5-bis(trifluoromethyl)benzyl]-(tetrazol-5- yl)amino}-2-ethyl-6-trifluoromethyl-3,4-dihydro-2H-quinoline-1-carboxylic acid ethyl ester (45 mg). MS (m/z): 611 [M+H]⁺

(3) (2R,4S)-4-{[3,5-Bis(trifluoromethyl)benzyl]-(tetrazol-5-yl)}amino-2-ethyl-6-trifluoromethyl-3,4-dihydro-2H-quinoline-1-carboxylic acid ethyl ester (150 mg) is dissolved in tetrahydrofuran (2.5 ml), and thereto is added sodium hydride (62.7%, 9.6 mg), and the mixture is stirred for 10 minutes. To the mixture is added propane 1-bromide (23 µl), and the mixture is stirred for 27 hours. Distilled water is added to the mixture, and the mixture is extracted with ethyl acetate. The extract is washed with a saturated brine, and the organic layer is dried over magnesium sulfate, and concentrated under reduced pressure. The resulting residue is purified by column chromatography (silica gel; hexane:ethyl acetate=10:1→4:1) to give (2R,4S)-4-{[3,5-bis(trifluoromethyl)benzyl]-(2-propyl-2H-tetrazol-5-yl)}amino-2-ethyl-6-trifluoromethyl-3,4-dihydro-2H-quinoline-1-carboxylic acid ethyl ester (26 mg). MS (m/z): 653 [M+H]⁺

Examples 29-30

The corresponding starting compounds are treated in a similar manner to Example 28-(3) to give the compounds as listed in Table 3.

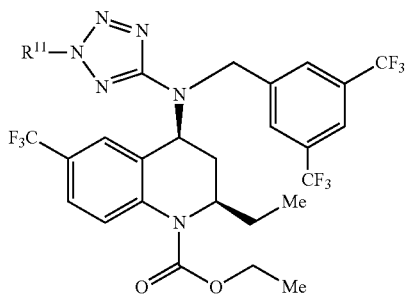

TABLE 3

| Example | R¹¹ | Physical properties, etc. |
|---|---|---|
| 29 | HO~~~ | MS (m/z): 655 [M + H]⁺ |
| 30 | HO~~~~ | MS (m/z): 669 [M + H]⁺ |

Example 31

(2R,4S)-4-{[3,5-Bis(trifluoromethyl)benzyl]-(tetrazol-5-yl)}amino-2-ethyl-6-trifluoromethyl-3,4-dihydro-2H-quinoline-1-carboxylic acid ethyl ester (100 mg) is dissolved in N,N-dimethylformamide (1 ml), and thereto are added 3-bromopropionic acid methyl ester (103.6 µl), triethylamine (2 ml) and a catalytic amount of potassium iodide, and the mixture stirred at 70° C. for 48 hours. Distilled water is added to the mixture, and the mixture is extracted with ether. The extract is dried over magnesium sulfate, and concentrated under reduced pressure. The resulting residue is purified by column chromatography (silica gel; hexane:ethyl acetate=9:1→4:1) to give (2R,4S)-4-{[3,5-bis(trifluoromethyl)benzyl]-[2-(2-methoxy-carbonylethyl)-2H-tetrazol-5-yl]}amino-2-ethyl-6-trifluoromethyl-3,4-dihydro-2H-quinoline-1-carboxylic acid ethyl ester (581 mg). MS (m/z): 697 [M+H]⁺

Examples 32-34

The corresponding starting compounds are treated in a similar manner to Example 31 to give the compounds as listed in Table 4.

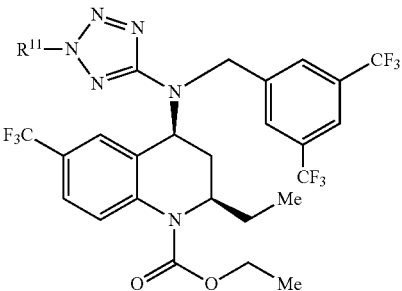

TABLE 4

| Example | R¹¹ | Physical properties, etc. |
|---|---|---|
| 32 | (Me)(Me)C(OH)Et | MS (m/z): 683 [M + H]⁺ |
| 33 | Me-CH₂-O-C(O)-C(Me)(Me)- | MS (m/z): 725 [M + H]⁺ |
| 34 | Me-CH₂-O-C(O)-CH₂-CH₂- | MS (m/z): 697 [M + H]⁺ |

Example 35

(2R,4S)-4-{[3,5-Bis(trifluoromethyl)benzyl]-(tetrazol-5-yl)}amino-2-ethyl-6-trifluoromethyl-3,4-dihydro-2H-quinoline-1-carboxylic acid ethyl ester (200 mg) is dissolved in tetrahydrofuran (5 ml), and thereto are added 2-dimethylaminoethanol (50 µl), a 40% solution of diethyl azo-dicarboxylate in toluene (220 µl) and triphenylphosphine (131.1 mg), and the mixture is stirred at room temperature for 1.5 hours. Distilled water is added thereto, and the mixture is extracted with ethyl acetate. The extract is dried over magnesium sulfate, and concentrated under reduced pressure. The resulting residue is purified by column chromatography (silica gel; hexane:ethyl acetate=9:1→4:1) to give (2R,4S)-4-{[3,5-bis(trifluoro-methyl)benzyl]-[2-(2-dimethylamino-ethyl)-2H-tetrazol-5-yl]}amino-2-ethyl-6-trifluoromethyl-3,4-dihydro-2H-quinoline-1-carboxylic acid ethyl ester (155 mg). MS (m/z): 682 [M+H]⁺

Examples 36-45

The corresponding starting compounds are treated in a similar manner to Example 35 to give the compounds as listed in Table 5.

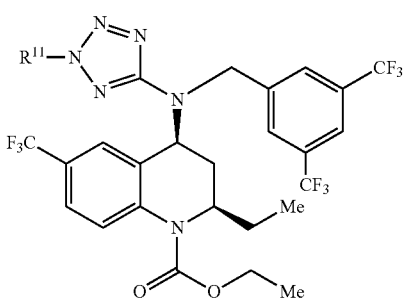

TABLE 5

| Example | R^11 | Physical properties, etc. |
|---|---|---|
| 36 | (propyl-morpholine) | MS (m/z): 724 [M + H]+ |
| 37 | (propyl-pyrrolidine) | MS (m/z): 708 [M + H]+ |
| 38 | (propyl-azepane) | MS (m/z): 736 [M + H]+ |
| 39 | Me-O-propyl | MS (m/z): 683 [M + H]+ |
| 40 | (4-methyl-tetrahydropyran) | MS (m/z): 695 [M + H]+ |
| 41 | Me-O-C(O)-C(Me)(Me)-CH2 | MS (m/z): 725 [M + H]+ |
| 42 | Me-S-propyl | MS (m/z): 685 [M + H]+ |
| 43 | (2,2-dimethyl-1,3-dioxolan-4-yl)ethyl | MS (m/z): 725 [M + H]+ |
| 44 | (epoxide)-ethyl | MS (m/z): 667 [M + H]+ |
| 45 | Me-S-butyl | MS (m/z): 699 [M + H]+ |

Example 46

(2R,4S)-4-{[3,5-Bis(trifluoromethyl)benzyl]-[2-(2-methoxycarbonyl-2-methylpropyl)-2H-tetrazol-5-yl]}amino-2-ethyl-6-trifluoromethyl-3,4-dihydro-2H-quinoline-1-carboxylic acid ethyl ester (300 mg) is dissolved in a mixture of ethanol (3 ml) and distilled water (0.5 ml), and thereto is added lithium hydroxide monohydrate (34.7 mg) under ice-cooling. The mixture is stirred at room temperature for 4 days, and thereto is added a saturated aqueous citric acid solution, and the mixture is extracted with methylene chloride. The organic layer is washed with a saturated brine, dried over magnesium sulfate, and concentrated under reduced pressure. The resulting residue is purified by column chromatography (silica gel; hexane:ethyl acetate=2:1→1:2) to give (2R,4S)-4-{[3,5-bis(trifluoromethyl)-benzyl]-[2-(2-carboxy-2-methylpropyl)-2H-tetrazol-5-yl]}amino-2-ethyl-6-trifluoromethyl-3,4-dihydro-2H-quinoline-1-carboxylic acid ethyl ester (262 mg). MS (m/z): 709 [M−H]−

Examples 47-49

The corresponding starting compounds are treated in a similar manner to Example 46 to give the compounds as listed in Table 6.

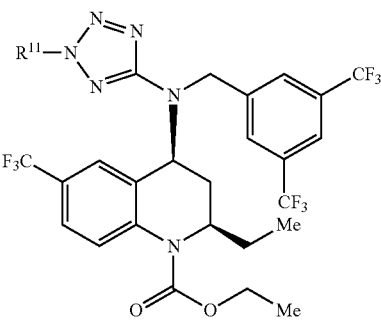

TABLE 6

| Example | R^11 | Physical properties, etc. |
|---|---|---|
| 47 | HO-C(O)-CH2CH2CH2- | MS (m/z): 683 [M + H]+ |
| 48 | HO-C(O)-CH2CH2- | MS (m/z): 669 [M + H]+ |
| 49 | HO-C(O)-C(Me)(Me)-CH2- | MS (m/z): 697 [M + H]+ |

Example 50

(2R,4S)-4-{[3,5-Bis(trifluoromethyl)benzyl]-[2-(3-methylthiopropyl)-2H-tetrazol-5-yl]}amino-2-ethyl-6-trifluoromethyl-3,4-dihydro-2H-quinoline-1-carboxylic acid ethyl ester (175 mg) is dissolved in chloroform (2 ml), and thereto is added m-chloroperbenzoic acid (422.8 mg), and the mixture is stirred at room temperature for 30 minutes. To the mixture is added a saturated aqueous sodium hydrogen carbonate solution, and the mixture is extracted with ethyl acetate. The organic layer is washed with a saturated brine, dried over magnesium sulfate, and concentrated under reduced pressure. The resulting residue is purified by column chromatography (silica gel; hexane:ethyl acetate=7:3→1:1) to give (2R,4S)-4-{[3,5-bis(trifluoromethyl)benzyl]-[2-(3-methanesulfonylpropyl)-2H-tetrazol-5-yl]}amino-2-ethyl-6-trifluoromethyl-3,4-dihydro-2H-quinoline-1-carboxylic acid ethyl ester (180 mg). MS (m/z): 731 [M+H]+

Example 51

(2R,4S)-4-{[3,5-Bis(trifluoromethyl)benzyl]-[2-(2-methylthioethyl)-2H-tetrazol-5-yl]}amino-2-ethyl-6-trifluoromethyl-3,4-dihydro-2H-quinoline-1-carboxylic acid ethyl ester (200 mg) is dissolved in chloroform (2 ml), and thereto is added m-chloroperbenzoic acid (100.1 mg), and the mixture is stirred at room temperature for 2.5 hours. To the mixture is added a saturated aqueous sodium hydrogen carbonate solution, and the mixture is extracted with methylene chloride. The organic layer is washed with a saturated brine, dried over magnesium sulfate, and concentrated under reduced pressure. The resulting residue is purified by column chromatography (silica gel; chloroform:methanol=49:1→19:1) to give (2R,4S)-4-{[3,5-bis(trifluoromethyl)benzyl]-[2-(2-methanesulfinylethyl)-2H-tetrazol-5-yl]}amino-2-ethyl-6-trifluoromethyl-3,4-dihydro-2H-quinoline-1-carboxylic acid ethyl ester (91.9 mg, MS (m/z): 701 [M+H]$^+$) and (2R,4S)-4-{[3,5-bis(trifluoromethyl)benzyl]-[2-(2-methanesulfonylethyl)-2H-tetrazol-5-yl]}amino-2-ethyl-6-trifluoromethyl-3,4-dihydro-2H-quinoline-1-carboxylic acid ethyl ester (118.6 mg, MS (m/z): 717 [M+H]$^+$).

Example 52

(2R,4S)-4-{[3,5-Bis(trifluoromethyl)benzyl]-[2-(2,2-dimethyl-[1,3]dioxolan-4-ylmethyl)-2H-tetrazol-5-yl]}amino-2-ethyl-6-trifluoromethyl-3,4-dihydro-2H-quinoline-1-carboxylic acid ethyl ester (260 mg) is dissolved in ethanol (2 ml), and thereto is added Dowex [H$^+$-type] (manufactured by The Dow Chemical Company) (4 g), and the mixture is stirred at room temperature for 39.5 hours. The mixture is filtered by using methanol, and the filtrate is concentrated under reduced pressure. The resulting residue is purified by column chromatography (silica gel; hexane:ethyl acetate=9:1→4:1) to give (2R,4S)-4-{[3,5-bis(trifluoromethyl)benzyl]-[2-(2,3-dihydroxypropyl)-2H-tetrazol-5-yl]}amino-2-ethyl-6-trifluoromethyl-3,4-dihydro-2H-quinoline-1-carboxylic acid ethyl ester (200 mg). MS (m/z): 685 [M+H]$^+$

Example 53

(2R,4S)-4-{[3,5-Bis(trifluoromethyl)benzyl]-(2-oxolanylmethyl-2H-tetrazol-5-yl)}amino-2-ethyl-6-trifluoromethyl-3,4-dihydro-2H-quinoline-1-carboxylic acid ethyl ester (100 mg) is dissolved in a solution which is previously prepared by adding sodium hydride (62.7%, 0.6 mg) into ethanol (2 ml), and stirred at room temperature for 5 minutes, and the mixture is stirred for 18 hours and 40 minutes. Distilled water is added thereto, and the mixture is extracted with ether. The organic layer is dried over magnesium sulfate, and concentrated under reduced pressure. The resulting residue is purified by column chromatography (silica gel; hexane:ethyl acetate=9:1→3:1) to give (2R,4S)-4-{[3,5-bis(trifluoromethyl)-benzyl]-[2-(3-ethoxy-2-hydroxypropyl)-2H-tetrazol-5-yl]}amino-2-ethyl-6-trifluoromethyl-3,4-dihydro-2H-quinoline-1-carboxylic acid ethyl ester (92.7 mg). MS (m/z): 713 [M+H]$^+$

Example 54

(2R,4S)-4-{[3,5-Bis(trifluoromethyl)benzyl]-(2-oxolanylmethyl-2H-tetrazol-5-yl)}amino-2-ethyl-6-trifluoromethyl-3,4-dihydro-2H-quinoline-1-carboxylic acid ethyl ester (120 mg) is dissolved in ethanol (1 ml), and thereto is added a 28% aqueous ammonia (1 ml). The mixture is stirred at room temperature for 18.5 hours. The reaction solution is concentrated under reduced pressure, and the resulting residue is purified by column chromatography (silica gel; chloroform:methanol=49:1→19:1) to give (2R,4S)-4-{[2-(3-amino-2-hydroxypropyl)-2H-tetrazol-5-yl]-[3,5-bis(trifluoro-methyl)benzyl]}amino-2-ethyl-6-trifluoromethyl-3,4-dihydro-2H-quinoline-1-carboxylic acid ethyl ester (51.2 mg). MS (m/z): 684 [M+H]$^+$

Examples 55-58

The corresponding starting compounds are treated in a similar manner to Example 54 to give the compounds as listed in Table 7.

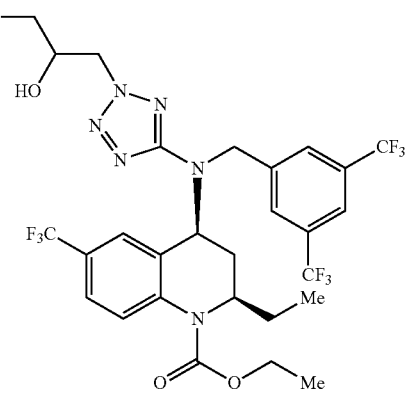

TABLE 7

| Example | R | Physical properties, etc. |
|---|---|---|
| 55 | Me—NH— | MS (m/z): 698 [M + H]$^+$ |
| 56 | Me$_2$N— | MS (m/z): 712 [M + H]$^+$ |
| 57 | morpholino— | MS (m/z): 754 [M + H]$^+$ |
| 58 | Me—N(piperazinyl)N— | MS (m/z): 767 [M + H]$^+$ |

Example 59

(1) (2R,4S)-4-{[3,5-Bis(trifluoromethyl)benzyl]cyano}amino-2-ethyl-6-trifluoromethyl-3,4-dihydro-2H-quinoline-1-carboxylic acid ethyl ester (15 g) is dissolved in ethanol (150 ml), and thereto are added hydroxylamine hydrochloride (2.1 g) and triethylamine (4.2 ml), and the mixture is stirred at room temperature for 18 hours. Distilled water is added to the mixture, and the mixture is extracted with ether. The organic layer is washed with a saturated brine, dried over magnesium sulfate, and concentrated under reduced pressure. The resulting residue is purified by column chromatography (silica gel; hexane:ethyl acetate=19:1→7:3) to give (2R,4S)-4-{[amino(hydroxyimino)methyl]-[3,5-bis(trifluoromethyl)benzyl]}amino-2-ethyl-6-trifluoromethyl-3,4-dihydro-2H-quinoline-1-carboxylic acid ethyl ester (5.02 g). MS (m/z): 601 [M+H]$^+$ (2) (2R,4S)-4-{[Amino(hydroxyimino)methyl]-[3,5-bis(trifluoromethyl)-benzyl]}amino-2-ethyl-6-trifluoromethyl-3,4-dihydro-2H-quinoline-1-carboxylic acid ethyl ester (60 mg) is dissolved in methylene chloride (1 ml) and thereto are added diisopropylethylamine (35 µl) and hexanoic acid chloride (18 µl), and the mixture is stirred for 16 hours. Distilled water is added to the mixture, and the mixture is extracted with ether. The organic layer is washed with a saturated brine, dried over magnesium sulfate, and concentrated under reduced pressure. The resulting residue is purified by column chromatography (silica gel; hexane:ethyl acetate=19:1→9:1) to give (2R,4S)-4-[(amino){[(1-oxohexyl)oxy]imino}methyl]-[3,5-bis(trifluoro-methyl)benzyl]]amino-2-ethyl-6-trifluoromethyl-3,4-dihydro-2H-quinoline-1-carboxylic acid ethyl ester (60.6 mg). MS (m/z): 699 [M+H]$^+$ (3) (2R,4S)-4-[(Amino){[(1-oxohexyl)oxy]imino}methyl])-[3,5-bis(trifluoro-methyl)benzyl]]amino-2-ethyl-6-trifluoromethyl-3,4-dihydro-2H-quinoline-1-carboxylic acid ethyl ester (37 mg) is dissolved in ethanol (1 ml), and thereto is added sodium methoxide (0.3 mg), and the mixture is stirred for one hour. Distilled water is added to the mixture, and the mixture is extracted with ether. The organic layer is washed with a saturated brine, dried over magnesium sulfate, and concentrated under reduced pressure. The resulting residue is purified by column chromatography (silica gel; hexane:ethyl acetate=9:1) to give (2R,4S)-4-{[3,5-bis(trifluoromethyl)-benzyl]-(5-pentyl-[1,2,4]oxadiazole-3-yl)}amino-2-ethyl-6-trifluoromethyl-3,4-dihydro-2H-quinoline-1-carboxylic acid ethyl ester (60.6 mg). MS (m/z): 681 [M+H]$^+$ Example 60

(2R,4S)-4-{[Amino(hydroxyimino)methyl]-[3,5-bis(trifluoromethyl)-benzyl]}amino-2-ethyl-6-trifluoromethyl-3,4-dihydro-2H-quinoline-1-carboxylic acid ethyl ester (154 mg) is dissolved in methylene chloride (1.5 ml), and thereto are added diisopropylethylamine (89 µl) and methoxy-acetic acid chloride (30 µl), and the mixture is stirred for 18 hours. Distilled water is added to the mixture, and the mixture is extracted with ether. The organic layer is washed with a saturated brine, dried over magnesium sulfate, and concentrated under reduced pressure. The resulting residue is purified by column chromatography (silica gel; hexane:ethyl acetate=2:1) to give (2R,4S)-4-{[3,5-bis(trifluoromethyl)-benzyl]-(5-methoxymethyl-[1,2,4]oxadiazol-3-yl)}amino-2-ethyl-6-trifluoro-methyl-3,4-dihydro-2H-quinoline-1-carboxylic acid ethyl ester (118.3 mg). MS (m/z): 655 [M+H]$^+$ Examples 61-63

The corresponding starting compounds are treated in a similar manner to Example 60 to give the compounds as listed in Table 8.

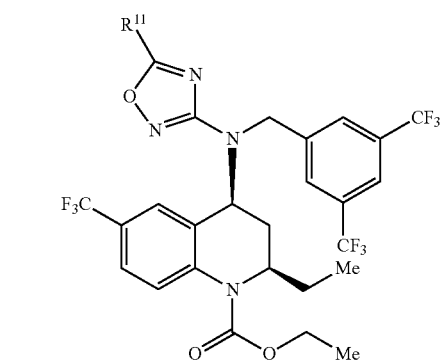

TABLE 8

| Example | R$^{11}$ | Physical properties, etc. |
| --- | --- | --- |
| 61 | Me-C(=O)-O-CH2CH3 (Me, O, O attached) | MS (m/z): 683 [M + H]$^+$ |
| 62 | phenyl-CH2-O-CH2CH3 | MS (m/z): 731 [M + H]$^+$ |
| 63 | Br-CH2CH2- | MS (m/z): 703/705 [M + H]$^+$ |

Example 64

(2R,4S)-4-{(5-Acetoxymethyl-[1,2,4]oxadiazol-3-yl)-[3,5-bis(trifluoro-methyl)benzyl]}amino-2-ethyl-6-trifluoromethyl-3,4-dihydro-2H-quinoline-1-carboxylic acid ethyl ester (30 mg) is dissolved in ethanol (1 ml), and thereto is added potassium carbonate (60.8 mg), and the mixture is stirred for 30 minutes. Distilled water is added, and the mixture is extracted with ether. The organic layer is washed with a saturated brine, dried over magnesium sulfate, and concentrated under reduced pressure. The resulting residue is purified by column chromatography (silica gel; hexane:ethyl acetate=4:1→7:3) to give (2R,4S)-4-{[3,5-bis(trifluoromethyl)-benzyl]-(5-hydroxymethyl-[1,2,4]oxadiazol-3-yl)}amino-2-ethyl-6-trifluoro-methyl-3,4-dihydro-2H-quinoline-1-carboxylic acid ethyl ester (22 mg). MS (m/z): 641 [M+H]$^+$ Example 65

(2R,4S)-4-{[3,5-Bis(trifluoromethyl)benzyl]-(5-bromomethyl-[1,2,4]-oxadiazol-3-yl)}amino-2-ethyl-6-trifluoromethyl-3,4-dihydro-2H-quinoline-1-carboxylic acid ethyl ester (100 mg) is dissolved in a mixture of methanol (0.5 ml) and tetrahydrofuran (0.5 ml), and thereto is added morpholine (0.1 ml). The mixture is stirred at 45° C. for 2 hours. The mixture is allowed to cool to room temperature, and thereto is added 1N hydrochloric acid, and the mixture is extracted with ether. The organic layer is washed with a saturated brine, dried over magnesium sulfate, and concentrated under reduced pressure. The resulting residue is purified by column chromatography (silica gel; hexane:ethyl acetate=4:1→7:3) to give (2R,4S)-4-{[3,5-bis(trifluoromethyl)benzyl]-[5-(morpholin-4-yl)methyl-[1,2,4]oxadiazol-3-yl]}amino-2- ethyl-6-trifluoromethyl-3,4-dihydro-2H-quinoline-1-carboxylic acid ethyl ester (69 mg). MS (m/z): 710 [M+H]⁺

Examples 66-67

The corresponding starting compounds are treated in a similar manner to Example 65 to give the compounds as listed in Table 9.

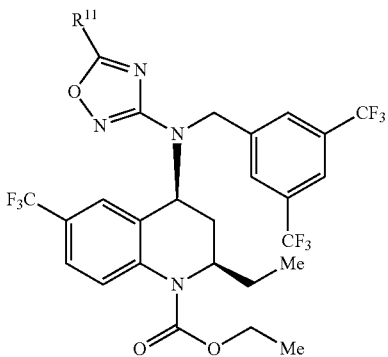

TABLE 9

| Example | R¹¹ | Physical properties, etc. |
|---|---|---|
| 66 | Me-N(Et)-CH₂-N(Me)- | MS (m/z): 668 [M + H]⁺ |
| 67 | Me₃C-O-C(O)-CH(S)-(pyrrolidin-1-yl-Et) | MS (m/z): 794 [M + H]⁺ |

Example 68

(2R,4S)-4-([3,5-Bis(trifluoromethyl)benzyl]-{[5-(2S)-2-tert-butoxy-carbonylpyrrolidin-1-yl)methyl]-[1,2,4]oxadiazol-3-yl})amino-2-ethyl-6-trifluoromethyl-3,4-dihydro-2H-quinoline-1-carboxylic acid ethyl ester (55 mg) is dissolved in a 4 N hydrochloride 1,4-dioxane solution (0.5 ml), and the mixture is stirred at room temperature overnight. The reaction solution is concentrated under reduced pressure, and the resulting residue is purified by column chromatography (silica gel; hexane:ethyl acetate=4:1→chloroform) to give (2R,4S)-4-([3,5-bis(trifluoromethyl)benzyl]-{[5-(2S)-2-carboxypyrrolidin-1-yl)methyl]-[1,2,4]oxadiazol-3-yl})amino-2-ethyl-6-trifluoromethyl-3,4-dihydro-2H-quinoline-1-carboxylic acid ethyl ester (27.5 mg). MS (m/z): 738 [M+H]⁺

Example 69

(1) (2R,4S)-4-Amino-2-ethyl-6-trifluoromethyl-3,4-dihydro-2H-quinoline-1-carboxylic acid ethyl ester (1 g), 4,6-dichloropyrimidine (1.9 g), and diisopropylamine (824 mg) are dissolved in N,N-dimethylformamide (15 ml), and the mixture is stirred at 80° C. for 3 hours. The reaction solution is cooled to room temperature, and thereto are added water and ethyl acetate. The organic layer is washed with a saturated brine, dried over magnesium sulfate, and concentrated under reduced pressure. The resulting residue is purified by column chromatography (silica gel; hexane:ethyl acetate=19:1→7:3) to give (2R,4S)-4-(6-chloropyrimidin-4-yl)amino-2-ethyl-6-trifluoromethyl-3,4-dihydro-2H-quinoline-1-carboxylic acid ethyl ester (1.088 g). MS (m/z): 429/431 [M+H]⁺

(2) (2R,4S)-4-(6-Chloropyrimidin-4-yl)amino-2-ethyl-6-trifluoromethyl-3,4-dihydro-2H-quinoline-1-carboxylic acid ethyl ester (100 mg), 3,5-bis-(trifluoromethyl)benzyl bromide (143 mg), and sodium hydride (62.7%, 18 mg) are dissolved in N,N-dimethylformamide (2 ml), and the mixture is stirred at 55° C. for 15 minutes. The reaction solution is cooled to room temperature, and thereto are added an aqueous citric acid solution and ethyl acetate. The organic layer is washed with a saturated brine, dried over magnesium sulfate, and concentrated under reduced pressure. The resulting residue is purified by column chromatography (silica gel; hexane:ethyl acetate=49:1→3:1) to give (2R,4S)-4-{[3,5-bis(trifluoro-methyl)benzyl]-(6-chloropyrimidin-4-yl)}amino-2-ethyl-6-trifluoromethyl-3,4-dihydro-2H-quinoline-1-carboxylic acid ethyl ester (75 mg). MS (m/z): 655/657 [M+H]⁺

(3) A mixture of (2R,4S)-4-{[3,5-bis(trifluoromethyl)benzyl]-(6-chloro-pyrimidin-4-yl)}amino-2-ethyl-6-trifluoromethyl-3,4-dihydro-2H-quinoline-1-carboxylic acid ethyl ester (220 mg) and morpholine (4 ml) is stirred at 70° C. for 20 minutes. The reaction solution is cooled to room temperature, and thereto are added water and ethyl acetate. The organic layer is washed with a saturated brine, dried over magnesium sulfate, and concentrated under reduced pressure. The resulting residue is purified by column chromatography (silica gel; hexane:ethyl acetate=19:1→3:2) to give (2R,4S)-4-{[3,5-bis(trifluoromethyl)benzyl]-[6-(morpholin-4-yl)-pyrimidin-4-yl]}amino-2-ethyl-6-trifluoromethyl-3,4-dihydro-2H-quinoline-1-carboxylic acid ethyl ester (110 mg). MS (m/z): 706 [M+H]⁺

Examples 70-75

The corresponding starting compounds are treated in a similar manner to Example 69-(3) to give the compounds as listed in Table 10.

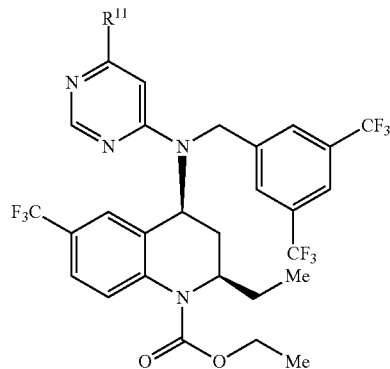

TABLE 10

| Example | R[11] | Physical properties, etc. |
|---------|-------|---------------------------|
| 70 | Me—N(piperazine)N— | MS (m/z): 719 [M + H]$^+$ |
| 71 | Me\N(Me)-CH$_2$CH$_2$-NH— | MS (m/z): 707 [M + H]$^+$ |
| 72 | Me\N(Me)-CH$_2$CH$_2$-N(Me)— | MS (m/z): 721 [M + H]$^+$ |
| 73 | Me-O-CH$_2$CH$_2$-NH— | MS (m/z): 708 [M + H]$^+$ |
| 74 | HO-CH$_2$CH$_2$-NH— | MS (m/z): 680 [M + H]$^+$ |
| 75 | HO-CH$_2$CH$_2$-N(Me)— | MS (m/z): 694 [M + H]$^+$ |

Example 76

(1) (2R,4S)-4-Amino-2-ethyl-6-trifluoromethyl-3,4-dihydro-2H-quinoline-1-carboxylic acid ethyl ester (1 g), 4-chloro-2-methylthio-pyrimidine (2.04 g), and diisopropylethylamine (890 μl) are dissolved in N,N-dimethylformamide (15 ml), and the mixture is stirred at 100° C. overnight. The reaction solution is cooled to room temperature, and thereto are added an aqueous citric acid solution and ethyl acetate. The organic layer is washed with a saturated brine, dried over magnesium sulfate, and concentrated under reduced pressure. The resulting residue is purified by column chromatography (silica gel; hexane: ethyl acetate=9:1→3:2) to give (2R,4S)-2-ethyl-4-(2-methylthiopyrimidin-4-yl)amino-6-trifluoromethyl-3,4-dihydro-2H-quinoline-1-carboxylic acid ethyl ester (1.07 g). MS (m/z): 441 [M+H]$^+$ (2) (2R,4S)-2-Ethyl-4-(2-methylthiopyrimidin-4-yl)amino-6-trifluoro-methyl-3,4-dihydro-2H-quinoline-1-carboxylic acid ethyl ester (1.05 g) and 3,5-bis(trifluoromethyl)benzyl bromide (1.465 g) are dissolved in N,N-dimethylformamide (10 ml), and thereto is added sodium hydride (62.7%, 137 mg) at room temperature, and the mixture is stirred for one hour. To the reaction solution is added acetic acid, and thereto are added water and ether. The organic layer is washed with a saturated brine, dried over magnesium sulfate, and concentrated under reduced pressure. The resulting residue is purified by column chromatography (silica gel; hexane:ethyl acetate=9:1→7:3) to give (2R,4S)-4-{[3,5-bis(trifluoro-methyl)benzyl]-(2-methylthiopyrimidin-4-yl)}amino-2-ethyl-6-trifluoro-methyl-3,4-dihydro-2H-quinoline-1-carboxylic acid ethyl ester (1.35 g). MS (m/z): 667 [M+H]$^+$ Example 77

(2R,4S)-4-{[3,5-Bis(trifluoromethyl)benzyl]-(2-methylthiopyrimidin-4-yl)}amino-2-ethyl-6-trifluoromethyl-3,4-dihydro-2H-quinoline-1-carboxylic acid ethyl ester (133.2 mg) is dissolved in chloroform (3 ml), and thereto is added m-chloroperbenzoic acid (64.5 mg) at room temperature, and the mixture is stirred for 5 minutes. To the reaction solution is added NH-silica gel, and the NH-silica gel is removed by filtration, and the filtrate is concentrated under reduced pressure. The resulting residue is purified by column chromatography (silica gel; hexane:ethyl acetate=4:1→0:1) to give (2R, 4S)-4-{[3,5-bis(trifluoromethyl)benzyl]-(2-methylsulfinylpyrimidin-4-yl)}amino-2-ethyl-6-trifluoromethyl-3,4-dihydro-2H-quinoline-1-carboxylic acid ethyl ester (53 mg, MS (m/z): 683 [M+H]$^+$) and (2R,4S)-4-{[3,5-bis(trifluoromethyl)benzyl]-(2-methylsulfonylpyrimidin-4-yl)}amino-2-ethyl-6-trifluoromethyl-3,4-dihydro-2H-quinoline-1-carboxylic acid ethyl ester (66 mg, MS (m/z): 699 [M+H]$^+$).

Example 78

Hydroxylamine hydrochloride (269 mg) is suspended in dimethyl-sulfoxide (3 ml), and thereto is added triethylamine (0.54 ml). The insoluble materials are collected by filtration, and washed with tetrahydro-furan. Tetrahydrofuran is removed from the filtrate by evaporation under reduced pressure to give a solution of hydroxylamine in dimethylsulfoxide. To this solution is added (2R,4S)-4-{[3,5-bis(trifluoromethyl)benzyl]-(5-cyanopyrimidin-2-yl)}amino-2-ethyl-6-trifluoromethyl-3,4-dihydro-2H-quinoline-1-carboxylic acid ethyl ester (500 mg), and the mixture is stirred at 75° C. for 30 minutes. The mixture is allowed to cool to room temperature, and to the reaction solution are added ethyl acetate and a saturated brine. The organic layer is washed with a saturated brine, dried over magnesium sulfate, and concentrated under reduced pressure to give (2R,4S)-4-{[3,5-bis(trifluoromethyl)benzyl]-[5-(N-hydroxycarbamimidoyl)-pyrimidin-2-yl]}amino-2-ethyl-6-trifluoromethyl-3,4-dihydro-2H-quinoline-1-carboxylic acid ethyl ester (520 mg). MS (m/z): 679 [M+H]$^+$ Example 79

(2R,4S)-4-{[3,5-Bis(trifluoromethyl)benzyl]-(2-methylsulfonyl-pyrimidin-4-yl)}amino-2-ethyl-6-trifluoromethyl-3,4-dihydro-2H-quinoline-1-carboxylic acid ethyl ester (100 mg) and an excess amount of 2-amino-ethanol are dissolved in 1,3-dimethylimidazolidinone (2 ml), and the mixture is stirred at 90° C. for one hour. The reaction solution is cooled to room temperature, and thereto are added water and ethyl acetate. The organic layer is washed with a saturated brine, dried over magnesium sulfate, and concentrated under reduced pressure. The resulting residue is purified by column chromatography (silica gel; hexane:ethyl acetate=3:2→1:4) to give (2R,4S)-4-{[3,5-bis(trifluoromethyl)benzyl]-[2-(2-hydroxy-ethylamino)pyrimidin-4-yl]}amino-2-ethyl-6-trifluoromethyl-3,4-dihydro-2H-quinoline-1-carboxylic acid ethyl ester (72 mg). MS (m/z): 680 [M+H]$^+$ Examples 80-82

The corresponding starting compounds are treated in a similar manner to Example 79 to give the compounds as listed in Table 11.

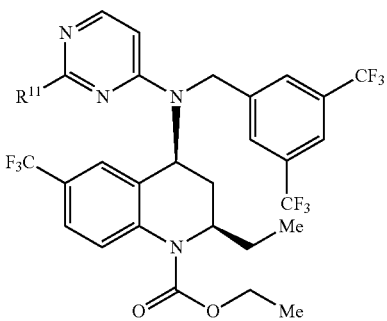

TABLE 11

| Example | R[11] | Physical properties, etc. |
|---|---|---|
| 80 | HO⌒⌒N(Me)⌒ | MS (m/z): 694 [M + H]+ |
| 81 | HO⌒CH(OH)⌒N(Me)⌒ | MS (m/z): 724 [M + H]+ |
| 82 | HO⌒⌒N(⌒⌒OH)⌒ | MS (m/z): 724 [M + H]+ |

Example 83

4-Methoxybenzyl alcohol (136 mg) is dissolved in N,N-dimethyl-formamide (3 ml), and thereto is added sodium hydride (62.7%, 42 mg) at room temperature, and the mixture is stirred for 30 minutes. To the reaction mixture is further added (2R,4S)-4-{[3,5-bis(trifluoromethyl)-benzyl]-(2-methylsulfonylpyrimidin-4-yl)}amino-2-ethyl-6-trifluoromethyl-3,4-dihydro-2H-quinoline-1-carboxylic acid ethyl ester (686 mg), and the mixture is stirred for 5 hours. Acetic acid is added to the reaction solution, and thereto are added water and ethyl acetate. The organic layer is washed with a saturated brine, dried over magnesium sulfate, and concentrated under reduced pressure. The resulting residue is purified by column chromatography (silica gel; hexane:ethyl acetate=9:1→1:1) to give (2R,4S)-4-{[3,5-bis(trifluoromethyl)benzyl]-[2-(4-methoxybenzyloxy)-pyrimidin-4-yl]}amino-2-ethyl-6-trifluoromethyl-3,4-dihydro-2H-quinoline-1-carboxylic acid ethyl ester (600 mg). MS (m/z): 757 [M+H]+

Example 84

(1) (2R,4S)-4-{[3,5-Bis(trifluoromethyl)benzyl]-[2-(4-methoxybenzyloxy)-pyrimidin-4-yl]}amino-2-ethyl-6-trifluoromethyl-3,4-dihydro-2H-quinoline-1-carboxylic acid ethyl ester (570 mg) is dissolved in 1,4-dioxane (4 ml), and thereto is added conc. hydrochloric acid (4 ml) at room temperature. The reaction solution is stirred for 15 minutes, and neutralized with a saturated aqueous sodium hydrogen carbonate solution. Ethyl acetate is added to the reaction solution, and the organic layer is washed with a saturated brine, dried over magnesium sulfate, and concentrated under reduced pressure. The resulting residue is purified by column chromatography (silica gel; hexane:ethyl acetate=1:1→0:1) to give (2R,4S)-4-{[3,5-bis(trifluoromethyl)benzyl]-(2-hydroxypyrimidin-4-yl)}amino-2-ethyl-6-trifluoromethyl-3,4-dihydro-2H-quinoline-1-carboxylic acid ethyl ester (410 mg). MS (m/z): 637 [M+H]+

(2) (2R,4S)-4-{[3,5-Bis(trifluoromethyl)benzyl]-(2-hydroxypyrimidin-4-yl)}amino-2-ethyl-6-trifluoromethyl-3,4-dihydro-2H-quinoline-1-carboxylic acid ethyl ester (376 mg), 2-iodoethanol (305 mg), and cesium carbonate (1.152 g) are dissolved in N,N-dimethylformamide (5 ml), and the mixture is stirred at 60° C. for 3 hours. The reaction solution is cooled to room temperature, and thereto are added water and ethyl acetate. The organic layer is washed with a saturated brine, dried over magnesium sulfate, and concentrated under reduced pressure. The resulting residue is purified by column chromatography (NH-silica gel; hexane:ethyl acetate=1:1→0:1), further by column chromatography (silica gel; hexane:ethyl acetate=3:7 →0:1) to give (2R,4S)-4-{[3,5-bis(trifluoromethyl)benzyl]-[1-(2-hydroxy-ethyl)-2-oxo-1,2-dihydropyrimidin-4-yl]}amino-2-ethyl-6-trifluoromethyl-3,4-dihydro-2H-quinoline-1-carboxylic acid ethyl ester (240 mg, MS (m/z): 681 [M+H]+) and (2R,4S)-4-([3,5-bis(trifluoromethyl)benzyl]-{1-[2-(2-hydroxyethoxy)ethyl]-2-oxo-1,2-dihydro-pyrimidin-4-yl})amino-2-ethyl-6-trifluoromethyl-3,4-dihydro-2H-quinoline-1-carboxylic acid ethyl ester (7 mg, MS (m/z): 725 [M+H]+).

Example 86

(1) (2R,4S)-4-Amino-2-ethyl-6-trifluoromethyl-3,4-dihydro-2H-quinoline-1-carboxylic acid ethyl ester (5 g) is dissolved in toluene (50 ml), and thereto are added tris(dibenzylideneacetone)dipalladium (293 mg), sodium tert-butoxide (3.8 g), 2-(di-tert-butylphosphino)biphenyl (376 mg), and 2,6-dichloropyrazine (4.7 g). The mixture is stirred at room temperature under nitrogen atmosphere for 23 hours. To the mixture is added a saturated aqueous sodium hydrogen carbonate solution, and the mixture is extracted with ether. The organic layer is washed with a saturated brine, dried over magnesium sulfate, and concentrated under reduced pressure. The resulting residue is purified by column chromatography (silica gel; hexane:ethyl acetate=6:1→3:1) to give (2R,4S)-4-(6-chloropyrazin-2-yl)amino-2-ethyl-6-trifluoromethyl-3,4-dihydro-2H-quinoline-1-carboxylic acid ethyl ester (5.3 g). MS (m/z): 429 [M+H]+

(2) (2R,4S)-4-(6-Chloropyrazin-2-yl)amino-2-ethyl-6-trifluoromethyl-3,4-dihydro-2H-quinoline-1-carboxylic acid ethyl ester (3 g) is dissolved in N,N-dimethylformamide (35 ml), and thereto are added sodium hydride (62.7%, 348 mg) and 3,5-bis(trifluoromethyl)benzyl bromide (9 mL), and the mixture is stirred at room temperature for 48 hours. Distilled water is added to the mixture, and the mixture is extracted with ether. The organic layer is washed with saturated brine, dried over magnesium sulfate, and concentrated under reduced pressure. The resulting residue is purified by column chromatography (silica gel; hexane: ethyl acetate=9:1→7:3) to give (2R,4S)-4-{[3,5-bis(trifluoromethyl)benzyl]-(6-chloropyrazin-2-yl)}amino-2-ethyl-6-trifluoromethyl-3,4-dihydro-2H-quinoline-1-carboxylic acid ethyl ester (1.6 g). MS (m/z): 655 [M+H]+

(3) (2R,4S)-4-{[3,5-Bis(trifluoromethyl)benzyl]-(6-chloropyrazin-2-yl)}amino-2-ethyl-6-trifluoromethyl-3,4-dihydro-2H-quinoline-1-carboxylic acid ethyl ester (200 mg) is dissolved in 1,3-dimethylimidazolidinone (2 ml), and thereto are added diisopropylethylamine (80 μl) and morpholine (140 μl). The mixture is stirred at 80° C. for 51 hours, and allowed to cool to room temperature. A saturated aqueous citric acid solution is added to the mixture, and the mixture is extracted with ether. The organic layer is washed with a saturated brine, dried over magnesium sulfate, and concentrated under reduced pressure. The resulting residue is purified by column chromatography (silica gel; hexane:ethyl acetate=4:1→13:7) to give (2R,4S)-4-{[3,5-bis(trifluoromethyl)benzyl]-[6-(morpholin-4-yl)pyrazin-2-yl]}amino-2-ethyl-6-trifluoromethyl-3,4-dihydro-2H-quinoline-1-carboxylic acid ethyl ester (132.8 mg). MS (m/z): 706 [M+H]$^+$ Example 87

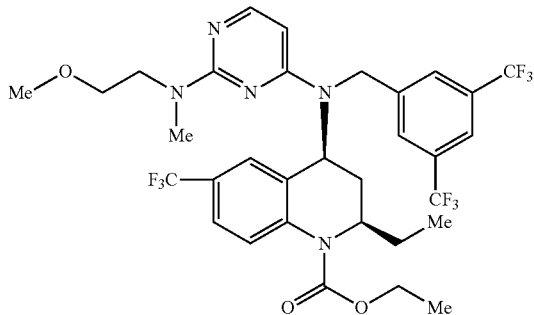

The corresponding starting compound is treated in a similar manner to Example 86 to give the compound of Example 87. MS (m/z): 708 [M+H]$^+$ Example 88

(1) (2R,4S)-4-Amino-2-ethyl-6-trifluoromethyl-3,4-dihydro-2H-quinoline-1-carboxylic acid ethyl ester (200 mg) and 2-chloro-5-nitro-thiazole (416 mg) are dissolved in N,N-dimethylformamide (1 ml), and the mixture is stirred at 100° C. for 3 hours. The reaction solution is cooled to room temperature, and thereto are added an aqueous citric acid solution and ethyl acetate. The organic layer is washed with a saturated brine, dried over magnesium sulfate, and concentrated under reduced pressure. The resulting residue is purified by column chromatography (silica gel; hexane:ethyl acetate=4:1→1:1) to give (2R,4S)-2-ethyl-4-(5-nitorthiazol-2-yl)amino-6-trifluoromethyl-3,4-dihydro-2H-quinoline-1-carboxylic acid ethyl ester (148 mg). MS (m/z): 445 [M+H]$^+$ (2) (2R,4S)-2-Ethyl-4-(5-nitrothiazol-2-yl)amino-6-trifluoromethyl-3,4-dihydro-2H-quinoline-1-carboxylic acid ethyl ester (133 mg) and 3,5-bis(trifluoromethyl)benzyl bromide (179 mg) are dissolved in tetrahydro-furan (3 ml), and thereto is added sodium hydride (62.7%, 34 mg), and the mixture is stirred at room temperature overnight. To the reaction solution is added acetic acid, and thereto are added water and ethyl acetate. The organic layer is washed with a saturated brine, dried over magnesium sulfate, and concentrated under reduced pressure. The resulting residue is purified by column chromatography (silica gel; hexane:ethyl acetate=4:1 →2:1) to give (2R,4S)-4-{[3,5-bis(trifluoromethyl)benzyl]-(5-nitrothiazol-2-yl)}amino-2-ethyl-6-trifluoromethyl-3,4-dihydro-2H-quinoline-1-carboxylic acid ethyl ester (58 mg). MS (m/z): 671 [M+H]$^+$ Example 89

(1) (2R,4S)-4-{[3,5-Bis(trifluoromethyl)benzyl]-cyano}amino-2-ethyl-6-trifluoromethyl-3,4-dihydro-2H-quinoline-1-carboxylic acid ethyl ester (327.9 mg) is dissolved in tetrahydrofuran (3 ml), and thereto is added sodium hydride (62.7%, 13.9 mg). The mixture is stirred with ice-cooling under nitrogen atmosphere for one hour. To the reaction solution is slowly added dropwise a solution of 3-buten-1-ol (41.8 mg) in tetrahydrofuran (4 ml) under ice-cooling, and the mixture is stirred at room temperature for 29 hours. Distilled water is added under ice-cooling, and the mixture is extracted with ethyl acetate. The organic layer is dried over magnesium sulfate, and concentrated under reduced pressure. The resulting residue is purified by column chromatography (silica gel; hexane:ethyl acetate=4:1) to give (2R,4S)-4-{1-[3,5-bis(trifluoromethyl)benzyl]-2-(3-buten-1-yl)}isoureido-2-ethyl-6-trifluoromethyl-3,4-dihydro-2H-quinoline-1-carboxylic acid ethyl ester (186.3 mg). MS (m/z): 640 [M+H]$^+$ (2) (2R,4S)-4-{1-[3,5-Bis(trifluoromethyl)benzyl]-2-(3-buten-1-yl)}isoureido-2-ethyl-6-trifluoromethyl-3,4-dihydro-2H-quinoline-1-carboxylic acid ethyl ester (172 mg) is dissolved in chloroform (3 ml), and thereto is added N-iodosuccimide (72.5 mg). The mixture is stirred at room temperature for 1.5 hours, and thereto is added a saturated aqueous sodium thiosulfate solution. The mixture is extracted with ether, and the organic layer is washed with a saturated brine, dried over magnesium sulfate, and concentrated under reduced pressure to give (2R,4S)-4-{[3,5-bis(trifluoromethyl)benzyl]-(4-iodomethyl-5,6-dihydro-4H-[1,3]oxadin-2-yl)}-amino-2-ethyl-6-trifluoromethyl-3,4-dihydro-2H-quinoline-1-carboxylic acid ethyl ester (211 mg). MS (m/z): 766 [M+H]$^+$ Example 90

(1) (2R,4S)-4-(5-Bromopyrimidin-2-yl)amino-2-ethyl-6-trifluoromethyl-3,4-dihydro-2H-quinoline-1-carboxylic acid ethyl ester (100 mg) is dissolved in N,N-dimethylformamide (1 ml), and thereto is added sodium hydride (62.7%, 10.3 mg), and the mixture is stirred with ice-cooling under nitrogen atmosphere for 10 minutes. 3,5-Dimethoxybenzyl bromide (74 mg) is added to the mixture under ice-cooling, and the mixture is stirred at room temperature for 16.5 hours. Distilled water is added to the mixture under ice-cooling, and the mixture is extracted with ether. The organic layer is washed with a saturated brine, dried over magnesium sulfate, and concentrated under reduced pressure. The resulting residue is purified by column chromatography (silica gel; hexane:ethyl acetate=9:1→4:1) to give (2R,4S)-4-[(5-bromopyrimidin-2-yl)-(3,5-dimethoxy-benzyl)]amino-2-ethyl-6-trifluoromethyl-3,4-dihydro-2H-quinoline-1-carboxylic acid ethyl ester (95.1 mg). MS (m/z): 623/625 [M+H]$^+$ (2) (2R,4S)-4-[(5-Bromopyrimidin-2-yl)-(3,5-dimethoxybenzyl)]amino-2-ethyl-6-trifluoromethyl-3,4-dihydro-2H-quinoline-1-carboxylic acid ethyl ester (290 mg) is dissolved in toluene (4 ml), and tris(dibenzylidene-acetone)dipalladium (8.5 mg), sodium tert-butoxide (68.2 mg), 2-(di-tert-butylphosphino)biphenyl (11 mg) and morpholine (62 μl) are added thereto. The reaction mixture is stirred under nitrogen atmosphere at room temperature for 4 days. The reaction solution is stirred at 80° C. for 5.5 hours, and allowed to cool to room temperature. Distilled water is added to the mixture, and the mixture is extracted with ether. The organic layer is washed with a saturated brine, dried over magnesium sulfate, and concentrated under reduced pressure. The resulting residue is purified by column chromatography (NH-silica gel; hexane:ethyl acetate=4:1→3:2) to give (2R,4S)-4-{(3,5-dimethoxybenzyl)-[5-(morpholin-4-yl)pyrimidin-2-yl]}-amino-2-ethyl-6-trifluoromethyl-3,4-dihydro-2H-quinoline-1-carboxylic acid ethyl ester (141.5 mg). MS (m/z): 630 [M+H]+

Examples 91-94

The corresponding starting compounds are treated in a similar manner to Example 90 to give the compounds as listed in Table 12.

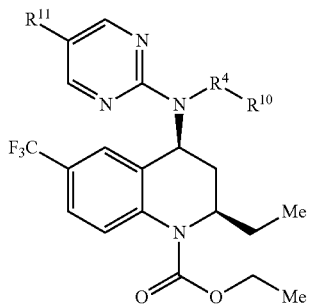

solution are added an aqueous citric acid solution and ethyl acetate, and the organic layer is washed with a saturated brine, dried over magnesium sulfate, and concentrated under reduced pressure. The resulting residue is purified by column chromatography (silica gel; hexane:ethyl acetate=9:1→2:3) to give (6-bromopyridin-2-yl)methanol (3.92 g). MS (m/z): 188/190 [M+H]+

(2) (6-Bromopyridin-2-yl)methanol (3.9 g) and triphenylphosphine (7.6 g) are dissolved in methylene chloride (50 ml), and thereto is added carbon tetrabromide (8.25 g) under ice-cooling. The reaction solution is concentrated under reduced pressure, and the resulting residue is purified by column chromatography (silica gel; hexane:ethyl acetate=49:1→47:3) to give 2-bromo-6-bromomethylpyridine (2.96 g). MS (m/z): 250/252 [M+H]+

(3) (2R,4S)-4-(5-Bromopyrimidin-2-yl)amino-2-ethyl-6-trifluoromethyl-3,4-dihydro-2H-quinoline-1-carboxylic acid ethyl ester (400 mg) is dissolved in N,N-dimethylformamide (4 ml), and thereto is added at 10° C. sodium hydride (62.7%, 42 mg). The mixture is stirred at the same temperature for 10 minutes, and to the reaction solution is added 2-bromo-6-bromomethylpyridine (318 mg). The mixture is stirred at the same temperature for 15 minutes, and thereto is added acetic acid. A saturated aqueous sodium hydrogen carbonate solution and ethyl acetate are added to the mixture. The organic layer is washed with a saturated brine, dried over magnesium sulfate, and concentrated under reduced pressure. The resulting residue is purified by column chromatography (silica gel; hexane:ethyl acetate=48:2→3:2) to give (2R,4S)-4-[(6-bromo-pyridin-2-yl)methyl-(5-bromopyrimidin-2-yl)]amino-2-

TABLE 12

| Example | R11 | R4—R10 | Physical properties, etc. |
|---|---|---|---|
| 91 | morpholin-4-yl | 3,5-dimethylbenzyl | MS (m/z): 598 [M + H]+ |
| 92 | morpholin-4-yl | 3-methoxybenzyl | MS (m/z): 600 [M + H]+ |
| 93 | morpholin-4-yl | 3-cyanobenzyl | MS (m/z): 595 [M + H]+ |
| 94 | (2-methoxyethyl)(methyl)amino | 3-cyanobenzyl | MS (m/z): 597 [M + H]+ |

Example 95

(1) 6-Bromopyridin-2-carbaldehyde (5 g) is dissolved in a mixture of methanol (10 ml) and tetrahydrofuran (15 ml), and thereto is added sodium borohydride (3.05 g) at 0° C., and the mixture is stirred for 10 minutes. To the reaction ethyl-6-trifluoro-methyl-3,4-dihydro-2H-quinoline-1-carboxylic acid ethyl ester (470 mg). MS (m/z): 642/644 [M+H]+

(4) (2R,4S)-4-[(6-bromopyridin-2-yl)methyl-(5-bromopyrimidin-2-yl)]amino-2-ethyl-6-trifluoromethyl-3,4-dihydro-2H-quinoline-1-carboxylic acid ethyl ester (150 mg), tetrakis(triphenylphosphine)palladium (28 mg) and zinc cyanide (71.2 mg) are dissolved in N,N-dimethylformamide (3 ml), and the mixture is stirred at 95° C. under nitrogen atmosphere overnight. The reaction solution is cooled to room temperature, and thereto are added a saturated aqueous sodium hydrogen carbonate solution and ethyl acetate. The organic layer is dried over magnesium sulfate, and concentrated under reduced pressure. The resulting residue is purified by column chromatography (silica gel; hexane:ethyl acetate=47:3→2:3) to give (2R, 4S)-4-[(6-cyanopyridin-2-yl)methyl-(5-cyanopyrimidin-2-yl)]amino-2-ethyl-6-trifluoromethyl-3,4-dihydro-2H-quinoline-1-carboxylic acid ethyl ester (105 mg). MS (m/z): 536 [M+H]$^+$ Examples 96-97

(2R*,4S*)-4-Amino-2-ethyl-6-methoxy-3,4-dihydro-2H-quinoline-1-carboxylic acid ethyl ester is treated in a similar manner to Example 1 to give the compounds as listed in Table 13.

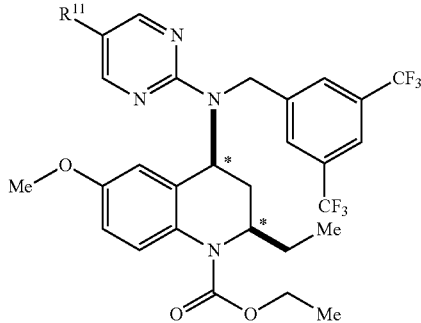

TABLE 13

| Example | Configuration | R$^{11}$ | Physical properties, etc. |
|---------|---------------|----------|---------------------------|
| 96 | (2R*,4S*) | morpholinyl-CH$_2$- | MS (m/z): 668 [M + H]$^+$ |
| 97 | (2R*,4S*) | Me-O-CH$_2$CH$_2$-N(Me)- | MS (m/z): 670 [M + H]$^+$ |

Example 98

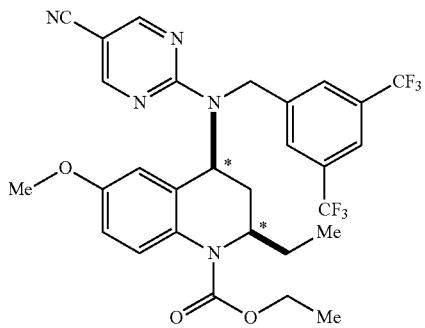

The corresponding starting compound is treated in a similar manner to Example 10 to give the compound of Example 98. MS (m/z): 608 [M+H]$^+$ Example 99

(2R*,4S*)-4-{[3,5-Bis(trifluoromethyl)benzyl]-(5-bromopyrimidin-2-yl)}amino-2-ethyl-6-methoxy-3,4-dihydro-2H-quinoline-1-carboxylic acid ethyl ester (284 mg), acrylic acid benzyl ester (125 mg), tris(dibenzylidene-acetone)dipalladium (292 mg), dicyclohexylmethylamine (110 µl), and tri(tert-butyl)phosphonium tetrafluoroborate (308 mg) are dissolved in 1,4-dioxane (4 ml), and the mixture is stirred at room temperature under nitrogen atmosphere overnight. The reaction solution is concentrated under reduced pressure, and the resulting residue is purified by column chromatography (silica gel; hexane:ethyl acetate=9:1→4:1) to give (2R*, 4S*)-4-{[5-(2-benzyloxycarbonylvinyl)pyrimidin-2-yl]-[3, 5-bis(trifluoro-methyl)benzyl]}amino-2-ethyl-6-methoxy-3, 4-dihydro-2H-quinoline-1-carboxylic acid ethyl ester (266 mg). MS (m/z): 743 [M+H]$^+$ Example 100

(2R*,4S*)-4-{[5-(2-Benzyloxycarbonylvinyl)pyrimidin-2-yl]-[3,5-bis(trifluoromethyl)benzyl]}amino-2-ethyl-6-methoxy-3,4-dihydro-2H-quinoline-1-carboxylic acid ethyl ester (265 mg) is dissolved in a mixture of methanol (4 ml) and tetrahydrofuran (1 ml), and thereto is added a catalytic amount of 10% palladium-carbon, and the mixture is stirred at room temperature under hydrogen atmosphere for 3 hours. The catalyst (10% palladium-carbon) is removed by filtration, and the filtrate is concentrated under reduced pressure. The resulting residue is purified by column chromatography (silica gel; hexane:ethyl acetate=4:1) to give (2R*,4S*)-4-{[3,5-bis(trifluoromethyl)benzyl]-[5-(2-carboxyvinyl)pyrimidin-2-yl]}amino-2-ethyl-6-methoxy-3,4-dihydro-2H-quinoline-1-carboxylic acid ethyl ester (176 mg). MS (m/z): 653 [M+H]$^+$ Example 101

(2R*,4S*)-4-{[3,5-Bis(trifluoromethyl)benzyl]-[5-(2-carboxyvinyl)-pyrimidin-2-yl]}amino-2-ethyl-6-methoxy-3,4-dihydro-2H-quinoline-1-carboxylic acid ethyl ester (120 mg) is dissolved in a mixture of methanol (4 ml) and tetrahydrofuran (1 ml), and a catalytic amount of 10% palladium-carbon is added thereto, and the mixture is stirred at room temperature under hydrogen atmosphere overnight. The catalyst is removed by filtration, and the filtrate is concentrated under reduced pressure. The resulting residue is purified by column chromatography (silica gel; hexane:ethyl acetate=4:1) to give (2R*,4S*)-4-{[3,5-bis(trifluoromethyl)benzyl]-[5-(2-carboxyethyl)pyrimidin-2-yl]}amino-2-ethyl-6-methoxy-3,4-dihydro-2H-quinoline-1-carboxylic acid ethyl ester (35 mg). MS (m/z): 655 [M+H]$^+$ Example 102

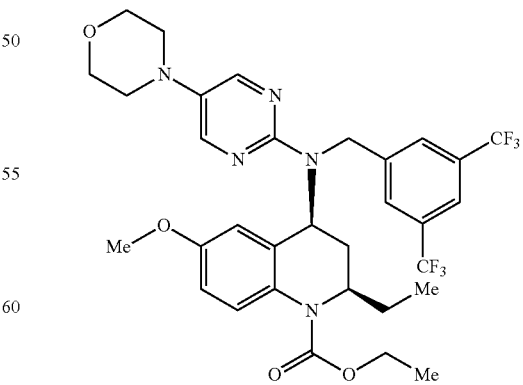

(2R,4S)-4-Amino-2-ethyl-6-methoxy-3,4-dihydro-2H-quinoline-1-carboxylic acid ethyl ester is treated in a similar manner to Example 1 to give the compound of Example 102. MS (m/z): 668 [M+H]$^+$

Example 103

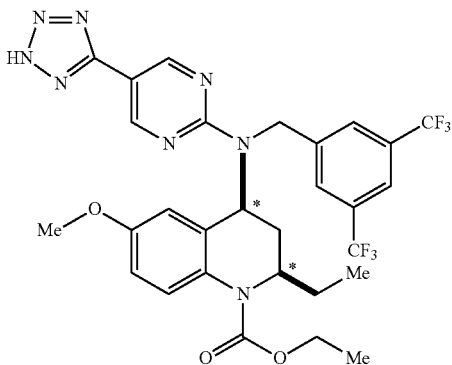

The corresponding starting compound is treated in a similar manner to Example 19 to give the compound of Example 103. MS (m/z): 651 [M+H]⁺

Examples 104-105

The corresponding starting compounds are treated in a similar manner to Example 20 to give the compounds as listed in Table 14.

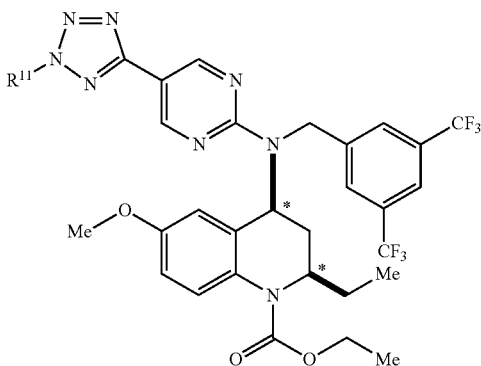

TABLE 14

| Example | Configuration | R¹¹ | Physical properties, etc. |
|---|---|---|---|
| 104 | (2R*,4S*) | CH₃— | MS (m/z): 665 [M + H]⁺ |
| 105 | (2R*,4S*) | HO⌒⌒ | MS (m/z): 695 [M + H]⁺ |

Examples 106-109

The corresponding starting compounds are treated in a similar manner to Example 35 to give the compounds as listed in Table 15.

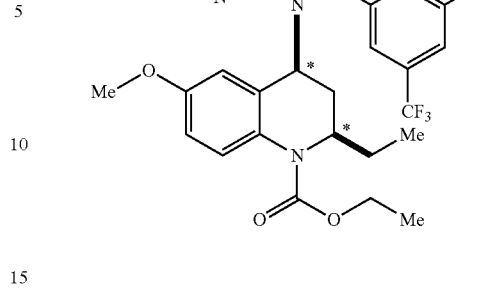

TABLE 15

| Example | Configuration | R¹¹ | Physical properties, etc. |
|---|---|---|---|
| 106 | (2R*,4S*) | Me∼S∼∼ | MS (m/z): 647 [M + H]⁺ |
| 107 | (2R*,4S*) | Me∼N∼∼ ·HCl, Me | MS (m/z): 644 [M + H]⁺ |
| 108 | (2R*,4S*) | Me,Me dioxolane-ethyl | MS (m/z): 687 [M + H]⁺ |
| 109 | (2R*,4S*) | Me-O-C(Me)(Me)-C(=O)-O-Me | MS (m/z): 687 [M + H]⁺ |

Example 110

(2R*,4S*)-4-{[3,5-Bis(trifluoromethyl)benzyl]-[2-(2-methylthioethyl)-2H-tetrazol-5-yl]}amino-2-ethyl-6-methoxy-3,4-dihydro-2H-quinoline-1-carboxylic acid ethyl ester (226 mg) is dissolved in methylene chloride (3 ml), and thereto is added m-chloroperbenzoic acid (75 mg) at room temperature, and the mixture is stirred overnight. To the reaction solution is added an aqueous potassium carbonate solution, and the organic layer is washed with a saturated brine, dried over magnesium sulfate, and concentrated under reduced pressure. The resulting residue is purified by column chromatography (silica gel; chloroform:methanol=1:0→20:1) to give (2R*,4S*)-4-{[3,5-bis(trifluoromethyl)benzyl]-[2-(2-methylsulfinylethyl)-2H-tetrazol-5-yl]}amino-2-ethyl-6-methoxy-3,4-dihydro-2H-quinoline-1-carboxylic acid ethyl ester (176 mg). MS (m/z): 663 [M+H]⁺

Example 111

(2R*,4S*)-4-{[3,5-Bis(trifluoromethyl)benzyl]-[2-(2-methylsulfinyl-ethyl)-2H-tetrazol-5-yl]}amino-2-ethyl-6-methoxy-3,4-dihydro-2H-quinoline-1-carboxylic acid ethyl ester (117 mg) is dissolved in methylene chloride (2 ml), and thereto is added m-chloroperbenzoic acid (76 mg) at room temperature. The mixture is stirred overnight, and to the reaction solution is added an aqueous potassium carbonate solution. The organic layer is washed with a saturated brine, dried over magnesium sulfate, and concentrated under reduced pressure. The resulting residue is purified by column chromatography (silica gel; hexane:ethyl acetate=2:1→1:1) to give (2R*,4S*)-4-{[3,5-bis(trifluoromethyl)benzyl]-[2-(2-methylsulfonylethyl)-2H-tetrazol-5-yl]}amino-2-ethyl-6-methoxy-3,4-dihydro-2H-quinoline-1-carboxylic acid ethyl ester (108 mg). MS (m/z): 679 [M+H]$^+$ Example 112

(2R*,4S*)-4-{[3,5-Bis(trifluoromethyl)benzyl]-[2-(2,2-dimethyl-[1,3]-dioxolan-4-ylmethyl)-2H-tetrazol-5-yl]}amino-2-ethyl-6-methoxy-3,4-dihydro-2H-quinoline-1-carboxylic acid ethyl ester (129 mg) is dissolved in a mixture of methanol (3 ml) and water (0.3 ml), and thereto are added at room temperature a strongly acidic resin (IR-120, manufactured by Organo Corporation) (50 mg) and a 6N hydrochloric acid (2 ml), and the mixture is stirred overnight. The resin is removed by filtration, and to the filtrate are added a saturated aqueous sodium hydrogen carbonate solution and ethyl acetate. The organic layer is washed with a saturated brine, dried over sodium sulfate, and concentrated under reduced pressure to give (2R*,4S*)-4-{[3,5-bis(trifluoromethyl)benzyl]-[2-(2,3-dihydroxypropyl)-2H-tetrazol-5-yl]}amino-2-ethyl-6-methoxy-3,4-dihydro-2H-quinoline-1-carboxylic acid ethyl ester (123 mg). MS (m/z): 647 [M+H]$^+$ Example 113

The corresponding starting compound is treated in a similar manner to Example 46 to give the compound of the following formula. MS (m/z): 673 [M+H]$^+$

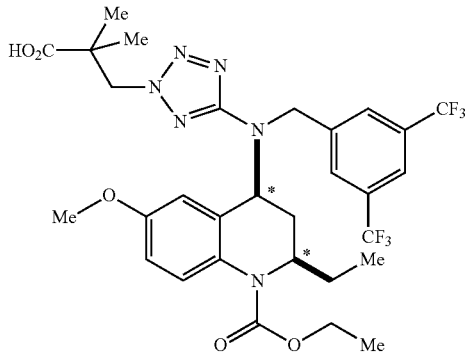

Examples 114-115

The corresponding starting compounds are treated in a similar manner to Example 60 to give the compounds as listed in Table 16.

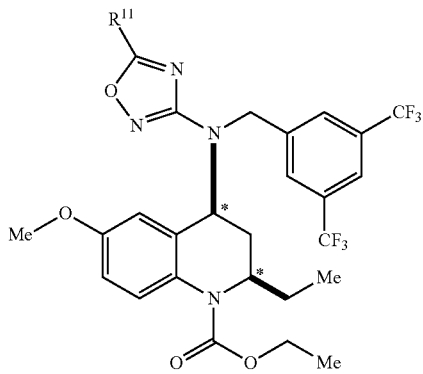

TABLE 16

| Example | Configuration | R$^{11}$ | Physical properties, etc. |
|---|---|---|---|
| 114 | (2R*,4S*) | Me–O–\~ | MS (m/z): 634 [M + H$_2$O]$^+$ |
| 115 | (2R*,4S*) | Me–C(=O)–O–\~ | MS (m/z): 662 [M + H$_2$O]$^+$ |

Example 116

The corresponding starting compound is treated in a similar manner to Example 64 to give the compound of the following formula. MS (m/z): 620 [M+H$_2$O]$^+$

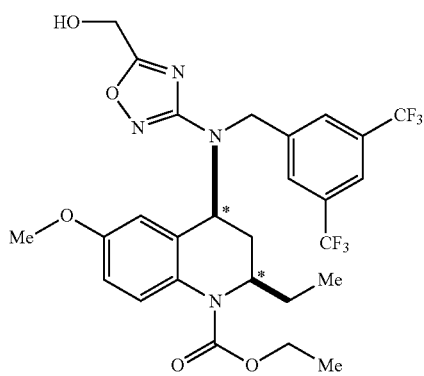

Example 117

(2R*,4S*)-4-{[3,5-Bis(trifluoromethyl)benzyl]-[5-bromopyrimidin-2-yl]}amino-6-bromo-2-ethyl-3,4-dihydro-2H-quinoline-1-carboxylic acid ethyl ester (1.48 g), tris(dibenzylideneacetone)dipalladium (190 mg), sodium tert-butoxide (401 mg), 2-(di-tert-butylphosphino)biphenyl (124 mg), and morpholine (197 µl) are dissolved in toluene (15 ml), and the mixture is stirred under nitrogen atmosphere at room temperature for 96 hours. To the reaction solution are added a saturated brine and ethyl acetate, and the organic layer is dried over magnesium sulfate, and concentrated under reduced pressure. The resulting residue is purified by column chromatography (NH-silica gel; hexane:ethyl acetate=9:1→67:33) to give (2R*,4S*)-4-{[3,5-bis(trifluoromethyl)benzyl]-[5-(morpholin-4-yl)pyrimidin-2-yl]}amino-2-ethyl-6-(morpholin-4-yl)-3,4-dihydro-2H-quinoline-1-carboxylic acid ethyl ester (320 mg, MS (m/z): 723 [M+H]$^+$) and (2R*,4S*)-4-{[3,5-bis(trifluoromethyl)benzyl]-[5-(morpholin-4-yl)pyrimidin-2-yl]}amino-6-bromo-2-ethyl-3,4-dihydro-2H-quinoline-1-carboxylic acid ethyl ester (568 mg, MS (m/z): 716/718 [M+H]$^+$).

Example 118

The corresponding starting compound is treated in a similar manner to Example 1 to give the compound of the following formula. MS (m/z): 696 [M+H]$^+$

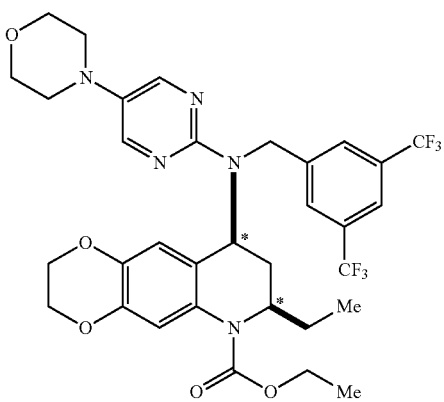

Example 119

(2R,4S)-4-{[3,5-Bis(trifluoromethyl)benzyl]-[5-(N-hydroxy-carbamimidoyl)pyrimidin-2-yl]}amino-2-ethyl-6-trifluoromethyl-3,4-dihydro-2H-quinoline-1-carboxylic acid ethyl ester (200 mg) and 1,1'-carbonyldimidazole (72 mg) are dissolved in acetonitrile (5 ml), and the mixture is refluxed for 2 hours. The mixture is allowed to cool to room temperature, and to the reaction solution are added ethyl acetate and a saturated aqueous sodium hydrogen carbonate solution. The organic layer is washed with a saturated brine, dried over magnesium sulfate, and concentrated under reduced pressure. The resulting residue is purified by silica gel column chromatography (hexane:ethyl acetate=4:1→1:1) to give (2R,4S)-4-{[3,5-bis(trifluoromethyl)benzyl]-[5-(5-oxo-4,5-dihydro-[1,2,4]-oxadiazol-3-yl)pyrimidin-2-yl]}amino-2-ethyl-6-trifluoromethyl-3,4-dihydro-2H-quinoline-1-carboxylic acid ethyl ester (60 mg). MS (m/z): 705 [M+H]+

Example 120

(1) (2R,4S)-4-{[3,5-Bis(trifluoromethyl)benzyl]-(5-bromopyrimidin-2-yl)}amino-2-ethyl-6-trifluoromethyl-3,4-dihydro-2H-quinoline-1-carboxylic acid ethyl ester (1.83 g), copper(I) iodide (150 mg), sodium iodide (2.36 g), and N,N'-dimethylethylenediamine (168 µl) are dissolved in 1,4-dioxane (8 ml), and the mixture is stirred at 105° C. under nitrogen atmosphere for 23 hours. The reaction solution is cooled to room temperature, and water and ethyl acetate are added thereto. The organic layer is washed with a saturated brine, dried over magnesium sulfate, and concentrated under reduced pressure. The resulting residue is purified by silica gel column chromatography (hexane: ethyl acetate=9:1→6:1) to give (2R,4S)-4-{[3,5-bis(trifluoromethyl)benzyl]-(5-iodopyrimidin-2-yl)}amino-2-ethyl-6-trifluoro-methyl-3,4-dihydro-2H-quinoline-1-carboxylic acid ethyl ester (1.70 g). MS (m/z): 747 [M+H]+

(2) (2R,4S)-4-{[3,5-Bis(trifluoromethyl)benzyl]-(5-iodopyrimidin-2-yl)}-amino-2-ethyl-6-trifluoromethyl-3,4-dihydro-2H-quinoline-1-carboxylic acid ethyl ester (1.69 g), sodium 3-methoxy-3-oxopropane-1-sulfinate (1.58 g), and copper(I) iodide (1.72 g) are dissolved in dimethylsulfoxide (20 ml), and the mixture is stirred at 110° C. under nitrogen atmosphere for 2.5 hours. The reaction solution is cooled to room temperature, and thereto are added water and ethyl acetate. The precipitated insoluble materials are removed by filtration through Celite™, and the organic layer is washed with a saturated brine, dried over magnesium sulfate, and concentrated under reduced pressure. The resulting residue is purified by silica gel column chromatography (hexane:ethyl acetate=4:1→2:1) to give (2R,4S)-4-{[3,5-bis(trifluoromethyl)benzyl]-[5-(2-methoxycarbonylethanesulfonyl)-pyrimidin-2-yl]}amino-2-ethyl-6-trifluoromethyl-3,4-dihydro-2H-quinoline-1-carboxylic acid ethyl ester (1.41 g). MS (m/z): 771 [M+H]+

Examples 121-123

The corresponding starting compounds are treated in a similar manner to Example 1-(3) to give the compounds as listed in Table 17.

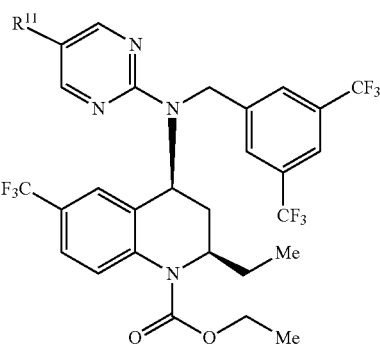

TABLE 17

| Example | R11 | Physical properties, etc. |
|---|---|---|
| 121 | ![](piperidine-4-carboxylic acid ethyl ester N-linked) | MS (m/z): 776 [M + H]+ |
| 122 | ![](4-methyl-piperidine-4-carboxylic acid ethyl ester N-linked) | MS (m/z): 790 [M + H]+ |
| 123 | ![](tert-butyl 3-(dimethylamino)propanoate) | MS (m/z): 778 [M + H]+ |

Example 124

(2R,4S)-4-{[3,5-Bis(trifluoromethyl)benzyl]-[5-(4-ethoxycarbonyl-piperidin-1-yl)pyrimidin-2-yl]}amino-2-ethyl-6-trifluoromethyl-3,4-dihydro-2H-quinoline-1-carboxylic acid ethyl ester (265 mg) is dissolved in ethanol (3 ml), and thereto is added a 2N aqueous sodium hydroxide solution (0.342 ml), and the mixture is stirred at 50° C. for one hour. The mixture is cooled to room temperature, and the reaction solution is acidified with 1N hydrochloric acid. The mixture is extracted with ethyl acetate, and the organic layer is washed with a saturated brine, dried over magnesium sulfate, and concentrated under reduced pressure. The resulting residue is purified by silica gel column chromatography (chloroform:methanol=1:0→9:1) to give (2R,4S)-4-{[3,5-bis(trifluoromethyl)benzyl]-[5-(4-carboxypiperidin-1-yl)pyrimidin-2-yl]}amino-2-ethyl-6-trifluoromethyl-3,4-dihydro-2H-quinoline-1-carboxylic acid ethyl ester (241 mg). MS (m/z): 748 [M+H]+

Example 125

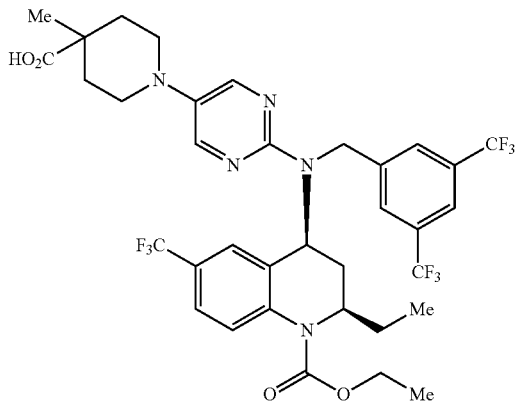

The corresponding starting compound is treated in a similar manner to Example 124 to give the compound of Example 125. MS (m/z): 762 [M+H]+

Example 126

(2R,4S)-4-{[3,5-Bis(trifluoromethyl)benzyl]-[5-(2-methoxycarbonyl-ethanesulfonyl)-pyrimidin-2-yl]}amino-2-ethyl-6-trifluoromethyl-3,4-dihydro-2H-quinoline-1-carboxylic acid ethyl ester (700 mg) and a 2N aqueous sodium hydroxide solution (1.8 ml) are dissolved in ethanol (10 ml), and the mixture is stirred at 50° C. for 30 minutes. The reaction solution is cooled to room temperature, and thereto are added a 2N aqueous hydrochloric acid solution (1.8 ml) and ethyl acetate under ice-cooling. The organic layer is washed with a saturated brine, dried over magnesium sulfate, and concentrated under reduced pressure. The resulting residue is purified by silica gel column chromatography (chloroform:methanol=99:1→4:1) to give (2R,4S)-4-{[3,5-bis(trifluoro-methyl)benzyl]-(5-sulfopyrimidin-2-yl)}amino-2-ethyl-6-trifluoromethyl-3,4-dihydro-2H-quinoline-1-carboxylic acid ethyl ester (384 mg). MS (m/z): 699 [M−H]−

Example 127

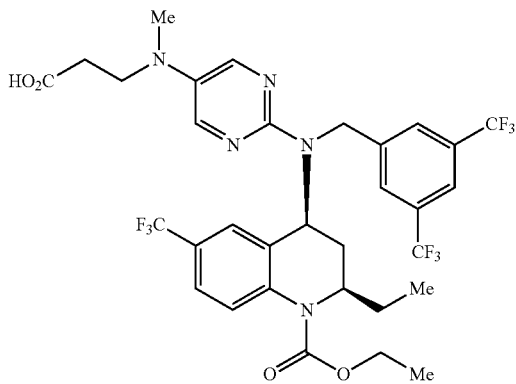

The corresponding starting compound is treated in a similar manner to Example 68 to give the compound of Example 127. MS (m/z): 722 [M+H]+

Example 128

(2R,4S)-4-{[3,5-Bis(trifluoromethyl)benzyl]-(5-sulfopyrimidin-2-yl)}amino-2-ethyl-6-trifluoromethyl-3,4-dihydro-2H-quinoline-1-carboxylic acid ethyl ester (225 mg) is dissolved in thionyl chloride (5 ml), and the mixture is stirred at 80° C. for 2 hours. The reaction solution is cooled to room temperature, and concentrated under reduced pressure. To the resulting residue is added chloroform (3 ml), and thereto is added a 2 N solution of methyl amine in tetrahydrofuran (3 ml) under ice-cooling. The mixture is stirred at room temperature for 2 hours, and thereto are added water and ethyl acetate. The organic layer is washed with a saturated brine, dried over magnesium sulfate, and concentrated under reduced pressure. The resulting residue is purified by silica gel column chromatography (hexane:ethyl acetate=4:1→2:1) to give (2R,4S)-4-{[3,5-bis(trifluoromethyl)benzyl]-(5-methylsulfamoylpyrimidin-2-yl)}amino-2-ethyl-6-trifluoromethyl-3,4-dihydro-2H-quinoline-1-carboxylic acid ethyl ester (68 mg). MS (m/z): 714 [M+H]+

Example 129

(2R,4S)-4-{[3,5-Bis(trifluoromethyl)benzyl]-(5-sulfopyrimidin-2-yl)}amino-2-ethyl-6-trifluoromethyl-3,4-dihydro-2H-quinoline-1-carboxylic acid ethyl ester (584 mg) is dissolved in thionyl chloride (5 ml), and the mixture is stirred at 80° C. for 2 hours. The reaction solution is cooled to room temperature, and concentrated under reduced pressure. To the resulting residue is added chloroform (3 ml), and thereto is further added a 7N solution of ammonia in methanol (3 ml) under ice-cooling. The mixture is stirred at room temperature for 2 hours, and water and ethyl acetate are added thereto. The organic layer is washed with a saturated brine, dried over magnesium sulfate, and concentrated under reduced pressure. The resulting residue is purified by silica gel column chromatography (hexane:ethyl acetate=4:1→2:1) to give (2R,4S)-4-{[3,5-bis(trifluoro-methyl)benzyl]-(5-methoxysulfinylpyrimidin-2-yl)}amino-2-ethyl-6-trifluoromethyl-3,4-dihydro-2H-quinoline-1-carboxylic acid ethyl ester (340 mg, MS (m/z): 699 [M+H]+) and (2R,4S)-4-{[3,5-bis(trifluoromethyl)benzyl]-(5-sulfamoylpyrimidin-2-yl)}amino-2-ethyl-6-trifluoromethyl-3,4-dihydro-2H-quinoline-1-carboxylic acid ethyl ester (22 mg, MS (m/z): 700 [M+H]+).

Examples 130-133

The corresponding starting compounds are treated in a similar manner to Example 90 to give the compounds as listed in Table 18.

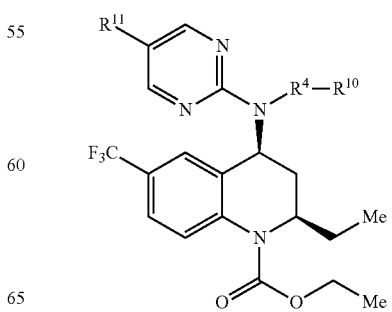

TABLE 18

| Example | R¹¹ | R⁴—R¹⁰ | Physical properties, etc. |
|---|---|---|---|
| 130 | morpholin-4-yl | 3,5-dibromobenzyl | MS (m/z): 726/728/730 [M + H]⁺ |
| 131 | morpholin-4-yl | 3-ethyl-5-cyano-benzyl with CF₃ | MS (m/z): 663 [M + H]⁺ |
| 132 | 4-acetylpiperazin-1-yl | 3,5-dimethoxy-benzyl with ethyl | MS (m/z): 671 [M + H]⁺ |
| 133 | 4-acetylpiperazin-1-yl | 3-ethyl-5-cyano-benzyl with CF₃ | MS (m/z): 704 [M + H]⁺ |

Example 134

(2R,4S)-4-{(3,5-Dibromobenzyl)-[(5-morpholin-4-yl)pyrimidin-2-yl]}-amino-2-ethyl-6-trifluoromethyl-3,4-dihydro-2H-quinoline-1-carboxylic acid ethyl ester (200 mg) is dissolved in N,N-dimethylformamide (4 ml), and thereto are added zinc cyanide (71 mg) and a catalytic amount of tetrakis-(triphenylphosphine)palladium, and the mixture is stirred at 110° C. under nitrogen atmosphere for 2.5 hours. The mixture is allowed to cool to room temperature, and thereto is added a saturated aqueous sodium hydrogen carbonate solution, and the mixture is extracted with ethyl acetate. The organic layer is washed with a saturated brine, dried over magnesium sulfate, and concentrated under reduced pressure. The resulting residue is purified by silica gel column chromatography (hexane:ethyl acetate=4:1 →3:2) to give (2R,4S)-4-{(3,5-dicyanobenzyl)-[(5-morpholin-4-yl)-pyrimidin-2-yl]}amino-2-ethyl-6-trifluoromethyl-3,4-dihydro-2H-quinoline-1-carboxylic acid ethyl ester (124 mg). MS (m/z): 620 [M+H]⁺

Examples 135-136

The corresponding starting compounds are treated in a similar manner to Example 99 to give the compounds as listed in Table 19.

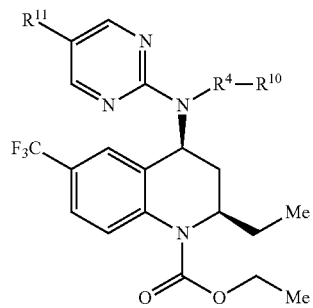

TABLE 19

| Example | R¹¹ | R⁴—R¹⁰ | Physical properties, etc. |
|---|---|---|---|
| 135 | benzyl crotonate group | 3,5-dimethoxy-benzyl with ethyl | MS (m/z): 705 [M + H]⁺ |

TABLE 19-continued

| Example | R11 | R4—R10 | Physical properties, etc. |
|---|---|---|---|
| 136 | 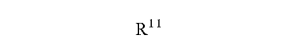 | 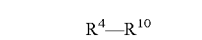 | MS (m/z): 738 [M + H]+ |

Example 137

(1) (2R,4S)-4-(5-Bromopyrimidin-2-yl)amino-2-ethyl-6-trifluoromethyl-3,4-dihydro-2H-quinoline-1-carboxylic acid ethyl ester (18 g) is dissolved in tetrahydrofuran (180 ml), and thereto are added di-tert-butyl dicarbonate (12.4 g) and a catalytic amount of 4-dimethylaminopyridine, and the mixture is stirred at room temperature overnight. To the reaction solution is added a saturated aqueous sodium hydrogen carbonate solution, and the mixture is extracted with ethyl acetate. The organic layer is washed with a saturated brine, dried over magnesium sulfate, and concentrated under reduced pressure. The resulting residue is purified by silica gel column chromatography (hexane:ethyl acetate=8:1) to give (2R,4S)-4-[(tert-butoxycarbonyl)-(5-bromopyrimidin-2-yl)]amino-2-ethyl-6-trifluoromethyl-3,4-dihydro-2H-quinoline-1-carboxylic acid ethyl ester (22.5 g). MS (m/z): 473/475 [M+H]+

(2) (2R,4S)-4-[(tert-Butoxycarbonyl)-(5-bromopyrimidin-2-yl)]amino-2-ethyl-6-trifluoromethyl-3,4-dihydro-2H-quinoline-1-carboxylic acid ethyl ester (5 g) is dissolved in 1,4-dioxane (60 ml), and thereto are added acrylic acid benzyl ester (2.83 g), tris(dibenzylideneacetone)dipalladium (1.2 g), tri(tert-butyl)phosphonium tetrafluoroborate (760 mg), and N,N-dicyclohexylmethylamine (1.87 g). The mixture is stirred at room temperature under nitrogen atmosphere for 2.5 hours, and thereto is added a saturated aqueous sodium hydrogen carbonate solution. The mixture is extracted with ethyl acetate, and the organic layer is washed with a saturated brine, dried over magnesium sulfate, and concentrated under reduced pressure. The resulting residue is purified by column chromatography (silica gel; hexane:ethyl acetate=4:1→3:2) to give (2R,4S)-4-{(tert-butoxycarbonyl)-[5-(2-benzyloxycarbonylvinyl)pyrimidin-2-yl]}amino-2-ethyl-6-trifluoromethyl-3,4-dihydro-2H-quinoline-1-carboxylic acid ethyl ester (3.65 g). MS (m/z): 655 [M+H]+

(3) (2R,4S)-4-{(tert-Butoxycarbonyl)-[5-(2-benzyloxycarbonylvinyl)-pyrimidin-2-yl]}amino-2-ethyl-6-trifluoromethyl-3,4-dihydro-2H-quinoline-1-carboxylic acid ethyl ester (1.65 g) is dissolved in methylene chloride (10 ml), and thereto is added trifluoroacetic acid (1 ml). The mixture is stirred at room temperature overnight, and concentrated under reduced pressure. The resulting residue is purified by column chromatography (NH-silica gel; hexane:ethyl acetate=4:1→3:2) to give (2R,4S)-4-[5-(2-benzyloxycarbonyl-vinyl)pyrimidin-2-yl]amino-2-ethyl-6-trifluoromethyl-3,4-dihydro-2H-quinoline-1-carboxylic acid ethyl ester (1.38 g). MS (m/z): 555 [M+H]+

(4) (2R,4S)-4-[5-(2-Benzyloxycarbonylvinyl)pyrimidin-2-yl]amino-2-ethyl-6-trifluoromethyl-3,4-dihydro-2H-quinoline-1-carboxylic acid ethyl ester (3.41 g) is dissolved in N,N-dimethylformamide (30 ml), and thereto is added sodium hydride (62.7%, 360 mg) under ice-cooling. The mixture is stirred under ice-cooling for 30 minutes, and thereto is added 3,5-dibromobenzyl bromide (3 g). The mixture is stirred at room temperature for one hour. To the reaction solution is added a saturated aqueous sodium hydrogen carbonate solution, and the mixture is extracted with ethyl acetate. The organic layer is washed with a saturated brine, dried over magnesium sulfate, and concentrated under reduced pressure. The resulting residue is purified by chromatography (silica gel; hexane:ethyl acetate=9:1→7:3) to give (2R,4S)-4-{[5-(2-benzyloxycarbonyl-vinyl)pyrimidin-2-yl]-(3,5-dibromobenzyl)}amino-2-ethyl-6-trifluoromethyl-3,4-dihydro-2H-quinoline-1-carboxylic acid ethyl ester (1.84 g). MS (m/z): 801/803/805 [M+H]+

Example 138

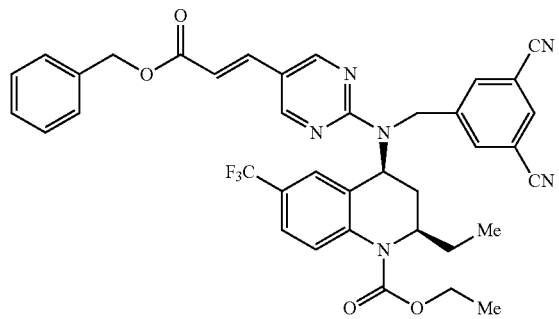

The corresponding starting compound is treated in a similar manner to Example 134 to give the compound of Example 138. MS (m/z): 695[M+H]+

Examples 139-141

The corresponding starting compounds are treated in a similar manner to Example 18-(2) to give the compounds as listed in Table 20.

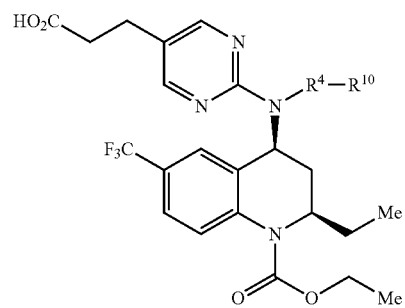

TABLE 20

| Example | R⁴—R¹⁰ | Physical properties, etc. |
|---|---|---|
| 139 | 3,5-dimethoxy-benzyl (ethyl substituent) | MS (m/z): 617 [M + H]⁺ |
| 140 | 3-CF₃, 5-CN benzyl (ethyl substituent) | MS (m/z): 650 [M + H]⁺ |
| 141 | 3,5-dicyano benzyl (ethyl substituent) | MS (m/z): 607 [M + H]⁺ |

Example 142

(2R,4S)-4-{[5-(2-Carboxyethyl)pyrimidin-2-yl]-(3,5-dimethoxy-benzyl)}amino-2-ethyl-6-trifluoromethyl-3,4-dihydro-2H-quinoline-1-carboxylic acid ethyl ester (145 mg) and triethylamine (98 μl) are dissolved in tetrahydrofuran (3 ml), and thereto is added dropwise ethyl chloro-carbonate (67 μl) at 0° C. The mixture is stirred at the same temperature for 30 minutes, and thereto is added sodium borohydride (44 mg). The mixture is further stirred at the same temperature for 3 hours. To the reaction solution are added an aqueous sodium hydrogen carbonate solution and ethyl acetate. The organic layer is washed with a saturated brine, dried over magnesium sulfate, and concentrated under reduced pressure. The resulting residue is purified by silica gel column chromatography (hexane:ethyl acetate=4:1→1:1) to give (2R,4S)-4-{(3,5-dimethoxy-benzyl)-[5-(3-hydroxypropyl)pyrimidin-2-yl]}amino-2-ethyl-6-trifluoro-methyl-3,4-dihydro-2H-quinoline-1-carboxylic acid ethyl ester (68 mg). MS (m/z): 603 [M+H]⁺

Example 143

(2R,4S)-4-[(3,5-Dimethoxybenzyl)-(5-iodopyrimidin-2-yl)]amino-2-ethyl-6-trifluoromethyl-3,4-dihydro-2H-quinoline-1-carboxylic acid ethyl ester (302 mg) is dissolved in N,N-dimethylformamide (2.5 ml), and thereto are added tetrakis(triphenylphosphine)palladium (104 mg), pyrimidine-5-boronic acid (112 mg) and sodium carbonate (114 mg). The mixture is stirred at 100° C. under nitrogen atmosphere for 4 hours. The mixture is allowed to cool to room temperature, and water is added thereto. The mixture is extracted with ethyl acetate, and the organic layer is washed with a saturated brine, dried over magnesium sulfate, and concentrated under reduced pressure. The resulting residue is purified by NH-silica gel column chromatography (hexane:ethyl acetate=2:1) to give (2R,4S)-4-[(5,5']bipyrimidin-2-yl)-(3,5-dimethoxy-benzyl)]amino-2-ethyl-6-trifluoro-methyl-3,4-dihydro-2H-quinoline-1-carboxylic acid ethyl ester (106 mg). MS (m/z): 623 [M+H]⁺

Example 144

(1) (2R,4S)-4-[(3,5-Dimethoxybenzyl)-(5-iodopyrimidin-2-yl)]amino-2-ethyl-6-trifluoromethyl-3,4-dihydro-2H-quinoline-1-carboxylic acid ethyl ester (3.89 g) is dissolved in toluene (12 ml), and thereto are added benzyl alcohol (1.2 ml), copper(I) iodide (221 mg), cesium carbonate (1.89 g), and 1,10-phenanthroline (418 mg), and the mixture is stirred at 100° C. for one day. To the reaction solution are added water and ethyl acetate, and the mixture is filtered through Celite™ to remove the insoluble materials. The organic layer is washed with a saturated brine, dried over magnesium sulfate, and concentrated under reduced pressure. The resulting residue is dissolved in toluene (12 ml), and thereto are added benzyl alcohol (0.3 ml), copper(I) iodide (221 mg), cesium carbonate (1.89 g), and 1,10-phenanthroline (418 mg). The mixture is stirred at 100° C. for one day, and allowed to cool to room temperature. To the reaction solution are added water and ethyl acetate, and the mixture is filtered through Celite™ to remove the insoluble materials. The organic layer is washed with a saturated brine, dried over magnesium sulfate, and concentrated under reduced pressure. The resulting residue is purified by silica gel column chromatography (hexane:ethyl acetate=9:1→4:1) to give (2R,4S)-4-[(3,5-dimethoxybenzyl)-(5-benzyloxypyrimidin-2-yl)]amino-2-ethyl-6-trifluoromethyl-3,4-dihydro-2H-quinoline-1-carboxylic acid ethyl ester (3.09 g). MS (m/z): 651 [M+H]⁺

(2) (2R,4S)-4-[(3,5-Dimethoxybenzyl)-(5-benzyloxypyrimidin-2-yl)]amino-2-ethyl-6-trifluoromethyl-3,4-dihydro-2H-quinoline-1-carboxylic acid ethyl ester (3.05 g) is dissolved in methanol (10 ml), and thereto is added 10% palladium-carbon (1 g). The mixture is stirred at room temperature under hydrogen atmosphere for one hour. The reaction solution is filtered, and concentrated under reduced pressure. The resulting residue is purified by silica gel column chromatography (hexane:ethyl acetate=4:1→1:1) to give (2R,4S)-4-[(3,5-dimethoxybenzyl)-(5-hydroxypyrimidin-2-yl)]amino-2-ethyl-6-trifluoromethyl-3,4-dihydro-2H-quinoline-1-carboxylic acid ethyl ester (1.84 g). MS (m/z): 561 [M+H]⁺

(3) (2R,4S)-4-[(3,5-Dimethoxybenzyl)-(5-hydroxypyrimidin-2-yl)]amino-2-ethyl-6-trifluoromethyl-3,4-dihydro-2H-quinoline-1-carboxylic acid ethyl ester (200 mg) is dissolved in tetrahydrofuran (2 ml), and thereto are added 2-methylsulfanylethanol (0.05 ml), triphenylphosphine (150 mg), a 40% solution of diethyl azodicarboxylate in toluene (0.25 ml), and the mixture is stirred at room temperature for 2.5 hours. Water is added to the mixture, and the mixture is extracted with ethyl acetate. The organic layer is washed with a saturated brine, dried over magnesium sulfate, and concentrated under reduced pressure. The resulting residue is purified by silica gel column chromatography (hexane:ethyl acetate=4:1→3:2) to give (2R,4S)-4-{(3,5-dimethoxybenzyl)-[5-(2-methylsulfanylethoxy)pyrimidin-2-yl]}amino-2-ethyl-6-trifluoromethyl-3,4-dihydro-2H-quinoline-1-carboxylic acid ethyl ester (224 mg). MS (m/z): 635 [M+H]⁺

Example 145

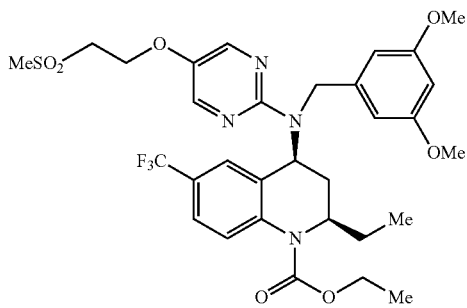

The corresponding starting compound is treated in a similar manner to Example 50 to give the compound of Example 145. MS (m/z): 667 [M+H]⁺

Examples 146-149

The corresponding starting compounds are treated in a similar manner to Example 96 to give the compounds as listed in Table 21.

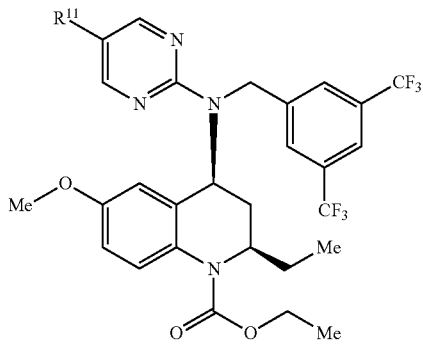

TABLE 21

| Example | R¹¹ | Physical properties, etc. |
|---|---|---|
| 146 | Me—N⌐N— | MS (m/z): 681 [M + H]⁺ |
| 147 | BnO-C(O)-N⌐N— | MS (m/z): 801 [M + H]⁺ |
| 148 | EtO-C(O)-piperidin-N— | MS (m/z): 738 [M + H]⁺ |

TABLE 21-continued

| Example | R¹¹ | Physical properties, etc. |
|---|---|---|
| 149 | Me₃C-O-C(O)-CH₂CH₂-N(Me)- | MS (m/z): 740 [M + H]⁺ |

Example 150

(2R,4S)-4-{[5-(4-Benzyloxycarbonylpiperazin-1-yl)pyrimidin-2-yl]-[3,5-bis(trifluoromethyl)benzyl]}amino-2-ethyl-6-methoxy-3,4-dihydro-2H-quinoline-1-carboxylic acid ethyl ester (1.78 g) is dissolved in ethanol (50 ml), and thereto is added 10% palladium-carbon (300 mg). The mixture is stirred at room temperature under hydrogen atmosphere for 3 hours. The catalyst (10% palladium-carbon) is removed by filtration, and the filtrate is concentrated under reduced pressure, and the resulting residue is purified by column chromatography (NH-silica gel; hexane:ethyl acetate=4:1→1:1) to give (2R,4S)-4-{[3,5-bis(trifluoromethyl)benzyl]-[5-(piperazin-1-yl)pyrimidin-2-yl]}amino-2-ethyl-6-methoxy-3,4-dihydro-2H-quinoline-1-carboxylic acid ethyl ester (470 mg). MS (m/z): 667 [M+H]⁺

Example 151

(1) (2R,4S)-4-{[3,5-Bis(trifluoromethyl)benzyl]-[5-(piperazin-1-yl)-pyrimidin-2-yl]}amino-2-ethyl-6-methoxy-3,4-dihydro-2H-quinoline-1-carboxylic acid ethyl ester (100 mg) and pyridine (18 μl) are dissolved in methylene chloride (1 ml), and thereto is added acetoxyacetic acid chloride (19.4 μl) at room temperature. The mixture is stirred overnight, and washed with a 1N hydrochloric acid. The organic layer is washed with a saturated brine, dried over magnesium sulfate, and concentrated under reduced pressure. The resulting residue is purified by column chromatography (silica gel; hexane:ethyl acetate=7:3→2:3) to give (2R,4S)-4-({5-[4-(2-acetoxyacetyl)piperazin-1-yl]pyrimidin-2-yl}-[3,5-bis(trifluoromethyl)-benzyl])amino-2-ethyl-6-methoxy-3,4-dihydro-2H-quinoline-1-carboxylic acid ethyl ester (110 mg). MS (m/z): 767 [M+H]⁺

(2) (2R,4S)-4-({5-[4-(2-Acetoxyacetyl)piperazin-1-yl]pyrimidin-2-yl}-[3,5-bis(trifluoromethyl)benzyl])amino-2-ethyl-6-methoxy-3,4-dihydro-2H-quinoline-1-carboxylic acid ethyl ester (87 mg) is dissolved in ethanol (1 ml), and thereto is added potassium carbonate (23 mg) at room temperature, and the mixture is stirred overnight. The insoluble materials are removed by filtration, and the filtrate is concentrated under reduced pressure to give (2R,4S)-4-([3,5-bis(trifluoromethyl)benzyl]-{5-[4-(2-hydroxyacetyl)piperazin-1-yl]pyrimidin-2-yl}) amino-2-ethyl-6-methoxy-3,4-dihydro-2H-quinoline-1-carboxylic acid ethyl ester (83 mg). MS (m/z): 725 [M+H]⁺

Example 152

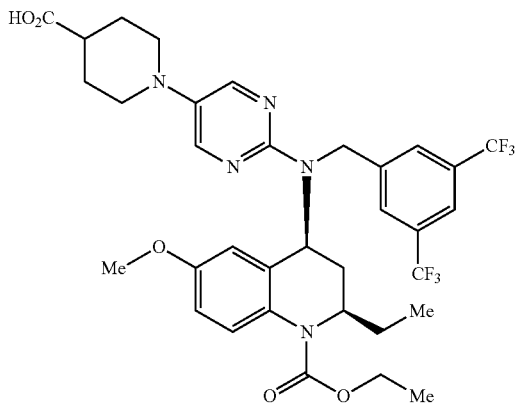

The corresponding starting compound is treated in a similar manner to Example 124 to give the compound of Example 152. MS (m/z): 710 [M+H]$^+$

Example 153

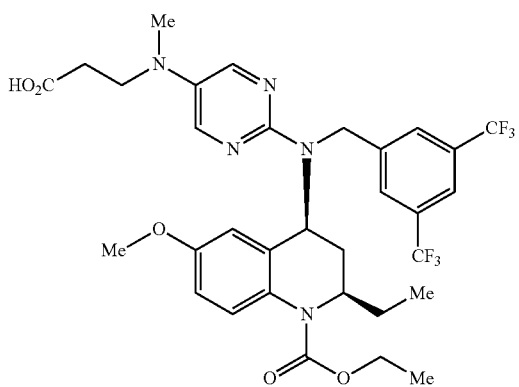

The corresponding starting compound is treated in a similar manner to Example 68 to give the compound of Example 153. MS (m/z): 684 [M+H]$^+$

Examples 154-156

The corresponding starting compounds are treated in a similar manner to Example 90 to give the compounds as listed in Table 22.

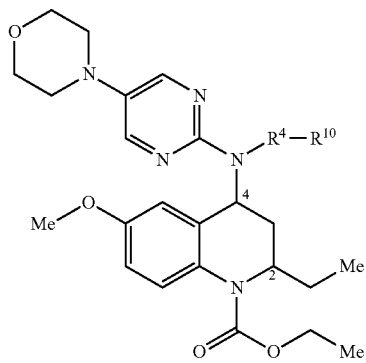

TABLE 22

| Example | Configuration | R$^4$—R$^{10}$ | Physical properties, etc. |
|---|---|---|---|
| 154 | (2R, 4S) | 3,5-dimethoxy-benzyl with ethyl | MS (m/z): 592 [M + H]$^+$ |
| 155 | (2R, 4S) | 3,5-dimethyl-benzyl with ethyl | MS (m/z): 560 [M + H]$^+$ |
| 156 | (2R*, 4S*) | 3,5-dibromo-benzyl with ethyl | MS (m/z): 688/690/692 [M + H]$^+$ |

Example 157

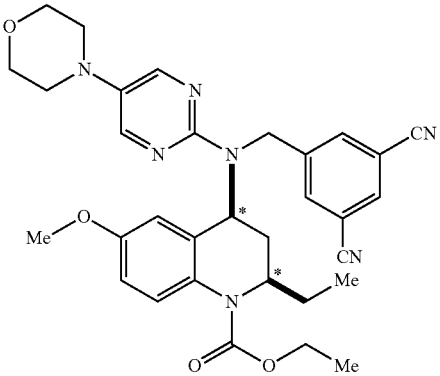

The corresponding starting compound is treated in a similar manner to Example 134 to give the compound of Example 157. MS (m/z): 582 [M+H]$^+$

Example 158

(2R,4S)-4-{[3,5-Bis(trifluoromethyl)benzyl]-(6-chloro-pyrimidin-4-yl)}amino-2-ethyl-6-trifluoromethyl-3,4-dihydro-2H-quinoline-1-carboxylic acid ethyl ester (200 mg), an excess amount of triethylamine, and aminoacetic acid tert-butyl ester (501 mg) are dissolved in 1,3-dimethyl-imidazolidinone (4 ml), and the mixture is stirred at 90° C. for 3 days. The reaction solution is cooled to room temperature, and thereto are added a saturated aqueous citric acid solution and ethyl acetate. The organic layer is washed with a saturated brine, dried over magnesium sulfate, and concentrated under reduced pressure. The resulting residue is purified by silica gel column chromatography (hexane:ethyl acetate=19:1→13:7) to give (2R,4S)-4-{[3,5-bis(trifluoromethyl)benzyl]-[6-(tert-butoxycarbonyl-methylamino)pyrimidin-4-yl]}amino-2-ethyl-6-trifluoromethyl-3,4-dihydro-2H-quinoline-1-carboxylic acid ethyl ester (22 mg). MS (m/z): 750 [M+H]$^+$

Examples 159-161

The corresponding starting compounds are treated in a similar manner to Example 158 to give the compounds as listed in Table 23.

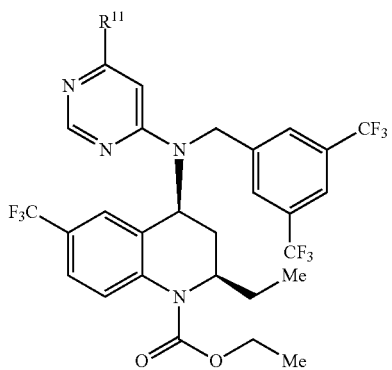

TABLE 23

| Example | R{11} | Physical properties, etc. |
|---|---|---|
| 159 | Me-C(Me)(Me)-O-C(O)-CH2-CH2-NH-Me | MS (m/z): 764 [M + H]+ |
| 160 | Me-CH2-O-C(O)-CH2-CH2-CH2-NH-Me | MS (m/z): 750 [M + H]+ |
| 161 | HO-CH2-CH2-CH2-NH-Me | MS (m/z): 694 [M + H]+ |

Examples 162-163

The corresponding starting compounds are treated in a similar manner to Example 68 to give the compounds as listed in Table 24.

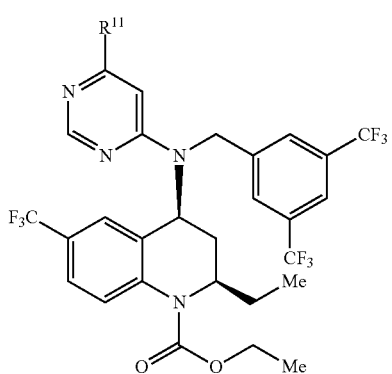

TABLE 24

| Example | R{11} | Physical properties, etc. |
|---|---|---|
| 162 | HO-C(O)-CH2-NH-Me | MS (m/z): 694 [M + H]+ |
| 163 | HO-C(O)-CH2-CH2-NH-Me | MS (m/z): 708 [M + H]+ |

Example 164

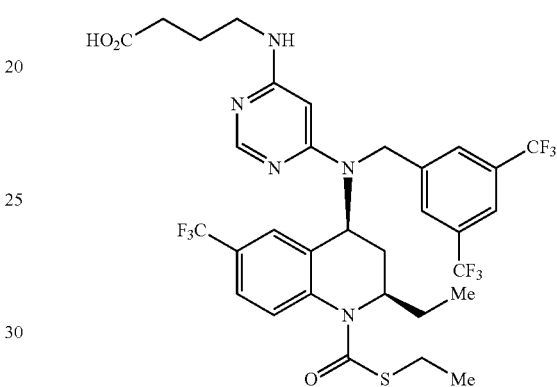

The corresponding starting compound is treated in a similar manner to Example 124 to give the compound of Example 164. MS (m/z): 722 [M+H]+

Example 165

(1) (2R,4S)-4-Amino-2-ethyl-6-trifluoromethyl-3,4-dihydro-2H-quinoline-1-carboxylic acid ethyl ester (1.5 g) and 3-bromobenzaldehyde (974 mg) are dissolved in 1,2-dichloroethane (15 ml), and thereto is added triacetoxy sodium borohydride (2.14 g) at room temperature. The mixture is stirred for 3 hours, and thereto are added an aqueous sodium hydrogen carbonate solution and ethyl acetate. The organic layer is washed with a saturated brine, dried over magnesium sulfate, and concentrated under reduced pressure. The resulting residue is purified by silica gel column chromatography (hexane:ethyl acetate=19:1→7:3) to give (2R,4S)-4-(3-bromobenzyl)amino-2-ethyl-6-trifluoromethyl-3,4-dihydro-2H-quinoline-1-carboxylic acid ethyl ester (2.45 g). MS (m/z): 485/487 [M+H]+

(2) (2R,4S)-4-(3-Bromobenzyl)amino-2-ethyl-6-trifluoromethyl-3,4-dihydro-2H-quinoline-1-carboxylic acid ethyl ester (2.32 g), bromocyane (609 mg), and sodium hydrogen carbonate (1.22 g) are suspended in ethanol (30 ml), and the mixture is stirred at room temperature overnight. To the reaction solution are added an aqueous sodium hydrogen carbonate solution and ethyl acetate. The organic layer is washed with a saturated brine, dried over magnesium sulfate, and concentrated under reduced pressure to give (2R,4S)-4-[cyano-(3-bromobenzyl)]amino-2-ethyl-6-trifluoromethyl-3,4-dihydro-2H-quinoline-1-carboxylic acid ethyl ester (2.43 g). MS (m/z): 527/529 [M+H2O]+

(3) (2R,4S)-4-[Cyano-(3-bromobenzyl)]amino-2-ethyl-6-trifluoromethyl-3,4-dihydro-2H-quinoline-1-carboxylic acid ethyl ester (2.43 g), sodium azide (3.12 g), and ammonium chloride (2.56 g) are dissolved in N,N-dimethylformamide (20 ml), and the mixture is stirred at 95° C. overnight. The reaction solution is cooled to room temperature, and thereto are added water and ethyl acetate. The organic layer is washed with a saturated brine, dried over magnesium sulfate, and concentrated under reduced pressure to give (2R,4S)-4-[(3-bromobenzyl)-(tetrazol-5-yl)]amino-2-ethyl-6-trifluoromethyl-3,4-dihydro-2H-quinoline-1-carboxylic acid ethyl ester (2.58 g). MS (m/z): 553/555 [M+H]$^+$ (4) (2R,4S)-4-[(3-Bromobenzyl)-(tetrazol-5-yl)]amino-2-ethyl-6-trifluoromethyl-3,4-dihydro-2H-quinoline-1-carboxylic acid ethyl ester (500 mg), 2-bromoethanol (271 mg), and potassium carbonate (375 mg) are dissolved in N,N-dimethylformamide (3 ml), and the mixture is stirred at 50° C. overnight. The reaction solution is cooled to room temperature, and thereto are added water and ethyl acetate. The organic layer is washed with a saturated brine, dried over magnesium sulfate, and concentrated under reduced pressure. The resulting residue is purified by silica gel column chromatography (hexane:ethyl acetate=9:1→2:3) to give (2R,4S)-4-{(3-bromobenzyl)-[2-(2-hydroxyethyl)-2H-tetrazol-5-yl]}amino-2-ethyl-6-trifluoromethyl-3,4-dihydro-2H-quinoline-1-carboxylic acid ethyl ester (394 mg). MS (m/z): 597/599 [M+H]$^+$ Example 166

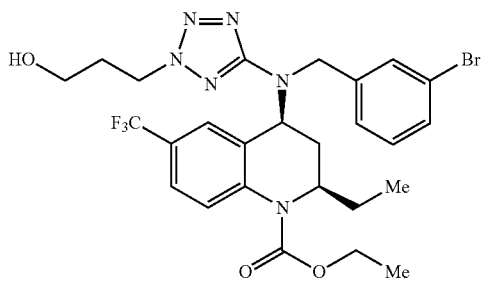

The corresponding starting compound is treated in a similar manner to Example 165-(4) to give the compound of Example 166. MS (m/z): 611/613 [M+H]$^+$ Example 167

(1) (2R,4S)-4-[(3-Bromobenzyl)-(tetrazol-5-yl)]amino-2-ethyl-6-trifluoromethyl-3,4-dihydro-2H-quinoline-1-carboxylic acid ethyl ester (500 mg), glycidol (89 µl), and triphenylphosphine (711 mg) are dissolved in tetrahydrofuran (3 ml), and thereto is added 40% azodicarboxylic acid diethyl ester in toluene (1180 mg) at room temperature, and the mixture is stirred for 15 minutes. To the reaction solution are added water and ethyl acetate, and the organic layer is washed with a saturated brine, dried over magnesium sulfate, and concentrated under reduced pressure. The resulting residue is purified by silica gel column chromatography (hexane:ethyl acetate=19:1→3:2) to give (2R,4S)-4-[(3-bromobenzyl)-(2-oxiranylmethyl-2H-tetrazol-5-yl)]amino-2-ethyl-6-trifluoromethyl-3,4-dihydro-2H-quinoline-1-carboxylic acid ethyl ester (347 mg). MS (m/z): 609/611 [M+H]$^+$ (2) (2R,4S)-4-[(3-Bromobenzyl)-(2-o)dranylmethyl-2H-tetrazol-5-yl)]amino-2-ethyl-6-trifluoromethyl-3,4-dihydro-2H-quinoline-1-carboxylic acid ethyl ester (330 mg) and morpholine (1 ml) are dissolved in ethanol (3 ml), and the mixture is stirred at room temperature overnight. To the reaction solution are added water and ethyl acetate, and the organic layer is washed with a saturated brine, dried over magnesium sulfate, and concentrated under reduced pressure. The resulting residue is purified by silica gel column chromatography (hexane:ethyl acetate=2:3→0:1) to give (2R,4S)-4-{(3-bromobenzyl)-[2-(2-hydroxy-3-morpholin-4-ylpropyl)-2H-tetrazol-5-yl]}amino-2-ethyl-6-trifluoromethyl-3,4-dihydro-2H-quinoline-1-carboxylic acid ethyl ester (315 mg). MS (m/z): 696/698 [M+H]$^+$ Example 168

(1) (2R,4S)-4-[(3-Bromobenzyl)-(tetrazol-5-yl)]amino-2-ethyl-6-trifluoromethyl-3,4-dihydro-2H-quinoline-1-carboxylic acid ethyl ester (500 mg) is treated in a similar manner to Example 167-(1) to give (2R,4S)-4-{(3-bromobenzyl)-[2-(2-methylsulfanylethyl)-2H-tetrazol-5-yl]}amino-2-ethyl-6-trifluoromethyl-3,4-dihydro-2H-quinoline-1-carboxylic acid ethyl ester (524 mg). MS (m/z): 627/629 [M+H]$^+$ (2) (2R,4S)-4-{(3-Bromobenzyl)-[2-(2-methylsulfanylethyl)-2H-tetrazol-5-yl]}amino-2-ethyl-6-trifluoromethyl-3,4-dihydro-2H-quinoline-1-carboxylic acid ethyl ester (520 mg) is treated in a similar manner to Example 50 to give (2R,4S)-4-{(3-bromobenzyl)-[2-(2-methylsulfonylethyl)-2H-tetrazol-5-yl]}amino-2-ethyl-6-trifluoromethyl-3,4-dihydro-2H-quinoline-1-carboxylic acid ethyl ester (474 mg). MS (m/z): 659/661 [M+H]$^+$ Examples 169-172

The corresponding starting compounds are treated in a similar manner to Example 10 to give the compounds as listed in Table 25.

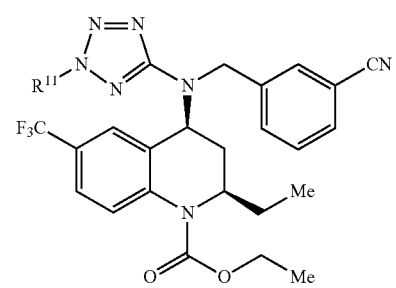

TABLE 25

| Example | R$^{11}$ | Physical properties, etc. |
|---|---|---|
| 169 | HO⌇⌇ | MS (m/z): 544 [M + H]$^+$ |
| 170 | HO⌇⌇⌇ | MS (m/z): 558 [M + H]$^+$ |
| 171 | (morpholine-CH$_2$-CH(OH)-CH$_2$-) | MS (m/z): 643 [M + H]$^+$ |

TABLE 25-continued

| Example | R[11] | Physical properties, etc. |
|---|---|---|
| 172 | Me-S(=O)(=O)-CH2CH2CH3 | MS (m/z): 606 [M + H]+ |

Example 173

(1) (2R*,4S*)-(4-Benzyloxycarbonylamino-2-ethyl-6-trifluoromethyl-3,4-dihydro-2H-quinoline (112.8 g) is dissolved in ethanol (1000 ml), and thereto is added 10% palladium-carbon (5.64 g), and the mixture is stirred at room temperature under hydrogen atmosphere overnight. The catalyst (10% palladium-carbon) is removed by filtration, and filtrate is concentrated under reduced pressure. To the residue is added hexane, and the precipitated crystals are collected by filtration to give (2R*,4S*)-4-amino-2-ethyl-6-trifluoromethyl-3,4-dihydro-2H-quinoline (70.3 g). MS (m/z): 245 [M+H]+

(2) (2R*,4S*)-4-Amino-2-ethyl-6-trifluoromethyl-3,4-dihydro-2H-quinoline (70.0 g) is dissolved in tetrahydrofuran (500 ml), and thereto is added di-tert-butyl dicarbonate (68.2 g). The mixture is stirred at room temperature overnight, and concentrated under reduced pressure. Hexane is added to the residue, and the precipitated crystals are collected by filtration to give (2R*,4S*)-4-tert-butoxycarbonylamino-2-ethyl-6-trifluoromethyl-3,4-dihydro-2H-quinoline (90.7 g). MS (m/z): 345 [M+H]+

(3) (2R*,4*S)-4-tert-Butoxycarbonylamino(2-ethyl-6-trifluoromethyl-3,4-dihydro-2H-quinoline (90.58 g) and triethylamine (44 ml) are dissolved in methylene chloride (900 ml), and thereto is added triphosgene (31.2 g) under ice-cooling. The reaction solution is stirred at room temperature for one hour, and concentrated under reduced pressure. The resulting residue is dissolved in tetrahydrofuran (900 ml), and thereto are added benzyl alcohol (54.4 ml), and sodium hydride (60%, 20.2 g) under ice-cooling. The mixture is stirred at the same temperature for 3 hours. Water and ethyl acetate are added to the reaction mixture, and the mixture is separated. The organic layer is washed with a saturated brine, dried over magnesium sulfate, and concentrated under reduced pressure. The residue is crystallized from diisopropyl ether to give (2R*,4S*)-4-tert-butoxycarbonylamino-2-ethyl-6-trifluoromethyl-3,4-dihydro-2H-quinoline-1-carboxylic acid benzyl ester (104.7 g). MS (m/z): 496 [M+H2O]+

(4) (2R*,4*S)-4-tert-Butoxycarbonylamino-2-ethyl-6-trifluoromethyl-3,4-dihydro-2H-quinoline-1-carboxylic acid benzyl ester (104.5 g) is dissolved in chloroform (500 ml), and thereto are added a 4N hydrochloric acid in ethyl acetate (500 ml) at room temperature. The mixture is stirred for 30 minutes, and concentrated under reduced pressure. To the residue is added diisopropyl ether, and the precipitated crystals are collected by filtration to give (2R*,4S*)-4-amino-2-ethyl-6-trifluoromethyl-3,4-dihydro-2H-quinoline-1-carboxylic acid benzyl ester hydrochloride (88.0 g). MS (m/z): 379 [M+H]+

(5) (2R*,4S*)-4-Amino-2-ethyl-6-trifluoromethyl-3,4-dihydro-2H-quinoline-1-carboxylic acid benzyl ester hydrochloride (25.0 g) is dissolved in a mixture of ethyl acetate and a saturated aqueous sodium hydrogen carbonate solution, and the organic layer is washed with a saturated brine, dried over magnesium sulfate, and concentrated under reduced pressure. The resulting residue (23 g) and 5-bromo-2-chloropyrimidine (29.3 g) are dissolved in 1,4-dioxane (100 ml), and thereto is added N,N-diisopropylethylamine (32 ml), and the mixture is refluxed overnight. The reaction solution is cooled to room temperature, and thereto are added water and diethyl ether, and the mixture is separated. The organic layer is washed with a saturated brine, dried over magnesium sulfate, and concentrated under reduced pressure. The resulting residue is purified by silica gel column chromatography (hexane:ethyl acetate=6:1→2:1) to give (2R*,4S*)-4-(5-bromopyrimidin-2-yl)amino-2-ethyl-6-trifluoromethyl-3,4-dihydro-2H-quinoline-1-carboxylic acid benzyl ester (24.0 g). MS (m/z): 535/537 [M+H]+

(6) (2R*,4S*)-4-(5-Bromopyrimidin-2-yl)amino-2-ethyl-6-trifluoromethyl-3,4-dihydro-2H-quinoline-1-carboxylic acid benzyl ester (13 g) is treated in a similar manner to Example 1-(2) to give (2R*,4S*)-4-{[3,5-bis(trifluoromethyl)benzyl]-(5-bromopyrimidin-2-yl)}amino-2-ethyl-3,4-dihydro-2H-quinoline-1-carboxylic acid benzyl ester (20.6 g). MS (m/z): 761/763 [M+H]+

(7) (2R*,4S*)-4-{[3,5-Bis(trifluoromethyl)benzyl]-(5-bromopyrimidin-2-yl)}amino-2-ethyl-3,4-dihydro-2H-quinoline-1-carboxylic acid benzyl ester (18.3 g) is treated in a similar manner to Example 1-(3) to give (2R*,4S*)-4-{[3,5-bis(trifluoromethyl)benzyl]-[5-(morpholin-4-yl)pyrimidin-2-yl]}amino-2-ethyl-3,4-dihydro-6-trifluoromethyl-2H-quinoline-1-carboxylic acid benzyl ester (11.2 g). MS (m/z): 768 [M+H]+

(8) (2R*,4S*)-4-{[3,5-Bis(trifluoromethyl)benzyl]-[5-(morpholin-4-yl)-pyrimidin-2-yl]}amino-2-ethyl-6-trifluoromethyl-3,4-dihydro-2H-quinoline-1-carboxylic acid benzyl ester (11.2 g) is treated in a similar manner to Example 150 to give (2R*,4S*)-4-{[3,5-bis(trifluoromethyl)benzyl]-[5-(morpholin-4-yl)pyrimidin-2-yl]}amino-2-ethyl-6-trifluoromethyl-3,4-dihydro-2H-quinoline (8.9 g). MS (m/z): 634 [M+H]+

Example 174

(2R*,4S*)-4-{[3,5-Bis(trifluoromethyl)benzyl]-[5-(morpholin-4-yl)pyrimidin-2-yl]}amino-2-ethyl-6-trifluoromethyl-3,4-dihydro-2H-quinoline (500 mg) and triethylamine (132 μl) are dissolved in methylene chloride (5 ml), and thereto is added triphosgene (94 mg) at room temperature, and the mixture is stirred for one hour. The reaction solution is concentrated under reduced pressure, and the resulting residue is separated into ethyl acetate and a saturated aqueous sodium hydrogen carbonate solution. The organic layer is washed with a saturated brine, dried over magnesium sulfate, and concentrated under reduced pressure. The resulting residue is dissolved in tetrahydrofuran (5 ml), and ethylene glycol (0.5 ml), triethylamine (295 ml) and 4-dimethylaminopyridine (26 mg) are added thereto. The mixture is stirred at room temperature overnight. The reaction solution is separated into ethyl acetate and a saturated aqueous sodium hydrogen carbonate solution. The organic layer is washed with a saturated brine, dried over magnesium sulfate, and concentrated under reduced pressure. The residue is purified by silica gel column chromatography (hexane:ethyl acetate=3:1→2:3) to give (2R*,4S*)-4-{[3,5-bis(trifluoromethyl)benzyl]-[(5-morpholin-4-yl)pyrimidin-2-yl]}amino-2-ethyl-6-trifluoromethyl-3,4-dihydro-2H-quinoline-1-carboxylic acid 2-hydroxyethyl ester (430 mg). MS (m/z): 722 [M+H]+

Example 175

(1) (2R,4S)-4-Amino-2-ethyl-6-trifluoromethyl-3,4-dihydro-2H-quinoline-1-carboxylic acid ethyl ester (1.28 g), 2-chloroxazole-4-carboxylic acid ethyl ester (1.44 g) and diisopropylethylamine (1.42 ml) are dissolved in 1,4-dioxane (10 ml), and the mixture is stirred at 130° C. overnight. The reaction solution is cooled to room temperature, and water and ethyl acetate are added thereto. The organic layer is washed with a saturated brine, dried over sodium sulfate, and concentrated under reduced pressure. The resulting residue is purified by silica gel column chromatography (hexane:ethyl acetate=4:1→1:1) to give (2R,4S)-4-(4-ethoxycarbonyloxazol-2-yl)amino-2-ethyl-6-trifluoromethyl-3,4-dihydro-2H-quinoline-1-carboxylic acid ethyl ester (1.13 g). MS (m/z): 456 [M+H]$^+$ (2) (2R,4S)-4-(4-Ethoxycarbonyloxazol-2-yl)amino-2-ethyl-6-trifluoro-methyl-3,4-dihydro-2H-quinoline-1-carboxylic acid ethyl ester (1.12 g) is treated in a similar manner to Example 1-(2) to give (2R,4S)-4-{[3,5-bis-(trifluoromethyl)benzyl]-(4-ethoxycarbonyloxazol-2-yl)}amino-2-ethyl-6-trifluoromethyl-3,4-dihydro-2H-quinoline-1-carboxylic acid ethyl ester (928 mg). MS (m/z): 682 [M+H]$^+$ Example 176

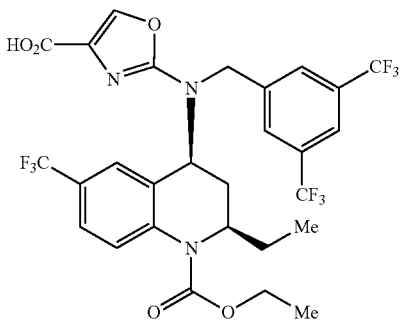

The corresponding starting compound is treated in a similar manner to Example 124 to give the compound of Example 176. MS (m/z): 654 [M+H]$^+$ Example 177

(1) (2R,4S)-4-{[3,5-Bis(trifluoromethyl)benzyl]-(5-bromopyrimidin-2-yl)}amino-2-ethyl-6-trifluoromethyl-3,4-dihydro-2H-quinoline-1-carboxylic acid ethyl ester (32.25 g), [1,1'-bis(diphenylphosphino)ferrocene]-dichloropalladium (1.012 g), potassium acetate (13.6 g), and bis-(pinacolate)diboron (17.56 g) are dissolved in dimethylsulfoxide (200 ml), and the mixture is stirred at 80° C. under nitrogen atmosphere for one hour. The reaction solution is cooled to room temperature, and thereto are added water and ethyl acetate. The organic layer is washed with a saturated brine, dried over magnesium sulfate, and concentrated under reduced pressure. The resulting residue is dissolved in tetrahydrofuran (100 ml), and thereto is added dropwise a 30% aqueous hydrogen peroxide solution (70 ml) under ice-cooling. One hour thereafter, a saturated aqueous sodium thiosulfate solution is added to the mixture, and the excess hydrogen peroxide is consumed. The mixture is separated into water and ethyl acetate. The organic layer is washed with a saturated brine, dried over magnesium sulfate, and concentrated under reduced pressure. The resulting residue is purified by silica gel column chromatography (hexane:ethyl acetate=5:1→3:1) to give (2R,4S)-4-{[3,5-bis(trifluoro-methyl)benzyl]-(5-hydroxypyrimidin-2-yl)}amino-2-ethyl-6-trifluoromethyl-3,4-dihydro-2H-quinoline-1-carboxylic acid ethyl ester (19.22 g). MS (m/z): 637 [M+H]$^+$ (2) (2R,4S)-4-{[3,5-Bis(trifluoromethyl)benzyl]-(5-hydroxypyrimidin-2-yl)}amino-2-ethyl-6-trifluoromethyl-3,4-dihydro-2H-quinoline-1-carboxylic acid ethyl ester (6.5 g) and 4-bromobutyric acid ethyl ester (2.19 g) are dissolved in N,N-dimethylformamide (50 ml), and thereto is added potassium carbonate (1.69 g), and the mixture is stirred at 45° C. overnight. Ethyl acetate and water are added to the mixture, and the organic layer is washed with a saturated brine, dried over magnesium sulfate, and concentrated under reduced pressure. The resulting residue is purified by silica gel column chromatography (hexane:ethyl acetate=95:5→3:1) to give (2R,4S)-4-{[3,5-bis(trifluoromethyl)benzyl]-[5-(3-ethoxycarbonylpropoxy)-pyrimidin-2-yl]}amino-2-ethyl-6-trifluoromethyl-3,4-dihydro-2H-quinoline-1-carboxylic acid ethyl ester (6.52 g). MS (m/z): 751 [M+H]$^+$ (3) (2R,4S)-4-{[3,5-Bis(trifluoromethyl)benzyl]-[5-(3-ethoxycarbonyl-propoxy)pyrimidin-2-yl]}amino-2-ethyl-6-trifluoromethyl-3,4-dihydro-2H-quinoline-1-carboxylic acid ethyl ester (6.5 g) is dissolved in ethanol (65 ml), and thereto is added a 2N aqueous sodium hydroxide solution (13 ml). The mixture is stirred at room temperature overnight. The reaction solution is concentrated under reduced pressure, and to the residue are added ethyl acetate and a 1N aqueous hydrochloric acid, and the mixture is separated. The organic layer is washed with a saturated brine, dried over magnesium sulfate and concentrated under reduced pressure. The resulting residue is purified by silica gel column chromatography (chloroform:methanol=1:0→95:5) to give (2R,4S)-4-{[3,5-bis(trifluoromethyl)benzyl]-[5-(3-carboxypropoxy)pyrimidin-2-yl]}amino-2-ethyl-6-trifluoromethyl-3,4-dihydro-2H-quinoline-1-carboxylic acid ethyl ester (6.16 g). MS (m/z): 723 [M+H]$^+$ Example 178

(2R,4S)-4-{[3,5-Bis(trifluoromethyl)benzyl]-[5-(3-carboxypropoxy)-pyrimidin-2-yl]}amino-2-ethyl-6-trifluoromethyl-3,4-dihydro-2H-quinoline-1-carboxylic acid ethyl ester (300 mg) is dissolved in ethanol (3 ml), and thereto is added a 2N aqueous sodium hydroxide solution (207 µl). The reaction solution is concenrated to dryness under reduced pressure to give (2R,4S)-4-{[3,5-bis(trifluoromethyl)benzyl]-[5-(3-carboxypropoxy)pyrimidin-2-yl]}amino-2-ethyl-6-trifluoromethyl-3,4-dihydro-2H-quinoline-1-carboxylic acid ethyl ester sodium salt (308 mg). MS (m/z): 721 [M−Na]$^−$ Example 179

(2R,4S)-4-{[3,5-Bis(trifluoromethyl)benzyl]-[5-(3-carboxypropoxy)-pyrimidin-2-yl]}amino-2-ethyl-6-trifluoromethyl-3,4-dihydro-2H-quinoline-1-carboxylic acid ethyl ester sodium salt (258 mg) is suspended in water (10 ml), and thereto is added a solution of calcium chloride (154 mg) in water (0.6 ml), and the mixture is stirred at room temperature overnight. Chloroform and water are added to the mixture, and the mixture is separated. The organic layer is washed with a saturated brine, dried over magnesium sulfate and concentrated under reduced pressure. The residue is dissolved in ethyl acetate, and thereto is added n-hexane. The precipitated crystals are collected by filtration to give (2R,4S)-4-{[3,5-bis(trifluoromethyl)benzyl]-[5-(3-carboxypropoxy)pyrimidin-2-yl]}amino-2-ethyl-6-trifluoromethyl-3,4-dihydro-2H-quinoline-1-carboxylic acid ethyl ester hemicalcium salt (169 mg). MS (m/z): 721 [M−1/2Ca]−

Example 180

(2R,4S)-4-{[3,5-Bis(trifluoromethyl)benzyl]-[5-(3-carboxypropoxy)-pyrimidin-2-yl]}amino-2-ethyl-6-trifluoromethyl-3,4-dihydro-2H-quinoline-1-carboxylic acid ethyl ester (250 mg) is dissolved in ethanol (2 ml), and thereto is added a 2N aqueous potassium hydroxide solution (173 µl). The reaction solution is concentrated to dryness under reduced pressure to give (2R,4S)-4-{[3,5-bis(trifluoromethyl)benzyl]-[5-(3-carboxypropoxy)-pyrimidin-2-yl]} amino-2-ethyl-6-trifluoromethyl-3,4-dihydro-2H-quinoline-1-carboxylic acid ethyl ester potassium salt (266 mg). MS (m/z): 721 [M−K]−

Examples 181-186

The corresponding starting compounds are treated in a similar manner to Example 177 (2) to give the compounds as listed in Table 26.

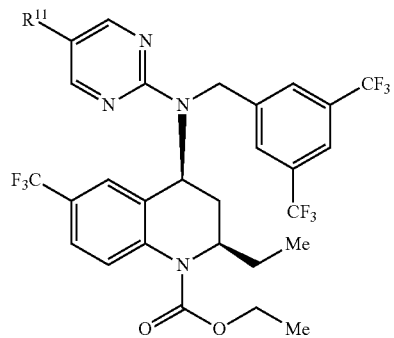

TABLE 26

| Ex. No. | $R^{11}$ | Physical properties, etc. |
|---|---|---|
| 181 | Me-O-C(=O)-CH2-O-Me | MS (m/z): 723 [M + H]+ |
| 182 | Me-O-C(=O)-(CH2)3-O-Me | MS (m/z): 765 [M + H]+ |
| 183 | Me-O-C(=O)-(CH2)4-O-Me | MS (m/z): 779 [M + H]+ |
| 184 | Me-O-C(=O)-(CH2)5-O-Me | MS (m/z): 793 [M + H]+ |
| 185 | Me-O-C(=O)-(4-C6H4)-CH2-O-Me | MS (m/z): 785 [M + H]+ |
| 186 | Me-O-C(=O)-(3-C6H4)-CH2-O-Me | MS (m/z): 785 [M + H]+ |

Example 187

(1) (2R,4S)-4-{[3,5-Bis(trifluoromethyl)benzyl]-(5-hydroxypyrimidin-2-yl)}amino-2-ethyl-6-trifluoromethyl-3,4-dihydro-2H-quinoline-1-carboxylic acid ethyl ester (2.0 g) is dissolved in N,N-dimethylformamide (30 ml), and thereto are added ethyl bromoacetate (520 µl), potassium carbonate (650 mg). The mixture is stirred at room temperature for 3.5 hours. Water and ethyl acetate are added to the mixture, and the mixture is separated. The organic layer is washed with a saturated brine, dried over magnesium sulfate, and concentrated under reduced pressure. The resulting residue is purified by silica gel column chromatography (hexane:ethyl acetate=19:1→41:9) to give (2R,4S)-4-{[3,5-bis(trifluoromethyl)benzyl]-(5-ethoxy-carbonylmethoxypyrimidin-2-yl)}amino-2-ethyl-6-trifluoromethyl-3,4-dihydro-2H-quinoline-1-carboxylic acid ethyl ester (2.07 g). MS (m/z): 723 [M+H]$^+$ (2) (2R,4S)-4-{[3,5-Bis(trifluoromethyl)benzyl]-(5-ethoxy-carbonyl-methoxypyrimidin-2-yl)}amino-2-ethyl-6-trifluoromethyl-3,4-dihydro-2H-quinoline-1-carboxylic acid ethyl ester (2.07 g) is dissolved in ethanol (30 ml), and thereto is added dropwise a 1N aqueous sodium hydroxide solution. The mixture is stirred for 2.5 hours, and thereto are added a 6N hydrochloric acid and ethyl acetate. The mixture is separated, and the organic layer is washed with a saturated brine, dried over magnesium sulfate and concentrated under reduced pressure. The resulting residue is purified by silica gel column chromatography (chloroform:methanol=1:0→9:1) to give (2R,4S)-4-{[3,5-bis(trifluoromethyl)benzyl]-(5-carboxy-methoxypyrimidin-2-yl)}amino-2-ethyl-6-trifluoromethyl-3,4-dihydro-2H-quinoline-1-carboxylic acid ethyl ester (1.83 g). MS (m/z): 695 [M+H]$^+$ (3) (2R,4S)-4-{[3,5-Bis(trifluoromethyl)benzyl]-(5-carboxymethoxy-pyrimidin-2-yl)}amino-2-ethyl-6-trifluoromethyl-3,4-dihydro-2H-quinoline-1-carboxylic acid ethyl ester (200 mg) is dissolved in tetrahydrofuran (4 ml), and thereto are added ethyl aminoacetate hydrochloride (48 mg), 1-hydroxybenzotriazole dihydrate (47 mg), 1-ethyl-3-(3-dimethylamino-propyl)carbodiimide hydrochloride (66 mg), and triethylamine (49 µl), and the mixture is stirred at room temperature for one hour. Water and ethyl acetate are added to the mixture, and the mixture is separated. The organic layer is washed with a saturated brine, dried over magnesium sulfate and concentrated under reduced pressure. The resulting residue is purified by silica gel column chromatography (hexane:ethyl acetate=4:1 →3:2) to give (2R,4S)-4-([3,5-bis(trifluoromethyl)benzyl]-{5-[(ethoxycarbonylmethylcarbamoyl)methoxy]pyrimidin-2-yl})amino-2-ethyl-6-trifluoromethyl-3,4-dihydro-2H-quinoline-1-carboxylic acid ethyl ester (165 mg). MS (m/z): 780 [M+H]$^+$

Examples 188-190

The corresponding starting compounds are treated in a similar manner to Example 187 (3) to give the compounds as listed in Table 27.

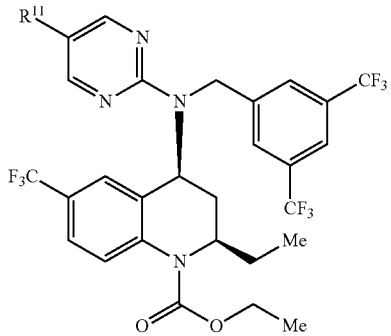

TABLE 27

| Ex. No. | R$^{11}$ | Physical properties, etc. |
|---|---|---|
| 188 | Me~O~\~N(Me)~\~O~Me (ethyl N-methyl-N-(methoxyacetyl)glycinate group) | MS (m/z): 794 [M + H]$^+$ |
| 189 | Me~O~C(O)~piperidine-N-C(O)CH$_2$OMe | MS (m/z): 834 [M + H]$^+$ |
| 190 | (S)-prolinyl N-C(O)CH$_2$OMe, CO$_2$Me | MS (m/z): 806 [M + H]$^+$ |

Example 191

(1) (2R,4S)-4-{[3,5-Bis(trifluoromethyl)benzyl]-(5-hydroxypyrimidin-2-yl)}amino-2-ethyl-6-trifluoromethyl-3,4-dihydro-2H-quinoline-1-carboxylic acid ethyl ester (300 mg) is dissolved in tetrahydrofuran (4 ml), and thereto are added (2S,4R)-1-benzyloxycarbonyl-2-methoxycarbonyl-4-hydroxy-pyrrolidine (395 mg) and triphenylphosphine (740 mg). To the mixture is added dropwise a 40% solution of diethyl azodicarboxylate in toluene (1.23 ml) under ice-cooling, and the mixture is stirred at room temperature overnight. Water and ethyl acetate are added to the mixture, and the mixture is separated. The organic layer is washed with a saturated brine, dried over magnesium sulfate, and concentrated under reduced pressure. The resulting residue is purified by silica gel column chromatography (hexane:ethyl acetate=9:1→4:1) to give (2R,4S)-4-([3,5-bis(trifluoro-methyl)benzyl]-{5-[(S)-2-((S)-methoxycarbonyl)-1-benzyloxycarbonyl-pyrrolidin-4-yloxy]pyrimidin-2-yl}) amino-2-ethyl-6-trifluoromethyl-3,4-dihydro-2H-quinoline-1-carboxylic acid ethyl ester (543 mg) as a crude product. MS (m/z): 898 [M+H]$^+$ (2) The crude (2R,4S)-4-([3,5-Bis(trifluoromethyl)benzyl]-{5-[(S)-2-((S)-methoxycarbonyl)-1-benzyloxycarbonylpyrrolidin-4-yloxy]pyrimidin-2-yl})-amino-2-ethyl-6-trifluoromethyl-3,4-dihydro-2H-quinoline-1-carboxylic acid ethyl ester (1.39 g) is dissolved in methanol (15 ml), and thereto is added 10% palladium-carbon (300 mg). The mixture is stirred under hydrogen atmosphere for 3 hours, filtered, and concentrated under reduced pressure. The resulting residue is purified by silica gel column chromatography (hexane:ethyl acetate=3:2→2:3→0:1) to give (2R,4S)-4-([3,5-bis(trifluoromethyl)benzyl]-{5-[(S)-2-((S)-methoxycarbonyl)pyrrolidin-4-yl]pyrimidin-2-yloxy}) amino-2-ethyl-6-trifluoromethyl-3,4-dihydro-2H-quinoline-1-carboxylic acid ethyl ester (667 mg). MS (m/z): 764 [M+H]$^+$

Example 192

(2R,4S)-4-([3,5-Bis(trifluoromethyl)benzyl]-{5-[(S)-2-((S)-methoxy-carbonyl)pyrrolidin-4-yloxy]pyrimidin-2-yl}) amino-2-ethyl-6-trifluoromethyl-3,4-dihydro-2H-quinoline-1-carboxylic acid ethyl ester (200 mg) is dissolved in tetrahydrofuran (5 ml), and thereto are added acetyl chloride (44 μl) and triethylamine (88 μl) under ice-cooling. The mixture is stirred at room temperature for 4 hours, and separated into a saturated aqueous sodium hydrogen carbonate solution and ethyl acetate. The organic layer is washed with a saturated brine, dried over magnesium sulfate and concentrated under reduced pressure. The resulting residue is purified by silica gel column chromatography (hexane:ethyl acetate=3:2→2:3) to give (2R,4S)-4-([3,5-bis(trifluoromethyl)benzyl]-{5-[(S)-2-((S)-methoxycarbonyl)-1-acetylpyrrolidin-4-yloxy]pyrimidin-2-yl})amino-2-ethyl-6-trifluoromethyl-3,4-dihydro-2H-quinoline-1-carboxylic acid ethyl ester (212 mg). MS (m/z): 806 [M+H]$^+$

Example 193

(1) (2R,4S)-4-{[3,5-Bis(trifluoromethyl)benzyl]-(5-hydroxypyrimidin-2-yl)}amino-2-ethyl-6-trifluoromethyl-3,4-dihydro-2H-quinoline-1-carboxylic acid ethyl ester (1.5 g) is dissolved in N,N-dimethylformamide (20 ml), and thereto are added 2-bromoethanol (1.25 ml) and potassium carbonate (490 mg), and the mixture is stirred at 60° C. overnight. The reaction solution is cooled to room temperature, and water and ethyl acetate are added thereto, and the mixture is separated. The organic layer is washed with a saturated brine, dried over magnesium sulfate and concentrated under reduced pressure. The resulting residue is purified by silica gel column chromatography (hexane: ethyl acetate=4:1→1:1) to give (2R,4S)-4-{[3,5-bis(trifluoromethyl)benzyl]-[5-(2-hydroxyethoxy)pyrimidin-2-yl]}amino-2-ethyl-6-trifluoromethyl-3,4-dihydro-2H-quinoline-1-carboxylic acid ethyl ester (493 mg). MS (m/z): 681 [M+H]$^+$ (2) (2R,4S)-4-{[3,5-Bis(trifluoromethyl)benzyl]-[5-(2-hydroxyethoxy)-pyrimidin-2-yl]}amino-2-ethyl-6-trifluoromethyl-3,4-dihydro-2H-quinoline-1-carboxylic acid ethyl ester (493 mg) is dissolved in methylene chloride (10 ml), and thereto are added triphenylphosphine (380 mg) and carbon tetrabromide (480 mg). The mixture is stirred at room temperature for 30 minutes, and thereto are added a saturated aqueous sodium hydrogen carbonate solution and chloroform, and the mixture is separated. The organic layer is washed with a saturated brine, dried over magnesium sulfate and concentrated under reduced pressure. The resulting residue is purified by silica gel column chromatography (hexane:ethyl acetate=9:1→4:1) to give (2R,4S)-4-{[3,5-bis(trifluoromethyl)benzyl]-[5-(2-bromoethoxy)pyrimidin-2-yl]}amino-2-ethyl-6-trifluoromethyl-3,4-dihydro-2H-quinoline-1-carboxylic acid ethyl ester (298 mg). MS (m/z): 743/745 [M+H]$^+$ (3) (2R,4S)-4-{[3,5-Bis(trifluoromethyl)benzyl]-[5-(2-bromoethoxy)-pyrimidin-2-yl]}amino-2-ethyl-6-trifluoromethyl-3,4-dihydro-2H-quinoline-1-carboxylic acid ethyl ester (298 mg) is dissolved in N,N-dimethyl-formamide (5 ml), and piperidine-4-carboxylic acid ethyl ester (185 μl) and potassium carbonate (166 mg) are added thereto, and the mixture is stirred at room temperature for 1.5 hour. The mixture is stirred at 60° C. for 2.5 hours. A saturated aqueous sodium hydrogen carbonate solution and ethyl acetate are added to the mixture, and the mixture is separated. The organic layer is washed with a saturated brine, dried over magnesium sulfate and concentrated under reduced pressure. The resulting residue is purified by silica gel column chromatography (hexane:ethyl acetate=1:1→1:4) to give (2R,4S)-4-([3,5-bis(trifluoromethyl)benzyl]-{5-[2-(4-ethoxycarbonylpiperidin-1-yl)ethoxy]pyrimidin-2-yl})amino-2-ethyl-6-trifluoromethyl-3,4-dihydro-2H-quinoline-1-carboxylic acid ethyl ester (245 mg). MS (m/z): 820 [M+H]$^+$

Example 194

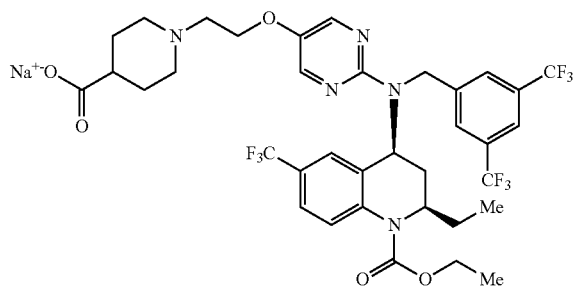

The corresponding starting compound is treated in a similar manner to Example 177 (3) and Example 178 to give the compound of Example 194. MS (m/z): 790 [M-Na]⁻

Example 195

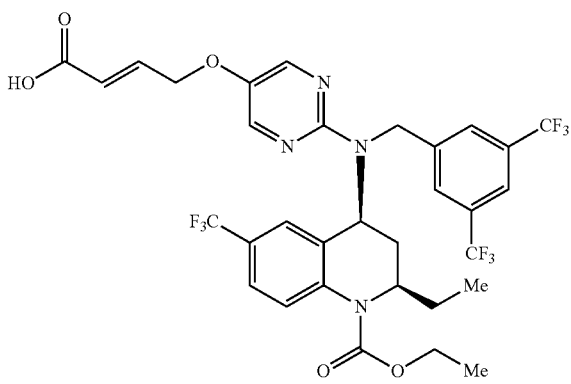

The corresponding starting compound is treated in a similar manner to Example 177 (2)-(3) to give the compound of Example 195. MS (m/z): 721 [M+H]⁺

Example 196

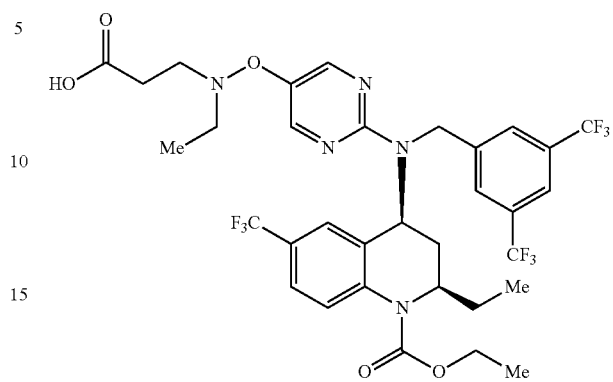

The corresponding starting compound is treated in a similar manner to Example 187 (3) and Example 177 (3) to give the compound of Example 196. MS (m/z): 794 [M+H]⁺

Examples 197-208

The corresponding starting compounds are treated in a similar manner to Example 177 (3) to give the compounds as listed in Table 28.

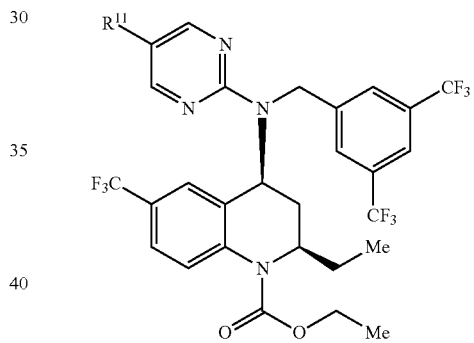

TABLE 28

| Ex. No. | R¹¹ | Physical properties, etc. |
|---|---|---|
| 197 | HO-C(=O)-CH₂-O-CH₃ | MS (m/z): 695 [M + H]⁺ |
| 198 | HO-C(=O)-(CH₂)₃-O-CH₃ | MS (m/z): 737 [M + H]⁺ |
| 199 | HO-C(=O)-(CH₂)₄-O-CH₃ | MS (m/z): 751 [M + H]⁺ |
| 200 | HO-C(=O)-(CH₂)₅-O-CH₃ | MS (m/z): 765 [M + H]⁺ |

TABLE 28-continued

| Ex. No. | R[11] | Physical properties, etc. |
|---|---|---|
| 201 | 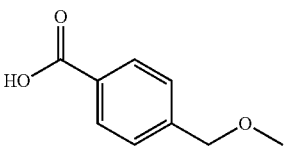 | MS (m/z): 771 [M + H]+ |
| 202 | 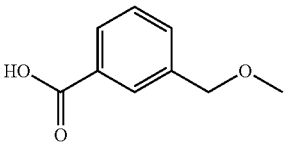 | MS (m/z): 771 [M + H]+ |
| 203 | 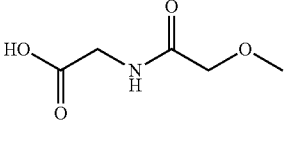 | MS (m/z): 752 [M + H]+ |
| 204 | 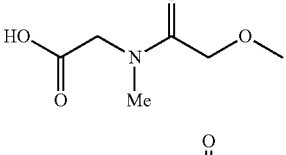 | MS (m/z): 766 [M + H]+ |
| 205 | 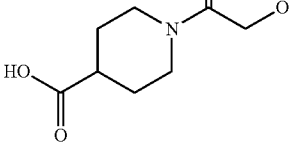 | MS (m/z): 806 [M + H]+ |
| 206 | 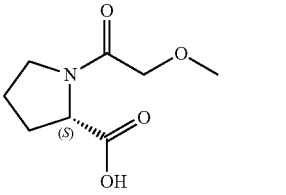 | MS (m/z): 792 [M + H]+ |
| 207 | 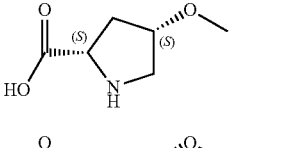 | MS (m/z): 750 [M + H]+ |
| 208 | 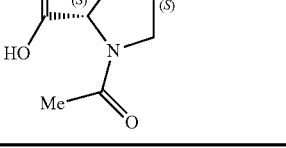 | MS (m/z): 792 [M + H]+ |

Example 209

(2R,4S)-4-{[3,5-Bis(trifluoromethyl)benzyl]-(5-hydroxy-pyrimidin-2-yl)}amino-2-ethyl-6-trifluoromethyl-3,4-dihydro-2H-quinoline-1-carboxylic acid ethyl ester (300 mg) is dissolved in tetrahydrofuran (3 ml), and thereto are added potassium tert-butoxide (53 mg) and β-propiolactone (30 μl) at room temperature. The reaction solution is stirred at room temperature overnight, and thereto are added ethyl acetate and 1N hydrochloric acid, and the mixture is separated. The organic layer is washed with a saturated brine, and dried over magnesium sulfate and concentrated under reduced pressure. The resulting residue is dissolved in a mixture of tetrahydrofuran and methanol (5:1,2 ml), and thereto is added a 2M solution of trimethylsilyldiazomethane in hexane (353 μl). Thirty minutes thereafter, the reaction solution is concentrated under reduced pressure, and the resulting residue is purified by NH-silica gel column chromatography (hexane: ethyl acetate=95:5→3:1) to give (2R,4S)-4-{[3,5-bis-(trifluoromethyl)benzyl]-[5-(2-methoxycarbonylethoxy)pyrimidin-2-yl]}-amino-2-ethyl-6-trifluoromethyl-3,4-dihydro-2H-quinoline-1-carboxylic acid ethyl ester (27 mg). MS (m/z): 723 [M+H]+

Example 210

(2R,4S)-4-{[3,5-Bis(trifluoromethyl)benzyl]-(5-hydroxypyrimidin-2-yl)}amino-2-ethyl-6-trifluoromethyl-3,4-dihydro-2H-quinoline-1-carboxylic acid ethyl ester (900 mg) is dissolved in tetrahydrofuran (9 ml), and thereto are added potassium tert-butoxide (158 mg) and β-propiolactone (89 μl) at room temperature. The reaction solution is stirred at room temperature overnight, and thereto are added ethyl acetate and 1N hydrochloric acid, and the mixture is separated. The organic layer is washed with a saturated brine, dried over magnesium sulfate and concentrated under reduced pressure. The resulting residue is purified by silica gel column chromatography (chloroform:methanol=1:0→9:1) to give (2R,4S)-4-{[3,5-bis(trifluoromethyl)benzyl]-[5-(2-carboxyethoxy)pyrimidin-2-yl]}amino-2-ethyl-6-trifluoromethyl-3,4-dihydro-2H-quinoline-1-carboxylic acid ethyl ester (178 mg). MS (m/z): 709 [M+H]+

Example 211

(1) (2R,4S)-4-{[3,5-Bis(trifluoromethyl)benzyl]-(5-hydroxypyrimidin-2-yl)}amino-2-ethyl-6-trifluoromethyl-3,4-dihydro-2H-quinoline-1-carboxylic acid ethyl ester (500 mg) is dissolved in N,N-dimethylformamide (5 ml), and thereto are added 2-(2-chloroethoxy)ethanol (830 μl), and potassium carbonate (1.09 g), and the mixture stirred at room temperature for 3 hours. The reaction mixture is stirred at 60° C. overnight. The reaction solution is cooled to room temperature, and the mixture is separated into water and ethyl acetate. The organic layer is washed with a saturated brine, dried over magnesium sulfate and concentrated under reduced pressure. The resulting residue is purified by silica gel column chromatography (hexane:ethyl acetate=4:1→3:2) to give (2R,4S)-4-([3,5-bis(trifluoromethyl)benzyl]-{5-[2-(2-hydroxyethoxy)ethoxy]pyrimidin-2-yl}) amino-2-ethyl-6-trifluoro methyl-3,4-dihydro-2H-quinoline-1-carboxylic acid ethyl ester (710 mg) as a crude product. MS (m/z): 725 [M+H]+
(2) The crude (2R,4S)-4-([3,5-bis(trifluoromethyl)benzyl]-{5-[2-(2-hydroxyethoxy)ethoxy]pyrimidin-2-yl})amino-2-ethyl-6-trifluoromethyl-3,4-dihydro-2H-quinoline-1-carboxylic acid ethyl ester (706 mg) is dissolved in methylene chloride (10 ml), and thereto is added 1,1,1-tris(acetoxy)-1,1-dihydro-1,2-benziodoxol-3-(1H)-one (826 mg), and the mixture is stirred at room temperature overnight. A saturated aqueous sodium hydrogen carbonate solution and ethyl acetate are added, and the mixture is separated. The organic layer is washed with a saturated brine, dried over magnesium sulfate and concentrated under reduced pressure. The resulting residue is purified by silica gel column chromatography (hexane:ethyl acetate=4:1→3:2) to give (2R,4S)-4-{[3,5-bis(trifluoromethyl)benzyl]-[5-(2-formylmethoxyethoxy)pyrimidin-2-yl]}amino-2-ethyl-6-trifluoromethyl-3,4-dihydro-2H-quinoline-1-carboxylic acid ethyl ester (190 mg). MS (m/z): 723 [M+H]+

Example 212

(2R,4S)-4-([3,5-Bis(trifluoromethyl)benzyl]-{5-[2-(2-oxoethoxy)-ethoxy]pyrimidin-2-yl})amino-2-ethyl-6-trifluoromethyl-3,4-dihydro-2H-quinoline-1-carboxylic acid ethyl ester (160 mg) is dissolved in a mixture of tert-butanol (3 ml) and water (0.8 ml), and thereto are added potassium dihydrogen phosphate dihydrate (41.4 mg), sodium chlorite (85 mg), and 2-methyl-2-butene (103 μl), and the mixture is stirred at room temperature for 2 hours. To the reaction solution are added 1N hydrochloric acid and ethyl acetate under ice-cooling, and the mixture is separated. The organic layer is washed with a saturated brine, dried over magnesium sulfate and concentrated under reduced pressure. The resulting residue is purified by silica gel column chromatography (chloroform:methanol=1:0→9:1) to give (2R,4S)-4-{[3,5-bis(trifluoromethyl)benzyl]-[5-(2-carboxymethoxyethoxy)pyrimidin-2-yl]}amino-2-ethyl-6-trifluoromethyl-3,4-dihydro-2H-quinoline-1-carboxylic acid ethyl ester (132 mg). MS (m/z): 739 [M+H]+

Example 213

(1) (2R,4S)-4-{[3,5-Bis(trifluoromethyl)benzyl]-(5-hydroxypyrimidin-2-yl)}amino-2-ethyl-6-trifluoromethyl-3,4-dihydro-2H-quinoline-1-carboxylic acid ethyl ester (500 mg) is dissolved in N,N-dimethylformamide (5 ml), and thereto is added 2-chloroethylcarbamic acid benzyl ester (402 mg) and potassium carbonate (260 mg), and the mixture is stirred at 80° C. overnight. The reaction solution is cooled to room temperature, and thereto are added water and ethyl acetate, and the mixture is separated. The organic layer is washed with a saturated brine, dried over magnesium sulfate and concentrated under reduced pressure. The resulting residue is purified by NH-silica gel column chromatography (hexane:ethyl acetate=9:1→4:1) to give (2R,4S)-4-{[5-(2-benzyloxycarbonylaminoethoxy)pyrimidin-2-yl]-[3,5-bis(trifluoromethyl)benzyl]}amino-2-ethyl-6-trifluoromethyl-3,4-dihydro-2H-quinoline-1-carboxylic acid ethyl ester (249 mg). MS (m/z): 814 [M+H]+
(2) (2R,4S)-4-{[5-(2-Benzyloxycarbonylaminoethoxy)pyrimidin-2-yl]-[3,5-bis(trifluoromethyl)benzyl]}amino-2-ethyl-6-trifluoromethyl-3,4-dihydro-2H-quinoline-1-carboxylic acid ethyl ester (240 mg) is dissolved in methanol (5 ml), and thereto is added 10% palladium-carbon (100 mg), and the mixture is stirred under hydrogen atmosphere for 2 hours. The reaction solution is filtered and concentrated under reduced pressure. The resulting residue is purified by NH-silica gel column chromatography (hexane:ethyl acetate=7:3→2:3) to give (2R,4S)-4-{[5-(2-aminoethoxy)-pyrimidin-2-yl]-[3,5-bis(trifluoromethyl)benzyl]}amino-2-ethyl-6-trifluoro-methyl-3,4-dihydro-2H-quinoline-1-carboxylic acid ethyl ester (167 mg). MS (m/z): 680 [M+H]+

Example 214

(2R,4S)-4-{[3,5-Bis(trifluoromethyl)benzyl]-(5-hydroxypyrimidin-2-yl)}amino-2-ethyl-6-trifluoromethyl-3,4-dihydro-2H-quinoline-1-carboxylic acid ethyl ester (975 mg) is dissolved in N,N-dimethylformamide (4.5 ml), and thereto is added sodium hydride (62.7%, 70 mg) under ice-cooling, and the mixture is stirred for 10 minutes. To the reaction solution is added 4-bromobutyronitrile (0.2 ml), and the mixture is stirred at room temperature for one hour. To the reaction solution are added water and ethyl acetate under ice-cooling, and the mixture is separated. The organic layer is washed with a saturated brine, dried over magnesium sulfate and concentrated under reduced pressure. The resulting residue is purified by silica gel column chromatography (hexane:ethyl acetate=4:1→3:2) to give (2R,4S)-4-{[3,5-bis(trifluoromethyl)benzyl]-[5-(3-cyanopropoxy)pyrimidin-2-yl]}amino- 2-ethyl-6-trifluoromethyl-3,4-dihydro-2H-quinoline-1-carboxylic acid ethyl ester (1.1 g). MS (m/z): 704 [M+H]$^+$ Example 215

(2R,4S)-4-{[3,5-Bis(trifluoromethyl)benzyl]-[5-(3-cyanopropoxy)-pyrimidin-2-yl]}amino-2-ethyl-6-trifluoromethyl-3,4-dihydro-2H-quinoline-1-carboxylic acid ethyl ester (300 mg), sodium azide (462 mg), and ammonium chloride (380 mg) are dissolved in N,N-dimethylformamide (1 ml), and the mixture is stirred at 120° C. for 27 hours. The reaction solution is cooled to room temperature, and thereto are added 1N hydrochloric acid and ethyl acetate, and the mixture is separated. The organic layer is washed with a saturated brine, dried over magnesium sulfate and concentrated under reduced pressure. The resulting residue is purified by silica gel column chromatography (chloroform:methanol=1:0 →9:1) to give (2R,4S)-4-([3,5-bis(trifluoromethyl)benzyl]-{5-[3-(tetrazol-5-yl)propoxy]pyrimidin-2-yl})amino-2-ethyl-6-trifluoromethyl-3,4-dihydro-2H-quinoline-1-carboxylic acid ethyl ester (169 mg). MS (m/z): 747 [M+H]$^+$ Example 216

(2R,4S)-4-{[3,5-Bis(trifluoromethyl)benzyl]-[5-(3-cyanopropoxy)-pyrimidin-2-yl]}amino-2-ethyl-6-trifluoromethyl-3,4-dihydro-2H-quinoline-1-carboxylic acid ethyl ester (700 mg), hydroxylamine hydrochloride (140 mg) and sodium carbonate (212 mg) are dissolved in ethanol (3 ml), and the mixture is refluxed for 41 hours. The reaction solution is cooled to room temperature, and thereto are added water and ethyl acetate, and the mixture is separated. The organic layer is washed with a saturated brine, dried over magnesium sulfate and concentrated under reduced pressure. The resulting residue is purified by silica gel column chromatography (hexane:ethyl acetate=7:3→1:1) to give (2R,4S)-4-([3,5-bis(trifluoro-methyl)benzyl]-{5-[3-(N-hydroxycarbamimidoyl)propoxy]pyrimidin-2-yl})-amino-2-ethyl-6-trifluoromethyl-3,4-dihydro-2H-quinoline-1-carboxylic acid ethyl ester (502 mg). MS (m/z): 737 [M+H]$^+$ Example 217

(2R,4S)-4-([3,5-Bis(trifluoromethyl)benzyl]-{5-[3-(N-hydroxy-carbamimidoyl)propoxy]pyrimidin-2-yl})amino-2-ethyl-6-trifluoromethyl-3,4-dihydro-2H-quinoline-1-carboxylic acid ethyl ester (200 mg), and 1,1'-carbonyldiimidazole (66 mg) are dissolved in acetonitrile (1.5 ml), and the mixture is stirred at 60° C. for 16.5 hours. The reaction solution is cooled to room temperature, and thereto are added water and ethyl acetate, and the mixture is separated. The organic layer is washed with a saturated brine, dried over magnesium sulfate and concentrated under reduced pressure. The resulting residue is purified by silica gel column chromatography (hexane:ethyl acetate=7:3→1:1) to give (2R,4S)-4-([3,5-bis(trifluoro-methyl)benzyl]-{5-[3-(5-oxo-4,5-dihydro [1,2,4]oxadiazol-3-yl)propoxy]pyrimidin-2-yl})amino-2-ethyl-6-trifluoromethyl-3,4-dihydro-2H-quinoline-1-carboxylic acid ethyl ester (115 mg). MS (m/z): 763 [M+H]$^+$ Example 218

(2R,4S)-4-([3,5-Bis(trifluoromethyl)benzyl]-{5-[3-(N-hydroxy-carbamimidoyl)propoxy]pyrimidin-2-yl})amino-2-ethyl-6-trifluoromethyl-3,4-dihydro-2H-quinoline-1-carboxylic acid ethyl ester (240 mg) and pyridine (106 µl) are dissolved in tetrahydrofuran (7.5 ml), and thereto is added dropwise a solution of thionyl chloride (48 µl) in methylene chloride (3 ml), and the mixture is stirred for 2 hours and 40 minutes. The reaction solution is concentrated under reduced pressure, and thereto are added water and ethyl acetate, and the mixture is separated. The organic layer is washed with a saturated brine, dried over magnesium sulfate and concentrated under reduced pressure. The resulting residue is purified by silica gel column chromatography (hexane:ethyl acetate=4:1→1:1) to give (2R,4S)-4-([3,5-bis(trifluoromethyl)benzyl]-{5-[3-(2-oxo-3H-[1,2,3,5]-oxothiazol-4-yl)propoxy]pyrimidin-2-yl})amino-2-ethyl-6-trifluoromethyl-3,4-dihydro-2H-quinoline-1-carboxylic acid ethyl ester (181 mg). MS (m/z): 783 [M+H]$^+$ Example 219

3-Chloropropane-1-sulfonyl chloride (0.38 ml) is dissolved in methylene chloride (15 ml), and ammonia gas is blown into the mixture for 15 minutes. The reaction solution is stirred overnight, and the resulting ammonium chloride is removed by filtration. The filtrate is concentrated, and the resulting 3-chloropropane-1-sulfonamide and (2R,4S)-4-{[3,5-bis(trifluoromethyl)benzyl]-(5-hydroxypyrimidin-2-yl)}amino-2-ethyl-6-trifluoromethyl-3,4-dihydro-2H-quinoline-1-carboxylic acid ethyl ester (500 mg), potassium iodide (1.3 g), and potassium hydroxide (352 mg) are dissolved in dimethylsulfoxide (4 ml), and the mixture is stirred at 60° C. for 24 hours. The mixture is cooled to room temperature, and thereto are added water and ethyl acetate, and the mixture is separated. The organic layer is washed with a saturated brine, dried over magnesium sulfate and concentrated under reduced pressure. The resulting residue is purified by silica gel column chromatography (hexane:ethyl acetate=9:1→1:1) to give (2R,4S)-4-{[3,5-bis(trifluoromethyl)benzyl]-[5-(3-sulfamoylpropoxy)-pyrimidin-2-yl]}amino-2-ethyl-6-trifluoromethyl-3,4-dihydro-2H-quinoline-1-carboxylic acid ethyl ester (22 mg). MS (m/z): 758 [M+H]$^+$ Example 220

(1) (2R,4S)-4-{[3,5-Bis(trifluoromethyl)benzyl]-(5-hydroxypyrimidin-2-yl)}amino-2-ethyl-6-trifluoromethyl-3,4-dihydro-2H-quinoline-1-carboxylic acid ethyl ester (300 mg) is dissolved in tetrahydrofuran (5 ml), and thereto are added ethyl 4-(hydroxymethyl)cyclohexylacetate (141 mg) and triphenylphosphine (370 mg). To the mixture is added dropwise a 40% solution of diethyl azodicarboxylate in toluene (600 µl) under ice-cooling, and the mixture is stirred at room temperature for 2.5 hours. Water and ethyl acetate are added to the mixture, and the mixture is separated. The organic layer is washed with a saturated brine, dried over magnesium sulfate and concentrated under reduced pressure. The resulting residue is purified by NH-silica gel column chromatography (hexane:ethyl acetate=19:1→4:1) to give (2R,4S)-4-{[3,5-bis(trifluoromethyl)benzyl]-[5-(4-ethoxy-carbonylmethylcyclohexylmethoxy)pyrimidin-2-yl]}amino-2-ethyl-6-trifluoromethyl-3,4-dihydro-2H-quinoline-1-carboxylic acid ethyl ester (275 mg). MS (m/z): 819 [M+H]$^+$ (2) (2R,4S)-4-{[3,5-Bis(trifluoromethyl)benzyl]-[5-(4-ethoxycarbonyl-methylcyclohexylmethoxy)pyrimidin-2-yl]}amino-2-ethyl-6-trifluoromethyl-3,4-dihydro-2H-quinoline-1-carboxylic acid ethyl ester (220 mg) is dissolved in ethanol (5 ml), and thereto is added dropwise a 1N aqueous sodium hydroxide solution (1 ml), and the mixture is stirred at room temperature overnight. To the mixture are added 1N hydrochloric acid and ethyl acetate, and the mixture is separated. The organic layer is washed with a saturated brine, dried over magnesium sulfate and concentrated under reduced pressure. The resulting residue is purified by silica gel column chromatography (chloroform:methanol=1:0→9:1) to give (2R,4S)-4-{[3,5-bis(trifluoromethyl)benzyl]-[5-(4-carboxymethylcyclohexylmethoxy)pyrimidin-2-yl]}amino-2-ethyl-6-trifluoromethyl-3,4-dihydro-2H-quinoline-1-carboxylic acid ethyl ester (181 mg). MS (m/z): 791 [M+H]$^+$ Example 221

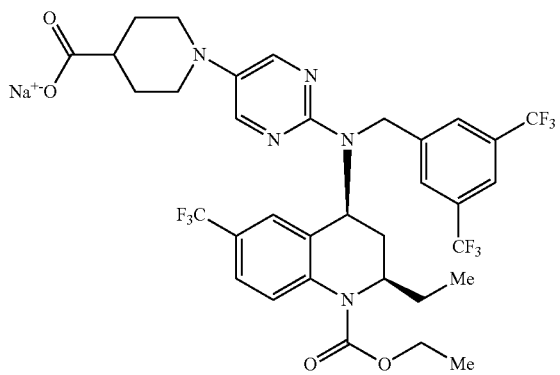

The corresponding starting compound is treated in a similar manner to Example 178 to give the compound of Example 221. MS (m/z): 746 [M–Na]$^-$ Examples 222-224

The corresponding starting compounds are treated in a similar manner to Example 1(3) to give the compounds as listed in Table 29.

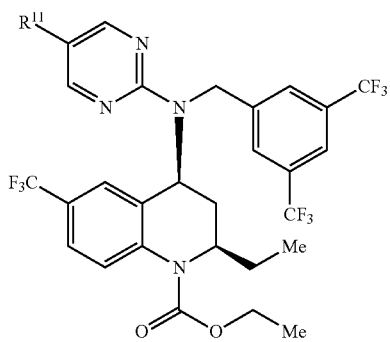

TABLE 29

| Ex. No. | R$^{11}$ | Physical properties, etc. |
|---|---|---|
| 222 | Me–\O–\C(=O)–CH2–[piperidin-4-yl]–N–Me | MS (m/z): 790 [M + H]$^+$ |

TABLE 29-continued

| Ex. No. | R$^{11}$ | Physical properties, etc. |
|---|---|---|
| 223 | Me–\O–C(=O)–CH2–[piperidin-3-yl]–N–Me | MS (m/z): 790 [M + H]$^+$ |
| 224 | Me3C–O–C(=O)–CH2CH2–N(Me)(Et) | MS (m/z): 792 [M + H]$^+$ |

Examples 225-226

The corresponding starting compounds are treated in a similar manner to Example 177 (3) to give the compounds as listed in Table 30.

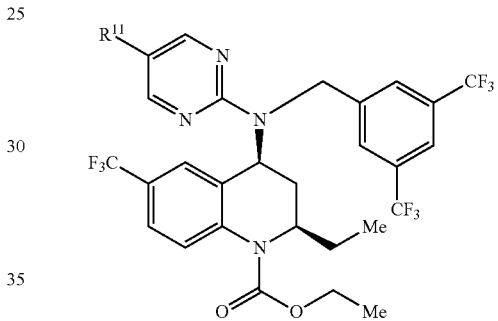

TABLE 30

| Ex. No. | R$^{11}$ | Physical properties, etc. |
|---|---|---|
| 225 | HO–C(=O)–CH2–[piperidin-4-yl]–N–Me | MS (m/z): 762 [M + H]$^+$ |
| 226 | HO–C(=O)–CH2–[piperidin-3-yl]–N–Me | MS (m/z): 762 [M + H]$^+$ |

Example 227

(2R,4S)-4-[[3,5-Bis(trifluoromethyl)benzyl]-(5-{[ethyl-(2-tert-butoxy-carbonylethyl)]amino}pyrimidin-2-yl)]amino-2-ethyl-6-trifluoromethyl-3,4-dihydro-2H-quinoline-1-carboxylic acid ethyl ester (70 mg) is dissolved in a 4N hydrogen chloride in ethyl acetate (0.5 ml), and the mixture is stirred at room temperature for 3 hours. To the reaction solution are added a saturated aqueous sodium hydrogen carbonate solution and ethyl acetate, and the mixture is separated. The organic layer is washed with a saturated brine, dried over magnesium sulfate and concentrated under reduced pressure to give (2R,4S)-4-[[3,5-bis(trifluoromethyl)benzyl]-(5-

{[ethyl-(2-carboxyethyl)]amino}pyrimidin-2-yl)]amino-2-ethyl-6-trifluoromethyl-3,4-dihydro-2H-quinoline-1-carboxylic acid ethyl ester (65 mg). MS (m/z): 736 [M+H]+

Example 228

(1) (2R,4S)-4-{[3,5-Bis(trifluoromethyl)benzyl]-(5-iodopyrimidin-2-yl)}-amino-2-ethyl-6-trifluoromethyl-3,4-dihydro-2H-quinoline-1-carboxylic acid ethyl ester (1.0 g), copper iodide (13 mg), potassium carbonate (370 mg), ethylene glycol (0.15 ml), and 4-mercaptobutanol (0.14 ml) are dissolved in isopropyl alcohol (1.5 ml), and the mixture is stirred at 80° C. under nitrogen atmosphere for 15 hours. The mixture is cooled to room temperature, and thereto is added ethyl acetate. The insoluble materials are removed by filtration, and the filtrate is concentrated under reduced pressure. The resulting residue is purified by silica gel column chromatography (hexane:ethyl acetate=9:1→7:3) to give (2R,4S)-4-{[3,5-bis-(trifluoromethyl)benzyl]-[5-(4-hydroxybutylsulfanyl)pyrimidin-2-yl]}amino-2-ethyl-6-trifluoromethyl-3,4-dihydro-2H-quinoline-1-carboxylic acid ethyl ester (705 mg). MS (m/z): 725 [M+H]+

(2) (2R,4S)-4-{[3,5-Bis(trifluoromethyl)benzyl]-[5-(4-hydroxybutyl-sulfanyl)pyrimidin-2-yl]}amino-2-ethyl-6-trifluoromethyl-3,4-dihydro-2H-quinoline-1-carboxylic acid ethyl ester (500 mg) is dissolved in chloroform (2 ml), and thereto is added m-chloroperbenzoic acid (75%, 636 mg) under ice-cooling. The mixture is stirred at room temperature for one hour, and thereto are added a saturated aqueous sodium hydrogen carbonate solution and ethyl acetate, and the mixture is separated. The organic layer is washed with a saturated brine, dried over magnesium sulfate and concentrated under reduced pressure. The resulting residue is purified by NH-silica gel column chromatography (hexane:ethyl acetate=7:3→1:1) to give (2R,4S)-4-{[3,5-bis(trifluoromethyl)benzyl]-[5-(4-hydroxybutylsulfonyl)-pyrimidin-2-yl]}amino-2-ethyl-6-trifluoromethyl-3,4-dihydro-2H-quinoline-1-carboxylic acid ethyl ester (309 mg). MS (m/z): 757 [M+H]+

(3) (2R,4S)-4-{[3,5-Bis(trifluoromethyl)benzyl]-[5-(4-hydroxybutyl-sulfonyl)pyrimidin-2-yl]}amino-2-ethyl-6-trifluoromethyl-3,4-dihydro-2H-quinoline-1-carboxylic acid ethyl ester (300 mg) and 1,1,1-tris(acetoxy)-1,1-dihydro-1,2-benziodoxol-3-(1H)-one (269 mg) are dissolved in methylene chloride (2 ml), and the mixture is stirred for 2.5 hours. Water and ethyl acetate are added to the mixture, and the mixture is separated. The organic layer is washed with a saturated brine, dried over magnesium sulfate and concentrated under reduced pressure. The resulting residue is purified by silica gel column chromatography (hexane:ethyl acetate=9:1→1:1) to give (2R,4S)-4-{[3,5-bis(trifluoromethyl)benzyl]-[5-(3-carboxy-propylsulfonyl)pyrimidin-2-yl]}amino-2-ethyl-6-trifluoromethyl-3,4-dihydro-2H-quinoline-1-carboxylic acid ethyl ester (103 mg). MS (m/z): 771 [M+H]+

Example 229

(1) (2R,4S)-4-Amino-2-ethyl-6-trifluoromethyl-3,4-dihydro-2H-quinoline-1-carboxylic acid ethyl ester (3 g), 2-chloro-4-methylthiazole-5-carboxylic acid ethyl ester (5.85 g) and diisopropylethylamine (3.3 ml) are dissolved in 1,4-dioxane (25 ml), and the mixture is stirred at 130° C. for one week. The reaction solution is cooled to room temperature, and water and ethyl acetate are added thereto, and the mixture is separated. The organic layer is washed with a saturated brine, dried over magnesium sulfate and concentrated under reduced pressure. The resulting residue is purified by silica gel column chromatography (hexane:ethyl acetate=6:1→4:1) to give (2R,4S)-4-(5-ethoxycarbonyl-4-methylthiazol-2-yl)amino-2-ethyl-6-trifluoromethyl-3,4-dihydro-2H-quinoline-1-carboxylic acid ethyl ester (1.93 g). MS (m/z): 486 [M+H]+

(2) (2R,4S)-4-(5-Ethoxycarbonyl-4-methylthiazol-2-yl)amino-2-ethyl-6-trifluoromethyl-3,4-dihydro-2H-quinoline-1-carboxylic acid ethyl ester (1.9 g) is dissolved in N,N-dimethylformamide (20 ml), and thereto is added sodium hydride (62.7%, 282 mg) under ice-cooling. The reaction mixture is stirred at room temperature for 30 minutes, and thereto is added 3,5-bis(trifluoromethyl)benzyl bromide (1.56 ml) under ice-cooling. The mixture is stirred at room temperature for 3 hours, and a saturated aqueous citric acid solution and ethyl acetate are added thereto, and the mixture is separated. The organic layer is washed with a saturated brine, dried over magnesium sulfate and concentrated under reduced pressure. The resulting residue is purified by silica gel column chromatography (hexane:ethyl acetate=9:1→4:1) to give (2R,4S)-4-{[3,5-bis(trifluoro-methyl)benzyl]-(5-ethoxycarbonyl-4-methylthiazol-2-yl)}amino-2-ethyl-6-trifluoromethyl-3,4-dihydro-2H-quinoline-1-carboxylic acid ethyl ester (1.62 g). MS (m/z): 712 [M+H]+

Example 230

(2R,4S)-4-{[3,5-Bis(trifluoromethyl)benzyl]-(5-ethoxycarbonyl-4-methylthiazol-2-yl)}amino-2-ethyl-6-trifluoromethyl-3,4-dihydro-2H-quinoline-1-carboxylic acid ethyl ester (250 mg) and lithium hydroxide monohydrate (147 mg) are dissolved in a mixture of ethanol (5 ml) and a 2N aqueous sodium hydroxide solution (703 µl), and the mixture is stirred at 70° C. for 2 hours. The reaction solution is cooled to room temperature, and acidified with a 2N aqueous hydrochloric acid. Subsequently, to the mixture is added ethyl acetate, and the mixture is separated. The organic layer is washed with a saturated brine, dried over magnesium sulfate and concentrated under reduced pressure. The resulting residue is purified by silica gel column chromatography (chloroform:methanol=1:0→19:1) to give (2R,4S)-4-{[3,5-bis(trifluoromethyl)benzyl]-(5-carboxy-4-methylthiazol-2-yl)}amino-2-ethyl-6-trifluoromethyl-3,4-dihydro-2H-quinoline-1-carboxylic acid ethyl ester (189 mg). MS (m/z): 684 [M+H]+

Example 231

(1) (2R,4S)-4-Amino-2-ethyl-6-trifluoromethyl-3,4-dihydro-2H-quinoline-1-carboxylic acid ethyl ester (10.0 g), 2,5-dibromopyridine (15 g), tris(dibenzylideneacetone)dipalladium (2.9 g), 2-dicyclohexylphosphino-2'-(N,N-dimethylamino)biphenyl (2.5 g) and sodium tert-butoxide (6.1 g) are dissolved in toluene (100 ml), and the mixture is stirred at 80° C. for 15 hours under nitrogen atmosphere. The mixture is cooled to room temperature, and water and ethyl acetate are added thereto, and the mixture is separated. The organic layer is washed with water and a saturated brine, and thereto is added NH-silica gel, and the mixture is filtered. The filtrate is concentrated under reduced pressure, and the resulting residue is purified by silica gel column chromatography (hexane:ethyl acetate=9:1→4:1) to give (2R,4S)-4-(5-bromopyridin-2- yl)amino-2-ethyl-6-trifluoromethyl-3,4-dihydro-2H-quinoline-1-carboxylic acid ethyl ester (3.56 g). MS (m/z): 472/474 [M+H]⁺

(2) (2R,4S)-4-(5-Bromopyridin-2-yl)amino-2-ethyl-6-trifluoromethyl-3,4-dihydro-2H-quinoline-1-carboxylic acid ethyl ester (2.4 g) is dissolved in N,N-dimethylformamide (15 ml), and thereto is added sodium hydride (40%, 335 mg) under ice-cooling. The mixture is stirred at room temperature for 30 minutes, and thereto is added 3,5-bis(trifluoromethyl-benzyl bromide (1.1 ml). The mixture is stirred at room temperature for 5 hours. To the mixture are added water and diethyl ether under ice-cooling, and the mixture is separated. The organic layer is washed with 1N hydro-chloric acid, water and a saturated brine, dried over magnesium sulfate and concentrated under reduced pressure. The resulting residue is purified by silica gel column chromatography (hexane:ethyl acetate=9:1 →7:3) to give (2R,4S)-4-{[3,5-bis(trifluoromethyl)benzyl]-(5-bromopyridin-2-yl)}amino-2-ethyl-6-trifluoromethyl-3,4-dihydro-2H-quinoline-1-carboxylic acid ethyl ester (1.72 g). MS (m/z): 698/700 [M+H]⁺

(3) (2R,4S)-4-{[3,5-Bis(trifluoromethyl)benzyl]-(5-bromopyridin-2-yl)}-amino-2-ethyl-6-trifluoromethyl-3,4-dihydro-2H-quinoline-1-carboxylic acid ethyl ester (1.72 g), [1,1'-bis(diphenylphosphino)ferrocene]dichloro-palladium (54 mg), potassium acetate (725 mg) and bis(pinacolate)diboron (938 mg) are dissolved in deaerated dimethylsulfoxide (7 ml), and the mixture is stirred at 80° C. for one hour. The reaction solution is cooled to room temperature, and water and ethyl acetate are added thereto, and the mixture is separated. The organic layer is washed with a saturated brine, dried over magnesium sulfate and concentrated under reduced pressure. The resulting residue is dissolved in tetrahydrofuran (7.5 ml), and thereto is added a 30% aqueous hydrogen peroxide solution (2.8 ml) under ice-cooling, and the mixture is stirred for 3 hours. A saturated aqueous sodium thiosulfate solution and ethyl acetate are added to the mixture under ice-cooling, and the mixture is separated. The organic layer is washed with water and a saturated brine, dried over magnesium sulfate and concentrated under reduced pressure. The resulting residue is purified by silica gel column chromatography (hexane:ethyl acetate=4:1→3:2) to give (2R,4S)-4-{[3,5-bis(trifluoromethyl)benzyl]-(5-hydroxypyridin-2-yl)}amino-2-ethyl-6-trifluoromethyl-3,4-dihydro-2H-quinoline-1-carboxylic acid ethyl ester (851 mg). MS (m/z): 636 [M+H]⁺

(4) (2R,4S)-4-{[3,5-Bis(trifluoromethyl)benzyl]-(5-hydroxypyridin-2-yl)}amino-2-ethyl-6-trifluoromethyl-3,4-dihydro-2H-quinoline-1-carboxylic acid ethyl ester (200 mg) is dissolved in N,N-dimethylformamide (1.5 ml), and thereto is added sodium hydride (15 mg) under ice-cooling. The mixture is stirred for 15 minutes, and thereto is added 4-bromobutyric acid ethyl ester (69 μl), and the mixture is stirred at room temperature for 1.5 hour. To the reaction solution are added water and ethyl acetate, and the mixture is separated. The organic layer is washed with a saturated brine, dried over magnesium sulfate and concentrated under reduced pressure. The resulting residue is purified by silica gel column chromatography (hexane:ethyl acetate=9:1→4:1) to give (2R,4S)-4-{[3,5-bis-(trifluoromethyl)benzyl]-[5-(3-ethoxycarbonylpropoxy)pyridin-2-yl]}amino-2-ethyl-6-trifluoromethyl-3,4-dihydro-2H-quinoline-1-carboxylic acid ethyl ester (132 mg). MS (m/z): 750 [M+H]⁺

(5) (2R,4S)-4-{[3,5-Bis(trifluoromethyl)benzyl]-[5-(3-ethoxycarbonyl-propoxy)pyridin-2-yl]}amino-2-ethyl-6-trifluoromethyl-3,4-dihydro-2H-quinoline-1-carboxylic acid ethyl ester (120 mg) is dissolved in ethanol (0.8 ml), and thereto is added a 2N aqueous sodium hydroxide solution (0.24 ml), and the mixture is stirred for 3 hours. To the reaction solution are added a 2N hydrochloric acid solution (0.24 ml) and ethyl acetate, and the mixture is separated. The organic layer is washed with water and a saturated brine, dried over magnesium sulfate and concentrated under reduced pressure. The resulting residue is purified by silica gel column chromatography (hexane:ethyl acetate=7:3→1:1) to give (2R,4S)-4-{[3,5-bis(trifluoromethyl)benzyl]-[5-(3-carboxypropoxy)pyridin-2-yl]}amino-2-ethyl-6-trifluoromethyl-3,4-dihydro-2H-quinoline-1-carboxylic acid ethyl ester (105 mg). MS (m/z): 722 [M+H]⁺

Example 232

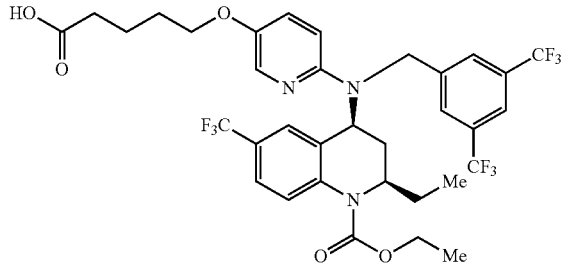

The corresponding starting compound is treated in a similar manner to Example 231 (4)-(5) to give the compound of Example 232. MS (m/z): 736 [M+H]⁺

Example 233

(1) (2R,4S)-4-(5-Bromopyrimidin-2-yl)amino-2-ethyl-6-trifluoromethyl-3,4-dihydro-2H-quinoline-1-carboxylic acid ethyl ester (18 g) is dissolved in tetrahydrofuran (180 ml), and thereto are added di-tert-butyl dicarbonate (24.8 g) and a catalytic amount of dimethylaminopyridine, and the mixture is stirred at room temperature overnight. To the mixture are added a saturated aqueous sodium hydrogen carbonate solution and ethyl acetate, and the mixture is separated. The organic layer is washed with a saturated brine, dried over magnesium sulfate and concentrated under reduced pressure. The resulting residue is purified by NH-silica gel column chromatography (hexane:ethyl acetate=8:1) to give (2R,4S)-4-[(5-bromopyrimidin-2-yl)-tert-butoxycarbonyl]amino-2-ethyl-6-trifluoromethyl-3,4-dihydro-2H-quinoline-1-carboxylic acid ethyl ester (22.5 g). MS (m/z): 573/575 [M+H]⁺

(2) (2R,4S)-4-[(5-Bromopyrimidin-2-yl)-tert-butoxycarbonyl]amino-2-ethyl-6-trifluoromethyl-3,4-dihydro-2H-quinoline-1-carboxylic acid ethyl ester (22.5 g) is dissolved in 1,4-dioxane (110 ml), and thereto are added copper (I) iodide (375 mg), sodium iodide (11.8 g) and N,N'-dimethylethane-1,2-diamine (0.42 ml), and the mixture is refluxed under nitrogen atmosphere overnight. The reaction solution is cooled to room temperature, and thereto are added water and ethyl acetate, and the mixture is separated. The organic layer is washed with a saturated brine, dried over magnesium sulfate and concentrated under reduced pressure. The resulting residue is purified by silica gel column chromatography (hexane:ethyl acetate=4:1) to give (2R,4S)-4-[tert-butoxycarbonyl-(5-iodopyrimidin-2-yl)]amino-2-ethyl-6-trifluoromethyl-3,4-dihydro-2H-quinoline-1-carboxylic acid ethyl ester (21.6 g). MS (m/z): 621 [M+H]$^+$ (3) (2R,4S)-4-[tert-Butoxycarbonyl-(5-iodopyrimidin-2-yl)]amino-2-ethyl-6-trifluoromethyl-3,4-dihydro-2H-quinoline-1-carboxylic acid ethyl ester (1.0 g), [1,1'-bis(diphenylphosphino)ferrocene]dichloropalladium (35 mg), potassium acetate (475 mg) and bis(pinacolate)diboron (615 mg) are dissolved in deaerated dimethylsulfoxide (8 ml), and the mixture is stirred at 80° C. for 18 hours. The reaction solution is cooled to room temperature, and water and ethyl acetate are added thereto, and the mixture is separated. The organic layer is washed with a saturated brine, dried over magnesium sulfate and concentrated under reduced pressure. The resulting residue is dissolved in tetrahydrofuran (8 ml), and thereto is added an excess amount of a 30% aqueous hydrogen peroxide solution under ice-cooling, and the mixture is stirred for 6 hours. A saturated aqueous sodium thiosulfate solution and ethyl acetate are added to the mixture under ice-cooling, and the mixture is separated. The organic layer is washed with a saturated brine, dried over magnesium sulfate and concentrated under reduced pressure. The resulting residue is purified by silica gel column chromatography (chloroform:methanol=1:0→19:1) to give (2R,4S)-4-[tert-butoxycarbonyl-(5-hydroxypyrimidin-2-yl)]amino-2-ethyl-6-trifluoromethyl-3,4-dihydro-2H-quinoline-1-carboxylic acid ethyl ester (1.7 g). MS (m/z): 511 [M+H]$^+$ (4) (2R,4S)-4-[tert-Butoxycarbonyl-(5-hydroxypyrimidin-2-yl)]amino-2-ethyl-6-trifluoromethyl-3,4-dihydro-2H-quinoline-1-carboxylic acid ethyl ester (800 mg) is dissolved in N,N-dimethylformamide (5 ml), and thereto is added sodium hydride (62.7%, 72 mg) under ice-cooling. The mixture is stirred at room temperature for 15 minutes, and thereto is added 1-chloro-2-methylsulfanylethane (259 mg), and the mixture is stirred at room temperature for 24 hours. Water and ethyl acetate are added to the reaction mixture under ice-cooling, and the mixture is separated. The organic layer is washed with a saturated brine, dried over magnesium sulfate and concentrated under reduced pressure. The resulting residue is purified by silica gel column chromatography (hexane:ethyl acetate=4:1→3:7) to give (2R,4S)-4-{tert-butoxycarbonyl-[5-(2-methylsulfanyl-ethoxy)pyrimidin-2-yl]}amino-2-ethyl-6-trifluoromethyl-3,4-dihydro-2H-quinoline-1-carboxylic acid ethyl ester (200 mg). MS (m/z): 585 [M+H]$^+$ (5) (2R,4S)-4-{tert-Butoxycarbonyl-[5-(2-methylsulfanylethoxy)-pyrimidin-2-yl]}amino-2-ethyl-6-trifluoromethyl-3,4-dihydro-2H-quinoline-1-carboxylic acid ethyl ester (200 mg) is dissolved in a 4N hydrogen chloride in 1,4-dioxane (1.5 ml), and the mixture is stirred at room temperature for 17.5 hours. To the reaction solution are added a 2N aqueous sodium hydroxide solution (3 ml) and diethyl ether, and the mixture is separated. The organic layer is concentrated under reduced pressure, and the resulting residue is purified by silica gel column chromatography (hexane:ethyl acetate=4:1→1:1) to give (2R,4S)-2-ethyl-4-[5-(2-methylsulfanylethoxy)pyrimidin-2-yl]amino-6-trifluoromethyl-3,4-dihydro-2H-quinoline-1-carboxylic acid ethyl ester (170 mg). MS (m/z): 485 [M+H]$^+$ (6) (2R,4S)-2-Ethyl-4-[5-(2-methylsulfanylethoxy)pyrimidin-2-yl]amino-6-trifluoromethyl-3,4-dihydro-2H-quinoline-1-carboxylic acid ethyl ester (160 mg) is dissolved in N,N-dimethylformamide (1.5 ml), and thereto is added sodium hydride (62.7%, 15 mg) under ice-cooling. The mixture is stirred at room temperature for 30 minutes, and thereto is added 3,5-dibromobenzyl bromide (141 mg), and the mixture is stirred at room temperature for 19 hours. To the reaction mixture is added a 0.5N hydrochloric acid and diethyl ether under ice-cooling, and the mixture is separated. The organic layer is washed with a saturated brine, dried over magnesium sulfate and concentrated under reduced pressure. The resulting residue is purified by silica gel column chromatography (hexane:ethyl acetate=9:1→7:3) to give (2R,4S)-4-{(3,5-dibromobenzyl)-[5-(2-methylsulfanyl-ethoxy)pyrimidin-2-yl]}amino-2-ethyl-6-trifluoromethyl-3,4-dihydro-2H-quinoline-1-carboxylic acid ethyl ester (110 mg). MS (m/z): 733 [M+H]$^+$ (7) (2R,4S)-4-{(3,5-Dibromobenzyl)-[5-(2-methylsulfanylethoxy)-pyrimidin-2-yl]}amino-2-ethyl-6-trifluoromethyl-3,4-dihydro-2H-quinoline-1-carboxylic acid ethyl ester (100 mg) is dissolved in N,N-dimethyl-formamide (2 ml), and thereto are added zinc cyanide (35.3 mg) and a catalytic amount of tetrakis(triphenylphosphine)palladium, and the mixture is stirred at 110° C. for 17.5 hours. The reaction solution is cooled to room temperature, and water and diethyl ether are added thereto, and the mixture is separated. The organic layer is washed with a saturated brine, dried over magnesium sulfate and concentrated under reduced pressure. The resulting residue is purified by silica gel column chromatography (hexane:ethyl acetate=9:1→7:3) to give (2R,4S)-4-{(3-bromo-5-cyanobenzyl)-[5-(2-methylsulfanylethoxy)pyrimidin-2-yl]}amino-2-ethyl-6-trifluoromethyl-3,4-dihydro-2H-quinoline-1-carboxylic acid ethyl ester (28 mg, MS (m/z): 678/680 [M+H]$^+$), and (2R,4S)-4-{(3,5-dicyanobenzyl)-[5-(2-methylsulfanylethoxy)pyrimidin-2-yl]}amino-2-ethyl-6-trifluoromethyl-3,4-dihydro-2H-quinoline-1-carboxylic acid ethyl ester (50 mg, MS (m/z): 625 [M+H]$^+$).

(8) (2R,4S)-4-{(3-Bromo-5-cyanobenzyl)-[5-(2-methylsulfanylethoxy)-pyrimidin-2-yl]}amino-2-ethyl-6-trifluoromethyl-3,4-dihydro-2H-quinoline-1-carboxylic acid ethyl ester (25 mg) is dissolved in chloroform (0.5 ml), and thereto is added m-chloroperbenzoic acid (75%, 17 mg), and the mixture is stirred at room temperature for 35 minutes. A saturated aqueous sodium hydrogen carbonate solution and ethyl acetate are added to the mixture, and the mixture is separated. The organic layer is concentrated under reduced pressure, and the resulting residue is purified by silica gel column chromatography (hexane:ethyl acetate=7:3→1:1) to give (2R,4S)-4-{(3-bromo-5-cyanobenzyl)-[5-(2-methylsulfonylethoxy)-pyrimidin-2-yl]}amino-2-ethyl-6-trifluoromethyl-3,4-dihydro-2H-quinoline-1-carboxylic acid ethyl ester (29 mg). MS (m/z): 710/712 [M+H]$^+$ Example 234

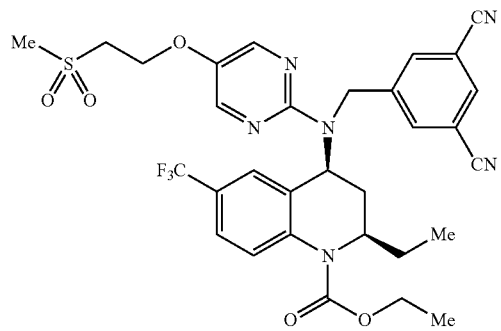

The corresponding starting compound is treated in a similar manner to Example 233 (8) to give the compound of Example 234. MS (m/z): 657 [M+H]+

Example 235

(1) (2R,4S)-4-(5-Bromopyrimidin-2-yl)amino-2-ethyl-6-trifluoromethyl-3,4-dihydro-2H-quinoline-1-carboxylic acid ethyl ester (1.0 g) is dissolved in N,N-dimethylformamide (10 ml), and thereto is added sodium hydride (62.7%, 89 mg) under ice-cooling. The mixture is stirred at room temperature for 15 minutes, and thereto are added 3-cyano-5-trifluoromethylbenzyl bromide (669 mg), and the mixture is stirred at room temperature for 20 hours. Water and diethyl ether are added to the mixture, and the mixture is separated. The organic layer is washed with water and a saturated brine, dried over magnesium sulfate, and concentrated under reduced pressure. The resulting residue is purified by silica gel column chromatography (hexane:ethyl acetate=9:1→4:1) to give (2R,4S)-4-[(5-bromopyrimidin-2-yl)-(3-cyano-5-trifluoromethylbenzyl)]-amino-2-ethyl-6-trifluoromethyl-3,4-dihydro-2H-quinoline-1-carboxylic acid ethyl ester (1.08 g). MS (m/z): 656/658 [M+H]+

(2) (2R,4S)-4-[(5-Bromopyrimidin-2-yl)-(3-cyano-5-trifluoromethyl-benzyl)]amino-2-ethyl-6-trifluoromethyl-3,4-dihydro-2H-quinoline-1-carboxylic acid ethyl ester (250 mg), tris(dibenzylideneacetone)dipalladium (35 mg), 2-(di-tert-butylphosphino)diphenyl (45 mg), sodium tert-butoxide (55 mg), and piperidine-4-carboxylic acid ethyl ester (88 µl) are dissolved in toluene (2 ml), and the mixture is stirred at room temperature for 2.5 hours. The reaction solution is stirred at 80° C. for 15 hours. To the reaction solution are added water and ethyl acetate, and the mixture is separated. The organic layer is washed with a saturated aqueous sodium hydrogen carbonate solution and water, a saturated brine, dried over magnesium sulfate, and concentrated under reduced pressure. The resulting residue is purified by silica gel column chromatography (hexane:ethyl acetate=4:1→3:2) to give (2R,4S)-4-{(3-cyano-5-trifluoromethylbenzyl)-[5-(4-ethoxycarbonylpiperidin-1-yl)pyrimidin-2-yl]}amino-2-ethyl-6-trifluoromethyl-3,4-dihydro-2H-quinoline-1-carboxylic acid ethyl ester (126.8 mg). MS (m/z): 733 [M+H]+

(3) (2R,4S)-4-{(3-Cyano-5-trifluoromethylbenzyl)-[5-(4-ethoxycarbonyl-piperidin-1-yl)pyrimidin-2-yl]}amino-2-ethyl-6-trifluoromethyl-3,4-dihydro-2H-quinoline-1-carboxylic acid ethyl ester (120 mg) is dissolved in ethanol (4 ml), and thereto is added 2N aqueous sodium hydroxide solution (1 ml), and the mixture is stirred at room temperature for 3 hours. To the mixture are added 2N hydrochloric acid (1 ml) and ethyl acetate, and the mixture is separated. The organic layer is concentrated under reduced pressure, and the resulting residue is purified by silica gel column chromatography (hexane:ethyl acetate=7:3→1:1) and by LC/MS (CAPCEL PAK MG II (Shiseido Co., Ltd.), water:methanol=60:40→methanol, 40 ml/min) to give (2R,4S)-4-{[5-(4-carboxypiperidin-1-yl)pyrimidin-2-yl]-(3-cyano-5-trifluoromethylbenzyl)}amino-2-ethyl-6-trifluoromethyl-3,4-dihydro-2H-quinoline-1-carboxylic acid ethyl ester (18.6 mg). MS (m/z): 719 [M+H]+

Example 236

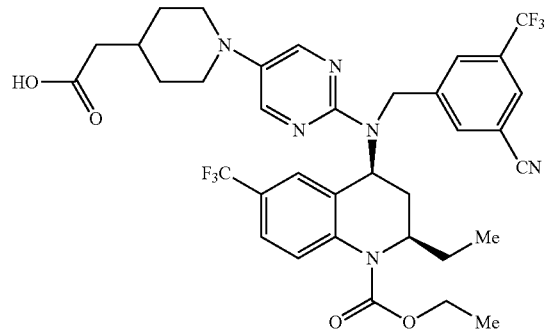

The corresponding starting compound is treated in a similar manner to Example 235 (2)-(3) to give the compound of Example 236. MS (m/z): 719 [M+H]+

Example 237

(1) (2R,4S)-4-[(5-Bromopyrimidin-2-yl)-(3-cyano-5-trifluoromethyl-benzyl)]amino-2-ethyl-6-trifluoromethyl-3,4-dihydro-2H-quinoline-1-carboxylic acid ethyl ester (10 g), [1,1'-bis(diphenylphosphino)ferrocene]-dichloropalladium (395 mg), potassium acetate (5.3 g) and bis(pinacolate)-diboron (6.8 g) are dissolved in deaerated dimethylsulfoxide (50 ml), and the mixture is stirred at 80° C. for 30 minutes. The reaction solution is cooled to room temperature, and thereto are added water and ethyl acetate, and the mixture is separated. The organic layer is washed with a saturated brine, dried over magnesium sulfate and concentrated under reduced pressure. The resulting residue is dissolved in tetrahydrofuran (50 ml), and thereto is added a 30% aqueous hydrogen peroxide solution (9 ml) under ice-cooling, and the mixture is stirred for 16 hours. A saturated aqueous sodium thiosulfate solution and ethyl acetate are added to the mixture under ice-cooling, and the mixture is separated. The organic layer is washed with a saturated brine, dried over sodium sulfate, and concentrated under reduced pressure. The resulting residue is purified by silica gel column chromatography (hexane:ethyl acetate=9:1→7:3) to give (2R,4S)-4-[(3-cyano-5-trifluoromethylbenzyl)-(5-hydroxy-pyrimidin-2-yl)]amino-2-ethyl-6-trifluoromethyl-3,4-dihydro-2H-quinoline-1-carboxylic acid ethyl ester (7.7 g). MS (m/z): 594 [M+H]+

(2) (2R,4S)-4-[(3-Cyano-5-trifluoromethylbenzyl)-(5-hydroxypyrimidin-2-yl)]amino-2-ethyl-6-trifluoromethyl-3,4-dihydro-2H-quinoline-1-carboxylic acid ethyl ester (500 mg) is dissolved in N,N-dimethylformamide (2.5 ml), and sodium hydride (62.7%, 119 mg) is added thereto under ice-cooling, and the mixture is stirred at room temperature for 30 minutes. To the reaction solution is added 4-bromobutyric acid ethyl ester (185 µl), and the mixture is stirred at room temperature for 17 hours. To the reaction solution are added water and ethyl acetate under ice-cooling, and the mixture is separated. The organic layer is washed with 1N hydrochloric acid, water and a saturated brine, dried over magnesium sulfate and concentrated under reduced pressure. The resulting residue is purified by silica gel column chromatography (hexane:ethyl acetate=9:1→7:3) to give (2R,4S)-4-{(3-cyano-5-trifluoromethylbenzyl)-[5-(3-ethoxycarbonylpropoxy)pyrimidin-2-yl]}amino-2-ethyl-6-trifluoromethyl-3,4-dihydro-2H-quinoline-1-carboxylic acid ethyl ester (380 mg). MS (m/z): 708 [M+H]+

(3) (2R,4S)-4-{(3-Cyano-5-trifluoromethylbenzyl)-[5-(3-ethoxycarbonyl-propoxy)pyrimidin-2-yl]}amino-2-ethyl-6-trifluoromethyl-3,4-dihydro-2H-quinoline-1-carboxylic acid ethyl ester (370 mg) is dissolved in a mixture of ethanol (1.5 ml) and tetrahydrofuran (1 ml), and thereto is added a 2N aqueous sodium hydroxide solution (0.79 ml), and the mixture is stirred at room temperature for 3 hours. To the reaction solution is added a 2N hydrochloric acid (0.8 ml), and the mixture is concentrated under reduced pressure. To the resulting residue are added water and ethyl acetate, and the mixture is separated. The organic layer is washed with a saturated brine, dried over magnesium sulfate, and concentrated under reduced pressure. The resulting residue is purified by silica gel column chromatography (hexane:ethyl acetate=9:1→7:3), and LC/MS (CAPCEL PAK MG II (Shiseido Co. Ltd.), water:methanol=50:50→methanol, 40 ml/min) to give (2R,4S)-4-{[5-(3-carboxypropoxy)pyrimidin-2-yl]-(3-cyano-5-trifluoromethylbenzyl)}amino-2-ethyl-6-trifluoromethyl-3,4-dihydro-2H-quinoline-1-carboxylic acid ethyl ester (167 mg). MS (m/z): 680 [M+H]+

Example 238

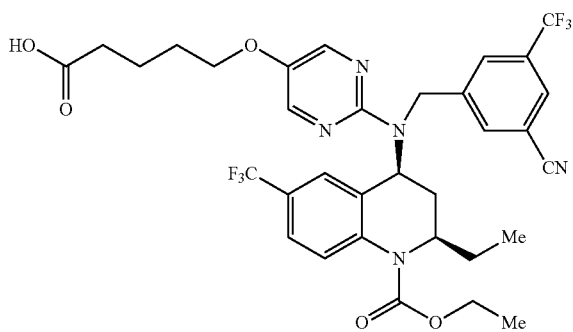

The corresponding starting compound is treated in a similar manner to Example 237 (2)-(3) to give the compound of Example 238. MS (m/z): 694 [M+H]+

Example 239

(1) (2R,4S)-4-{[3,5-Bis(trifluoromethyl)benzyl]-(5-bromopyrimidin-2-yl)}amino-2-ethyl-6-methoxy-3,4-dihydro-2H-quinoline-1-carboxylic acid ethyl ester (330 mg) is dissolved in dimethylsulfoxide (2.5 ml), and thereto are added [1,1'-bis(diphenylphosphino)ferrocene]dichloropalladium (11 mg), potassium acetate (147 mg) and bis(pinacolate)diboron (190 mg), and the mixture is stirred at 80° C. under nitrogen atmosphere for one hour. The reaction solution is cooled to room temperature, and thereto are added a saturated brine and ethyl acetate, and the mixture is separated. The organic layer is washed with a saturated brine, dried over magnesium sulfate and concentrated under reduced pressure. The resulting residue is dissolved in tetrahydrofuran (3 ml), and thereto is added a 2N aqueous sodium hydroxide solution (0.3 ml), and further thereto is added dropwise a 30% aqueous hydrogen peroxide solution (3 ml) under ice-cooling. The mixture is stirred at room temperature for one hour, and a saturated aqueous sodium thiosulfate solution is added thereto under ice-cooling. Then, a 10% aqueous citric acid solution and ethyl acetate are added to the mixture, and the organic layer is washed with a saturated brine, dried over magnesium sulfate and concentrated under reduced pressure. The resulting residue is purified by silica gel column chromatography (hexane:ethyl acetate=4:1→3:1) to give (2R,4S)-4-{[3,5-bis(trifluoro-methyl)benzyl]-(5-hydroxypyrimidin-2-yl)}amino-2-ethyl-6-methoxy-3,4-dihydro-2H-quinoline-1-carboxylic acid ethyl ester (144 mg). MS (m/z): 599 [M+H]+

(2) (2R,4S)-4-{[3,5-Bis(trifluoromethyl)benzyl]-(5-hydroxypyrimidin-2-yl)}amino-2-ethyl-6-methoxy-3,4-dihydro-2H-quinoline-1-carboxylic acid ethyl ester (141 mg) is dissolved in N,N-dimethylformamide (1.5 ml), and thereto are added potassium carbonate (65 mg) and 4-bromobutyric acid ethyl ester (44 µl). The mixture is stirred at room temperature overnight. A saturated brine and ethyl acetate are added to the mixture, and the mixture is separated. The organic layer is washed with a saturated brine, dried over magnesium sulfate and concentrated under reduced pressure. The resulting residue is purified by silica gel column chromatography (hexane:ethyl acetate=4:1→3:1) to give (2R,4S)-4-{[3,5-bis(trifluoromethyl)-benzyl]-[5-(3-ethoxycarbonylpropoxy)pyrimidin-2-yl]}amino-2-ethyl-6-methoxy-3,4-dihydro-2H-quinoline-1-carboxylic acid ethyl ester (141 mg). MS (m/z): 713 [M+H]+

(3) (2R,4S)-4-{[3,5-Bis(trifluoromethyl)benzyl]-[5-(3-ethoxycarbonyl-propoxy)pyrimidin-2-yl]}amino-2-ethyl-6-methoxy-3,4-dihydro-2H-quinoline-1-carboxylic acid ethyl ester (137 mg) is dissolved in 1,4-dioxane (1 ml), and thereto is added a 2N aqueous sodium hydroxide solution (1 ml), and the mixture is stirred at 40° C. for one hour. The reaction solution is cooled to room temperature, and acidified with a 10% aqueous citric acid solution. Subsequently, ethyl acetate is added to the mixture, and the organic layer is washed with a saturated brine, dried over magnesium sulfate and concentrated under reduced pressure. The resulting residue is purified by silica gel column chromatography (chloroform:methanol=19:1) to give (2R,4S)-4-{[3,5-bis(trifluoromethyl)benzyl]-[5-(3-carboxy-propoxy)pyrimidin-2-yl]}amino-2-ethyl-6-methoxy-3,4-dihydro-2H-quinoline-1-carboxylic acid ethyl ester (123 mg). MS (m/z): 685 [M+H]+

Example 240

(1) (2R,4S)-4-{[3,5-Bis(trifluoromethyl)benzyl]-(5-bromopyrimidin-2-yl)}amino-2-ethyl-6-hydroxy-3,4-dihydro-2H-quinoline-1-carboxylic acid ethyl ester (2.28 g) is dissolved in tetrahydrofuran (7 ml), and thereto is added sodium hydride (63%, 107 mg) under ice-cooling, and the mixture is stirred at 0° C. under nitrogen atmosphere for 30 minutes. To the reaction mixture is added chloromethyl methyl ether (0.40 ml) under ice-cooling, and the mixture is stirred at room temperature for one hour. A saturated aqueous sodium hydrogen carbonate solution and ethyl acetate are added to the mixture, and the mixture is separated. The organic layer is washed with a saturated brine, dried over magnesium sulfate and concentrated under reduced pressure. The resulting residue is purified by silica gel column chromatography (hexane:ethyl acetate=10:1) to give (2R,4S)-4-{[3,5-bis(trifluoromethyl)benzyl]-(5-bromopyrimidin-2-yl)}amino-2-ethyl-6-methoxymethoxy-3,4-dihydro-2H-quinoline-1-carboxylic acid ethyl ester (1.95 g). MS (m/z): 693/691 [M+H]+

(2) (2R,4S)-4-{[3,5-Bis(trifluoromethyl)benzyl]-(5-bromopyrimidin-2-yl)}amino-2-ethyl-6-methoxymethoxy-3,4-dihydro-2H-quinoline-1-carboxylic acid ethyl ester (1.93 g) is dissolved in dimethylsulfoxide (8 ml), and the mixture is deaerated. To the mixture are added [1,1'-bis(diphenyl-phosphino)ferrocene]dichloropalladium (61 mg), potassium acetate (822 mg) and bis(pinacolate)diboron (1.06 g), and the mixture is stirred at 80° C. under nitrogen atmosphere for 45 minutes. The reaction solution is cooled to room temperature, and thereto are added a saturated brine and ethyl acetate, and the mixture is separated. The organic layer is washed with a saturated brine, dried over magnesium sulfate and concentrated under reduced pressure. The resulting residue is dissolved in tetrahydrofuran (24 ml), and thereto is added a 2N aqueous sodium hydroxide solution (14 ml), and further added dropwise a 30% aqueous hydrogen peroxide solution (10 ml) under ice-cooling. The mixture is stirred at the same temperature for 30 minutes, and thereto is added a saturated aqueous sodium thiosulfate solution under ice-cooling, and further thereto are added a 10% aqueous citric acid solution and ethyl acetate. The organic layer is washed with a saturated brine, dried over magnesium sulfate and concentrated under reduced pressure. The resulting residue is purified by silica gel column chromatography (hexane:ethyl acetate=4:1→3:1) to give (2R,4S)-4-{[3,5-bis(trifluoromethyl)benzyl]-(5-hydroxypyrimidin-2-yl)}amino-2-ethyl-6-methoxymethoxy-3,4-dihydro-2H-quinoline-1-carboxylic acid ethyl ester (1.49 g). MS (m/z): 629 [M+H]$^+$ (3) (2R,4S)-4-{[3,5-Bis(trifluoromethyl)benzyl]-(5-hydroxypyrimidin-2-yl)}amino-2-ethyl-6-methoxymethoxy-3,4-dihydro-2H-quinoline-1-carboxylic acid ethyl ester (1.49 mg) is dissolved in N,N-dimethylformamide (7 mL), and thereto is added sodium hydride (62.7%, 109 mg) under ice-cooling, and the mixture is stirred at room temperature for 40 minutes. To the reaction solution is added 4-bromobutyric acid ethyl ester (0.52 mL), and the mixture is stirred at room temperature for 3 hours. To the reaction solution are added water and ethyl acetate-hexane=4:1 under ice-cooling, and the mixture is separated. The organic layer is washed with a saturated brine, dried over magnesium sulfate and concentrated under reduced pressure. The resulting residue is purified by silica gel column chromatography (hexane:ethyl acetate=4:1→7:3) to give (2R,4S)-4-{[3,5-bis(trifluoromethyl)benzyl]-[5-(3-ethoxycarbonylpropoxy)pyrimidin-2-yl]}amino-2-ethyl-6-methoxymethoxy-3,4-dihydro-2H-quinoline-1-carboxylic acid ethyl ester (1.29 g). MS (m/z): 743 [M+H]$^+$ (4) (2R,4S)-4-{[3,5-Bis(trifluoromethyl)benzyl]-[5-(3-ethoxycarbonyl-propoxy)pyrimidin-2-yl]}amino-2-ethyl-6-methoxymethoxy-3,4-dihydro-2H-quinoline-1-carboxylic acid ethyl ester (1.29 g) is dissolved in tetrahydrofuran (5.2 mL), and thereto is added a 6N hydrochloric acid (0.58 mL) under ice-cooling, and the mixture is stirred at 50° C. for 2.5 hours. The reaction solution is cooled to room temperature, and thereto are added water and ethyl acetate, and the mixture is separated. The organic layer is washed with a saturated brine, dried over magnesium sulfate, and concentrated under reduced pressure. The resulting residue is purified by silica gel column chromatography (hexane:ethyl acetate=4:1→7:3→chloroform:methanol=9:1) to give (2R,4S)-4-{[3,5-bis(trifluoromethyl)benzyl]-[5-(3-ethoxycarbonylpropoxy)pyrimidin-2-yl]}amino-2-ethyl-6-hydroxy-3,4-dihydro-2H-quinoline-1-carboxylic acid ethyl ester (614 mg, MS (m/z): 699 [M+H]$^+$) and (2R,4S)-4-{[3,5-bis(trifluoromethyl)benzyl]-[5-(3-carboxypropoxy)pyrimidin-2-yl]}amino-2-ethyl-6-hydroxy-3,4-dihydro-2H-quinoline-1-carboxylic acid ethyl ester (550 mg, MS (m/z): 671 [M+H]$^+$).

(5) (2R,4S)-4-{[3,5-Bis(trifluoromethyl)benzyl]-[5-(3-ethoxycarbonyl-propoxy)pyrimidin-2-yl]}amino-2-ethyl-6-hydroxy-3,4-dihydro-2H-quinoline-1-carboxylic acid ethyl ester (610 mg), and pyridine (424 μl) are dissolved in methylene chloride (4 mL), and thereto is added dropwise trifluoromethanesulfonic anhydride (354 μl) under ice-cooling. The reaction solution is stirred for 3.5 hours, and thereto are added a saturated aqueous citric acid solution and diethyl ether, and the mixture is separated. The organic layer is washed with a saturated brine, dried over magnesium sulfate and concentrated under reduced pressure. The resulting residue is purified by silica gel column chromatography (hexane:ethyl acetate=9:1→7:3) to give (2R,4S)-4-{[3,5-bis(trifluoromethyl)benzyl]-[5-(3-ethoxy-carbonylpropoxy)pyrimidin-2-yl]}amino-2-ethyl-6-trifluoromethane-sulfonyloxy-3,4-dihydro-2H-quinoline-1-carboxylic acid ethyl ester (555 mg). MS (m/z): 831 [M+H]$^+$ (6) (2R,4S)-4-{[3,5-Bis(trifluoromethyl)benzyl]-[5-(3-ethoxycarbonyl-propoxy)pyrimidin-2-yl]}amino-2-ethyl-6-trifluoromethane sulfonyloxy-3,4-dihydro-2H-quinoline-1-carboxylic acid ethyl ester (220 mg), dimethylamine (a 2N tetrahydrofuran solution, 0.16 mL), palladium acetate (0.6 mg), 2-(di-tert-butylphosphino)diphenyl (3.3 mg) and sodium tert-butoxide (36 mg) are dissolved in toluene (0.52 mL), and the mixture is stirred at 80° C. for 21 hours under nitrogen atmosphere in a sealed vessel. The reaction solution is cooled to room temperature, and thereto are added water and ethyl acetate, and the mixture is separated. The organic layer is washed with a saturated brine, dried over magnesium sulfate and concentrated under reduced pressure. The resulting residue is purified by silica gel column chromatography (hexane:ethyl acetate=4:1→7:3) to give (2R,4S)-4-{[3,5-bis(trifluoromethyl)benzyl]-[5-(3-ethoxycarbonylpropoxy)pyrimidin-2-yl]}amino-6-dimethylamino-2-ethyl-3,4-dihydro-2H-quinoline-1-carboxylic acid ethyl ester (53 mg). MS (m/z): 726 [M+H]$^+$ (7) (2R,4S)-4-{[3,5-Bis(trifluoromethyl)benzyl]-[5-(3-ethoxycarbonyl-propoxy)pyrimidin-2-yl]}amino-6-dimethylamino-2-ethyl-3,4-dihydro-2H-quinoline-1-carboxylic acid ethyl ester (48 mg) is dissolved in ethanol (0.3 mL), and thereto is added a 2N aqueous sodium hydroxide solution (0.1 mL), and the mixture is stirred at room temperature for 30 minutes. To the reaction solution are added a saturated aqueous citric acid solution and ethyl acetate, and the mixture is separated. The organic layer is washed with water and a saturated brine, dried over sodium sulfate, and concentrated under reduced pressure. The resulting residue is purified by silica gel column chromatography (hexane:ethyl acetate=4:1→1:1) to give (2R,4S)-4-{[3,5-bis(trifluoromethyl)benzyl]-[5-(3-carboxypropoxy)pyrimidin-2-yl]}amino-6-dimethylamino-2-ethyl-3,4-dihydro-2H-quinoline-1-carboxylic acid ethyl ester (29 mg). MS (m/z): 698 [M+H]$^+$ Example 241

(1) (2R*,4*S)-4-Benzyloxycarbonylamino-2-ethyl-6-trifluoromethyl-1,2,3,4-tetrahydroquinoline (112.8 g) is dissolved in methanol (1000 ml) and thereto is added 10% palladium-carbon (5.64 g), and the mixture is stirred at room temperature under hydrogen atmosphere overnight. The palladium carbon is removed by filtration, and the filtrate is concentrated under reduced pressure. To the resulting residue is added n-hexane, and the precipitated crystals are collected by filtration and washed to give (2R*,4S*)-(4-amino-2-ethyl-6-trifluoromethyl-1,2,3,4-tetrahydroquinoline (70.3 g). MS (m/z): 245 [M+H]$^+$ (2) (2R*,4S*)-(4-Amino-2-ethyl-6-trifluoromethyl-1,2,3,4-tetrahydroquinoline (70 g) and di-tert-butyl dicarbonate (68.2 g) are dissolved in tetrahydrofuran (500 ml), and the mixture is stirred at room temperature overnight. The reaction solution is concentrated under reduced pressure, and thereto is added n-hexane. The precipitated crystals are collected by filtration to give (2R*,4S*)-4-tert-butoxycarbonylamino-2-ethyl-6-trifluoromethyl-1,2,3,4-tetrahydro-quinoline (90.7 g). MS (m/z): 345 [M+H]$^+$ (3) (2R*,4*S)-4-tert-Butoxycarbonylamino-2-ethyl-6-trifluoromethyl-1,2,3,4-tetrahydroquinoline (90.58 g) and triethylamine (44 ml) are dissolved in methylene chloride (900 ml), and thereto is added triphosgene (31.2 g) under ice-cooling, and the mixture is stirred at room temperature for one hour. The reaction solution is concentrated under reduced pressure, and the resulting residue and benzyl alcohol (54.4 ml) are dissolved in tetrahydrofuran (900 ml), and thereto is added sodium hydride (20.2 g) under ice-cooling, and the mixture is stirred at the same temperature for 3 hours. Water and ethyl acetate are added to the mixture, and the mixture is separated. The organic layer is washed with a saturated brine, dried over magnesium sulfate, and concentrated under reduced pressure. The residue is crystallized from isopropyl ether to give (2R*,4*S)-4-tert-butoxycarbonylamino-2-ethyl-6-trifluoromethyl-3,4-dihydro-2H-quinoline-1-carboxylic acid benzyl ester (104.7 g). MS (m/z): 496 [M+H$_2$O]$^+$ (4) (2R*,4S*)-4-tert-Butoxycarbonylamino-2-ethyl-6-trifluoromethyl-3,4-dihydro-2H-quinoline-1-carboxylic acid benzyl ester (104.5 g) is dissolved in chloroform (500 ml), and thereto is added a 4N hydrochloric acid in ethyl acetate (500 ml), and the mixture is stirred at room temperature for 30 minutes. The reaction solution is concentrated under reduced pressure, and to the resulting residue is added isopropyl ether, and the precipitated crystals are collected by filtration and washed to give (2R*,4S*)-4-amino-2-ethyl-6-trifluoromethyl-3,4-dihydro-2H-quinoline-1-carboxylic acid benzyl ester hydrochloride (88.0 g). MS (m/z): 379 [M—HCl]$^+$ (5) (2R*,4S*)-4-Amino-2-ethyl-6-trifluoromethyl-3,4-dihydro-2H-quinoline-1-carboxylic acid benzyl ester hydrochloride (12 g) is dissolved in a mixture of a 2N aqueous sodium hydroxide solution and ethyl acetate, and the mixture is separated. The organic layer is washed with a saturated brine, dried over magnesium sulfate and concentrated under reduced pressure. The resulting residue, and 5-bromo-2-chloropyrimidine (16.8 g) and diisopropylethylamine (15 ml) are dissolved in 1,4-dioxane (100 ml), and the mixture is stirred at 130° C. for 24 hours. The reaction solution is cooled to room temperature, and water and ethyl acetate are added thereto, and the mixture is separated. The organic layer is washed with a saturated brine, dried over magnesium sulfate and concentrated under reduced pressure. The resulting residue is purified by silica gel column chromatography (hexane:ethyl acetate=9:1→4:1) to give (2R*,4S*)-4-(5-bromopyrimidin-2-yl)amino-2-ethyl-6-trifluoromethyl-3,4-dihydro-2H-quinoline-1-carboxylic acid benzyl ester (9.39 g). MS (m/z): 535/537 [M+H]$^+$ (6) (2R*,4S*)-4-(5-Bromopyrimidin-2-yl)amino-2-ethyl-6-trifluoromethyl-3,4-dihydro-2H-quinoline-1-carboxylic acid benzyl ester (5 g), tris(dibenzylideneacetone)dipalladium (1.71 g), sodium tert-butoxide (1.35 g), 2-(di-tert-butylphosphino)biphenyl (2.22 g), and morpholine (1.22 ml) are dissolved in toluene (50 ml), and the mixture is stirred at 50° C. under nitrogen atmosphere for 5 hours. The reaction solution is cooled to room temperature, and thereto are added water and ethyl acetate, and the mixture is separated. The organic layer is washed with a saturated brine, dried over magnesium sulfate and concentrated under reduced pressure. The resulting residue is purified by silica gel column chromatography (hexane:ethyl acetate=2:1→1:1), then by NH-silica gel column chromatography (hexane:ethyl acetate=2:1→1:1) to give (2R*,4S*)-2-ethyl-4-[5-(morpholin-4-yl)pyrimidin-2-yl]amino-6-trifluoromethyl-3,4-dihydro-2H-quinoline-1-carboxylic acid benzyl ester (2.58 g). MS (m/z): 542 [M+H]$^+$ (7) (2R*,4S*)-2-Ethyl-4-[5-(morpholin-4-yl)pyrimidin-2-yl]amino-6-trifluoromethyl-3,4-dihydro-2H-quinoline-1-carboxylic acid benzyl ester (2.57 g) is dissolved in N,N-dimethylformamide (20 ml), and thereto is added sodium hydride (62.7%, 257 mg) under ice-cooling, and the mixture is stirred at room temperature for 30 minutes. To the mixture is added 3,5-dibromobenzyl bromide (2.64 g) under ice-cooling, and the mixture is stirred at room temperature overnight. To the reaction solution are added water and ethyl acetate, and the mixture is separated. The organic layer is washed with a saturated brine, dried over magnesium sulfate and concentrated under reduced pressure. The resulting residue is purified by silica gel column chromatography (hexane:ethyl acetate=6:1→4:1) to give (2R*,4S*)-4-{(3,5-dibromobenzyl)-[5-(morpholin-4-yl)pyrimidin-2-yl]}amino-2-ethyl-6-trifluoromethyl-3,4-dihydro-2H-quinoline-1-carboxylic acid benzyl ester (2.41 g). MS (m/z): 788/780 [M+H]$^+$ (8) (2R*,4S*)-4-{(3,5-Dibromobenzyl)-[5-(morpholin-4-yl)pyrimidin-2-yl]}amino-2-ethyl-6-trifluoromethyl-3,4-dihydro-2H-quinoline-1-carboxylic acid benzyl ester (2.38 g), a catalytic amount of tetrakis(triphenyl-phosphine)palladium and zinc cyanide (779 mg) are dissolved in N,N-dimethylformamide (40 ml), and the mixture is stirred at 110° C. under nitrogen atmosphere for 4 hours. The reaction solution is cooled to room temperature, and thereto are added water and ethyl acetate, and the organic layer is washed with a saturated brine, dried over magnesium sulfate and concentrated under reduced pressure. The resulting residue is purified by silica gel column chromatography (hexane:ethyl acetate=4:1 →2:1) to give (2R*,4S*)-4-{(3,5-dicyanobenzyl)-[5-(morpholin-4-yl)-pyrimidin-2-yl]}amino-2-ethyl-6-trifluoromethyl-3,4-dihydro-2H-quinoline-1-carboxylic acid benzyl ester (1.66 g). MS (m/z): 682 [M+H]$^+$ Example 242

(1) (2R*,4S*)-4-{(3,5-Dicyanobenzyl)-[5-(morpholin-4-yl)pyrimidin-2-yl]}amino-2-ethyl-6-trifluoromethyl-3,4-dihydro-2H-quinoline-1-carboxylic acid benzyl ester (1.6 g) is dissolved in a mixture of methanol (10 ml) and tetrahydrofuran (10 ml), and thereto is added a catalytic amount of 10% palladium-carbon, and the mixture is stirred at room temperature under hydrogen atmosphere for one hour. The catalyst is removed by filtration, and the filtrate is concentrated under reduced pressure. The resulting residue is purified by silica gel column chromatography (hexane:ethyl acetate=2:1→1:1) to give (2R*,4S*)-4-{(3,5-dicyanobenzyl)-[5-(morpholin-4-yl)pyrimidin-2-yl]}amino-2-ethyl-6-trifluoromethyl-1,2,3,4-tetrahydroquinoline (1.07 g). MS (m/z): 548 [M+H]$^+$ (2) (2R*,4S*)-4-{(3,5-Dicyanobenzyl)-[5-(morpholin-4-yl)pyrimidin-2-yl]}-amino-2-ethyl-6-trifluoromethyl-1,2,3,4-tetrahydroquinoline (150 mg) and triethylamine (76 µl) are dissolved in dichloromethane (1.5 ml), and thereto is added triphosgene (33 mg) under ice-cooling, and the mixture is stirred at room temperature for 3 hours. To the reaction solution are added water and ethyl acetate, and the organic layer is washed with a saturated brine, dried over magnesium sulfate and concentrated under reduced pressure. The resulting residue and ethylene glycol (1 ml) are dissolved in tetrahydrofuran (2.5 ml), and thereto are added triethylamine (400 µl) and a catalytic amount of 4-dimethylaminopyridine under ice-cooling, and the mixture is stirred at room temperature for one hour. To the reaction solution are added water and ethyl acetate, and the organic layer is washed with a saturated brine, dried over magnesium sulfate and concentrated under reduced pressure. The resulting residue is purified by silica gel column chromatography (hexane:ethyl acetate=1:2→1:4) to give (2R*,4S*)-4-{(3,5-dicyanobenzyl)-[5-(morpholin-4-yl)pyrimidin-2-yl]}amino-2-ethyl-6-trifluoromethyl-3,4-dihydro-2H-quinoline-1-carboxylic acid 2-hydroxyethyl ester (156 mg). MS (m/z): 636 [M+H]$^+$ Example 243

(2R*,4S*)-4-{(3,5-Dicyanobenzyl)-[5-(morpholin-4-yl)pyrimidin-2-yl]}amino-2-ethyl-6-trifluoromethyl-1,2,3,4-tetrahydroquinoline (200 mg) and 2-bromoethyl isocyanate (200 µl) are dissolved in toluene (2 ml), and the mixture is stirred at 90° C. for 8 hours. The reaction solution is cooled to room temperature, and thereto are added water and ethyl acetate, and the mixture is separated. The organic layer is washed with a saturated brine, dried over magnesium sulfate and concentrated under reduced pressure. The resulting residue is dissolved in N,N-dimethylformamide (2 ml), and thereto is added sodium hydride (62.7%, 100 mg) under ice-cooling. The mixture is stirred at 90° C. for 30 minutes. The reaction solution is cooled to room temperature, and thereto are added water and ethyl acetate, and the mixture is separated. The organic layer is washed with a saturated brine, dried over magnesium sulfate and concentrated under reduced pressure. The resulting residue is purified by silica gel column chromatography (hexane:ethyl acetate=1:4→0:1) to give (2R*,4S*)-4-{(3,5-dicyanobenzyl)-[5-(morpholin-4-yl)pyrimidin-2-yl]}amino-1-(4,5-dihydrooxazol-2-yl)-2-ethyl-6-trifluoromethyl-1,2,3,4-tetrahydroquinoline (97 mg). MS (m/z): 617 [M+H]$^+$ Example 244

(1) 4-Aminobenzotrifluoride (100 g) and benzotriazole (74 g) are dissolved in toluene (1200 ml), and thereto is added dropwise propionaldehyde (49.3 ml) under ice-cooling, and the reaction solution is stirred at room temperature overnight. Heptane (600 ml) is added, and the mixture is further stirred for 30 minutes. The precipitates are collected by filtration, and washed with heptane to give {[1-(benzotriazol-1-yl)propyl]-(4-trifluoromethylphenyl)}amine (140.9 g).

(2) {[1-(Benzotriazol-1-yl)propyl]-(4-trifluoromethylphenyl)}amine (140 g), (S)-vinylcarbamic acid 1-phenylethyl ester (83.5 g) and p-toluenesulfonic acid (1.66 g) are dissolved in toluene (1500 ml), and the mixture is stirred at 80° C. for 3 hours. To the mixture are added a 2N aqueous sodium hydroxide solution and ethyl acetate, and the mixture is separated. The organic layer is washed with a saturated brine, dried over magnesium sulfate and concentrated under reduced pressure. The resulting residue is recrystallized from isopropyl ether to give (2R,4S)-4-((S)-1-phenylethoxycarbonylamino)-2-ethyl-6-trifluoromethyl-1,2,3,4-tetrahydroquinoline (36.4 g). MS (m/z): 393 [M+H]$^+$ (3) (2R,4S)-4-((S)-1-Phenylethoxycarbonylamino)-2-ethyl-6-trifluoromethyl-1,2,3,4-tetrahydroquinoline (2.25 g) is dissolved in a mixture of methanol (15 ml) and tetrahydrofuran (5 ml), and thereto is added 10% palladium-carbon (200 mg). The mixture is stirred at room temperature under hydrogen atmosphere for 4 hours. The palladium-carbon is removed by filtration, and the filtrate is concentrated under reduced pressure to give (2R,4S)-4-amino-2-ethyl-6-trifluoromethyl-1,2,3,4-tetrahydroquinoline. MS (m/z): 245 [M+H]$^+$. The resulting compound is dissolved in tetrahydrofuran (15 ml), and thereto is added di-tert-butyl dicarbonate (1.25 g), and the mixture is stirred at room temperature overnight. The reaction solution is concentrated under reduced pressure, and the resulting residue is purified by silica gel column chromatography (hexane:ethyl acetate=95:5→7:3) to give (2R,4S)-4-tert-butoxycarbonylamino-2-ethyl-6-trifluoromethyl-1,2,3,4-tetrahydroquinoline (2.0 g). MS (m/z): 345 [M+H]$^+$ (4) (2R,4S)-4-(tert-Butoxycarbonylamino)-2-ethyl-6-trifluoromethyl-1,2,3,4-tetrahydroquinoline (2.0 g) and triethylamine (972 µl) are dissolved in methylene chloride (20 ml), and thereto is added triphosgene (690 mg) under ice-cooling, and the mixture is stirred at room temperature for one hour. Ethyl acetate and a saturated aqueous sodium hydrogen carbonate solution are added to the mixture, and the mixture is separated. The organic layer is washed with a saturated brine, dried over magnesium sulfate, and concentrated under reduced pressure. The residue and benzyl alcohol (1.2 ml) are dissolved in tetrahydrofuran (30 ml), and thereto is added sodium hydride (446 mg) under ice-cooling, and the mixture is stirred at room temperature overnight. Water and ethyl acetate are added to the mixture, and the mixture is separated. The organic layer is washed with a saturated brine, dried over magnesium sulfate and concentrated under reduced pressure. The residue is dissolved in chloroform (10 ml), and thereto is added a 4N hydrogen chloride in ethyl acetate (10 ml), and the mixture is stirred at room temperature for one hour. To the reaction solution are ethyl acetate and a saturated aqueous sodium hydrogen carbonate solution, and the mixture is separated. The organic layer is washed with a saturated brine, dried over magnesium sulfate, and concentrated under reduced pressure to give (2R,4S)-4-amino-2-ethyl-6-trifluoromethyl-3,4-dihydro-2H-quinoline-1-carboxylic acid benzyl ester (1.73 g). MS (m/z): 379: [M+H]$^+$ (5) (2R,4S)-4-Amino-2-ethyl-6-trifluoromethyl-3,4-dihydro-2H-quinoline-1-carboxylic acid benzyl ester (1.73 g) and 5-bromo-2-chloro-pyrimidine (2.21 g) are dissolved in 1,4-dioxane (20 ml), and thereto is added N,N-diisopropylethylamine (1.99 ml), and the mixture is refluxed overnight. To the reaction solution are added a saturated brine and ethyl acetate, and the mixture is separated. The organic layer is washed with a saturated brine, dried over magnesium sulfate and concentrated under reduced pressure. The residue is purified by silica gel column chromatography (hexane:ethyl acetate=95:5→3:1) to give (2R,4S)-4-(5-bromopyrimidin-2-yl)amino-2-ethyl-6-trifluoromethyl-3,4-dihydro-2H-quinoline-1-carboxylic acid benzyl ester (2.02 g). MS (m/z): 535/537 [M+H]$^+$ (6) (2R,4S)-4-(5-Bromopyrimidin-2-yl)amino-2-ethyl-6-trifluoromethyl-3,4-dihydro-2H-quinoline-1-carboxylic acid benzyl ester (2.0 g) is dissolved in N,N-dimethylformamide (15 ml), and thereto is added sodium hydride (177 mg) under ice-cooling. The mixture is stirred at the same temperature for 20 minutes, and thereto is added 3,5-bis(trifluoromethyl)benzyl bromide (1.03 ml), and the mixture is stirred at the same temperature for one hour. To the reaction solution are added ethyl acetate and water, and the mixture is separated. The organic layer is washed with a saturated brine, dried over magnesium sulfate and concentrated under reduced pressure. The residue is purified by silica gel column chromatography (hexane:ethyl acetate=95:5→3:1) to give (2R,4S)-4-{[3,5-bis(trifluoromethyl)benzyl]-(5-bromopyrimidin-2-yl)}amino-2-ethyl-6-trifluoromethyl-3,4-dihydro-2H-quinoline-1-carboxylic acid benzyl ester (2.19 g). MS (m/z): 761/763 [M+H]$^+$ (7) (2R,4S)-4-{[3,5-Bis(trifluoromethyl)benzyl]-(5-bromopyrimidin-2-yl)}amino-2-ethyl-6-trifluoromethyl-3,4-dihydro-2H-quinoline-1-carboxylic acid benzyl ester (2.15 g), isonipecotic acid ethyl ester (634 µl), sodium tert-butoxide (407 mg) and 2-(di-tert-butylphosphino)biphenyl (337 mg) are dissolved in toluene (20 ml), and thereto is added tris(dibenzylidene-acetone)dipalladium (258 mg), and the mixture is stirred at room temperature under nitrogen atmosphere overnight. To the reaction solution are added ethyl acetate and water, and the mixture is separated. The organic layer is washed with a saturated brine, dried over magnesium sulfate and concentrated under reduced pressure. The residue is purified by silica gel column chromatography (hexane:ethyl acetate=95:5→4:1) to give (2R,4S)-4-{[3,5-bis(trifluoromethyl)benzyl]-[5-(4-ethoxycarbonylpiperidin-1-yl)pyrimidin-2-yl]}amino-2-ethyl-6-trifluoro-methyl-3,4-dihydro-2H-quinoline-1-carboxylic acid benzyl ester (1.30 g). MS (m/z): 838 [M+H]$^+$ (8) (2R,4S)-4-{[3,5-Bis(trifluoromethyl)benzyl]-[5-(4-ethoxycarbonyl-piperidin-1-yl)pyrimidin-2-yl]}amino-2-ethyl-6-trifluoromethyl-3,4-dihydro-2H-quinoline-1-carboxylic acid benzyl ester (1.28 g) is dissolved in ethanol (15 ml), and thereto is added 10% palladium-carbon (200 mg), and the mixture is stirred at room temperature under hydrogen atmosphere for 1.5 hour. The palladium-carbon is removed by filtration, and the obtained filtrate is concentrated under reduced pressure. The residue is purified by silica gel column chromatography (hexane:ethyl acetate=95:5→4:1) to give (2R,4S)-4-{[3,5-bis(trifluoromethyl)benzyl]-[5-(4-ethoxycarbonylpiperidin-1-yl)pyrimidin-2-yl]}amino-2-ethyl-6-trifluoromethyl-1,2,3,4-tetrahydro-quinoline (1.02 g). MS (m/z): 704 [M+H]$^+$ (9) (2R,4S)-4-{[3,5-Bis(trifluoromethyl)benzyl]-[5-(4-ethoxycarbonyl-piperidin-1-yl)pyrimidin-2-yl]}amino-2-ethyl-6-trifluoromethyl-1,2,3,4-tetrahydroquinoline (250 mg) and triethylamine (60 µl) are dissolved in methylene chloride (3 ml), and thereto is added triphosgene (42 mg) under ice-cooling. The mixture is stirred at room temperature for 30 minutes, and thereto are added ethyl acetate and a saturated aqueous sodium hydrogen carbonate solution, and the mixture is separated. The organic layer is washed with a saturated brine, dried over magnesium sulfate and concentrated under reduced pressure. The residue is dissolved in tetrahydrofuran (1 ml), and thereto are added a 2-fluoroethanol (0.5 ml), triethylamine (0.5 ml) and 4-dimethylaminopyridine (10 mg), and the mixture is stirred at room temperature overnight. To the mixture are added water and ethyl acetate, and the mixture is separated. The organic layer is washed with a saturated brine, dried over magnesium sulfate, and concentrated under reduced pressure. The residue is purified by silica gel column chromatography (hexane:ethyl acetate=95:5→4:1) to give (2R,4S)-4-{[3,5-bis(trifluoromethyl)benzyl]-[5-(4-ethoxycarbonylpiperidin-1-yl)-pyrimidin-2-yl]}amino-2-ethyl-6-trifluoromethyl-3,4-dihydro-2H-quinoline-1-carboxylic acid 2-fluoroethyl ester (215 g). MS (m/z): 794 [M+H]$^+$ Examples 245-247

The corresponding starting compounds are treated in a similar manner to Example 244 (9) to give the compounds as listed in Table 31.

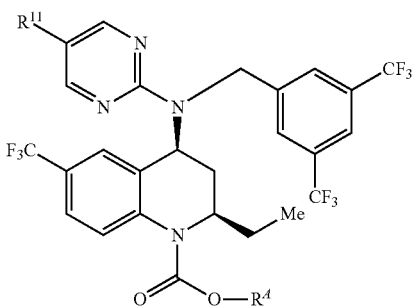

TABLE 31

| Ex. No. | R$^{11}$ | R$^A$ | Physical properties, etc. |
|---|---|---|---|
| 245 | ![structure] | ![structure] | MS (m/z): 812 [M + H]$^+$ |
| 246 | ![structure] | ![structure] | MS (m/z): 830 [M + H]$^+$ |

TABLE 31-continued

| Ex. No. | R[11] | R[4] | Physical properties, etc. |
|---|---|---|---|
| 247 |  |  | MS (m/z): 792 [M + H]+ |

Example 248

(1) (2R,4S)-4-{[3,5-Bis(trifluoromethyl)benzyl]-(5-bromopyrimidin-2-yl)}-amino-2-ethyl-6-trifluoro methyl-3,4-dihydro-2H-quinoline-1-carboxylic acid benzyl ester (4.87 g), [1,1'-bis(diphenylphosphino)ferrocene]-dichloropalladium (140 mg), potassium acetate (1.88 g), and bis(pinacolate)diboron (3.25 g) are dissolved in dimethylsulfoxide (45 ml), and the mixture is stirred at 80° C. under nitrogen atmosphere for one hour. The reaction solution is cooled to room temperature, and thereto are added water and ethyl acetate, and the mixture is separated. The organic layer is washed with a saturated brine, dried over magnesium sulfate and concentrated under reduced pressure. The resulting residue is dissolved in tetrahydrofuran (50 ml), and thereto is added dropwise a 30% aqueous hydrogen peroxide solution (10 ml) under ice-cooling. One hour thereafter, a saturated aqueous sodium thiosulfate solution is added to the reaction mixture under ice-cooling, and the excess amount of hydrogen peroxide is consumed. Water and ethyl acetate are added to the reaction mixture, and the mixture is separated. The organic layer is washed with a saturated brine, dried over magnesium sulfate and concentrated under reduced pressure. The resulting residue is purified by silica gel column chromatography (hexane:ethyl acetate=95:5→4:1) to give (2R,4S)-4-{[3,5-bis(trifluoromethyl)benzyl]-(5-hydroxypyrimidin-2-yl)}amino-2-ethyl-6-trifluoromethyl-3,4-dihydro-2H-quinoline-1-carboxylic acid benzyl ester (2.73 g). MS (m/z): 699 [M+H]+

(2) (2R,4S)-4-{[3,5-Bis(trifluoromethyl)benzyl]-(5-hydroxypyrimidin-2-yl)}amino-2-ethyl-6-trifluoromethyl-3,4-dihydro-2H-quinoline-1-carboxylic acid benzyl ester (2.71 g) and 4-bromobutyric acid ethyl ester (617 µl) are dissolved in N,N-dimethylformamide (10 ml), and thereto is added potassium carbonate (644 mg), and the mixture is stirred at 45° C. overnight. Ethyl acetate and a saturated brine are added to the mixture, and the mixture is separated. The organic layer is washed with a saturated brine, dried over magnesium sulfate and concentrated under reduced pressure. The resulting residue is purified by silica gel column chromatography (hexane:ethyl acetate=95:5→4:1) to give (2R,4S)-4-{[3,5-bis(trifluoro-methyl)benzyl]-[5-(3-ethoxycarbonylpropoxy)pyrimidin-2-yl]}amino-2-ethyl-6-trifluoromethyl-3,4-dihydro-2H-quinoline-1-carboxylic acid benzyl ester (2.78 g). MS (m/z): 813 [M+H]+

(3) (2R,4S)-4-{[3,5-Bis(trifluoromethyl)benzyl]-[5-(3-ethoxycarbonyl-propoxy)pyrimidin-2-yl]}amino-2-ethyl-6-trifluoromethyl-3,4-dihydro-2H-quinoline-1-carboxylic acid benzyl ester (2.77 g) is dissolved in ethanol (30 ml), and thereto is added 10% palladium-carbon (500 mg), and the mixture is stirred at room temperature under hydrogen atmosphere for 3 hours. The palladium-carbon is removed by filtration, and the obtained filtrate is concentrated under reduced pressure. The residue is purified by silica gel column chromatography (hexane:ethyl acetate=95:5→4:1) to give (2R,4S)-4-{[3,5-bis(trifluoromethyl)benzyl]-[5-(3-ethoxycarbonylpropoxy)-pyrimidin-2-yl]}amino-2-ethyl-6-trifluoromethyl-1,2,3,4-tetrahydro-quinoline (2.23 g). MS (m/z): 679 [M+H]+

(4) (2R,4S)-4-{[3,5-Bis(trifluoromethyl)benzyl]-[5-(3-ethoxycarbonyl-propoxy)pyrimidin-2-yl]}amino-2-ethyl-6-trifluoromethyl-1,2,3,4-tetra-hydroquinoline (319 mg) and triethylamine (79 µl) is dissolved in methylene chloride (2 ml), and thereto is added triphosgene (56 mg) under ice-cooling, and the mixture is stirred at room temperature for 30 minutes. To the mixture are added ethyl acetate and a saturated aqueous sodium hydrogen carbonate solution, and the mixture is separated. The organic layer is washed with a saturated brine, dried over magnesium sulfate and concentrated under reduced pressure. The residue is dissolved in tetrahydrofuran (1 ml), and thereto are added 2-fluoroethanol (0.5 ml), triethylamine (0.5 ml) and 4-dimethylaminopyridine (10 mg), and the mixture is stirred at room temperature overnight. Water and ethyl acetate are added to the mixture, and the mixture is separated. The organic layer is washed with a saturated brine, dried over magnesium sulfate and concentrated under reduced pressure. The residue is purified by silica gel column chromatography (hexane:ethyl acetate=95:5→4:1) to give (2R,4S)-4-{[3,5-bis(trifluoromethyl)benzyl]-[5-(3-ethoxycarbonylpropoxy)pyrimidin-2-yl]}amino-2-ethyl-6-trifluoromethyl-3,4-dihydro-2H-quinoline-1-carboxylic acid 2-fluoroethyl ester (173 mg). MS (m/z): 769 [M+H]+

Examples 249-253

The corresponding starting compounds are treated in a similar manner to Example 248 (4) to give the compounds as listed in Table 32.

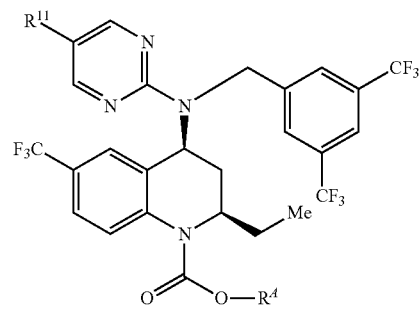

TABLE 32
| Ex. No. | R¹¹ | R⁴ | Physical properties, etc. |
|---|---|---|---|
| 249 | 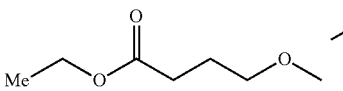 |  | MS (m/z): 805 [M + H]⁺ |
| 250 | 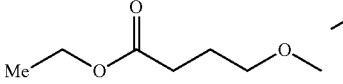 |  | MS (m/z): 779 [M + H]⁺ |
| 251 | 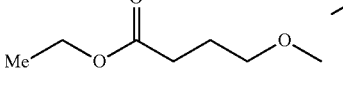 |  | MS (m/z): 793 [M + H]⁺ |
| 252 | 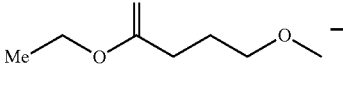 |  | MS (m/z): 765 [M + H]⁺ |
| 253 | 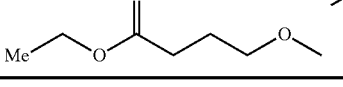 |  | MS (m/z): 781 [M + H]⁺ |
Examples 254-261
The corresponding starting compounds are treated in a similar manner to Example 177 (3) to give the compounds as listed in Table 33.
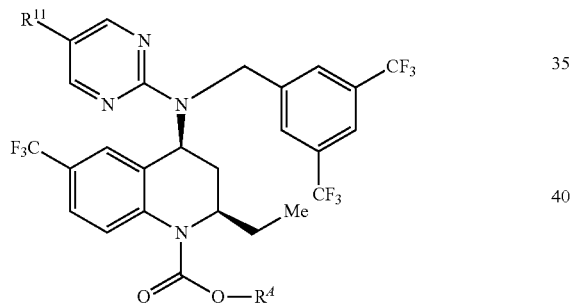
TABLE 33
| Ex. No. | R¹¹ | R⁴ | Physical properties, etc. |
|---|---|---|---|
| 254 | 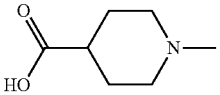 | 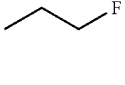 | MS (m/z): 766 [M + H]⁺ |
| 255 | 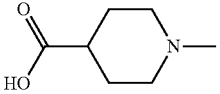 | 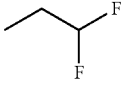 | MS (m/z): 784 [M + H]⁺ |
| 256 | 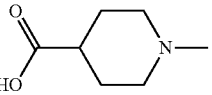 | 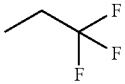 | MS (m/z): 802 [M + H]⁺ |
| 257 | 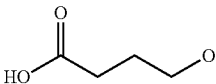 | 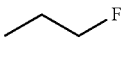 | MS (m/z): 741 [M + H]⁺ |

TABLE 33-continued

| Ex. No. | R[11] | R[4] | Physical properties, etc. |
|---|---|---|---|
| 258 | HO-C(=O)-CH2-CH2-CH2-O- | -CH2-CHF2 (with extra F) | MS (m/z): 777 [M + H]+ |
| 259 | HO-C(=O)-CH2-CH2-CH2-O- | -CH2-CH(Me)2 | MS (m/z): 751 [M + H]+ |
| 260 | HO-C(=O)-CH2-CH2-CH2-O- | -CH2-CH(Me)-CH2-Me | MS (m/z): 765 [M + H]+ |
| 261 | HO-C(=O)-CH2-CH2-CH2-O- | -CH(Me)2 | MS (m/z): 737 [M + H]+ |

Example 262

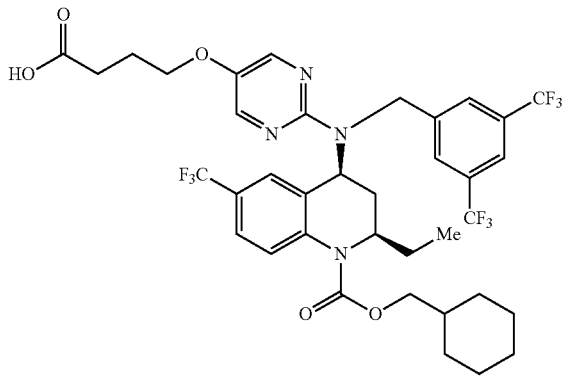

The corresponding starting compound is treated in a similar manner to Example 248 (4) and Example 177 (3) to give the compound of Example 262. MS (m/z): 791 [M+H]+

Example 263

(2R,4S)-4-{[3,5-Bis(trifluoromethyl)benzyl]-[5-(4-ethoxycarbonyl-piperidin-1-yl)pyrimidin-2-yl]}amino-2-ethyl-6-trifluoromethyl-3,4-dihydro-2H-quinoline-1-carboxylic acid 2-hydroxyethyl ester (215 mg) is dissolved in tetrahydrofuran (2 ml), and thereto is added a 1N aqueous sodium hydroxide solution (2 ml), and the mixture is stirred at 50° C. for 2 hours. The reaction solution is cooled to room temperature, and thereto are added ethyl acetate and 1N hydrochloric acid, and the mixture is separated. The organic layer is washed with a saturated brine, dried over magnesium sulfate and concentrated under reduced pressure. The resulting residue is purified by silica gel column chromatography (hexane:ethyl acetate=4:1→1:4) to give (2R,4S)-4-{[3,5-bis(trifluoromethyl)benzyl]-[5-(4-carboxy-piperidin-1-yl)pyrimidin-2-yl]}amino-2-ethyl-6-trifluoromethyl-3,4-dihydro-2H-quinoline-1-carboxylic acid 2-hydroxyethyl ester (47 mg, MS (m/z): 764 [M+H]+) and (2R,4S)-4-{[3,5-bis(trifluoromethyl)benzyl]-[5-(4-carboxy-piperidin-1-yl)pyrimidin-2-yl]}amino-2-ethyl-6-trifluoromethyl-1,2,3,4-tetrahydroquinoline (90 mg, MS (m/z): 676 [M+H]+).

Example 264

(2R,4S)-4-{[3,5-Bis(trifluoromethyl)benzyl]-[5-(3-ethoxycarbonyl-propoxy)pyrimidin-2-yl]}amino-2-ethyl-6-trifluoromethyl-3,4-dihydro-2H-quinoline-1-carboxylic acid 3-hydroxypropyl ester (165 mg) is dissolved in ethanol (2 ml), and thereto is added a 2N aqueous sodium hydroxide solution (317 µl), and the mixture is stirred at room temperature for 3 hours. To the mixture are added ethyl acetate and 1N hydrochloric acid, and the mixture is separated. The organic layer is washed with a saturated brine, dried over magnesium sulfate and concentrated under reduced pressure. The resulting residue is purified by thin layer silica gel column chromatography (hexane:ethyl acetate=1:1) to give (2R,4S)-4-{[3,5-bis(trifluoromethyl)benzyl]-[5-(3-carboxypropoxy)pyrimidin-2-yl]}-amino-2-ethyl-6-trifluoromethyl-3,4-dihydro-2H-quinoline-1-carboxylic acid 3-hydroxypropyl ester (37 mg, MS (m/z): 753 [M+H]+) and (2R,4S)-4-{[3,5-bis(trifluoromethyl)benzyl]-[5-(3-carboxypropoxy)pyrimidin-2-yl]}-amino-2-ethyl-6-trifluoromethyl-3,4-dihydro-2H-quinoline-1-carboxylic acid 3-acetoxypropyl ester (116 mg, MS (m/z): 795 [M+H]+).

Example 265

(1) (2R,4S)-4-(5-Bromopyrimidin-2-yl)amino-2-ethyl-6-trifluoromethyl-3,4-dihydro-2H-quinoline-1-carboxylic acid benzyl ester (7.9 g) is dissolved in N,N-dimethylformamide (35 ml), and thereto is added sodium hydride (737 mg) under ice-cooling. The mixture is stirred at the same temperature for 20 minutes, and thereto is added 3-bromomethyl-5-cyano-benzotrifluoride (5.85 g), and the mixture is stirred at the same temperature for one hour. To the reaction solution are added ethyl acetate and a saturated brine, and the mixture is separated. The organic layer is washed with a saturated brine, dried over magnesium sulfate and concentrated under reduced pressure. The residue is purified by silica gel column chromatography (hexane:ethyl acetate=95:5→3:1) to give (2R,4S)-4-[(5-bromopyrimidin-2-yl)-(3-cyano-5-trifluoromethylbenzyl)]amino-2-ethyl-6-trifluoromethyl-3,4-dihydro-2H-quinoline-1-carboxylic acid benzyl ester (4.84 g). MS (m/z): 718/720 [M+H]+

(2) (2R,4S)-4-[(5-Bromopyrimidin-2-yl)-(3-cyano-5-trifluoromethyl-benzyl)]amino-2-ethyl-6-trifluoromethyl-3,4- dihydro-2H-quinoline-1-carboxylic acid benzyl ester (4.82 g), [1,1'-bis(diphenylphosphino)-ferrocene]dichloropalladium (147 mg), and potassium acetate (1.98 g) and bis(pinacolate)diboron (2.56 g) are dissolved in dimethylsulfoxide (30 ml), and the mixture is stirred at 80° C. under nitrogen atmosphere for one hour. The reaction solution is cooled to room temperature, and thereto are added ethyl acetate and a saturated brine, and the mixture is separated. The organic layer is washed with a saturated brine, dried over magnesium sulfate and concentrated under reduced pressure. The resulting residue is dissolved in tetrahydrofuran (80 ml), and thereto is added dropwise a 30% aqueous hydrogen peroxide solution (50 ml) under ice-cooling. One hour thereafter, a saturated aqueous sodium thiosulfate solution is added to the mixture under ice-cooling, and an excess amount of hydrogen peroxide is consumed. To the mixture are added ethyl acetate and water, and the mixture is separated. The organic layer is washed with a saturated brine, dried over magnesium sulfate and concentrated under reduced pressure. The resulting residue is purified by silica gel column chromatography (hexane:ethyl acetate=9:1→7:3) to give (2R,4S)-4-[(3-cyano-5-trifluoromethylbenzyl)-(5-hydroxypyrimidin-2-yl)]amino-2-ethyl-6-trifluoromethyl-3,4-dihydro-2H-quinoline-1-carboxylic acid benzyl ester (2.47 g). MS (m/z): 656 [M+H]$^+$ (3) (2R,4S)-4-[(3-Cyano-5-trifluoromethylbenzyl)-(5-hydroxypyrimidin-2-yl)]amino-2-ethyl-6-trifluoromethyl-3,4-dihydro-2H-quinoline-1-carboxylic acid benzyl ester (2.46 g) and 4-bromobutyric acid ethyl ester (597 μl) are dissolved in N,N-dimethylformamide (20 ml), and thereto is added potassium carbonate (622 mg), and the mixture is stirred at 50° C. for 5 hours. The reaction solution is cooled to room temperature, and thereto are added ethyl acetate and water, and the mixture is separated. The organic layer is washed with a saturated brine, dried over magnesium sulfate and concentrated under reduced pressure. The resulting residue is purified by silica gel column chromatography (hexane:ethyl acetate=95:5→3:2) to give (2R,4S)-4-{(3-cyano-5-trifluoromethylbenzyl)-[5-(3-ethoxycarbonylpropoxy)pyrimidin-2-yl]}amino-2-ethyl-6-trifluoromethyl-3,4-dihydro-2H-quinoline-1-carboxylic acid benzyl ester (2.29 g). MS (m/z): 770 [M+H]$^+$ (4) (2R,4S)-4-{(3-Cyano-5-trifluoromethylbenzyl)-[5-(3-ethoxycarbonyl-propoxy)pyrimidin-2-yl]}amino-2-ethyl-6-trifluoromethyl-3,4-dihydro-2H-quinoline-1-carboxylic acid benzyl ester (2.28 g) is dissolved in ethanol (25 ml), and thereto is added 10% palladium-carbon (500 mg), and the mixture is stirred at room temperature under hydrogen atmosphere for one hour. The palladium-carbon is removed by filtration, and the filtrate is concentrated under reduced pressure. The residue is purified by silica gel column chromatography (hexane:ethyl acetate=95:5→3:1) to give (2R,4S)-4-{(3-cyano-5-trifluoromethylbenzyl)-[5-(3-ethoxycarbonylpropoxy)-pyrimidin-2-yl]}amino-2-ethyl-6-trifluoromethyl-1,2,3,4-tetrahydro-quinoline (1.77 g). MS (m/z): 636 [M+H]$^+$ (5) (2R,4S)-4-{(3-Cyano-5-trifluoromethylbenzyl)-[5-(3-ethoxycarbonyl-propoxy)pyrimidin-2-yl]}amino-2-ethyl-6-trifluoromethyl-1,2,3,4-tetra-hydroquinoline (500 mg) and triethylamine (132 μl) are dissolved in methylene chloride (5 ml), and thereto is added triphosgene (93 mg) under ice-cooling, and the mixture is stirred at room temperature for one hour. To the mixture are added ethyl acetate and a saturated aqueous sodium hydrogen carbonate solution, and the mixture is separated. The organic layer is washed with a saturated brine, dried over magnesium sulfate and concentrated under reduced pressure. The residue is dissolved in tetrahydrofuran (5 ml), and thereto are added 2,2,2-trifluoroethanol (0.5 ml) and triethylamine (0.5 ml), and the mixture is stirred at room temperature overnight. To the mixture are added water and ethyl acetate, and the mixture is separated. The organic layer is washed with a saturated brine, dried over magnesium sulfate and concentrated under reduced pressure. The residue is purified by silica gel column chromatography (hexane:ethyl acetate=95:5→7:3) to give (2R,4S)-4-{(3-cyano-5-trifluoromethylbenzyl)-[5-(3-ethoxycarbonylpropoxy)pyrimidin-2-yl]}amino-2-ethyl-6-trifluoromethyl-3,4-dihydro-2H-quinoline-1-carboxylic acid 2,2,2-trifluoroethyl ester (457 mg). MS (m/z): 762 [M+H]$^+$ (6) (2R,4S)-4-{(3-Cyano-5-trifluoromethylbenzyl)-[5-(3-ethoxycarbonyl-propoxy)pyrimidin-2-yl]}amino-2-ethyl-6-trifluoromethyl-3,4-dihydro-2H-quinoline-1-carboxylic acid 2,2,2-trifluoroethyl ester (436 mg) is dissolved in ethanol (2 ml), and thereto is added a 2N aqueous sodium hydroxide solution (859 μl), and the mixture is stirred at room temperature for one hour. To the mixture are added ethyl acetate and a saturated aqueous citric acid solution, and the mixture is separated. The organic layer is washed with a saturated brine, dried over magnesium sulfate and concentrated under reduced pressure. The resulting residue is purified by silica gel column chromatography (hexane:ethyl acetate=9:1→3:2) and LC/MS (CAPCEL PAK MG II (Shiseido Co. Ltd.), water:methanol=60:40→methanol, 40 ml/min) to give (2R,4S)-4-{[5-(3-carboxypropoxy)-pyrimidin-2-yl]-(3-cyano-5-trifluoromethylbenzyl)}amino-2-ethyl-6-trifluoro-methyl-3,4-dihydro-2H-quinoline-1-carboxylic acid 2,2,2-trifluoroethyl ester (82 mg, MS (m/z): 734 [M+H]$^+$) and (2R,4S)-4-{(3-carboxy-5-trifluoro-methylbenzyl)-[5-(3-ethoxycarbonylpropoxy)pyrimidin-2-yl]}amino-2-ethyl-6-trifluoromethyl-3,4-dihydro-2H-quinoline-1-carboxylic acid 2,2,2-trifluoroethyl ester (70 mg, MS (m/z): 781 [M+H]$^+$).

Example 266

(1) (2R*,4S*)-4-(5-Bromopyrimidin-2-yl)amino-2-ethyl-6-trifluoromethyl-3,4-dihydro-2H-quinoline-1-carboxylic acid benzyl ester (13 g) is dissolved in N,N-dimethylformamide (100 ml), and thereto is added sodium hydride (62.7%, 1.2 g) under ice-cooling and subsequently 3,5-bis(trifluoromethyl)benzyl bromide (6.68 ml), and the mixture is stirred at room temperature for 17.5 hours. Water and diethyl ether are added to the mixture, and the mixture is separated. The organic layer is washed with a saturated brine, dried over magnesium sulfate and concentrated under reduced pressure. The resulting residue is purified by silica gel column chromatography (hexane:ethyl acetate=9:1) to give (2R*,4S*)-4-{[3,5-bis(trifluoromethyl)benzyl]-(5-bromopyrimidin-2-yl)}amino-2-ethyl-6-trifluoromethyl-3,4-dihydro-2H-quinoline-1-carboxylic acid benzyl ester (20.6 g). MS (m/z): 761/763 [M+H]$^+$ (2) (2R*,4S*)-4-{[3,5-Bis(trifluoromethyl)benzyl]-(5-bromopyrimidin-2-yl)}amino-2-ethyl-6-trifluoromethyl-3,4-dihydro-2H-quinoline-1-carboxylic acid benzyl ester (18.3 g), tris(dibenzylideneacetone)dipalladium (439.5 mg), 2-(di-tert-butylphosphino)diphenyl (572.3 mg), sodium tert-butoxide (3.46 g), and morpholine (3.14 ml) are dissolved in toluene (120 ml), and the mixture is stirred at room temperature for one hour. The reaction solution is stirred at 80° C. for one hour. To the reaction solution is added NH-silica gel, and the mixture is filtered. To the filtrate are added a saturated aqueous sodium hydrogen carbonate solution and diethyl ether, and the mixture is separated. The organic layer is washed with a saturated brine, dried over magnesium sulfate and concentrated under reduced pressure. The resulting residue is purified by silica gel column chromatography (hexane:ethyl acetate=9:1 →6:1) to give (2R*,4S*)-4-{[3,5-bis(trifluoromethyl)benzyl]-[5-(morpholin-4-yl)pyrimidin-2-yl]}amino-2-ethyl-6-trifluoromethyl-3,4-dihydro-2H-quinoline-1-carboxylic acid benzyl ester (11.2 g). MS (m/z): 768 [M+H]$^+$ (3) (2R*,4S*)-4-{[3,5-Bis(trifluoromethyl)benzyl]-[5-(morpholin-4-yl)-pyrimidin-2-yl]}amino-2-ethyl-6-trifluoromethyl-3,4-dihydro-2H-quinoline-1-carboxylic acid benzyl ester (11.2 g) is dissolved in a mixture of tetrahydrofuran (90 ml) and methanol (30 ml), and thereto is added 10% palladium-carbon (5 g), and the mixture is stirred under hydrogen atmosphere for 21 hours. The catalyst is removed by filtration, and the filtrate is concentrated under reduced pressure. The residue is purified by NH-silica gel column chromatography (chloroform) and silica gel column chromatography (hexane:ethyl acetate=9:1→7:3) to give (2R*,4S*)-4-{[3,5-bis(trifluoromethyl)benzyl]-[5-(morpholin-4-yl)pyrimidin-2-yl]}amino-2-ethyl-6-trifluoromethyl-1,2,3,4-tetrahydroquinoline (8.9 g). MS (m/z): 634 [M+H]$^+$ (4) (2R*,4S*)-4-{[3,5-Bis(trifluoromethyl)benzyl]-[5-(morpholin-4-yl)-pyrimidin-2-yl]}amino-2-ethyl-6-trifluoromethyl-1,2,3,4-tetrahydro-quinoline (300 mg) is dissolved in methylene chloride (2.5 ml), and thereto are added triethylamine (197 µl) and triphosgene (147 mg), and the mixture is stirred at room temperature for 2 hours and 40 minutes. The reaction solution is concentrated, and the residue is dissolved in tetrahydrofuran (2.5 ml), and thereto are added triethylamine (0.6 ml), a catalytic amount of 4-(dimethylamino)pyridine, and pentane-1,5-diol (0.6 ml), and the mixture is stirred at room temperature for 14 hours. To the reaction solution are added water and ethyl acetate, and the mixture is separated. The organic layer is dried over magnesium sulfate and concentrated under reduced pressure. The resulting residue is purified by silica gel column chromatography (hexane:ethyl acetate=9:1→1:1) to give (2R*,4S*)-4-{[3,5-bis(trifluoromethyl)benzyl]-[5-(morpholin-4-yl)pyrimidin-2-yl]}amino-2-ethyl-6-trifluoromethyl-3,4-dihydro-2H-quinoline-1-carboxylic acid 5-hydroxypentyl ester (261 mg). MS (m/z): 764 [M+H]$^+$ Example 267

(1) (2R*,4S*)-4-{[3,5-Bis(trifluoromethyl)benzyl]-[5-(morpholin-4-yl)-pyrimidin-2-yl]}amino-2-ethyl-6-trifluoromethyl-1,2,3,4-tetrahydro-quinoline (500 mg) is dissolved in methylene chloride (3 ml), and thereto are added triethylamine (212 µl) and triphosgene (150 mg), and the mixture is stirred at room temperature for 2 hours. The reaction solution is concentrated under reduced pressure, and thereto are added a saturated aqueous sodium hydrogen carbonate solution and ethyl acetate, and the mixture is separated. The organic layer is washed with a saturated brine, dried over magnesium sulfate and concentrated under reduced pressure. The resulting residue is dissolved in tetrahydrofuran (5 ml), and thereto are added 4-hydroxymethyl-1-tert-butoxycarbonylpiperidine (204 mg) and sodium hydride (30 mg), and the mixture is stirred at room temperature for 3 days. To the mixture are added a saturated brine and ethyl acetate, and the mixture is separated. The organic layer is dried over magnesium sulfate and concentrated under reduced pressure. The resulting residue is purified by silica gel column chromatography (hexane:ethyl acetate=9:1 →3:2) to give (2R*,4S*)-4-{[3,5-bis(trifluoromethyl)benzyl]-[5-(morpholin-4-yl)pyrimidin-2-yl]}amino-2-ethyl-6-trifluoromethyl-3,4-dihydro-2H-quinoline-1-carboxylic acid (1-tert-butoxycarbonylpiperidin-4-yl)methyl ester (282 mg). MS (m/z): 875 [M+H]$^+$ (2) (2R*,4S*)-4-{[3,5-Bis(trifluoromethyl)benzyl]-[5-(morpholin-4-yl)pyrimidin-2-yl]}amino-2-ethyl-6-trifluoromethyl-3,4-dihydro-2H-quinoline-1-carboxylic acid (1-tert-butoxycarbonylpiperidin-4-yl)methyl ester (282 mg) is dissolved in ethyl acetate (3 ml), and thereto is added a 4N hydrogen chloride in ethyl acetate (1 ml), and the mixture is stirred at room temperature overnight. To the mixture are added a saturated aqueous sodium hydrogen carbonate solution and ethyl acetate, and the mixture is separated. The organic layer is washed with a saturated brine, dried over magnesium sulfate and concentrated under reduced pressure. The resulting residue is purified by silica gel column chromatography (chloroform:methanol=9:1→7:3) to give (2R*,4S*)-4-{[3,5-bis(trifluoro-methyl)benzyl]-[5-(morpholin-4-yl)pyrimidin-2-yl]}amino-2-ethyl-6-trifluoro-methyl-3,4-dihydro-2H-quinoline-1-carboxylic acid piperidin-4-ylmethyl ester (38 mg). MS (m/z): 775 [M+H]$^+$ Example 268

(1) (2R*,4S*)-4-{[3,5-Bis(trifluoromethyl)benzyl]-(5-bromopyrimidin-2-yl)}amino-2-ethyl-6-methoxy-3,4-dihydro-2H-quinoline-1-carboxylic acid ethyl ester (13.7 g) is dissolved in methylene chloride (100 ml), and the mixture is cooled to −70° C., and thereto is added dropwise boron tribromide (1 M methylene chloride solution, 41.4 ml) under nitrogen atmosphere. The reaction solution is gradually warmed to room temperature with stirring over a period of 1.5 hour. The mixture is further stirred at room temperature for 21 hours. To the reaction solution are added a saturated aqueous sodium hydrogen carbonate solution and ethyl acetate, and the mixture is separated. The organic layer is washed with a saturated brine, dried over magnesium sulfate and concentrated under reduced pressure. The resulting residue is purified by silica gel column chromatography (hexane:ethyl acetate=19:1→1:1) to give (2R*,4S*)-4-{[3,5-bis(trifluoromethyl)benzyl]-(5-bromopyrimidin-2-yl)}amino-2-ethyl-6-hydroxy-3,4-dihydro-2H-quinoline-1-carboxylic acid ethyl ester (3.1 g). MS (m/z): 647/649 [M+H]$^+$ (2) (2R*,4S*)-4-{[3,5-Bis(trifluoromethyl)benzyl]-(5-bromopyrimidin-2-yl)}amino-2-ethyl-6-hydroxy-3,4-dihydro-2H-quinoline-1-carboxylic acid ethyl ester (3.1 g), imidazole (0.98 g), and tert-butyldimethylsilyl chloride are dissolved in N,N-dimethylformamide (25 ml), and the mixture is stirred at room temperature for 15.5 hours. To the reaction solution are added water and ethyl acetate, and the mixture is separated. The organic layer is washed with water and a saturated brine, dried over magnesium sulfate, and concentrated under reduced pressure. The resulting residue is purified by silica gel column chromatography (hexane:ethyl acetate=9:1→4:1) to give (2R*,4S*)-4-{[3,5-bis(trifluoromethyl)benzyl]-(5-bromo-pyrimidin-2-yl)}amino-6-(tert-butyldimethylsilanyloxy)-2-ethyl-3,4-dihydro-2H-quinoline-1-carboxylic acid ethyl ester (3.88 g). MS (m/z): 761/763 [M+H]$^+$ (3) (2R*,4S*)-4-{[3,5-Bis(trifluoromethyl)benzyl]-(5-bromopyrimidin-2-yl)}amino-6-(tert-butyldimethylsilanyloxy)-2-ethyl-3,4-dihydro-2H-quinoline-1-carboxylic acid ethyl ester (3.85 g), [1,1'-bis(diphenyl-phosphino)ferrocene]dichloropalladium (111 mg), potassium acetate (1.5 g) and bis(pinacolate)diboron (1.9 g) are dissolved in deaerated dimethyl-sulfoxide (50 ml), and the mixture is stirred at 80° C. for 30 minutes. The reaction solution is cooled to room temperature, and thereto are added water and ethyl acetate, and the mixture is separated. The organic layer is washed with a saturated brine, dried over sodium sulfate, and concentrated under reduced pressure. The resulting residue is dissolved in tetrahydrofuran (15 ml), and thereto is added a 30% aqueous hydrogen peroxide solution (3.4 ml) under ice-cooling, and the mixture is stirred for one hour and 45 minutes. A saturated aqueous sodium thiosulfate solution and ethyl acetate are added to the mixture under ice-cooling, and the mixture is separated, The organic layer is washed with water and a saturated brine, dried over sodium sulfate, and concentrated under reduced pressure. The resulting residue is purified by silica gel column chromatography (hexane:ethyl acetate=4:1→1:1) to give (2R*,4S*)-4-{[3,5-bis(trifluoromethyl)benzyl]-(5-hydroxypyrimidin-2-yl)}amino-2-ethyl-6-hydroxy-3,4-dihydro-2H-quinoline-1-carboxylic acid ethyl ester (2.0 g). MS (m/z): 585 [M+H]$^+$ (4) (2R*,4S*)-4-{[3,5-Bis(trifluoromethyl)benzyl]-(5-hydroxypyrimidin-2-yl)}amino-2-ethyl-6-hydroxy-3,4-dihydro-2H-quinoline-1-carboxylic acid ethyl ester (2.0 g) is dissolved in N,N-dimethylformamide (10 ml), and thereto is added sodium hydride (62.7%, 144 mg) under ice-cooling, and the mixture is stirred at room temperature for 30 minutes. To the reaction solution is added 4-bromobutyric acid ethyl ester (502 µl), and the mixture is stirred at room temperature for 6 hours. To the reaction solution are added water and ethyl acetate under ice-cooling, and the organic layer is washed with a saturated brine, dried over magnesium sulfate and concentrated under reduced pressure. The resulting residue is purified by silica gel column chromatography (hexane:ethyl acetate=9:1→1:1) to give (2R*,4S*)-4-{[3,5-bis(trifluoromethyl)benzyl]-[5-(3-ethoxycarbonylpropoxy)-pyrimidin-2-yl]}amino-6-(3-ethoxycarbonylpropoxy)-2-ethyl-3,4-dihydro-2H-quinoline-1-carboxylic acid ethyl ester (578 mg). MS (m/z): 813 [M+H]$^+$ (5) (2R*,4S*)-4-{[3,5-Bis(trifluoromethyl)benzyl]-[5-(3-ethoxycarbonyl-propoxy)pyrimidin-2-yl]}amino-6-(3-ethoxycarbonylpropoxy)-2-ethyl-3,4-dihydro-2H-quinoline-1-carboxylic acid ethyl ester (300 mg) is dissolved in ethanol (1.75 ml), and thereto is added a 2N aqueous sodium hydroxide solution (0.55 ml), and the mixture is stirred at room temperature for 3 hours. To the mixture are added a 2N hydrochloric acid (0.55 ml) and ethyl acetate, and the mixture is separated. The organic layer is washed with a saturated brine, dried over magnesium sulfate, and concentrated under reduced pressure. The resulting residue is purified by silica gel column chromatography (chloroform:methanol=1:0→9:1) to give (2R*,4S*)-4-{[3,5-bis(trifluoromethyl)benzyl]-[5-(3-carboxypropoxy)-pyrimidin-2-yl]}amino-6-(3-carboxypropoxy)-2-ethyl-3,4-dihydro-2H-quinoline-1-carboxylic acid ethyl ester (207 mg). MS (m/z): 757 [M+H]$^+$ Example 269

(1) (2R*,4S*)-4-{[3,5-Bis(trifluoromethyl)benzyl]-[5-(morpholin-4-yl)pyrimidin-2-yl]}amino-2-ethyl-6-trifluoromethyl-1,2,3,4-tetrahydroquinoline (1.0 g), and triethylamine (424 µl) are dissolved in methylene chloride (6.5 ml), and thereto is added triphosgene (300 mg) under ice-cooling, and the mixture is stirred at room temperature for 2 hours. The reaction solution is concentrated under reduced pressure, and to the residue are added a saturated aqueous sodium hydrogen carbonate solution and ethyl acetate, and the mixture is separated. The organic layer is washed with a saturated brine, dried over magnesium sulfate and concentrated under reduced pressure. The resulting residue and 2-bromoethanol (1 ml) are dissolved in tetrahydrofuran (10 ml), and thereto are added triethylamine (460 µl) and a catalytic amount of 4-dimethylaminopyridine, and the mixture is stirred at room temperature for 3 days. To the reaction solution are added a saturated brine and ethyl acetate, and the mixture is separated. The organic layer is dried over magnesium sulfate, and concentrated under reduced pressure. The resulting residue is purified by silica gel column chromatography (hexane:ethyl acetate=9:1→7:3) to give (2R*,4S*)-4-{[3,5-bis(trifluoro-methyl)benzyl]-[5-(morpholin-4-yl)pyrimidin-2-yl]}amino-2-ethyl-6-trifluoromethyl-3,4-dihydro-2H-quinoline-1-carboxylic acid 2-bromoethyl ester (1.51 g) as a crude product. MS (m/z): 784/786 [M+H]$^+$ (2) The crude (2R*,4S*)-4-{[3,5-bis(trifluoromethyl)benzyl]-[5-(morpholin-4-yl)pyrimidin-2-yl]}amino-2-ethyl-6-trifluoromethyl-3,4-dihydro-2H-quinoline-1-carboxylic acid 2-bromoethyl ester (750 mg) is dissolved in N,N-dimethylformamide (5 ml), and thereto are added piperidine-4-carboxylic acid ethyl ester (442 µl) and potassium carbonate (400 mg), and the mixture is stirred at 60° C. overnight. To the reaction solution are added water and ethyl acetate, and the mixture is separated. The organic layer is washed with a saturated brine, dried over magnesium sulfate, and concentrated under reduced pressure. The resulting residue is purified by silica gel column chromatography (hexane:ethyl acetate=7:31:1) to give (2R*,4S*)-4-{[3,5-bis(trifluoromethyl)benzyl]-[5-(morpholin-4-yl)pyrimidin-2-yl]}amino-2-ethyl-6-trifluoromethyl-3,4-dihydro-2H-quinoline-1-carboxylic acid 2-(4-ethoxycarbonylpiperidin-1-yl)ethyl ester (439 mg). MS (m/z): 861 [M+H]$^+$ (3) (2R*,4S*)-4-{[3,5-Bis(trifluoromethyl)benzyl]-[5-(morpholin-4-yl)pyrimidin-2-yl]}amino-2-ethyl-6-trifluoromethyl-3,4-dihydro-2H-quinoline-1-carboxylic acid 2-(4-ethoxycarbonylpiperidin-1-yl)ethyl ester (439 mg) is dissolved in ethanol (8 ml), and thereto is added dropwise a 1N aqueous sodium hydroxide solution (4 ml), and the mixture is stirred at room temperature overnight. To the reaction solution are added a 1N hydrochloric acid and ethyl acetate, and the mixture is separated. The organic layer is washed with a saturated brine, dried over magnesium sulfate and concentrated under reduced pressure. The resulting residue is purified by silica gel column chromatography (chloroform:methanol=1:0→9:1) to give (2R*,4S*)-4-{[3,5-bis(trifluoromethyl)benzyl]-[5-(morpholin-4-yl)pyrimidin-2-yl]}amino-2-ethyl-6-trifluoromethyl-3,4-dihydro-2H-quinoline-1-carboxylic acid 2-(4-carboxypiperidin-1-yl)ethyl ester (307 mg). MS (m/z): 833 [M+H]$^+$

Example 270

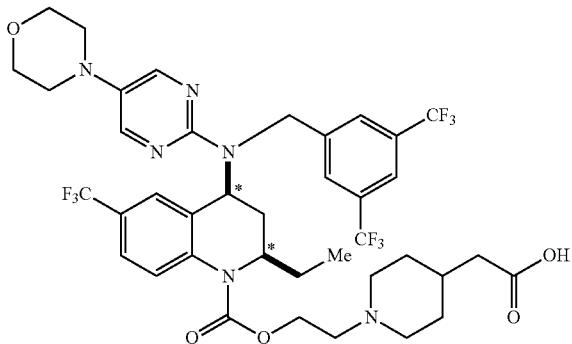

The corresponding starting compounds are treated in a similar manner to Example 269 to give the compound of Example 270. MS (m/z): 847 [M+H]+

Example 271

(1) (2R*,4S*)-4-{[3,5-Bis(trifluoromethyl)benzyl]-[5-(morpholin-4-yl)-pyrimidin-2-yl]}amino-2-ethyl-6-trifluoromethyl-3,4-dihydro-2H-quinoline-1-carboxylic acid 5-hydroxypentyl ester (200 mg) is dissolved in dichloromethane (1.5 ml), and thereto is added [1,1,1-tris(acetyloxy)-1,1-dihydro-1,2-benziodoxol-3-(1H)-one] (124 mg), and the mixture is stirred at room temperature for 30 minutes. To the reaction solution are added water and ethyl acetate, and the mixture is separated. The organic layer is concentrated under reduced pressure, and the resulting residue is purified by silica gel column chromatography (hexane:ethyl acetate=9:13:2) to give (2R*,4S*)-4-{[3,5-bis(trifluoromethyl)benzyl]-[5-(morpholin-4-yl)-pyrimidin-2-yl]}amino-2-ethyl-6-trifluoromethyl-3,4-dihydro-2H-quinoline-1-carboxylic acid 4-formylbutyl ester (104 mg). MS (m/z): 762 [M+H]+

(2) (2R*,4S*)-4-{[3,5-Bis(trifluoromethyl)benzyl]-[5-(morpholin-4-yl)pyrimidin-2-yl]}amino-2-ethyl-6-trifluoromethyl-3,4-dihydro-2H-quinoline-1-carboxylic acid 4-formylbutyl ester (100 mg) is dissolved in a mixture of tert-butanol:water (4:1, 1.5 ml), and thereto are added 2-methyl-2-butene (77 µl), sodium dihydrogenphosphate dihydrate (28 mg) and sodium chlorite (47 mg) at room temperature, and the mixture is stirred for 1.5 hour. To the reaction solution are added a 1N hydrochloric acid and ethyl acetate, and the mixture is separated. The organic layer is washed with water and a saturated brine, dried over magnesium sulfate, and concentrated under reduced pressure. The resulting residue is purified by silica gel column chromatography (chloroform:methanol=1:0→19:1) to give (2R*,4S*)-4-{[3,5-bis(trifluoromethyl)benzyl]-[5-(morpholin-4-yl)pyrimidin-2-yl]}amino-2-ethyl-6-trifluoromethyl-3,4-dihydro-2H-quinoline-1-carboxylic acid 4-carboxybutyl ester (43.1 mg). MS (m/z): 778 [M+H]+

Example 272

(1) (2R,4S)-4-{[3,5-Bis(trifluoromethyl)benzyl]-(5-bromopyrimidin-2-yl)}amino-2-ethyl-6-trifluoromethyl-3,4-dihydro-2H-quinoline-1-carboxylic acid ethyl ester (3 g) is dissolved in tetrahydrofuran:ethanol (1:1,30 ml), and thereto is added sodium hydroxide (858 mg), and the mixture is stirred at 80° C. for 9 hours. The reaction solution is cooled to room temperature, and thereto is added a 1N hydrochloric acid (22 ml), and the mixture is concentrated under reduced pressure. To the resulting residue are added water and diethyl ether, and the mixture is separated. The organic layer is washed with a saturated brine, dried over magnesium sulfate and concentrated under reduced pressure. The resulting residue is purified by silica gel column chromatography (hexane:ethyl acetate=9:13:1) and NH-silica gel column chromatography (hexane:ethyl acetate=9:13:1) to give (2R,4S)-4-{[3,5-bis(trifluoromethyl)benzyl]-(5-bromopyrimidin-2-yl)}amino-2-ethyl-6-trifluoromethyl-1,2,3,4-tetrahydroquinoline (1.79 g). MS (m/z): 626/628 [M+H]+

(2) (2R,4S)-4-{[3,5-Bis(trifluoromethyl)benzyl]-(5-bromopyrimidin-2-yl)}amino-2-ethyl-6-trifluoromethyl-3,4-dihydro-2H-quinoline (800 mg) is dissolved in dichloromethane (6 ml), and thereto is added triethylamine (444 µl) and triphosgene (303 mg), and the mixture is stirred at room temperature for 5 hours. The reaction solution is concentrated under reduced pressure, and the insoluble materials are removed by filtration with diethyl ether. The filtrate is concentrated under reduced pressure, and the resulting residue is dissolved in tetrahydrofuran (6 ml), and to the mixture are added a 60% sodium hydride (92 mg) and 1,5-pentanediol (400 mg) under ice-cooling. The mixture is stirred at room temperature for 30 minutes, and thereto are added water and ethyl acetate, and the mixture is separated. The organic layer is washed with a 1N hydrochloric acid, water, and a saturated brine, dried over magnesium sulfate and concentrated under reduced pressure. The resulting residue is purified by silica gel column chromatography (hexane:ethyl acetate=4:1→3:2) to give (2R,4S)-4-{[3,5-bis(trifluoromethyl)benzyl]-(5-bromopyrimidin-2-yl)}amino-2-ethyl-6-trifluoromethyl-3,4-dihydro-2H-quinoline-1-carboxylic acid 5-hydroxypentyl ester (643.6 mg). MS (m/z): 757/759 [M+H]+

(3) (2R,4S)-4-{[3,5-Bis(trifluoromethyl)benzyl]-(5-bromopyrimidin-2-yl)}amino-2-ethyl-6-trifluoromethyl-3,4-dihydro-2H-quinoline-1-carboxylic acid 5-hydroxypentyl ester (640 mg) is dissolved in acetone (5 ml), and thereto is added a 1.94M Jones reagent (1.38 ml) under ice-cooling, and the mixture is stirred for 1.5 hour. To the reaction solution are added sodium hydrogenesulfite and water under ice-cooling, and the mixture is concentrated under reduced pressure. To the resulting residue is added 1N hydrochloric acid and ethyl acetate, and the mixture is separated. The organic layer is washed with water and a saturated brine, dried over magnesium sulfate and concentrated under reduced pressure. The resulting residue is purified by silica gel column chromatography (hexane:ethyl acetate=4:1→1:1) to give (2R,4S)-4-{[3,5-bis(trifluoro-methyl)benzyl]-(5-bromopyrimidin-2-yl)}amino-2-ethyl-6-trifluoromethyl-3,4-dihydro-2H-quinoline-1-carboxylic acid 4-carboxybutyl ester (517.2 mg). MS (m/z): 771/773 [M+H]+

(4) (2R,4S)-4-{[3,5-Bis(trifluoromethyl)benzyl]-(5-bromopyrimidin-2-yl)}amino-2-ethyl-6-trifluoromethyl-3,4-dihydro-2H-quinoline-1-carboxylic acid 4-carboxybutyl ester (510 mg) is dissolved in tetrahydrofuran:methanol (5:1,6 ml), and thereto is added a 2M solution of trimethylsilyl-diazomethane in hexane (0.86 ml) under ice-cooling, and the mixture is stirred for one hour and 40 minutes. The reaction solution is concentrated under reduced pressure, and the resulting residue is purified by silica gel column chromatography (hexane:ethyl acetate=9:1→4:1) to give (2R,4S)-4-{[3,5-bis(trifluoromethyl)benzyl]-(5- bromopyrimidin-2-yl)}amino-2-ethyl-6-trifluoromethyl-3,4-dihydro-2H-quinoline-1-carboxylic acid 4-methoxycarbonylbutyl ester (466 mg). MS (m/z): 785/787 [M+H]$^+$ (5) (2R,4S)-4-{[3,5-Bis(trifluoromethyl)benzyl]-(5-bromopyrimidin-2-yl)}-amino-2-ethyl-6-trifluoromethyl-3,4-dihydro-2H-quinoline-1-carboxylic acid 4-methoxycarbonylbutyl ester (460 mg) is dissolved in toluene (3.5 ml), and thereto are added tris(dibenzylideneacetone)dipalladium (54 mg), 2-(di-tert-butylphosphino)biphenyl (36 mg), sodium tert-butoxide (112 mg) and morpholine (102 μl), and the mixture is stirred at room temperature for 3 hours. To the reaction solution are added water and ethyl acetate, and the mixture is separated. The organic layer is washed with a saturated aqueous citric acid solution, water, and a saturated brine, dried over sodium sulfate, and concentrated under reduced pressure. The resulting residue is purified by silica gel column chromatography (chloroform:methanol=1:0→9:1) to give (2R,4S)-4-{[3,5-bis(trifluoromethyl)benzyl]-[5-(morpholin-4-yl)pyrimidin-2-yl]}amino-2-ethyl-6-trifluoromethyl-3,4-dihydro-2H-quinoline-1-carboxylic acid 4-carboxybutyl ester (72.5 mg). MS (m/z): 778 [M+H]$^+$ Example 273

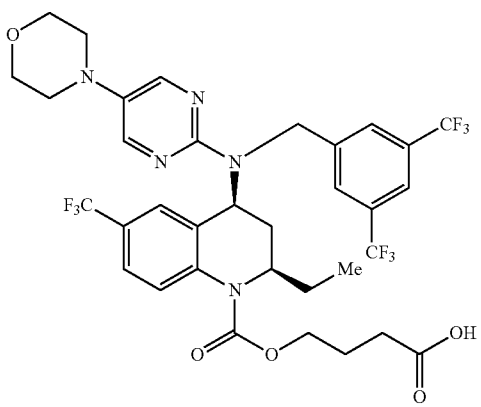

The corresponding starting compound is treated in a similar manner to Example 272 to give the compound of Example 273. MS (m/z): 764 M+H]$^+$ Example 274

(1) (2R,4S)-4-{[3,5-Bis(trifluoromethyl)benzyl]-(5-bromopyrimidin-2-yl)}amino-2-ethyl-6-trifluoromethyl-3,4-dihydro-2H-quinoline-1-carboxylic acid 6-methoxycarbonylhexyl ester (574 mg), which is obtained by treating the corresponding starting compounds in a similar manner to Example 272 (1)-(4), is dissolved in toluene (4.5 ml), and thereto are added tris(dibenzylideneacetone)dipalladium (0) (65 mg), 2-(di-tert-butyl-phosphino)biphenyl (84 mg), morpholine (123 μl), and sodium tert-butoxide (136 mg), and the mixture is stirred at room temperature under nitrogen atmosphere for 5 hours. The reaction mixture is neutralized with a 10% aqueous citric acid solution, and thereto is added a saturated brine, and the mixture is extracted with ethyl acetate. The organic layer is washed with a saturated brine, dried over magnesium sulfate, and concentrated under reduced pressure. The resulting residue is purified by silica gel column chromatography (hexane:ethyl acetate=4:1→2:1→chloro-form:methanol=100:1→19:1) to give (2R,4S)-4-{[3,5-bis(trifluoromethyl)-benzyl]-[5-(morpholin-4-yl)pyrimidin-2-yl]}amino-2-ethyl-6-trifluoromethyl-3,4-dihydro-2H-quinoline-1-carboxylic acid 6-methoxycarbonylhexyl ester (119 mg). MS (m/z): 820 [M+H]$^+$ (2) (2R,4S)-4-{[3,5-Bis(trifluoromethyl)benzyl]-[5-(morpholin-4-yl)-pyrimidin-2-yl]}amino-2-ethyl-6-trifluoromethyl-3,4-dihydro-2H-quinoline-1-carboxylic acid 6-methoxycarbonylhexyl ester (116 mg) is dissolved in a mixture of tetrahydrofuran (2 ml) and methanol (1 ml), and to the mixture is added a 1M aqueous sodium hydroxide solution (1 ml), and the mixture is stirred at room temperature for one hour. The reaction mixture is acidified with a 10% aqueous citric acid solution, and thereto is added a saturated brine, and the mixture is extracted with ethyl acetate. The organic layer is washed with a saturated brine, dried over magnesium sulfate, and concentrated under reduced pressure. The resulting residue is purified by silica gel column chromatography (hexane:ethyl acetate=4:1→3:2) to give (2R,4S)-4-{[3,5-bis(trifluoromethyl)benzyl]-[5-(morpholin-4-yl)pyrimidin-2-yl]}amino-2-ethyl-6-trifluoromethyl-3,4-dihydro-2H-quinoline-1-carboxylic acid 6-carboxyhexyl ester (85 mg). MS (m/z): 806 [M+H]$^+$ Example 275

(1) (2R,4S)-4-{[3,5-Bis(trifluoromethyl)benzyl]-(5-bromopyrimidin-2-yl)}amino-2-ethyl-6-trifluoromethyl-3,4-dihydro-2H-quinoline-1-carboxylic acid ethyl ester (3.01 g) is dissolved in chloroform (20 ml), and thereto is added trimethylsilyl iodide (5 g), and the mixture is stirred under nitrogen atmosphere at 55° C. overnight. To the reaction mixture is added a saturated aqueous sodium hydrogen carbonate solution, and the mixture is extracted with ethyl acetate. The organic layer is washed with a saturated brine, dried over magnesium sulfate, and concentrated under reduced pressure. The resulting residue is purified by NH-silica gel column chromatography (hexane:ethyl acetate=9:1) to give (2R,4S)-4-{[3,5-bis(trifluoromethyl)benzyl]-(5-bromopyrimidin-2-yl)}amino-2-ethyl-6-trifluoromethyl-1,2,3,4-tetrahydroquinoline (2.22 g). MS (m/z):626/628 [M+H]$^+$ (2) (2R,4S)-4-{[3,5-Bis(trifluoromethyl)benzyl]-(5-bromopyrimidin-2-yl)}amino-2-ethyl-6-trifluoromethyl-1,2,3,4-tetrahydroquinoline (500 mg) is dissolved in dichloromethane (4 ml), and thereto are added triethylamine (556 μl) and triphosgene (380 mg), and the mixture is stirred at room temperature for 1.5 hour. The reaction solution is concentrated under reduced pressure, and thereto is added diethyl ether, and the insoluble materials are removed by filtration. The filtrate is concentrated under reduced pressure, and the resulting residue is dissolved in tetrahydrofuran (4 ml), and thereto are added 6-hydroxyhexanoic acid ethyl ester (156 μl) and triethylamine (167 μl), and the mixture is stirred at room temperature for 30 minutes. To the mixture is added a 60% sodium hydride (38 mg) under ice-cooling, and the mixture is stirred for 30 minutes. To the reaction solution are added water and ethyl acetate, and the mixture is separated. The organic layer is washed with a 1N hydrochloric acid, water, and a saturated brine, dried over magnesium sulfate and concentrated under reduced pressure. The resulting residue is purified by silica gel column chromatography (hexane:ethyl acetate=9:1→4:1) to give (2R,4S)-4-{[3,5-bis(trifluoromethyl)benzyl]-(5-bromopyrimidin-2-yl)}amino-2-ethyl-6-trifluoromethyl- 3,4-dihydro-2H-quinoline-1-carboxylic acid 5-ethoxycarbonylpentyl ester (380 mg). MS (m/z): 813/815 [M+H]+

(3) (2R,4S)-4-{[3,5-Bis(trifluoromethyl)benzyl]-(5-bromopyrimidin-2-yl)}amino-2-ethyl-6-trifluoromethyl-3,4-dihydro-2H-quinoline-1-carboxylic acid 5-ethoxycarbonylpentyl ester (370 mg) is dissolved in toluene (2.5 ml), and thereto are added tris(dibenzylideneacetone)dipalladium (42 mg), 2-(di-tert-butylphosphino)biphenyl (27 mg), sodium tert-butoxide (87 mg) and morpholine (79 µl), and the mixture is stirred at room temperature for 30 minutes. The mixture is stirred at 80° C. for one hour and 45 minutes. The reaction solution is cooled to room temperature, and thereto are added water and ethyl acetate, and the mixture is separated. The organic layer is washed with a 1N hydrochloric acid, water, and a saturated brine, dried over magnesium sulfate and concentrated under reduced pressure. The resulting residue is purified by silica gel column chromatography (hexane:ethyl acetate=9:1→1:1) to give (2R,4S)-4-{[3,5-bis(trifluoro-methyl)benzyl]-[5-(morpholin-4-yl)pyrimidin-2-yl]}amino-2-ethyl-6-trifluoromethyl-3,4-dihydro-2H-quinoline-1-carboxylic acid 5-ethoxycarbonylpentyl ester (90.3 mg, MS (m/z): 820 [M+H]+) and (2R,4S)-4-{[3,5-bis(trifluoro-methyl)benzyl]-[5-(morpholin-4-yl)pyrimidin-2-yl]}amino-2-ethyl-6-trifluoro-methyl-3,4-dihydro-2H-quinoline-1-carboxylic acid 5-carboxypentyl ester (67.7 mg, MS (m/z): 792 [M+H]+).

(4) (2R,4S)-4-{[3,5-Bis(trifluoromethyl)benzyl]-[5-(morpholin-4-yl)-pyrimidin-2-yl]}amino-2-ethyl-6-trifluoromethyl-3,4-dihydro-2H-quinoline-1-carboxylic acid 5-ethoxycarbonylpentyl ester (90 mg) is dissolved in ethanol (1 ml), and thereto is added a 2N aqueous sodium hydroxide solution (0.16 ml), and the mixture is stirred at room temperature for 2 hours. To the reaction solution are added a 1N hydrochloric acid (0.32 ml) and ethyl acetate, and the mixture is separated. The organic layer is washed with water and a saturated brine, dried over magnesium sulfate and concentrated under reduced pressure. The resulting residue is purified by silica gel column chromatography (hexane:ethyl acetate=4:1→1:1) to give (2R,4S)-4-{[3,5-bis(trifluoromethyl)benzyl]-[5-(morpholin-4-yl)pyrimidin-2-yl]}amino-2-ethyl-6-trifluoromethyl-3,4-dihydro-2H-quinoline-1-carboxylic acid 5-carboxypentyl ester (53 mg). MS (m/z): 792 [M+H]+

Example 276

(1) (2R,4S)-4-{[3,5-Bis(trifluoromethyl)benzyl]-(5-bromopyrimidin-2-yl)}amino-2-ethyl-6-trifluoromethyl-1,2,3,4-tetrahydroquinoline (1 g) is dissolved in toluene (3.5 ml), and thereto are added tris(dibenzylidene-acetone)dipalladium (137 mg), 2-(di-tert-butylphosphino)biphenyl (95 mg), sodium tert-butoxide (460 mg) and morpholine (0.28 ml), and the mixture is stirred at room temperature for 17 hours. To the reaction solution are added a saturated aqueous sodium hydrogen carbonate solution and ethyl acetate, and the mixture is separated. The organic layer is washed with a saturated brine, dried over sodium sulfate and concentrated under reduced pressure. The resulting residue is purified by silica gel column chromatography (hexane:ethyl acetate=9:1→7:3) to give (2R,4S)-4-{[3,5-bis-(trifluoromethyl)benzyl]-[5-(morpholin-4-yl)pyrimidin-2-yl]}amino-2-ethyl-6-trifluoromethyl-1,2,3,4-tetrahydroquinoline (780.3 mg). MS (m/z): 634 [M+H]+

(2) (2R,4S)-4-{[3,5-Bis(trifluoromethyl)benzyl]-[5-(morpholin-4-yl)-pyrimidin-2-yl]}amino-2-ethyl-6-trifluoromethyl-1,2,3,4-tetrahydroquinoline (300 mg) is dissolved in dichloromethane (2 ml), and thereto are added triethylamine (310 µl) and triphosgene (208 mg), and the mixture is stirred at room temperature for one hour. The reaction solution is concentrated under reduced pressure, and thereto is added diethyl ether, and the insoluble materials are removed by filtration. The filtrate is concentrated under reduced pressure, and the resulting residue is dissolved in tetrahydrofuran (2 ml), and a 60% sodium hydride (36 mg) and 3-hydroxypropionic acid tert-butyl ester (131 µl) are added thereto under ice-cooling. The mixture is stirred at room temperature for 16 hours, and thereto are added water and ethyl acetate, and the mixture is separated. The organic layer is washed with a saturated brine, dried over sodium sulfate and concentrated under reduced pressure. The resulting residue is purified by silica gel column chromatography (hexane:ethyl acetate=9:1→3:2) to give (2R,4S)-4-{[3,5-bis(trifluoromethyl)benzyl]-[5-(morpholin-4-yl)pyrimidin-2-yl]}amino-2-ethyl-6-trifluoromethyl-3,4-dihydro-2H-quinoline-1-carboxylic acid 2-tert-butoxycarbonylethyl ester (207 mg). MS (m/z): 806 [M+H]+

(3) To (2R,4S)-4-{[3,5-Bis(trifluoromethyl)benzyl]-[5-(morpholin-4-yl)pyrimidin-2-yl]}amino-2-ethyl-6-trifluoromethyl-3,4-dihydro-2H-quinoline-1-carboxylic acid 2-tert-butoxycarbonylethyl ester (200 mg) is added a 4N hydrogen chloride in 1,4-dioxane (2 mL), and the mixture is stirred for 2 hours. The reaction solution is concentrated and the resulting residue is purified by silica gel column chromatography (chloroform:methanol=1:0→19:1) to give (2R,4S)-4-{[3,5-bis(trifluoromethyl)benzyl]-[5-(morpholin-4-yl)pyrimidin-2-yl]}amino-2-ethyl-6-trifluoromethyl-3,4-dihydro-2H-quinoline-1-carboxylic acid 2-carboxyethyl ester (176.3 mg). MS (m/z): 750 [M+H]+

Example 277

(1) (2R,4S)-4-{[3,5-Bis(trifluoromethyl)benzyl]-[5-(morpholin-4-yl)-pyrimidin-2-yl]}amino-2-ethyl-6-trifluoromethyl-1,2,3,4-tetrahydroquinoline (250 mg) is dissolved in methylene chloride (3 ml), and thereto is added triethylamine (111 µl), and further added under ice-cooling triphosgene (316 mg). Under nitrogen atmosphere, the mixture is stirred at the same temperature for one hour, and the reaction mixture is concentrated under reduced pressure. To the residue is added ether, and the precipitated insoluble materials are removed by filtration. The filtrate is concentrated under reduced pressure, and to the resulting residue are added tetrahydrofuran (4 ml), methyl glycolate (62 µl) and sodium hydride (62.7%, 30 mg), and the mixture is stirred under nitrogen atmosphere at room temperature for 2 hours. The reaction mixture is neutralized with a 10% aqueous citric acid solution, and thereto is added a saturated brine, and the mixture is extracted with ethyl acetate. The organic layer is washed with a saturated brine, dried over magnesium sulfate, and concentrated under reduced pressure. The resulting residue is purified by silica gel column chromatography (hexane:ethyl acetate=4:1) to give (2R,4S)-4-{[3,5-bis(trifluoromethyl)benzyl]-[5-(morpholin-4-yl)pyrimidin-2-yl]}amino-2-ethyl-6-trifluoromethyl-3,4-dihydro-2H-quinoline-1-carboxylic acid methoxycarbonylmethyl ester (166 mg). MS (m/z): 750 [M+H]⁺

(2) (2R,4S)-4-{[3,5-Bis(trifluoromethyl)benzyl]-[5-(morpholin-4-yl)-pyrimidin-2-yl]}amino-2-ethyl-6-trifluoromethyl-3,4-dihydro-2H-quinoline-1-carboxylic acid methoxycarbonylmethyl ester (163 mg) is dissolved in a mixture of tetrahydrofuran (2 ml) and methanol (2 ml), and thereto is added a 1N aqueous sodium hydroxide solution (1 ml), and the mixture is stirred at room temperature for one hour. The reaction mixture is acidified with a 10% aqueous citric acid solution, and thereto is added a saturated brine, and the mixture is extracted with ethyl acetate. The organic layer is washed with a saturated brine, dried over magnesium sulfate, and concentrated under reduced pressure. The resulting residue is purified by silica gel column chromatography (chloroform:methanol=1:0→19:1) to give (2R,4S)-4-{[3,5-bis(trifluoromethyl)benzyl]-[5-(morpholin-4-yl)pyrimidin-2-yl]}amino-2-ethyl-6-trifluoromethyl-3,4-dihydro-2H-quinoline-1-carboxylic acid carboxymethyl ester (125 mg). MS (m/z): 736 [M+H]⁺

Examples 278-282

The corresponding starting compounds are treated in a similar manner to Example 277 to give the compounds as listed in Table 34.

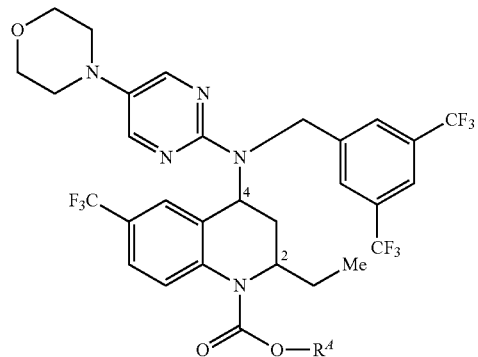

TABLE 34

| Ex. No. | Configuration | R⁴ | Physical properties, etc. |
|---|---|---|---|
| 278 | (2R*, 4S*) | (4-methylcyclohexanecarboxylic acid) | MS (m/z): 804 [M + H]⁺ |
| 279 | (2R*, 4S*) | (4-ethylcyclohexylacetic acid) | MS (m/z): 832 [M + H]⁺ |
| 280 | (2R*, 4S*) | (4-methylbenzoic acid) | MS (m/z): 812 [M + H]⁺ |
| 281 | (2R, 4S) | (2,2-dimethylbutanoic acid) | MS (m/z): 778 [M + H]⁺ |
| 282 | (2R, 4S) | (2,2-difluorobutanoic acid) | MS (m/z): 786 [M + H]⁺ |

Example 283

To (2R*,4S*)-4-{[3,5-bis(trifluoromethyl)benzyl]-[5-(morpholin-4-yl)pyrimidin-2-yl]}amino-2-ethyl-6-trifluoromethyl-3,4-dihydro-2H-quinoline-1-carboxylic acid [(2S, 4R)-(1-tert-butoxycarbonyl-2-methoxy-carbonyl)pyrrolidin-4-yl]ester (230 mg), which is prepared by treating the corresponding starting compounds in a similar manner to Example 277 (1), is added a 4N hydrogen chloride in 1,4-dioxane (1.5 ml), and the mixture is stirred at room temperature for one hour and 40 minutes. The reaction solution is concentrated under reduced pressure, and the resulting crude product (223 mg) is dissolved in methanol (3 ml), and thereto is added a 2N aqueous sodium hydroxide solution (0.4 ml), and the mixture is stirred at room temperature for 3.5 hours. To the reaction solution is added a 1N hydrochloric acid (0.14 ml), and the mixture is concentrated under reduced pressure. To the resulting residue is added diethyl ether, and the insoluble materials are removed by filtration. The filtrate is concentrated under reduced pressure, and to the resulting residue are added water and ethyl acetate, and the mixture is separated. The organic layer is concentrated under reduced pressure, and to the residue are added hexane and diethyl ether, and the mixture is dissolved with heating. The mixture is cooled to room temperature, and the resulting powdery product is dried under reduced pressure to give (2R*,4S*)-4-{[3,5-bis(trifluoromethyl)benzyl]-[5-(morpholin-4-yl)pyrimidin-2-yl]}amino-2-ethyl-6-trifluoromethyl-3,4-dihydro-2H-quinoline-1-carboxylic acid [(2S,4R)-2-carboxypyrrolidin-4-yl]ester (116 mg). MS (m/z): 791 [M+H]$^+$

Example 284

(1) (2R*,4S*)-4-{[3,5-Bis(trifluoromethyl)benzyl]-[5-(morpholin-4-yl)-pyrimidin-2-yl]}amino-2-ethyl-6-trifluoromethyl-3,4-dihydro-2H-quinoline (2.0 g) is dissolved in tetrahydrofuran (30 ml), and thereto are added acryloyl chloride (770 μl) and triethylamine (1.4 ml) under ice-cooling, and the mixture is stirred at room temperature overnight. To the reaction solution are added a saturated aqueous sodium hydrogen carbonate solution and ethyl acetate, and the mixture is separated. The organic layer is washed with a saturated brine, dried over magnesium sulfate and concentrated under reduced pressure. The resulting residue is purified by silica gel column chromatography (hexane:ethyl acetate=9:1→3:2) to give (2R*,4S*)-4-{[3,5-bis(trifluoromethyl)benzyl]-[5-(morpholin-4-yl)pyrimidin-2-yl]}amino-1-acryloyl-2-ethyl-6-trifluoromethyl-3,4-dihydro-2H-quinoline (1.52 g). MS (m/z): 688 [M+H]$^+$ (2) (2R*,4S*)-4-{[3,5-Bis(trifluoromethyl)benzyl]-[5-(morpholin-4-yl)-pyrimidin-2-yl]}amino-1-acryloyl-2-ethyl-6-trifluoromethyl-3,4-dihydro-2H-quinoline (500 mg) is dissolved in tetrahydrofuran (5 ml), and thereto is added piperidine-4-carboxylic acid ethyl ester (1.1 ml), and the mixture is stirred at 45° C. for 3 days. To the reaction solution are added a saturated aqueous ammonium chloride solution and ethyl acetate, and the mixture is separated. The organic layer is washed with a saturated brine, dried over magnesium sulfate and concentrated under reduced pressure. The resulting residue is purified by NH-silica gel column chromatography (hexane:ethyl acetate=4:1→3:2) to give (2R*,4S*)-4-{[3,5-bis(trifluoromethyl)benzyl]-[5-(morpholin-4-yl)pyrimidin-2-yl]}amino-2-ethyl-1-[2-(4-ethoxycarbonylpiperidin-1-yl)ethyl]carbonyl-6-trifluoromethyl-3,4-dihydro-2H-quinoline (539 mg). MS (m/z): 845 [M+H]$^+$ (3) (2R*,4S*)-4-{[3,5-Bis(trifluoromethyl)benzyl]-[5-(morpholin-4-yl)-pyrimidin-2-yl]}amino-2-ethyl-1-[2-(4-ethoxycarbonylpiperidin-1-yl)-ethyl]carbonyl-6-trifluoromethyl-3,4-dihydro-2H-quinoline (150 mg) is dissolved in ethanol (4 ml), and thereto is added dropwise a 1N aqueous sodium hydroxide solution (2 ml), and the mixture is stirred at room temperature overnight. To the reaction solution are added a 1N hydrochloric acid and ethyl acetate, and the mixture is separated. The organic layer is washed with a saturated brine, dried over magnesium sulfate and concentrated under reduced pressure. The resulting residue is purified by silica gel column chromatography (chloroform:methanol=49:1 →17:3) to give (2R*, 4S*)-4-{[3,5-bis(trifluoromethyl)benzyl]-[5-(morpholin-4-yl)pyrimidin-2-yl]}amino-2-ethyl-1-[2-(4-carboxypiperidin-1-yl)ethyl]carbonyl-6-trifluoromethyl-3,4-dihydro-2H-quinoline (128 mg). MS (m/z): 817 [M+H]$^+$

Example 285

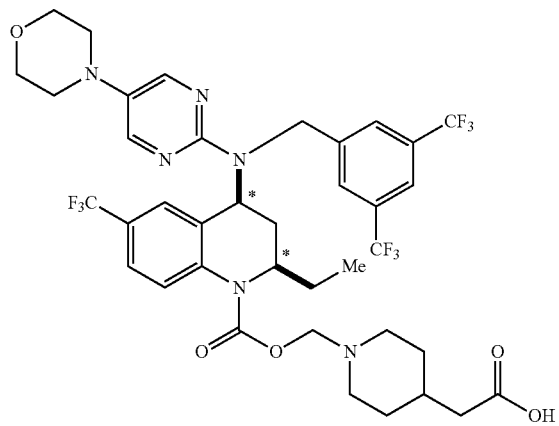

The corresponding starting compound is treated in a similar manner to Example 284 to give the compound of Example 285. MS (m/z): 831 [M+H]$^+$

Example 286

(1) (2R*,4S*)-4-{[3,5-Bis(trifluoromethyl)benzyl]-[5-(morpholin-4-yl)-pyrimidin-2-yl]}amino-2-ethyl-6-trifluoromethyl-1,2,3,4-tetrahydroquinoline (670 mg) is dissolved in dichloromethane (5 ml), and thereto are added pyridine (342 μl) and 4-chlorocarbonylbutyric acid methyl ester (440 μl), and the mixture is stirred at room temperature for 24 hours. To the reaction solution are added water and ethyl acetate, and the organic layer is washed with a saturated brine, dried over magnesium sulfate and concentrated under reduced pressure. The resulting residue is purified by silica gel column chromatography (hexane:ethyl acetate=4:1→1:1) to give (2R*,4S*)-4-{[3,5-bis(trifluoromethyl)benzyl]-[5-(morpholin-4-yl)pyrimidin-2-yl]}amino-2-ethyl-1-(3-methoxycarbonylpropyl)carbonyl-6-trifluoromethyl-3,4-dihydro-2H-quinoline (460.3 mg). MS (m/z): 762 [M+H]$^+$ (2) (2R*,4S*)-4-{[3,5-Bis(trifluoromethyl)benzyl]-[5-(morpholin-4-yl)-pyrimidin-2-yl]}amino-2-ethyl-1-(3-methoxycarbonylpropyl)carbonyl-6-trifluoromethyl-3,4-dihydro-2H-quinoline (100 mg) is dissolved in a mixture of tetrahydrofuran:methanol (1:1, 2 ml), and thereto is added a 2N aqueous sodium hydroxide solution (0.2 ml), and the mixture is stirred for 7.5 hours. To the reaction solution is added a 2N hydrochloric acid (0.2 ml), and the organic layer is washed with a saturated brine, dried over magnesium sulfate and concentrated under reduced pressure. The resulting residue is purified by silica gel column chromatography (chloroform:methanol=1:0→9:1) to give (2R*,4S*)-4-{[3,5-bis(trifluoro-methyl)benzyl]-[5-(morpholin-4-yl)pyrimidin-2-yl]}amino-1-(3-carboxypropyl)carbonyl-2-ethyl-6-trifluoromethyl-3,4-dihydro-2H-quinoline (92.6 mg). MS (m/z): 748 [M+H]$^+$ Example 287

(1) (2R*,4S*)-4-{[3,5-Bis(trifluoromethyl)benzyl]-[5-(morpholin-4-yl)pyrimidin-2-yl]}amino-2-ethyl-1-(3-methoxycarbonylpropyl)carbonyl-6-trifluoromethyl-3,4-dihydro-2H-quinoline (450 mg) is dissolved in tetrahydrofuran (6 ml), and thereto is added a 1M solution of borane-tetrahydrofuran complex in tetrahydrofuran (2.95 ml) under ice-cooling, and the mixture is stirred at room temperature for 2 hours. To the reaction solution is added an aqueous diethyl ether, and the mixture is stirred for 30 minutes. To the mixture are added ethyl acetate and water, and the mixture is separated. The organic layer is washed with a saturated brine, dried over magnesium sulfate and concentrated under reduced pressure. The resulting residue is purified by silica gel column chromatography (hexane:ethyl acetate=4:1→1:1) to give (2R*,4S*)-4-{[3,5-bis(trifluoro methyl)benzyl]-[5-(morpholin-4-yl)pyrimidin-2-yl]}amino-2-ethyl-1-(4-methoxycarbonylbutyl)-6-trifluoromethyl-3,4-dihydro-2H-quinoline (90.0 mg). MS (m/z): 747 [M+H]$^+$ (2) (2R*,4S*)-4-{[3,5-Bis(trifluoromethyl)benzyl]-[5-(morpholin-4-yl)-pyrimidin-2-yl]}amino-2-ethyl-1-(4-methoxycarbonylbutyl)-6-trifluoro-methyl-3,4-dihydro-2H-quinoline (85 mg) is dissolved in a mixture of tetrahydrofuran:methanol (1:1, 2 ml), and thereto is added a 2N aqueous sodium hydroxide solution (0.16 ml), and the mixture is stirred for 4.5 hours. To the reaction solution is added a 2N hydrochloric acid (0.16 ml), and the organic layer is washed with a saturated brine, dried over magnesium sulfate and concentrated under reduced pressure. The resulting residue is purified by silica gel column chromatography (chloro-form:methanol=1:0 →19:1) to give (2R*,4S*)-4-{[3,5-bis(trifluoromethyl)-benzyl]-[5-(morpholin-4-yl)pyrimidin-2-yl]}amino-2-ethyl-1-(4-carboxy-butyl)-6-trifluoromethyl-3,4-dihydro-2H-quinoline (82 mg). MS (m/z): 732 [M−H]$^−$ Example 288

(1) (2R,4S)-4-{[3,5-Bis(trifluoromethyl)benzyl]-(5-bromopyrimidin-2-yl)}-amino-2-ethyl-6-trifluoromethyl-1,2,3,4-tetrahydroquinoline (1 g) is dissolved in toluene (5 ml), and thereto are added tris(dibenzylideneacetone)dipalladium (147 mg), 2-(di-tert-butyl-phosphino)biphenyl (95 mg), sodium tert-butoxide (307 mg) and a 2N solution of dimethylamine in tetrahydrofuran (1.6 ml), and the mixture is stirred in a sealed vessel at room temperature for one hour. To the reaction solution are added water and ethyl acetate, and the mixture is separated. The organic layer is washed with a saturated brine, dried over magnesium sulfate and concentrated under reduced pressure. The resulting residue is purified by silica gel column chromatography (hexane:ethyl acetate=9:1→7:3) to give (2R,4S)-4-{[3,5-bis(trifluoromethyl)benzyl]-(5-dimethylaminopyrimidin-2-yl)}amino-2-ethyl-6-trifluoromethyl-1,2,3,4-tetrahydroquinoline (500 mg). MS (m/z): 592 [M+H]$^+$ (2) (2R,4S)-4-{[3,5-Bis(trifluoromethyl)benzyl]-(5-dimethylamino-pyrimidin-2-yl)}amino-2-ethyl-6-trifluoromethyl-1,2,3,4-tetrahydroquinoline (470 mg) is treated in a similar manner to Example 276 (2)-(3) to give (2R,4S)-4-{[3,5-bis(trifluoromethyl)benzyl]-(5-dimethylaminopyrimidin-2-yl)}amino-2-ethyl-6-trifluoromethyl-3,4-dihydro-2H-quinoline-1-carboxylic acid 2-carboxyethyl ester (195.5 mg). MS (m/z): 708 [M+H]$^+$ Example 289

(1) (2R,4S)-4-{[3,5-Bis(trifluoromethyl)benzyl]-(5-bromopyrimidin-2-yl)}amino-2-ethyl-6-trifluoromethyl-1,2,3,4-tetrahydroquinoline (7.00 g) is dissolved in methylene chloride (80 ml), and thereto is added triethylamine (4.2 ml), and further added triphosgene (2.99 g) under ice-cooling. Under nitrogen atmosphere, the mixture is stirred at the same temperature for 1.5 hour, and concentrated under reduced pressure, and thereto is added ether. The precipitated insoluble materials are removed by filtration, and the filtrate is concentrated under reduced pressure. To the resulting residue are added tetrahydrofuran (80 ml), tert-butyl 3-hydroxypropionate (2.64 ml) and sodium hydride (62.7%, 680 mg), and the mixture is stirred at room temperature under nitrogen atmosphere overnight. The reaction mixture is neutralized with a 10% aqueous citric acid solution, and thereto is added a saturated brine. The mixture is extracted with ethyl acetate, and the organic layer is washed twice with a saturated brine, dried over magnesium sulfate and concentrated under reduced pressure. The resulting residue is purified by silica gel column chromatography (hexane:ethyl acetate=10:1) to give (2R,4S)-4-{[3,5-bis(trifluoromethyl)-benzyl]-(5-bromopyrimidin-2-yl)}amino-2-ethyl-6-trifluoromethyl-3,4-dihydro-2H-quinoline-1-carboxylic acid 2-tert-butoxycarbonylethyl ester (6.10 g). MS (m/z): 801/799 [M+H]$^+$ (2) (2R,4S)-4-{[3,5-Bis(trifluoromethyl)benzyl]-(5-bromopyrimidin-2-yl)}amino-2-ethyl-6-trifluoromethyl-3,4-dihydro-2H-quinoline-1-carboxylic acid 2-tert-butoxycarbonylethyl ester (5.00 g) is dissolved in dimethyl-sulfoxide (20 ml), and the mixture is deaerated. To the mixture are added[1,1'-bis(diphenylphosphino)ferrocene]palladium (II) dichloride (177 mg), potassium acetate (1.84 g) and bis(pinacolato)diboron (2.38 g), and the mixture is stirred at 80° C. under nitrogen atmosphere for one hour. The reaction solution is cooled to room temperature, and thereto are added a saturated brine and ethyl acetate, and the organic layer is washed with a saturated brine, dried over magnesium sulfate and concentrated under reduced pressure. The resulting residue is dissolved in tetrahydrofuran (30 ml), and thereto is added dropwise a 30% aqueous hydrogen peroxide solution (10 ml) under ice-cooling, and the mixture is stirred at the same temperature for one hour. To the reaction mixture is added a saturated aqueous sodium thiosulfate solution under ice-cooling, and the mixture is extracted with ethyl acetate. The organic layer is washed with a saturated brine, dried over magnesium sulfate and concentrated under reduced pressure. The resulting residue is purified by silica gel column chromatography (hexane:ethyl acetate=4:1→3:1) to give (2R,4S)-4-{[3,5-bis(trifluoromethyl)benzyl]-(5-hydroxypyrimidin- 2-yl)}amino-2-ethyl-6-trifluoromethyl-3,4-dihydro-2H-quinoline-1-carboxylic acid 2-tert-butoxycarbonylethyl ester (2.94 g). MS (m/z): 737 [M+H]+

(3) (2R,4S)-4-{[3,5-Bis(trifluoromethyl)benzyl]-(5-hydroxypyrimidin-2-yl)}amino-2-ethyl-6-trifluoromethyl-3,4-dihydro-2H-quinoline-1-carboxylic acid 2-tert-butoxycarbonylethyl ester (300 mg) is dissolved in a mixture of tetrahydrofuran (2.5 ml) and N,N-dimethylformamide (1 ml), and thereto are added 4-bromobutyronitrile (244 µl) and potassium carbonate (281 mg), and the mixture is stirred at 60° C. for 1.5 hour. To the reaction mixture is added a saturated brine, and the mixture is extracted with ethyl acetate. The organic layer is washed with a saturated brine, dried over magnesium sulfate and concentrated under reduced pressure. The resulting residue is purified by thin layer silica gel chromatography (hexane:ethyl acetate=3:1) to give (2R,4S)-4-{[3,5-bis(trifluoromethyl)benzyl]-[5-(3-cyanopropoxy)-pyrimidin-2-yl]}amino-2-ethyl-6-trifluoromethyl-3,4-dihydro-2H-quinoline-1-carboxylic acid 2-tert-butoxycarbonylethyl ester (107 mg). MS (m/z): 804 [M+H]+

(4) (2R,4S)-4-{[3,5-Bis(trifluoromethyl)benzyl]-[5-(3-cyanopropoxy)-pyrimidin-2-yl]}amino-2-ethyl-6-trifluoromethyl-3,4-dihydro-2H-quinoline-1-carboxylic acid 2-tert-butoxycarbonylethyl ester (103 mg) is dissolved in methylene chloride (1 ml), and thereto is added a 4N hydrochloric acid in 1,4-dioxane (1 ml) under ice-cooling, and the mixture is stirred at room temperature for 2 hours. The reaction mixture is concentrated under reduced pressure, and thereto is added a small amount of a saturated aqueous sodium hydrogen carbonate solution, and the mixture is neutralized. Then, the mixture is made weakly acidic with a 10% aqueous citric acid solution, and extracted with ethyl acetate, and the organic layer is washed twice with a saturated brine, dried over magnesium sulfate and concentrated under reduced pressure. The resulting residue is purified by silica gel column chromatography (chloroform:methanol=19:1) to give (2R,4S)-4-{[3,5-bis(trifluoromethyl)benzyl]-[5-(3-cyanopropoxy)pyrimidin-2-yl]}amino-2-ethyl-6-trifluoromethyl-3,4-dihydro-2H-quinoline-1-carboxylic acid 2-carboxyethyl ester (71 mg). MS (m/z): 748 [M+H]+

Example 290

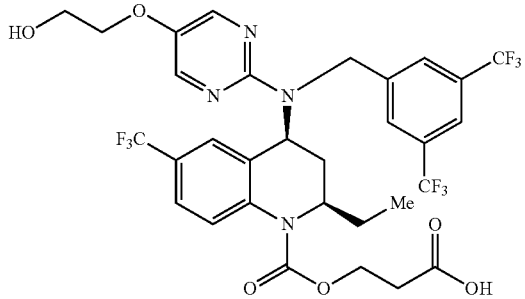

The corresponding starting compound is treated in a similar manner to Example 289 to give the compound of Example 290. MS (m/z): 725 [M+H]+

Example 291

(1) (2R,4S)-4-{[3,5-Bis(trifluoromethyl)benzyl]-(5-hydroxypyrimidin-2-yl)}amino-2-ethyl-6-trifluoromethyl-3,4-dihydro-2H-quinoline-1-carboxylic acid 2-tert-butoxycarbonylethyl ester (220 mg) is dissolved in tetrahydro-furan (1.5 ml), and thereto is added 2-methoxyethanol (35 µl) and triphenylphosphine (118 mg), and further added dropwise a 40% solution of diethyl azodicarboxylate in toluene (195 µl) under cooling with water. The mixture is stirred at room temperature for one hour, and to the reaction mixture is added a saturated brine, and the mixture is extracted with ethyl acetate. The organic layer is washed with a saturated brine, dried over magnesium sulfate and concentrated under reduced pressure. The resulting residue is purified by silica gel column chromatography (hexane:ethyl acetate=17:3→4:1) to give (2R,4S)-4-{[3,5-bis(trifluoro-methyl)benzyl]-[5-(2-methoxyethoxy)pyrimidin-2-yl]}amino-2-ethyl-6-trifluoromethyl-3,4-dihydro-2H-quinoline-1-carboxylic acid 2-tert-butoxycarbonylethyl ester (193 mg). MS (m/z): 795 [M+H]+

(2) To (2R,4S)-4-{[3,5-bis(trifluoromethyl)benzyl]-[5-(2-methoxyethoxy)-pyrimidin-2-yl]}amino-2-ethyl-6-trifluoromethyl-3,4-dihydro-2H-quinoline-1-carboxylic acid 2-tert-butoxycarbonylethyl ester (190 mg) is added a 4N hydrochloric acid in 1,4-dioxane (2 ml), and the mixture is stirred at room temperature for 2 hours. The reaction mixture is concentrated under reduced pressure, and thereto is added a saturated brine, and the mixture is extracted with ethyl acetate. The organic layer is washed twice with a saturated brine, dried over magnesium sulfate and concentrated under reduced pressure. The resulting residue is purified by silica gel column chromatography (chloroform:methanol=19:1) to give (2R,4S)-4-{[3,5-bis(trifluoromethyl)benzyl]-[5-(2-methoxyethoxy)pyrimidin-2-yl]}amino-2-ethyl-6-trifluoromethyl-3,4-dihydro-2H-quinoline-1-carboxylic acid 2-carboxyethyl ester (168 mg). MS (m/z): 739 [M+H]+

Example 292

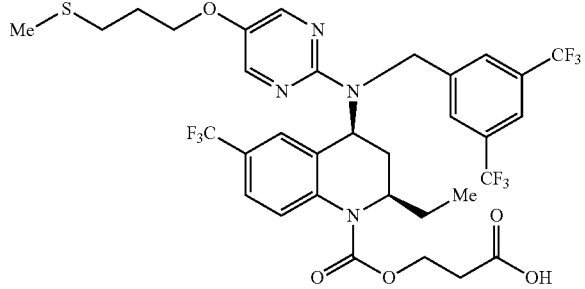

The corresponding starting compound is treated in a similar manner to Example 291 to give the compound of Example 292. MS (m/z): 769 [M+H]+

Example 293

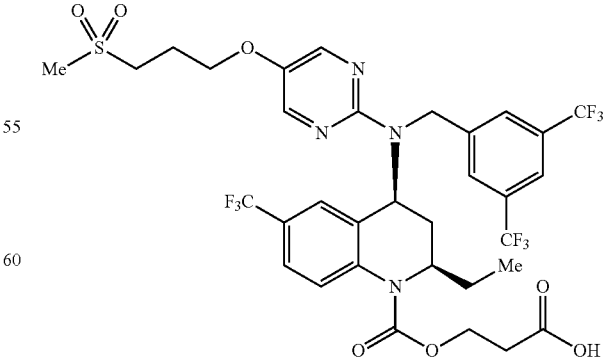

The corresponding starting compound is treated in a similar manner to Example 50 and Example 291(2) to give the compound of Example 293. MS (m/z): 801 [M+H]+

Example 294

(1) (2R,4S)-4-{[3,5-Bis(trifluoromethyl)benzyl]-(5-bromopyrimidin-2-yl)}-amino-2-ethyl-6-trifluoromethyl-3,4-dihydro-2H-quinoline-1-carboxylic acid 4-methoxycarbonylbutyl ester (1.08 g) is dissolved in dimethyl-sulfoxide (4 ml), and thereto are added [1,1'-bis(diphenylphosphino)-ferrocene]dichloropalladium, complex with dichloromethane (1:1,30 mg), potassium acetate (403 mg), and bis(pinacolato)diboron (522 mg), and the mixture is stirred at 80° C. for 2 hours. The reaction solution is cooled to room temperature, and thereto are added water and diethyl ether, and the mixture is separated. The organic layer is washed with a saturated brine, dried over magnesium sulfate and concentrated under reduced pressure. The resulting residue is dissolved in tetrahydrofuran (4 ml), and thereto is added a 30% aqueous hydrogen peroxide solution (1.0 ml) under ice-cooling, and the mixture is stirred at room temperature for 7.5 hours. To the reaction solution is added a saturated aqueous sodium thiosulfate solution under ice-cooling, and then further added diethyl ether, and the mixture is separated. The organic layer is washed with water and a saturated brine, dried over magnesium sulfate and concentrated under reduced pressure. The resulting residue is purified by silica gel column chromatography (hexane:ethyl acetate=4:1→3:2) to give (2R,4S)-4-{[3,5-bis(trifluoromethyl)benzyl]-(5-hydroxypyrimidin-2-yl)}amino-2-ethyl-6-trifluoromethyl-3,4-dihydro-2H-quinoline-1-carboxylic acid 4-methoxy-carbonylbutyl ester (1.06 mg). MS (m/z): 723 [M+H]⁺

(2) (2R,4S)-4-{[3,5-Bis(trifluoromethyl)benzyl]-(5-hydroxypyrimidin-2-yl)}amino-2-ethyl-6-trifluoromethyl-3,4-dihydro-2H-quinoline-1-carboxylic acid 4-methoxycarbonylbutyl ester (200 mg) is dissolved in tetrahydrofuran (3 ml), and thereto are added a 40% solution of diethyl azodicarboxylate in toluene (255 ml), triphenylphosphine (147 mg), and 2-methoxyethanol (44 µl), and the mixture is stirred at room temperature for 2 hours. To the reaction solution are added a saturated aqueous sodium hydrogen carbonate solution and ethyl acetate, and the mixture is separated. The organic layer is washed with water and a saturated brine, dried over magnesium sulfate and concentrated under reduced pressure. The resulting residue is purified by silica gel column chromatography (hexane:ethyl acetate=4:1→63:37) to give (2R,4S)-4-{[3,5-bis(trifluoro-methyl)benzyl]-[5-(2-methoxyethoxy)pyrimidin-2-yl]}amino-2-ethyl-6-trifluoromethyl-3,4-dihydro-2H-quinoline-1-carboxylic acid 4-methoxy-carbonylbutyl ester (171.4 mg). MS (m/z): 781 [M+H]⁺

(3) (2R,4S)-4-{[3,5-Bis(trifluoromethyl)benzyl]-[5-(2-methoxyethoxy)-pyrimidin-2-yl]}amino-2-ethyl-6-trifluoromethyl-3,4-dihydro-2H-quinoline-1-carboxylic acid 4-methoxycarbonylbutyl ester (163 mg) is dissolved in tetrahydrofuran:methanol (1:1,4 ml), and thereto is added a 2N aqueous sodium hydroxide solution (0.315 ml), and the mixture is stirred at room temperature for 15.5 hours. To the reaction solution is added a 1N hydrochloric acid (0.63 ml), and the organic layer is washed with a saturated brine, dried over magnesium sulfate and concentrated under reduced pressure. The resulting residue is purified by silica gel column chromatography (chloroform:methanol=1:0→24:1) and further by gel permeation column chromatography (JAIGEL-1H and JAIGEL-2H, manufactured by Japan Analytical Industry Co., Ltd.; 4 ml/min., chloroform) to give (2R,4S)-4-{[3,5-bis(trifluoromethyl)benzyl]-[5-(2-methoxyethoxy)pyrimidin-2-yl]}amino-2-ethyl-6-trifluoromethyl-3,4-dihydro-2H-quinoline-1-carboxylic acid 4-carboxybutyl ester (36.5 mg). MS (m/z): 767 [M+H]⁺

Example 295

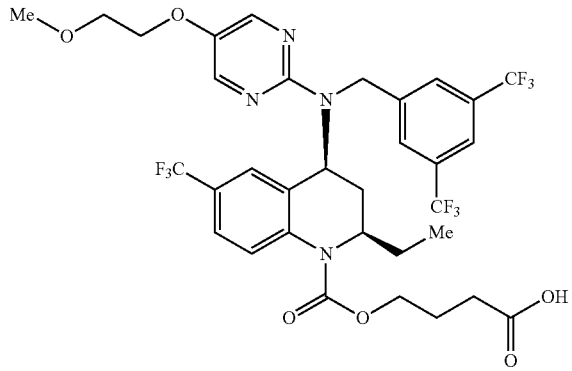

The corresponding starting compound is treated in a similar manner to Example 294 to give the compound of Example 295. MS (m/z): 753 [M+H]⁺

Example 296

(1) (2R,4S)-4-{[3,5-Bis(trifluoromethyl)benzyl]-(5-bromopyrimidin-2-yl)}-amino-2-ethyl-6-trifluoromethyl-3,4-dihydro-2H-quinoline-1-carboxylic acid 5-ethoxycarbonylpentyl ester (400 mg) is dissolved in dimethyl-sulfoxide (1.5 ml), and thereto are added [1,1'-bis(diphenylphosphino)-ferrocene]dichloropalladium, complex with dichloromethane (1:1,11 mg), potassium acetate (145 mg), and bis(pinacolato)diborone (187 mg), and the mixture is stirred at 80° C. for 2 hours and 20 minutes. The reaction solution is cooled to room temperature, and thereto are added water and ethyl acetate, and the mixture is separated. The organic layer is washed with a saturated brine, dried over magnesium sulfate and concentrated under reduced pressure. The resulting residue is dissolved in tetrahydro-furan (1.5 ml), and thereto is added a 30% aqueous hydrogen peroxide solution (0.56 ml) under ice-cooling, and the mixture is stirred at room temperature for 1.5 hour. To the reaction mixture is added a saturated aqueous sodium thiosulfate solution under ice-cooling, and the mixture is extracted with ethyl acetate. The organic layer is washed with a saturated brine, dried over magnesium sulfate and concentrated under reduced pressure. The resulting residue is purified by silica gel column chromatography (hexane:ethyl acetate=9:1→7:3) to give (2R,4S)-4-{[3,5-bis-(trifluoromethyl)benzyl]-(5-hydroxypyrimidin-2-yl)}amino-2-ethyl-6-trifluoromethyl-3,4-dihydro-2H-quinoline-1-carboxylic acid 5-ethoxy-carbonylpentyl ester (319 mg). MS (m/z): 751 [M+H]⁺

(2) (2R,4S)-4-{[3,5-Bis(trifluoromethyl)benzyl]-(5-hydroxypyrimidin-2-yl)}amino-2-ethyl-6-trifluoromethyl-3,4-dihydro-2H-quinoline-1-carboxylic acid 5-ethoxycarbonylpentyl ester (310 mg) is dissolved in N,N-dimethylformamide (4 ml), and thereto are added potassium carbonate (340 mg) and 2-bromoethanol (160 µl), and the mixture is stirred at room temperature for 23.5 hours. To the reaction solution are added a saturated aqueous citric acid solution and ethyl acetate, hexane, and the mixture is separated. The organic layer is washed with water and a saturated brine, dried over magnesium sulfate and concentrated under reduced pressure. The resulting residue is purified by silica gel column chromatography (hexane:ethyl acetate=4:1→3:2) to give (2R,4S)-4-{[3,5-bis(trifluoromethyl)benzyl]-[5-(2-hydroxyethoxy)pyrimidin-2-yl]}amino-2-ethyl-6-trifluoromethyl-3,4-dihydro-2H-quinoline-1-carboxylic acid 5-ethoxycarbonylpentyl ester (146 mg). MS (m/z): 795 [M+H]⁺

(3) (2R,4S)-4-{[3,5-Bis(trifluoromethyl)benzyl]-[5-(2-hydroxyethoxy)-pyrimidin-2-yl]}amino-2-ethyl-6-trifluoromethyl-3,4-dihydro-2H-quinoline-1-carboxylic acid 5-ethoxycarbonylpentyl ester (130 mg) is dissolved in ethanol (1.6 ml), and thereto is added a 2N aqueous sodium hydroxide solution (0.25 ml), and the mixture is stirred at room temperature for 4 hours. To the reaction solution is added a 2N hydrochloric acid, and the organic layer is washed with water and a saturated brine, dried over magnesium sulfate and concentrated under reduced pressure. The resulting residue is purified by silica gel column chromatography (chloroform:methanol=1:0→19:1) to give (2R,4S)-4-{[3,5-bis(trifluoro-methyl)benzyl]-[5-(2-hydroxyethoxy)pyrimidin-2-yl]}amino-2-ethyl-6-trifluoromethyl-3,4-dihydro-2H-quinoline-1-carboxylic acid 5-carboxyl-pentyl ester (119 mg). MS (m/z): 767 [M+H]⁺

Example 297

(1) (2R,4S)-4-{[3,5-Bis(trifluoromethyl)benzyl]-(5-hydroxypyrimidin-2-yl)}amino-2-ethyl-6-trifluoromethyl-3,4-dihydro-2H-quinoline-1-carboxylic acid 3-methoxycarbonylpropyl ester (130 mg) is dissolved in tetrahydrofuran (1.5 ml). 2-Acetoxyethanol (37 mg), triphenylphosphine (188 mg) and a 40% solution of diethyl azodicarboxylate in toluene (314 μl) are added thereto and the mixture is stirred at room temperature for 6 hours. Water is added to the mixture, and the mixture is extracted with diethyl ether. The organic layer is washed with a saturated brine, dried over magnesium sulfate, and concentrated under reduced pressure. The resulting residue is purified by silica gel column chromatography (hexane:ethyl acetate=9:1→7:3) to give (2R,4S)-4-{[3,5-bis(trifluoro methyl)benzyl]-[5-(2-acetoxyethoxy)pyrimidin-2-yl]}amino-2-ethyl-6-trifluoromethyl-3,4-dihydro-2H-quinoline-1-carboxylic acid 3-methoxycarbonylpropyl ester (145.1 mg). MS (m/z): 795 [M+H]⁺.

(2) (2R,4S)-4-{[3,5-Bis(trifluoromethyl)benzyl]-[5-(2-acetoxyethoxy)pyrimidin-2-yl]}amino-2-ethyl-6-trifluoromethyl-3,4-dihydro-2H-quinoline-1-carboxylic acid 3-methoxycarbonylpropyl ester (135 mg) is dissolved in tetrahydrofuran:methanol (1:1) (3 ml), thereto is added a 2N aqueous sodium hydroxide solution (0.25 ml) and the mixture is stirred at room temperature for 8.5 hours. To the reaction solution are added 1N hydrochloric acid (0.5 ml) and ethyl acetate, and the organic layer is washed with a saturated brine, dried over magnesium sulfate, and concentrated under reduced pressure. The resulting residue is purified by LC-MS (CAPCEL PAK MG II (Shiseido Co., Ltd.), 40 ml/min, a 10% aqueous ammonium carbonate solution:methanol=60:40→methanol) and silica gel column chromatography (chloroform:methanol=1:0→19:1) to give (2R,4S)-4-{[3,5-bis(trifluoromethyl)benzyl]-[5-(2-hydroxyethoxy)pyrimidin-2-yl]}amino-2-ethyl-6-trifluoromethyl-3,4-dihydro-2H-quinoline-1-carboxylic acid 3-carboxypropyl ester (41.8 mg). MS (m/z):739 [M+H]⁺.

Example 298

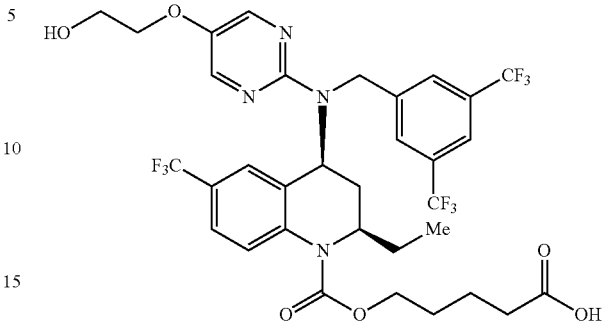

Corresponding starting compound is treated in a similar manner to Example 297 to give the compound of Example 298. MS (m/z): 753 [M+H]⁺.

Example 299

(1) (2R,4S)-4-{[3,5-Bis(trifluoromethyl)benzyl]-(5-bromopyrimidin-2-yl)}amino-2-ethyl-6-trifluoromethyl-3,4-dihydro-2H-quinoline (3 g) is dissolved in dichloromethane (25 ml). Triethylamine (2.0 ml) and triphosgene (1.4 g) are added to the solution under ice-cooling and the mixture is stirred at the same temperature for 30 minutes. The reaction solution is concentrated under reduced pressure, insoluble materials are removed by filtration with tetrahydrofuran and the filtrate is concentrated under reduced pressure. The resulting residue is dissolved in tetrahydrofuran (25 ml), thereto are added hydroxypivalic acid methyl ester (0.79 ml) and 62.7% sodium hydride (238 mg) under ice-cooling and the mixture is stirred at room temperature for 63 hours. The reaction solution is separated by adding water and ethyl acetate. The organic layer is washed with a saturated brine, dried over magnesium sulfate, and concentrated under reduced pressure. The resulting residue is purified by silica gel column chromatography (hexane:ethyl acetate=9:1→4:1) to give (2R,4S)-4-{[3,5-bis(trifluoromethyl)benzyl]-(5-bromopyrimidin-2-yl)}amino-2-ethyl-6-trifluoromethyl-3,4-dihydro-2H-quinoline-1-carboxylic acid 2-methoxycarbonyl-2-methylpropyl ester (3.08 g). MS (m/z): 785/787 [M+H]⁺.

(2) (2R,4S)-4-{[3,5-Bis(trifluoromethyl)benzyl]-(5-bromopyrimidin-2-yl)}amino-2-ethyl-6-trifluoromethyl-3,4-dihydro-2H-quinoline-1-carboxylic acid 2-methoxycarbonyl-2-methylpropyl ester (3.07 g) is dissolved in dimethylsulfoxide (20 ml). [1,1'-Bis(diphenylphosphino)ferrocene]dichloro-palladium, complex with dichloromethane (1:1) (163 mg), potassium acetate (1.15 g) and bis(pinacolato)diboron (1.49 g) are added to the solution and the mixture is heated to 80° C. for 3 hours. The reaction solution is cooled to room temperature and separated by adding water and ethyl acetate. The organic layer is washed with a saturated brine, dried over magnesium sulfate, and concentrated under reduced pressure. The resulting residue is dissolved in tetrahydrofuran (20 ml), thereto is added a 30% aqueous hydrogen peroxide solution (8.8 ml) under ice-cooling and the mixture is stirred at room temperature for an hour. The reaction solution is separated by adding a saturated aqueous sodium thiosulfate solution under ice-cooling followed by ethyl acetate. The organic layer is washed with a saturated brine, dried over magnesium sulfate, and concentrated under reduced pressure. The resulting residue is purified by silica gel column chromatography (hexane:ethyl acetate=4:1→1:1) to give (2R,4S)-4-{[3,5-Bis(trifluoromethyl)benzyl]-(5-hydroxypyrimidin-2-yl)}amino-2-ethyl-6-trifluoromethyl-3,4-dihydro-2H-quinoline-1-carboxylic acid 2-methoxycarbonyl-2-methylpropyl ester (2.37 g). MS (m/z): 723 [M+H]⁺.

(3) (2R,4S)-4-{[3,5-Bis(trifluoromethyl)benzyl]-(5-hydroxypyrimidin-2-yl)}amino-2-ethyl-6-trifluoromethyl-3,4-dihydro-2H-quinoline-1-carboxylic acid 2-methoxycarbonyl-2-methylpropyl ester (300 mg) is dissolved in N,N-dimethylformamide (2 ml), and thereto are added 62.7% sodium hydride (95 mg) and 2-bromoethanol (190 µl) under ice-cooling, and the mixture is stirred at room temperature for 19 hours. The reaction solution is separated by adding water and ethyl acetate. The organic layer is washed with a saturated brine, dried over magnesium sulfate, and concentrated under reduced pressure. The resulting residue is purified by NH-silica gel column chromatography (hexane:ethyl acetate=9:1→7:3) to give (2R,4S)-4-{[3,5-bis(trifluoromethyl)benzyl]-[5-(2-hydroxyethoxy)pyrimidin-2-yl]}amino-2-ethyl-6-trifluoromethyl-3,4-dihydro-2H-quinoline-1-carboxylic acid 2-methoxycarbonyl-2-methylpropyl ester (110 mg). MS (m/z): 767 [M+H]⁺.

(4) (2R,4S)-4-{[3,5-Bis(trifluoromethyl)benzyl]-[5-(2-hydroxyethoxy)pyrimidin-2-yl]}amino-2-ethyl-6-trifluoromethyl-3,4-dihydro-2H-quinoline-1-carboxylic acid 2-methoxycarbonyl-2-methylpropyl ester (100 mg) is dissolved in tetrahydrofuran:methanol (1:1) (1 ml), thereto is added a 2N aqueous sodium hydroxide solution (0.66 ml) and the mixture is stirred at room temperature for 3 hours. To the reaction solution are added 2N hydrochloric acid (0.66 ml) and ethyl acetate, and the organic layer is washed with a saturated brine, dried over magnesium sulfate, and concentrated under reduced pressure. The resulting residue is purified by silica gel column chromatography (chloroform:methanol=1:0→19:1) to give (2R,4S)-4-{[3,5-bis(trifluoromethyl)benzyl]-[5-(2-hydroxyethoxy)-pyrimidin-2-yl]}amino-2-ethyl-6-trifluoromethyl-3,4-dihydro-2H-quinoline-1-carboxylic acid 2-carboxy-2-methylpropyl ester (68.8 mg). MS (m/z): 753 [M+H]⁺.

Example 300

(1) (2R,4S)-4-{[3,5-Bis(trifluoromethyl)benzyl]-(5-hydroxypyrimidin-2-yl)}amino-2-ethyl-6-trifluoromethyl-3,4-dihydro-2H-quinoline-1-carboxylic acid 3-methoxycarbonylpropyl ester (250 mg) is dissolved in N,N-dimethylformamide (3 ml), and thereto is added sodium hydride (60%, 17.2 mg) under ice-cooling and the mixture is stirred at room temperature for 10 minutes. 4-Bromobutyronitrile (46 µl) is added to the reaction solution and the mixture is stirred at the same temperature for 3 hours.

Water and ethyl acetate are added to the reaction solution, the organic layer is washed with a saturated brine, dried over magnesium sulfate, and concentrated under reduced pressure. The resulting residue is purified by silica gel column chromatography (hexane:ethyl acetate=4:1→1:1) to give (2R,4S)-4-{[3,5-bis(trifluoromethyl)benzyl]-[5-(3-cyanopropoxy)pyrimidin-2-yl]}amino-2-ethyl-6-trifluoromethyl-3,4-dihydro-2H-quinoline-1-carboxylic acid 3-methoxycarbonylpropyl ester (68 mg). MS (m/z):776 [M+H]⁺.

(2) (2R,4S)-4-{[3,5-Bis(trifluoromethyl)benzyl]-[5-(3-cyanopropoxy)pyrimidin-2-yl]}amino-2-ethyl-6-trifluoromethyl-3,4-dihydro-2H-quinoline-1-carboxylic acid 3-methoxycarbonylpropyl ester (60 mg) is dissolved in tetrahydrofuran:methanol (1:1) (3 ml), and thereto is added 2N aqueous sodium hydroxide solution (600 µl), and the mixture is stirred at room temperature for 7 days. After adding 2N hydrochloric acid (600 µl) and ethyl acetate to the reaction solution, the organic layer is washed with a saturated brine, dried over magnesium sulfate, and concentrated under reduced pressure. The resulting residue is purified by silica gel column chromatography (chloroform:methanol=1:0→19:1) to give (2R,4S)-4-{[3,5-bis(trifluoromethyl)benzyl]-[5-(3-cyanopropoxy)pyrimidin-2-yl]}amino-2-ethyl-6-trifluoromethyl-3,4-dihydro-2H-quinoline-1-carboxylic acid 3-carboxypropyl ester (58.2 mg). MS (m/z):762 [M+H]⁺.

Examples 301-303

Corresponding starting compounds are treated in a similar manner to Example 300 to give the compounds of Examples 301-303.

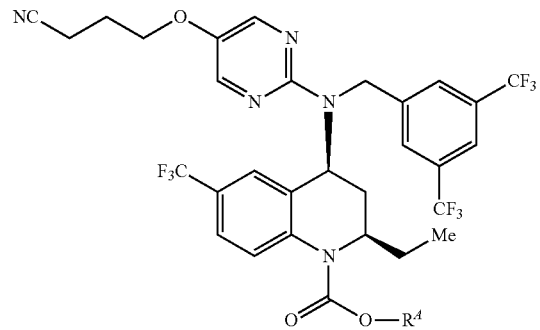

TABLE 35

| Ex. No. | Configuration | R⁴ | Physical properties, etc. |
|---|---|---|---|
| 301 | (2R, 4S) | pentyl-C(=O)OH | MS (m/z): 776 [M + H]⁺ |
| 302 | (2R, 4S) | -(CH₂)₄-C(=O)-CH(OH)- chain | MS (m/z): 790 [M + H]⁺ |
| 303 | (2R, 4S) | -CH₂-C(Me)(Me)-C(=O)OH | MS (m/z): 776 [M + H]⁺ |

Example 304

(1) (2R,4S)-4-{[3,5-Bis(trifluoromethyl)benzyl]-(5-hydroxypyrimidin-2-yl)}amino-2-ethyl-6-trifluoromethyl- 3,4-dihydro-2H-quinoline-1-carboxylic acid 5-ethoxycarbonylpentyl ester (300 mg) is dissolved in tetrahydrofuran (2 ml), and thereto are added 2-methoxyethanol (63 µl), triphenylphosphine (210 mg) and a 40% solution of diethyl azodicarboxylate in toluene (365 µl), and the mixture is stirred at room temperature for 2.5 hours. Water is added to the reaction solution and the mixture is extracted with ethyl acetate. The organic layer is washed with a saturated brine, dried over magnesium sulfate, and concentrated under reduced pressure. The resulting residue is purified by silica gel column chromatography (hexane:ethyl acetate=9:1→4:1) to give (2R,4S)-4-{[3,5-bis(trifluoromethyl)benzyl]-[5-(2-methoxyethoxy)pyrimidin-2-yl]}amino-2-ethyl-6-trifluoromethyl-3,4-dihydro-2H-quinoline-1-carboxylic acid 5-ethoxycarbonylpentyl ester (300 mg). MS (m/z):809 [M+H]$^+$.

(2)  (2R,4S)-4-{[3,5-Bis(trifluoromethyl)benzyl]-[5-(2-methoxyethoxy)-pyrimidin-2-yl]}amino-2-ethyl-6-trifluoromethyl-3,4-dihydro-2H-quinoline-1-carboxylic acid 5-ethoxycarbonylpentyl ester (293 mg) is dissolved in tetrahydrofuran:ethanol (1:1)(3 ml), and thereto is added 2N aqueous sodium hydroxide solution (0.5 ml), and the mixture is stirred at room temperature for 4 hours. To the reaction solution are added 2N hydrochloric acid (0.5 ml) and ethyl acetate, and the organic layer is washed with a saturated brine, dried over magnesium sulfate, and concentrated under reduced pressure. The resulting residue is purified by silica gel column chromatography (chloroform:methanol=1:0→47:3) to give (2R,4S)-4-{[3,5-bis(trifluoromethyl)benzyl]-[5-(2-methoxyethoxy)-pyrimidin-2-yl]}amino-2-ethyl-6-trifluoromethyl-3,4-dihydro-2H-quinoline-1-carboxylic acid 5-carboxypentyl ester (243 mg). MS (m/z): 781 [M+H]$^+$.

Example 305

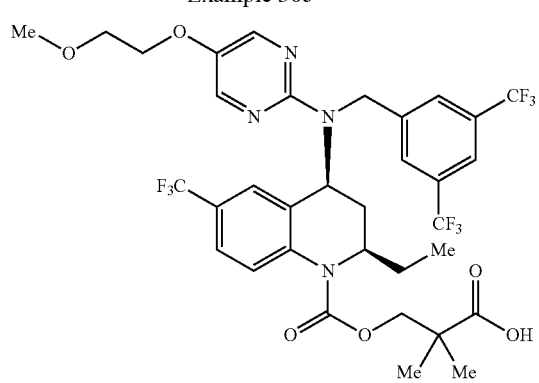

Corresponding starting compound is treated in a similar manner to Example 304 to give the compound of Example 305. MS (m/z): 767 [M+H]$^+$.

Examples 306-311

Corresponding starting compounds are treated in a similar manner to Example 291 to give the compounds of Examples 306-311.

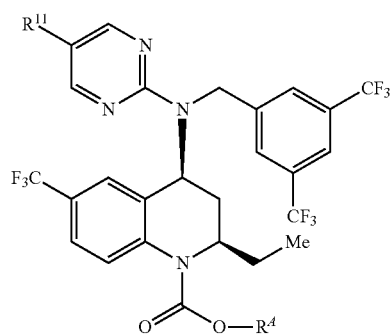

TABLE 36

| Ex. No. | Configuration | R$^{11}$ | R$^4$ | Physical properties, etc. |
|---|---|---|---|---|
| 306 | (2R, 4S) | Me–O–O– | –CH$_2$CH$_2$CH$_2$C(O)OH | MS (m/z): 753 [M + H]$^+$ |
| 307 | (2R, 4S) | Me–O–O– | –CH$_2$CH$_2$CH$_2$C(O)OH | MS (m/z): 753 [M + H]$^+$ |
| 308 | (2R, 4S) | Me$_2$CH–O–O– | –CH$_2$CH$_2$CH$_2$C(O)OH | MS (m/z): 767 [M + H]$^+$ |
| 309 | (2R, 4S) | Me–O–CH(Me)–O– | –CH$_2$CH$_2$CH$_2$C(O)OH | MS (m/z): 753 [M + H]$^+$ |
| 310 | (2R, 4S) | Me–O–CH(Me)–O– | –CH$_2$CH$_2$CH$_2$C(O)OH | MS (m/z): 767 [M + H]$^+$ |

TABLE 36-continued

| Ex. No. | Configuration | R[11] | R[4] | Physical properties, etc. |
|---|---|---|---|---|
| 311 | (2R, 4S) | Me–O–CH₂–CH(O–CH₂–Me)–CH₂–O– (glyceryl bis-ethyl ether group) | –CH₂CH₂C(=O)OH | MS (m/z): 811 [M + H]⁺ |

Example 312

(1) (2R,4S)-4-{[3,5-Bis(trifluoromethyl)benzyl]-(5-dimethylaminopyrimidin-2-yl)}amino-2-ethyl-6-trifluoromethyl-3,4-dihydro-2H-quinoline (255 mg) and triethylamine (144 µl) are dissolved in methylene chloride (3 ml), and thereto is added triphosgene (102 mg) under ice-cooling. The mixture is stirred at the same temperature for 45 minutes, and concentrated under reduced pressure. To the residue is added ether and insoluble materials are removed by filtration. The filtrate is concentrated under reduced pressure. The resulting residue is dissolved in tetrahydrofuran (3 ml), thereto are added 3-hydroxy-2,2-dimethylpropionic acid methyl ester (110 µl) and sodium hydride (62.7%, 33 mg) under ice-cooling, and the mixture is stirred at room temperature for 1.5 hours. The reaction solution is separated by adding a saturated brine and ethyl acetate, and organic layer is washed with a saturated brine, dried over magnesium sulfate, and concentrated under reduced pressure. The resulting residue is purified by silica gel column chromatography (hexane:ethyl acetate=4:1) to give (2R,4S)-4-{[3,5-bis(trifluoromethyl)benzyl]-(5-dimethylaminopyrimidin-2-yl)}amino-2-ethyl-6-trifluoromethyl-3,4-dihydro-2H-quinoline-1-carboxylic acid 2-methoxycarbonyl-2-methylpropyl ester (285 mg). MS (m/z):750 [M+H]⁺.

(2) (2R,4S)-4-{[3,5-Bis(trifluoromethyl)benzyl]-(5-dimethylaminopyrimidin-2-yl)}amino-2-ethyl-6-trifluoromethyl-3,4-dihydro-2H-quinoline-1-carboxylic acid 2-methoxycarbonyl-2-methylpropyl ester (275 mg) is dissolved in a mixture of methanol (1.5 ml) and tetrahydrofuran (4 ml), and thereto is added a 2N aqueous sodium hydroxide solution (1.8 ml). The reaction solution is stirred at room temperature for 4 hours, acidified slightly by adding 10% aqueous citric acid solution, and extracted with ethyl acetate. The organic layer is washed with a saturated brine, dried over magnesium sulfate, and concentrated under reduced pressure. The resulting residue is purified by silica gel column chromatography (chloroform:methanol=1:0→97:3) to give (2R,4S)-4-{[3,5-bis(trifluoromethyl)benzyl]-(5-dimethylamino pyrimidin-2-yl)}amino-2-ethyl-6-trifluoromethyl-3,4-dihydro-2H-quinoline-1-carboxylic acid 2-carboxy-2-methylpropyl ester (257 mg). MS (m/z):736 [M+H]⁺.

(3) (2R,4S)-4-{[3,5-Bis(trifluoromethyl)benzyl]-(5-dimethylaminopyrimidin-2-yl)}amino-2-ethyl-6-trifluoromethyl-3,4-dihydro-2H-quinoline-1-carboxylic acid 2-carboxy-2-methylpropyl ester (248 mg) is dissolved in ethanol (2 ml), thereto is added a 2M aqueous sodium hydroxide solution (169 µl), and the mixture is stirred at room temperature for 3 minutes. The reaction solution is concentrated to dryness under reduced pressure to give (2R,4S)-4-{[3,5-bis(trifluoromethyl)benzyl]-(5-dimethylaminopyrimidin-2-yl)}amino-2-ethyl-6-trifluoromethyl-3,4-dihydro-2H-quinoline-1-carboxylic acid 2-carboxy-2-methylpropyl ester sodium salt (254 mg). MS (m/z): 734 [M−Na]⁻.

Example 313

(1) (2R,4S)-4-{[3,5-Bis(trifluoromethyl)benzyl]-(5-bromopyrimidin-2-yl)}amino-2-ethyl-6-trifluoromethyl-3,4-dihydro-2H-quinoline-1-carboxylic acid 2-tert-butoxycarbonylethyl ester (300 mg) is dissolved in toluene (2 ml), and thereto are added cyclopropylboronic acid (42 mg), tripotassium phosphate (278 mg), a 20% solution of tricyclohexylphosphine in toluene solution (53 µl), water (84 µl) and palladium (II) acetate (4 mg). The mixture is heated to 95° C. under nitrogen flow and stirred for 3 hours. The reaction solution is allowed to cool to room temperature and separated by adding a saturated brine and ethyl acetate. The organic layer is washed with a saturated brine, dried over magnesium sulfate, and concentrated under reduced pressure. The resulting residue is purified by silica gel column chromatography (hexane:ethyl acetate=6:1→4:1) to give (2R,4S)-4-{[3,5-bis(trifluoromethyl)benzyl]-(5-cyclopropylpyrimidin-2-yl)}amino-2-ethyl-6-trifluoromethyl-3,4-dihydro-2H-quinoline-1-carboxylic acid 2-tert-butoxycarbonylethyl ester (258 mg). MS (m/z): 761 [M+H]⁺.

(2) (2R,4S)-4-{[3,5-Bis(trifluoromethyl)benzyl]-(5-cyclopropylpyrimidin-2-yl)}amino-2-ethyl-6-trifluoromethyl-3,4-dihydro-2H-quinoline-1-carboxylic acid 2-tert-butoxycarbonylethyl ester (255 mg) is dissolved in methylene chloride (2 ml), and thereto is added 4N hydrochloric acid in 1,4-dioxane (2 ml), and the mixture is stirred at room temperature for 5 hours. The reaction solution is neutralized with a saturated aqueous sodium hydrogen carbonate solution, acidified slightly by addition of 10% citric acid and extracted with ethyl acetate. The organic layer is washed with a saturated brine, dried over magnesium sulfate, and concentrated under reduced pressure. The resulting residue is purified by silica gel column chromatography (chloroform:methanol=19:1) to give (2R,4S)-4-{[3,5-bis(trifluoromethyl)benzyl]-(5-cyclo propylpyrimidin-2-yl)}amino-2-ethyl-6-trifluoromethyl-3,4-dihydro-2H-quinoline-1-carboxylic acid 2-carboxyethyl ester (228 mg). MS (m/z): 705 [M+H]⁺.

(3) (2R,4S)-4-{[3,5-Bis(trifluoromethyl)benzyl]-(5-cyclopropylpyrimidin-2-yl)}amino-2-ethyl-6-trifluoromethyl-3,4-dihydro-2H-quinoline-1-carboxylic acid 2-carboxyethyl ester (222 mg) is dissolved in ethanol (1 ml), and thereto is added 2M aqueous sodium hydroxide solution (158 µl), and the mixture is stirred at room temperature for 5 minutes. The reaction solution is concentrated to dryness under reduced pressure to give (2R,4S)-4-{[3,5-bis(trif-

189 luoromethyl)benzyl]-(5-cyclopropylpyrimidin-2-yl)}amino-2-ethyl-6-trifluoromethyl-3,4-dihydro-2H-quinoline-1-carboxylic acid 2-carboxyethyl ester sodium salt (223 mg). MS (m/z): 703 [M−Na]⁻.

Example 314

(2R,4S)-4-{[3,5-Bis(trifluoromethyl)benzyl]-[5-(4-carboxypiperidin-1-yl)pyrimidin-2-yl]}amino-2-ethyl-6-trifluoromethyl-3,4-dihydro-2H-quinoline-1-carboxylic acid ethyl ester sodium salt (2.7 g) is dissolved in water (100 ml) under heating and added dropwise to a solution (75 ml) of calcium chloride (1.56 g) in water at room temperature. The reaction solution is stirred overnight, and the precipitated residue is collected by filtration and washed with water to give (2R,4S)-4-{[3,5-bis(trifluoromethyl)benzyl]-[5-(4-carboxypiperidin-1-yl)pyrimidin-2-yl]}amino-2-ethyl-6-trifluoromethyl-3,4-dihydro-2H-quinoline-1-carboxylic acid ethyl ester hemicalcium salt (2.79 g). MS (m/z): 746 [M−1/2Ca]⁻.

Example 315

(1) (2R,4S)-4-[(5-Bromopyrimidin-2-yl)-(3-cyano-5-trifluoromethyl-benzyl)]amino-2-ethyl-6-trifluoromethyl-3,4-dihydro-2H-quinoline-1-carboxylic acid ethyl ester (570 mg) is dissolved in chloroform (2.5 ml), and thereto is added trimethylsilyl iodide (865 μl), and the mixture is stirred at 55° C. under nitrogen flow overnight. A saturated aqueous sodium hydrogen carbonate solution is added to the reaction mixture and extracted with ethyl acetate. The organic layer is washed with a saturated brine, dried over magnesium sulfate, and concentrated under reduced pressure. The resulting residue is purified by NH-silica gel column chromatography (hexane:ethyl acetate=10:1) to give (2R,4S)-4-[(5-bromopyrimidin-2-yl)-(3-cyano-5-trifluoromethylbenzyl)]amino-2-ethyl-6-trifluoromethyl-3,4-dihydro-2H-quinoline (362 mg). MS (m/z):583/585 [M]⁺.
(2) (2R,4S)-4-[(5-Bromopyrimidin-2-yl)-(3-cyano-5-trifluoromethylbenzyl)]amino-2-ethyl-6-trifluoromethyl-3,4-dihydro-2H-quinoline (412 mg) is treated in a similar manner to Example 276 to give (2R,4S)-4-{(3-cyano-5-trifluoromethylbenzyl)-[5-(morpholin-4-yl)pyrimidin-2-yl]}amino-2-ethyl-6-trifluoromethyl-3,4-dihydro-2H-quinoline-1-carboxylic acid 2-carboxyethyl ester (80 mg). MS (m/z): 707 [M+H]⁺.

Example 316

(1) (2R,4S)-4-{[3,5-Bis(trifluoromethyl)benzyl]-(5-bromopyridin-2-yl)}amino-2-ethyl-6-trifluoromethyl-3,4-dihydro-2H-quinoline-1-carboxylic acid ethyl ester (24.62 g) and sodium hydroxide (4.2 g) are dissolved in tetrahydrofuran:ethanol (1:1) (300 ml), and the mixture is heated to 80° C. and stirred for 5 hours. The reaction solution is cooled to room temperature and concentrated under reduced pressure. The mixture is separated by adding 2N hydrochloric acid and ethyl acetate. The organic layer is washed with a saturated brine, dried over magnesium sulfate, and concentrated under reduced pressure. The resulting residue is purified by silica gel column chromatography (hexane:ethyl acetate=10:1→7:3) to give a mixture of (2R,4S)-4-{[3,5-bis(trifluoromethyl)benzyl]-(5-bromopyridin-2-yl)}amino-2-ethyl-6-trifluoromethyl-3,4-dihydro-2H-quinoline and (2R,4R)-4-{[3,5-bis(trifluorom-

190 ethyl)benzyl]-(5-bromopyridin-2-yl)}amino-2-ethyl-6-trifluoromethyl-3,4-dihydro-2H-quinoline (9.1 g). MS (m/z):626/628 [M+H]⁺.
(2) A mixture of (2R,4S)-4-{[3,5-bis(trifluoromethyl)benzyl]-(5-bromopyridin-2-yl)}amino-2-ethyl-6-trifluoromethyl-3,4-dihydro-2H-quinoline and (2R,4R)-4-{[3,5-bis(trifluoromethyl)benzyl]-(5-bromopyridin-2-yl)}amino-2-ethyl-6-trifluoromethyl-3,4-dihydro-2H-quinoline (4 g) is dissolved in toluene (30 ml), and thereto are added tris-(dibenzylideneacetone)dipalladium (586 mg), 2-(di-tert-butylphosphino)-biphenyl (382 mg), sodium tert-butoxide (3.07 g) and a 2N dimethylamine tetrahydrofuran solution (16 ml), and the mixture is stirred at room temperature for 19 hours. The reaction solution is separated by adding water and ethyl acetate. The organic layer is washed with a saturated brine, dried over magnesium sulfate, and concentrated under reduced pressure. The resulting residue is purified by silica gel column chromatography (hexane:ethyl acetate=9:1→7:3) to give (2R,4S)-4-{[3,5-bis(trifluoromethyl)benzyl]-(5-dimethylaminopyridin-2-yl)}amino-2-ethyl-6-trifluoromethyl-3,4-dihydro-2H-quinoline (655 mg) (MS (m/z):591 [M+H]⁺) and (2R,4R)-4-{[3,5-bis(trifluoromethyl)benzyl]-(5-dimethylaminopyridin-2-yl)}amino-2-ethyl-6-trifluoromethyl-3,4-dihydro-2H-quinoline (380 mg) MS (m/z): 591 [M+H]⁺.
(3) (2R,4S)-4-{[3,5-Bis(trifluoromethyl)benzyl]-(5-dimethylaminopyridin-2-yl)}amino-2-ethyl-6-trifluoromethyl-3,4-dihydro-2H-quinoline (400 mg) is treated in a similar manner to Example 276 (2)-(3) to give (2R,4S)-4-{[3,5-bis(trifluoromethyl)benzyl]-(5-dimethylaminopyridin-2-yl)}amino-2-ethyl-6-trifluoromethyl-3,4-dihydro-2H-quinoline-1-carboxylic acid 2-carboxyethyl ester (272 mg). MS (m/z):707 [M+H]⁺.

Example 317

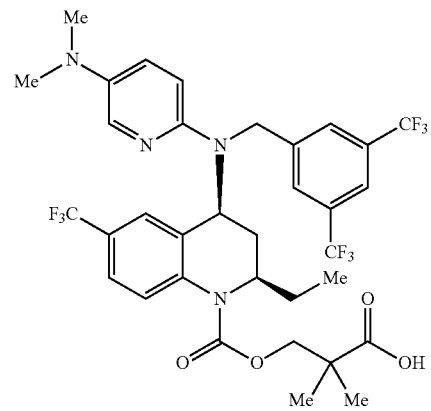

Corresponding starting compounds are treated in a similar manner to Example 312 (1)-(2) to give the compounds of Example 317. MS (m/z):735 [M+H]⁺.

Example 318

(1) (2R,4S)-4-{[3,5-Bis(trifluoromethyl)benzyl]-(5-bromopyridin-2-yl)}amino-2-ethyl-6-trifluoromethyl-3,4-dihydro-2H-quinolin-1-carboxylic acid ethyl ester (10 g) is dissolved in chloroform (45 ml), thereto is added trimethylsilyl iodide (14.2 ml) at room temperature, and the mixture is stirred at 50° C. for 4.5 hours. The reaction solution is cooled to room temperature and separated by adding a saturated aqueous sodium hydrogen carbonate solution and ethyl acetate under ice-cooling. The organic layer is washed with a saturated brine, dried over magnesium sulfate, and concentrated under reduced pressure. The resulting residue is purified by NH-silica gel column chromatography (hexane:ethyl acetate=19:1→4:1) to give (2R,4S)-4-{[3,5-bis(trifluoromethyl)benzyl]-(5-bromopyridin-2-yl)}amino-2-ethyl-6-trifluoromethyl-3,4-dihydro-2H-quinoline (3.56 g). MS (m/z): 626/628 [M+H]$^+$.

(2) (2R,4S)-4-{[3,5-Bis(trifluoromethyl)benzyl]-(5-bromopyridin-2-yl)}amino-2-ethyl-6-trifluoromethyl-3,4-dihydro-2H-quinoline (2.78 g) is dissolved in toluene (20 ml), and thereto are added tris(dibenzylidene-acetone)dipalladium (407 mg), sodium tert-butoxide (2.13 g), 2-(di-tert-butylphosphino)biphenyl (530 mg) and morpholine (1.94 ml). The reaction mixture is stirred under nitrogen atmosphere at room temperature for 60 hours. The reaction solution is separated by adding a saturated aqueous sodium hydrogen carbonate solution and ethyl acetate. The organic layer is washed with a saturated brine, dried over magnesium sulfate, and concentrated under reduced pressure. The resulting residue is purified by NH-silica gel column chromatography (hexane:ethyl acetate=19:1→4:1) to give (2R,4S)-4-{[3,5-bis(trifluoromethyl)benzyl]-[5-(morpholin-4-yl)pyridin-2-yl]}amino-2-ethyl-6-trifluoromethyl-3,4-dihydro-2H-quinoline (1.85 g). MS (m/z): 633 [M+H]$^+$.

(3) (2R,4S)-4-{[3,5-Bis(trifluoromethyl)benzyl]-[5-(morpholin-4-yl)pyridin-2-yl]}amino-2-ethyl-6-trifluoromethyl-3,4-dihydro-2H-quinoline (400 mg) is treated in a similar manner to Example 276 (2)-(3) to give (2R,4S)-4-{[3,5-bis(trifluoromethyl)benzyl]-[5-(morpholin-4-yl)pyridin-2-yl]}amino-2-ethyl-6-trifluoromethyl-3,4-dihydro-2H-quinolin-1-carboxylic acid 2-carboxyethyl ester (97 mg). MS (m/z): 749 [M+H]$^+$.

Example 319

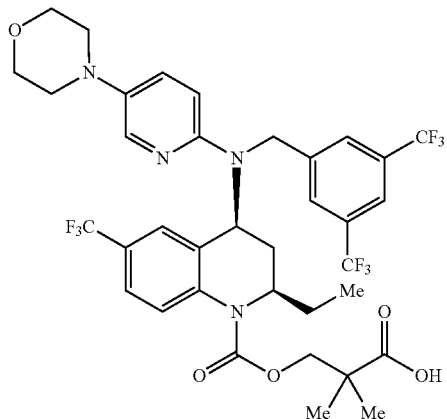

Corresponding starting compounds are treated in a similar manner to Example 312 (1)-(2) to give the compounds of Example 319. MS (m/z): 777 [M+H]$^+$.

Example 320

(1) (2R,4S)-4-{[3,5-Bis(trifluoromethyl)benzyl]-(5-bromopyridin-2-yl)}amino-2-ethyl-6-trifluoromethyl-3,4-dihydro-2H-quinoline (1.52 g) is dissolved in dimethylsulfoxide (10 ml), and thereto are added [1,1'-bis(diphenylphosphino)ferrocene]dichloropalladium, complex with dichloromethane (1:1) (396 mg), potassium acetate (715 mg) and bis(pinacolato)diboron (1.23 g), then the mixture is heated to 80° C. under nitrogen flow and stirred for an hour. The reaction solution is cooled to room temperature and separated by adding water and ethyl acetate. The organic layer is washed with a saturated brine, dried over magnesium sulfate, and concentrated under reduced pressure. The resulting residue is dissolved in tetrahydrofuran (20 ml), thereto is added a 30% aqueous hydrogen peroxide solution (15 ml) under ice-cooling, and the mixture is stirred at room temperature for an hour. The reaction solution is separated by adding a saturated aqueous sodium thiosulfate solution followed by ethyl acetate under ice-cooling. The organic layer is washed with a saturated brine, dried over magnesium sulfate, and concentrated under reduced pressure. The resulting residue is purified by silica gel column chromatography (hexane:ethyl acetate=9:1→77:23) to give (2R,4S)-4-{[3,5-bis(trifluoromethyl)benzyl]-(5-hydroxypyridin-2-yl)}amino-2-ethyl-6-trifluoromethyl-3,4-dihydro-2H-quinoline (1.10 g). MS (m/z): 564 [M+H]$^+$.

(2) (2R,4S)-4-{[3,5-Bis(trifluoromethyl)benzyl]-(5-hydroxypyridin-2-yl)}amino-2-ethyl-6-trifluoromethyl-3,4-dihydro-2H-quinoline (600 mg), triphenylphosphine (459 mg) and 2-methoxyethanol (138 μl) are dissolved in tetrahydrofuran (5 ml), and thereto is added a 40% solution of diethyl azodicarboxylate solution in toluene (797 μl), and the mixture is stirred at room temperature for 2 hours. The reaction solution is separated by adding a saturated aqueous sodium hydrogen carbonate solution and ethyl acetate. The organic layer is washed with water and a saturated brine, dried over magnesium sulfate, and concentrated under reduced pressure. The resulting residue is purified by silica gel column chromatography (hexane:ethyl acetate=97:3→4:1) to give (2R,4S)-4-{[3,5-bis(trifluoromethyl)benzyl]-[5-(2-methoxyethoxy)pyridin-2-yl]}amino-2-ethyl-6-trifluoromethyl-3,4-dihydro-2H-quinoline (416 mg). MS (m/z): 622 [M+H]$^+$.

(3) (2R,4S)-4-{[3,5-Bis(trifluoromethyl)benzyl]-[5-(2-methoxyethoxy)pyridin-2-yl]}amino-2-ethyl-6-trifluoromethyl-3,4-dihydro-2H-quinoline (170 mg) is treated in a similar manner to Example 276 (2)-(3) to give (2R,4S)-4-{[3,5-bis(trifluoromethyl)benzyl]-[5-(2-methoxyethoxy)pyridin-2-yl]}amino-2-ethyl-6-trifluoromethyl-3,4-dihydro-2H-quinoline-1-carboxylic acid 2-carboxyethyl ester (63 mg). MS (m/z):738 [M+H]$^+$.

Example 321

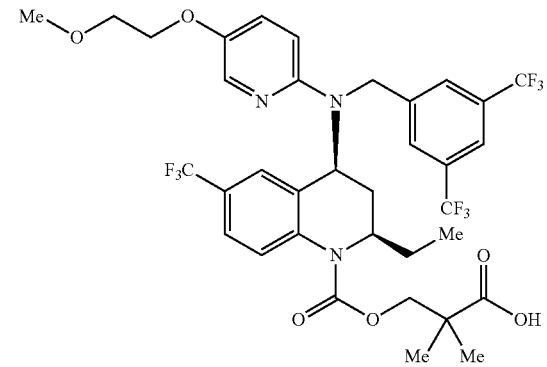

Corresponding starting compounds are treated in a similar manner to Example 312 (1)-(2) to give the compounds of Example 321. MS (m/z): 766 [M+H]$^+$.

Example 322

(1) (2R,4S)-4-{[3,5-Bis(trifluoromethyl)benzyl]-(5-hydroxypyridin-2-yl)}amino-2-ethyl-6-trifluoromethyl-3,4-dihydro-2H-quinoline (280 mg), 4-bromobutyronitrile (88 mg) and potassium carbonate (137 mg) are added to N,N-dimethylformamide (1 ml), and the mixture is stirred at 50° C. for 2 hours. The reaction solution is separated by adding a saturated aqueous sodium hydrogen carbonate solution and ethyl acetate. The organic layer is washed with water and a saturated brine, dried over magnesium sulfate, and concentrated under reduced pressure. The resulting residue is purified by silica gel column chromatography (hexane:ethyl acetate=85:15 →67:33) to give (2R,4S)-4-{[3,5-bis(trifluoromethyl)benzyl]-[5-(3-cyanopropoxy)pyridin-2-yl]}amino-2-ethyl-6-trifluoromethyl-3,4-dihydro-2H-quinoline (231 mg). MS (m/z): 631 [M+H]$^+$.

(2) (2R,4S)-4-{[3,5-Bis(trifluoromethyl)benzyl]-[5-(3-cyanopropoxy)pyridin-2-yl]}amino-2-ethyl-6-trifluoromethyl-3,4-dihydro-2H-quinoline (218 mg) is treated in a similar manner to Example 276 (2)-(3) to give (2R,4S)-4-{[3,5-bis(trifluoromethyl)benzyl]-[5-(3-cyanopropoxy)pyridin-2-yl]}amino-2-ethyl-6-trifluoromethyl-3,4-dihydro-2H-quinoline-1-carboxylic acid 2-carboxyethyl ester (29 mg). MS (m/z):747 [M+H]$^+$.

Example 323

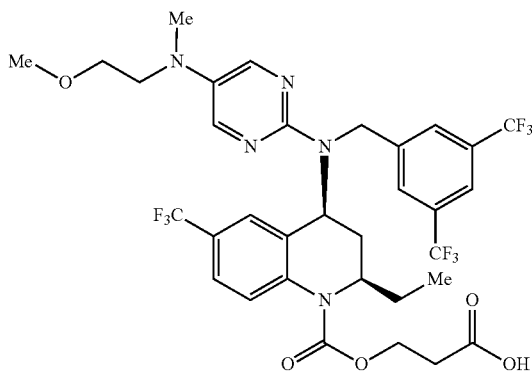

Corresponding starting compounds are treated in a similar manner to Example 288 to give The compounds of Example 323. MS (m/z):752 [M+H]$^+$.

Example 324

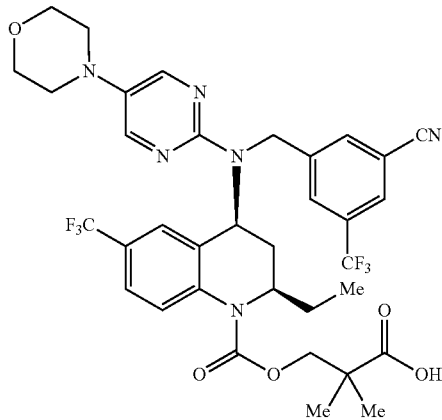

Corresponding starting compounds are treated in a similar manner to Example 312 (1)-(2) to give the compounds of Example 324. MS (m/z):735 [M+H]$^+$.

Reference Example 1

To a solution of sodium azide (19.2 g) in water (75 ml) is added dropwise under ice-cooling a solution of acryloyl chloride (20 ml) in toluene (75 ml), and the mixture is stirred at the same temperature for 3 hours. A saturated aqueous sodium hydrogen carbonate solution is added thereto, and the organic layer is washed with a saturated brine and dried over magnesium sulfate. The resulting toluene solution is added dropwise into a mixture of (S)-1-phenylethyl alcohol (38.6 ml), pyridine (9.9 ml) and hydroquinone (1.49 g) which is warmed at 85° C., and the mixture is stirred at the same temperature for 2 hours. The mixture is allowed to cool to room temperature, and thereto is added a saturated aqueous sodium hydrogen carbonate solution. The organic layer is washed with a saturated brine, dried over magnesium sulfate, and concentrated under reduced pressure. The resulting residue is purified by column chromatography (silica gel; hexane:ethyl acetate=8:1) to give vinylcarbamic acid (S)-1-phenylethyl ester (28.9 g). MS (m/z): 191 [M]$^+$

Reference Example 2

(1) To a solution of p-anisidine (50 g) and benzotriazole (48.4 g) in toluene (700 ml) is added dropwise a solution of propionaldehyde (32.2 ml) in toluene (40 ml) under ice-cooling, and the mixture is stirred at room temperature overnight. To the mixture is added heptane (700 ml), and the mixture is further stirred for one hour. The precipitates are collected by filtration, washed with heptane to give {[(1-benzotriazol-1-yl)propyl]-(4-methoxyphenyl)}amine (105.8 g).

(2) {[1-(Benzotriazol-1-yl)propyl]-(4-methoxyphenyl)}amine (45.8 g), vinylcarbamic acid (S)-1-phenylethyl ester (31 g) and p-toluenesulfonic acid (616 mg) are dissolved in toluene (500 ml), and the mixture is stirred at 80° C. for 4 hours. To the mixture are added a saturated aqueous sodium hydrogen carbonate solution and ethyl acetate, and the organic layer is washed with a saturated brine, dried over magnesium sulfate, and concentrated under reduced pressure. The resulting residue is purified by column chromatography (silica gel; hexane:ethyl acetate=6:1→3:1) to give a mixture (46.4 g) of (2R,4S)-2-ethyl-6-methoxy-4-((S)-1-phenylethoxycarbonylamino)-1,2,3,4-tetrahydroquinoline and (2S,4R)-2-ethyl-6-methoxy-4-((S)-1-phenylethoxycarbonylamino)-1,2,3,4-tetrahydroquinoline. MS (m/z): 355 [M+H]$^+$ (3) A mixture (45.1 g) of (2R,4S)-2-ethyl-6-methoxy-4-((S)-1-phenylethoxycarbonylamino)-1,2,3,4-tetrahydroquinoline and (2S,4R)-2-ethyl-6-methoxy-4-((S)-1-phenylethoxycarbonylamino)-1,2,3,4-tetrahydroquinoline is recrystallized from isopropyl ether (150 ml) to give (2R,4S)-(2-ethyl-6-methoxy-4-((S)-1-phenylethoxycarbonylamino)-1,2,3,4-tetrahydroquinoline (9.56 g). MS (m/z): 355 [M+H]$^+$ (4) (2R,4S)-(2-ethyl-6-methoxy-4-((S)-1-phenylethoxycarbonylamino)-1,2,3,4-tetrahydroquinoline (7.5 g) and pyridine (8.56 ml) are dissolved in methylene chloride (75 ml), and thereto is added dropwise a solution of ethyl chlorocarbonate (10.1 ml) in methylene chloride (20 ml) under ice-cooling, and the mixture is stirred at room temperature for 3 hours. The reaction solution is washed with a 1M aqueous sodium hydroxide solution, a 1N hydrochloric acid, and a saturated brine, dried over magnesium sulfate and concentrated under reduced pressure. The resulting residue is purified by column chromatography (silica gel; hexane:ethyl acetate=90:10→60:40) to give (2R,4S)-2-ethyl-6-methoxy-4-((S)-1-phenylethoxy-carbonylamino)-3,4-dihydro-2H-quinoline-1-carboxylic acid ethyl ester (7.61 g). MS (m/z): 444 [M+NH$_4$]$^+$ (5) To a solution of (2R,4S)-2-ethyl-6-methoxy-4-((S)-1-phenylethoxy-carbonylamino)-3,4-dihydro-2H-quinoline-1-carboxylic acid ethyl ester (9.32 g) in ethanol (100 ml) is added 10% palladium-carbon, and the mixture is stirred under hydrogen atmosphere for 3 hours. The catalyst is removed by filtration, and the filtrate is concentrated under reduced pressure to give (2R,4S)-4-amino-2-ethyl-6-methoxy-3,4-dihydro-2H-quinoline-1-carboxylic acid ethyl ester (6.09 g). MS (m/z): 279 [M+H]$^+$ Reference Example 3

(1) 3,4-Ethylenedioxyaniline (17.68 g) and benzotriazole (13.93 g) are dissolved in toluene (200 ml), and thereto is added dropwise propion-aldehyde (9.2 ml) under ice-cooling. The reaction solution is stirred at room temperature overnight. To the mixture is added heptane (200 ml), and the mixture is further stirred for one hour. The precipitates are collected by filtration, and washed with heptane to give {[1-(benzotriazol-1-yl)propyl]-(3,4-ethylenedioxyphenyl)}amine (35.48 g).

(2) {[1-(Benzotriazol-1-yl)propyl]-(3,4-ethylenedioxyphenyl)}amine (30.00 g), vinylcarbamic acid benzyl ester (17.13 g), and p-toluenesulfonic acid (184 mg) are dissolved in toluene (310 ml), and the mixture is stirred at 70° C. for 3 hours. To the mixture are added a 1N aqueous sodium hydroxide solution and ethyl acetate, and the mixture is separated. The organic layer is washed with water and a saturated brine, dried over magnesium sulfate, and concentrated under reduced pressure. The resulting residue is purified by silica gel column chromatography (chloroform:acetone=20:1) to give (2R*,4S*)-4-benzyloxycarbonylamino-2-ethyl-6,7-ethylenedioxy-1,2,3,4-tetrahydroquinoline (5.63 g). MS (m/z): 369 [M+H]$^+$ (3) ((2R*,4S*)-4-benzyloxycarbonylamino-2-ethyl-6,7-ethylenedioxy-1,2,3,4-tetrahydroquinoline (5.62 g) and pyridine (6.2 ml) are dissolved in methylene chloride (45 ml), and thereto is added dropwise a solution of ethyl chlorocarbonate (7.3 ml) in methylene chloride (15 ml) under ice-cooling, and the mixture is stirred at room temperature for 3 hours. To the reaction solution is added a 1N aqueous sodium hydroxide solution (83 ml), and the mixture is stirred at room temperature for 30 minutes. The mixture is separated and the organic layer is washed with a 1N hydrochloric acid, a saturated aqueous sodium hydrogen carbonate solution, and a saturated brine, dried over sodium sulfate, and concentrated under reduced pressure. The residue is dissolved in ethanol (40 ml), and thereto is added dropwise water (17 ml). The precipitated crystals are collected by filtration, and washed with a mixture of ethanol-water=7:3 to give (2R*,4S*)-2-ethyl-6,7-ethylenedioxy-4-benzyloxy-carbonylamino-3,4-dihydro-2H-quinoline-1-carboxylic acid ethyl ester (5.98 g). MS (m/z): 458 [M+H$_2$O]$^+$ (4) (2R*,4*S)-4-Benzyloxycarbonylamino-2-ethyl-6,7-ethylenedioxy-3,4-dihydro-2H-quinoline-1-carboxylic acid ethyl ester (5.97 g) is dissolved in methanol (60 ml), and thereto are added 10% palladium-carbon (0.5 g) and ammonium formate (2.14 g), and the mixture is stirred at 37° C. for one hour. The palladium-carbon is removed by filtration, and the filtrate is concentrated under reduced pressure. The residue is dissolved in chloroform (65 ml), and washed with a saturated aqueous sodium hydrogen carbonate solution and a saturated brine, dried over sodium sulfate, and concentrated under reduced pressure. To the resulting residue is added heptane (20 ml), and the mixture is stirred overnight. The precipitated crystals are collected by filtration and washed with heptane to give (2R*,4S*)-4-amino-2-ethyl-6,7-ethylenedioxy-3,4-dihydro-2H-quinoline-1-carboxylic acid ethyl ester (3.54 g). MS (m/z): 307 [M+H]$^+$ Reference Example 4

To (2R*,4S*)-6-bromo-2-ethyl-4-(benzyloxycarbonylamino)-3,4-dihydro-2H-quinoline-1-carboxylic acid ethyl ester (28.36 g), which prepared by treating the corresponding starting compounds in a similar manner to Reference Example 3 (1)-(3), is added a 25% solution of hydrogen bromide in acetic acid (140 ml), and the mixture is stirred at room temperature for 45 minutes. The reaction solution is concentrated under reduced pressure, and to the residue is added ether (200 ml), and the precipitates are collected by filtration and washed with ether. The precipitates are added to a saturated aqueous sodium hydrogen carbonate solution, and the mixture is extracted with ethyl acetate. The organic layer is washed with a saturated brine, dried over sodium sulfate and concentrated under reduced pressure. The residue is purified by silica gel column chromatography (ethyl acetate) and concentrated. To the residue is added heptane (150 ml), and the mixture is stirred at room temperature overnight. The precipitates are collected by filtration and washed with heptane to give (2R*,4S*)-4-amino-6-bromo-2-ethyl-3,4-dihydro-2H-quinoline-1-carboxylic acid ethyl ester (18.46 g). MS (m/z): 327/329 [M+H]$^+$ Reference Example 5

(1) Ethyl bromopyruvate (29.9 g) and urea (13.8 g) are dissolved in ethanol (110 ml) and the mixture is refluxed for 24 hours. The reaction solution is cooled to room temperature, and concentrated under reduced pressure. To the residue are added water and ether, and the pH value of the mixture is adjusted to 10 by addition of a 2N aqueous sodium hydroxide solution. The organic layer is dried over magnesium sulfate, and concentrated under reduced pressure. The resulting residue is crystallized from isopropyl ether to give 2-aminooxazole-4-carboxylic acid ethyl ester (7.53 g). MS (m/z): 157 [M+H]$^+$ (2) 2-Aminooxazol-4-carboxylic acid ethyl ester (7.3 g), tert-butyl nitrite (9.4 ml), and copper (II) chloride (9.4 g) are dissolved in acetonitrile (210 ml), and the mixture is stirred at 60-80° C. for 2 hours. The reaction solution is cooled to room temperature, and thereto are added a 2N aqueous hydrochloric acid solution and methylene chloride. The organic layer is washed with a saturated brine, dried over magnesium sulfate, and concentrated under reduced pressure. The resulting is purified by silica gel column chromatography (hexane:ethyl acetate=4:1→2:1) to give 2-chlorooxazole-4-carboxylic acid ethyl ester (5.57 g). MS (m/z): 176/178 [M+H]$^+$ Reference Example 6

2-Amino-4-methylthiazole-5-carboxylic acid ethyl ester (8.72 g), tert-butyl nitrite (9.4 ml) and copper (II) chloride (9.4 g) are dissolved in acetonitrile (210 ml), and the mixture is stirred at 80° C. for 2 hours. The reaction solution is cooled to room temperature, and thereto are added a 2N aqueous hydrochloric acid solution and methylene chloride, and the mixture is separated. The organic layer is washed with a saturated brine, dried over magnesium sulfate, and concentrated under reduced pressure. The resulting residue is purified by silica gel column chromatography (hexane:ethyl acetate=99:1→23:2) to give 2-chloro-4-methylthiazole-5-carboxylic acid ethyl ester (8.83 g). MS (m/z): 206/208 [M+H]$^+$ Reference Example 7

(1) 4-Oxocyclohexanecarboxylic acid ethyl ester (5 g) is dissolved in ethanol (20 ml), and thereto is added sodium hydroxide (1.29 g), and the mixture is stirred at room temperature for one hour. To the mixture is added ethyl diethylphosphonoacetate (6.4 ml), and thereto is further added dropwise a 21% solution of sodium ethoxide in ethanol (12 ml) under ice-cooling over a period of 30 minutes. The reaction solution is stirred under ice-cooling for 3.5 hours, and concentrated under reduced pressure. To the resulting residue are added a 2N hydrochloric acid and ethyl acetate, and the mixture is separated. The organic layer is washed with a saturated brine, dried over magnesium sulfate, and concentrated under reduced pressure. The resulting residue is purified by silica gel column chromatography (hexane:ethyl acetate=9:1→1:1) to give 4-(ethoxy-carbonylmethylene)cyclohexanecarboxylic acid (2.05 g) as a crude product. MS (m/z): 213 [M+H]$^+$ (2) The crude 4-(ethoxycarbonylmethylene)cyclohexanecarboxylic acid (2.05 g) is dissolved in ethanol (20 ml), and thereto are added 10% palladium-carbon (500 mg), ammonium formate (3.7 g) and acetic acid (4.2 ml), and the mixture is stirred at 60° C. overnight. The reaction solution is cooled to room temperature, and the reaction solution is filtered. To the filtrate are added a 2N hydrochloric acid and ethyl acetate, and the mixture is separated. The organic layer is washed with a saturated brine, dried over magnesium sulfate, and concentrated under reduced pressure. The resulting residue is purified by silica gel column chromatography (hexane:ethyl acetate=7:3→1:1) to give 4-(ethoxycarbonylmethyl)cyclo-hexanecarboxylic acid (1.97 g). MS (m/z): 215 [M+H]$^+$ (3) 4-(Ethoxycarbonylmethyl)cyclohexanecarboxylic acid (1.97 g) is dissolved in tetrahydrofuran (20 ml), and thereto are added ethyl chlorocarbonate (650 µl) and triethylamine (950 µl) under ice-cooling, and the mixture is stirred under ice-cooling for 30 minutes. The reaction solution is filtered, and the filtrate is added to a suspension of sodium borohydride (515 mg) in tetrahydrofuran (10 ml), and the mixture is stirred under ice-cooling for one hour. A 1N hydrochloric acid and ethyl acetate are added to the mixture, and the mixture is separated. The organic layer is washed with a saturated brine, dried over magnesium sulfate and concentrated under reduced pressure. The resulting residue is purified by silica gel column chromatography (hexane:ethyl acetate=4:1→1:1) to give ethyl 4-(hydroxymethyl)cyclohexane acetate (360 mg). MS (m/z): 201 [M+H]$^+$ Reference Example 8

The corresponding starting compound is treated in a similar manner to Reference Example 3 to give (2R*,4S*)-4-amino-2-ethyl-6-methoxy-3,4-dihydro-2H-quinoline-1-carboxylic acid ethyl ester.

The invention claimed is:

1. A method for treatment of arteriosclerosis dyslipidemia, or coronary artery disease, which comprises administering an effective amount of a compound of the formula (I):

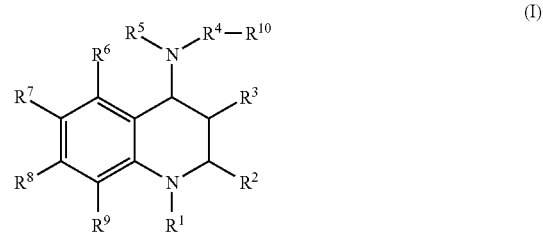

wherein $R^1$ is an alkoxycarbonyl group or an alkoxycarbonyl group substituted by 1 to 5 substituents selected independently from a carboxyl group, an alkoxycarbonyl group, a halogen atom, a hydroxy group and a cycloalkyl group;
$R^2$ is an alkyl group;
$R^3$ is a hydrogen atom;
$R^4$ is an alkylene group;
$R^5$ is a group of the formula:

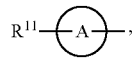

in which Ring A is a pyrimidinyl group or a pyridyl group and $R^{11}$ is an alkoxy group substituted by a carboxyl group, a cyano group, a hydroxy group, an alkoxy group, an alkylthio group or an alkylsulfonyl group; a mono- or di-alkylamino group; or a mono- or di-alkylamino group substituted by an alkoxy group;
$R^{10}$ is a phenyl group substituted by 1 to 3 substituents selected from a cyano group, an alkyl group, an alkyl group substituted by one or more halogen atom, and an alkoxy group;
$R^6$ and $R^9$ each are a hydrogen atom;
$R^7$ is an alkyl group, an alkyl group substituted by one or more halogen atom, an alkoxy group, or a mono- or di-alkylamino group; and
$R^8$ is a hydrogen atom,
or a pharmaceutically acceptable salt thereof.

2. The method according to claim 1, wherein $R^1$ is an ethoxycarbonyl group, a hydroxyethoxycarbonyl group, a 2-fluoroethoxycarbonyl group, a 2,2-difluoroethoxycarbonyl group or a 2,2,2-trifluoroethoxycarbonyl group; $R^2$ is an ethyl group;
$R^{10}$ is a phenyl group substituted by 1 to 2 substituents selected from a cyano group, a trifluoromethyl group and a methoxy group; and $R^7$ is a trifluoromethyl group or a methoxy group.

3. The method according to claim 1, wherein $R^1$ is a carboxy($C_{2-10}$alkoxy)carbonyl group or an alkoxycarbonyl($C_{2-10}$alkoxy)carbonyl group; $R^2$ is an ethyl group; $R^{10}$is a phenyl group substituted by 1 to 2 substituents selected from a cyano group, a trifluoromethyl group and a methoxy group; and $R^7$ is a trifluoromethyl group or a methoxy group.

4. The method according to claim 1, wherein the compound of the formula (I) is selected from the group consisting of:

(2R,4S)-4-[[3,5-Bis(trifluoromethyl)benzyl]-(5-{[methyl-(2-methoxyethyl)]-amino}pyrimidin-2-yl)]amino-2-ethyl-6-trifluoromethyl-3,4-dihydro-2H-quinoline-1-carboxylic acid ethyl ester;
(2R,4S)-4- {[3,5-Bis(trifluoromethyl)benzyl]-[5-(2-methoxyethoxy)pyrimidin-2-yl]}amino-2-ethyl-6-trifluoromethyl-3,4-dihydro-2H-quinoline-1-carboxylic acid ethyl ester;
(2R,4S)-4-{[3,5-Bis(trifluoromethyl)benzyl]-[5-(3-carboxypropoxy)pyrimidin-2-yl]}amino-2-ethyl-6-trifluoromethyl-3,4-dihydro-2H-quinoline-1-carboxylic acid ethyl ester;
(2R,4S)-4-{[3,5-Bis(trifluoromethyl)benzyl]-[5-(4-carboxybutoxy)pyrimidin-2-yl]}amino-2-ethyl-6-trifluoromethyl-3,4-dihydro-2H-quinoline-1-carboxylic acid ethyl ester;
(2R,4S)-4-{[3,5-Bis(trifluoromethyl)benzyl]-[5-(5-carboxypentyloxy)pyrimidin-2-yl ]}amino-2-ethyl-6-trifluoromethyl-3,4-dihydro-2H-quinoline-1-carboxylic acid ethyl ester;
(2R,4S)-4-{[3,5-Bis(trifluoromethyl)benzyl]-[5-(2-carboxyethoxy)pyrimidin-2-yl]}amino-2-ethyl-6-trifluoromethyl-3,4-dihydro-2H-quinoline-1-carboxylic acid ethyl ester;
(2R,4S)-4-{(3-Cyano-5-trifluoromethylbenzyl)-[5-(4-carboxybutoxy)pyrimidin-2-yl]amino-2-ethyl-6-trifluoromethyl-3,4-dihydro-2H-quinoline-1-carboxylic acid ethyl ester;
(2R,4S)-4-{[3,5-Bis(trifluoromethyl)benzyl]-[5-(3-carboxypropoxy)pyrimidin-2-yl ]}amino-2-ethyl-6-methoxy-3,4-dihydro-2H-quinoline-1-carboxylic acid ethyl ester;
(2R,4S)-4-{[3,5-Bis(trifluoromethyl)benzyl]-[5-(3-carboxypropoxy)pyrimidin-2-yl]}amino-2-ethyl-6-dimethylamino-3,4-dihydro-2H-quinoline-1-carboxylic acid ethyl ester;
(2R,4S)-4-{[3,5-Bis(trifluoromethypbenzyl]-[5-(3-carboxypropoxy)pyrimidin-2-yl]}amino-2-ethyl-6-trifluoromethyl-3,4-dihydro-2H-quinoline-1-carboxylic acid 2,2,2-trifluoroethyl ester; and
(2R,4S)-4-{(3-Cyano-5-trifluoromethylbenzyl)-[5-(3-carboxypropoxy)pyrimidin-2-yl]} amino-2-ethyl-6-trifluoromethyl-3,4-dihydro-2H-quinoline-1-carboxylic acid 2,2,2-trifluoroethyl ester,
or a pharmaceutically acceptable salt thereof.
5. The method according to claim 1, wherein the compound of the formula (I) is selected from the group consisting of:
(2R,4S)-4-{[3,5-Bis(trifluoromethyl)benzyl]-[5-(2-hydroxyethoxy)pyrimidin-2-yl]}amino-2-ethyl-6-trifluoromethyl-3,4-dihydro-2H-quinoline-1-carboxylic acid 3-carboxypropyl ester;
(2R,4S)-4-{[3,5-Bis(trifluoromethyl)benzyl]-[5-(2-hydroxyethoxy)pyrimidin-2-yl]}amino-2-ethyl-6-trifluoromethyl-3,4-dihydro-2H-quinoline-1-carboxylic acid 4-carboxybutyl ester;
(2R,4S)-4-{[3,5-Bis(trifluoromethypbenzyl]-[5-(2-hydroxyethoxy)pyrimidin-2-yl]}amino-2-ethyl-6-trifluoromethyl-3,4-dihydro-2H-quinoline-1-carboxylic acid 2-carboxy-2-methylpropyl ester;
(2R,4S)-4- {[3,5-Bis(trifluoromethyl)benzyl]-[5-(2-methoxyethoxy)pyrimidin-2-yl]}amino-2-ethyl-6-trifluoromethyl-3,4-dihydro-2H-quinoline- 1-carboxylic acid 2-carboxy-2-methylpropyl ester;
(2R,4S)-4-{[3,5-Bis(trifluoromethyl)benzyl]-[5-(2-methoxyethoxy)pyrimidin-2-yl]}amino-2-ethyl-6-trifluoromethyl-3,4-dihydro-2H-quinoline-1-carboxylic acid 5-carboxypentyl ester;
(2R,4S)-4-{[3,5-Bis(trifluoromethyl)benzyl]-[5-(3-cyanopropoxy)pyrimidin-2-yl]}amino-2-ethyl-6-trifluoromethyl-3,4-dihydro-2H-quinoline-1-carboxylic acid 3-carboxypropyl ester;
(2R,4S)-4-{[3,5-Bis(trifluoromethyl)benzyl]-[5-(3-cyanopropoxy)pyrimidin-2-yl]}amino-2-ethyl-6-trifluoromethyl-3,4-dihydro-2H-quinoline-1-carboxylic acid 4-carboxybutyl ester;
(2R,4S)-4-{[3,5-Bis(trifluoromethyl)benzyl]-[5-(3-cyanopropoxy)pyrimidin-2-yl]}amino-2-ethyl-6-trifluoromethyl-3,4-dihydro-2H-quinoline-1-carboxylic acid 2-carboxy-2-methylpropyl ester;
(2R,4S)-4-{[3,5-Bis(trifluoromethyl)benzyl]-[5-(3-cyanopropoxy)pyrimidin-2-yl]}amino-2-ethyl-6-trifluoromethyl-3,4-dihydro-2H-quinoline-1-carboxylic acid 5-carboxypentyl ester;
(2R,4S)-4-{[3,5-Bis(trifluoromethyl)benzyl]-(5-dimethylaminopyrimidin-2-yl)}amino-2-ethyl-6-trifluoromethyl-3,4-dihydro-2H-quinoline-1-carboxylic acid 3-carboxypropyl ester;
(2R,4S)-4-{[3,5-Bis(trifluoromethyl)benzyl]-(5-dimethylaminopyrimidin-2-yl)}amino-2-ethyl-6-trifluoromethyl-3,4-dihydro-2H-quinoline-1-carboxylic acid 4-carboxybutyl ester;
(2R,4S)-4-{[3,5-Bis(trifluoromethyl)benzyl]-(5-dimethyl aminopyrimidin-2-yl)}amino-2-ethyl-6-trifluoromethyl-3,4-dihydro-2 H-quinoline- 1-carboxylic acid 2-carboxy-2-methylpropyl ester;
(2R,4S)-4-{[3,5-Bis(trifluoromethyl)benzyl]-(5-dimethylaminopyrimidin-2-yl)}amino-2-ethyl-6-trifluoromethyl-3,4-dihydro-2H-quinoline-1-carboxylic acid 5-carboxypentyl ester;
(2R,4S)-4-{(3-Cyano-5-trifluoromethylbenzyl)[5-(2-methoxyethoxy)pyrimidin-2-yl]}amino-2-ethyl-6-trifluoromethyl-3,4-dihydro-2H-quinoline-1-carboxylic acid 2-carboxyethyl ester;
(2R,4S)-4-{(3-Cyano-5-trifluoromethylbenzyl)[5-(2-methoxyethoxy)pyrimidin-2-yl]}amino-2-ethyl-6-trifluoromethyl-3,4-dihydro-2H-quinoline-1-carboxylic acid 3-carboxypropyl ester;
(2R,4S)-4-{(3-Cyano-5-trifluoromethylbenzyl)[5-(2-methoxyethoxy)pyrimidin-2-yl]}amino-2-ethyl-6-trifluoromethyl-3,4-dihydro-2H-quinoline-1-carboxylic acid 4-carboxybutyl ester;
(2R,4S)-4-{(3-Cyano-5-trifluoromethylbenzyl)[5-(2-methoxyethoxy)pyrimidin-2-yl]}amino-2-ethyl-6-trifluoromethyl-3,4-dihydro-2H-quinoline-1-carboxylic acid 2-carboxy-2-methylpropyl ester;
(2R,4S)-4- {[3,5-Bis(trifluoromethyl)benzyl]-[5-(2-hydroxyethoxy)pyridin-2-yl[}amino-2-ethyl-6-trifluoromethyl-3,4-dihydro-2H-quinoline-1-carboxylic acid 2-carboxy-2-methylpropyl ester;
(2R,4S)-4-{[3,5-Bis(trifluoromethyl)benzyl]-[5-(2-methoxyethoxy)pyridin-2-yl]}amino-2-ethyl-6-trifluoromethyl-3,4-dihydro-2H-quinoline-1-carboxylic acid 2-carboxyethyl ester;
(2R,4S)-4-{[3,5-Bis(trifluoromethypbenzyl]-[5-(2-methoxyethoxy)pyridin-2-yl]}amino-2-ethyl-6-trifluoromethyl-3,4-dihydro-2H-quinoline-1-carboxylic acid 3-carboxypropyl ester;
(2R,4S)-4-{[3,5-Bis(trifluoromethyl)benzyl]-[5-(2-methoxyethoxy)pyridin-2-yl]}amino-2-ethyl-6-trifluoromethyl-3,4-dihydro-2H-quinoline-1-carboxylic acid 4-carboxybutyl ester;
(2R,4S)-4-{[3,5-Bis(trifluoromethypbenzyl]-[5-(2-methoxyethoxy)pyridin-2-yl]}amino-2-ethyl-6-trifluoromethyl-3,4-dihydro-2H-quinoline-1-carboxylic acid 2-carboxy-2-methylpropyl ester;

(2R,4S)-4- {[3,5-Bis(trifluoromethyl)benzyl]-[5-(3-cyanopropoxy)pyridin-2-yl]}amino-2-ethyl-6-trifluoromethyl-3,4-dihydro-2H-quinoline-1-carboxylic acid 2-carboxyethyl ester;

(2R,4S)-4-{[3,5-Bis(trifluoromethyl)benzyl]-(5-dimethylaminopyridin-2-yl)}amino-2-ethyl-6-trifluoromethyl-3,4-dihydro-2H-quinoline-1-carboxylic acid 2-carboxyethyl ester;

(2R,4S)-4-{[3,5-Bis(trifluoromethyl)benzyl]-(5-dimethylaminopyridin-2-yl)}amino-2-ethyl-6-trifluoromethyl-3,4-dihydro-2H-quinoline-1-carboxylic acid 3-carboxypropyl ester;

(2R,4S)-4- {[3,5-Bis(trifluoromethyl)benzyl]-(5-dimethyl aminopyridin-2-yl)}amino-2-ethyl-6-trifluoromethyl-3,4-dihydro-2H-quinoline-1-carboxylic acid 4-carboxybutyl ester;

(2R,4S)-4-{[3,5-Bis(trifluoromethyl)benzyl]-(5-dimethyl aminopyridin-2-yl)}amino-2-ethyl-6-trifluoromethyl-3,4-dihydro-2H-quinoline-1-carboxylic acid 2-carboxy-2-methylpropyl ester;

(2R,4S)-4- {(3-Cyano-5-trifluoromethylbenzyl)-[5-(2-methoxyethoxy)pyridin-2-yl]}amino-2-ethyl-6-trifluoromethyl-3,4-dihydro-2H-quinoline-1-carboxylic acid 2-carboxyethyl ester; and (2R,4S)-4-{(3-Cyano-5-trifluoromethylbenzyl)-[5-(2-methoxyethoxy)pyrimidin-2-yl]}amino-2-ethyl-6,7-ethylenedioxy-3,4-dihydro-2H-quinoline-1-carboxylic acid 2-carboxyethyl ester, or a pharmaceutically acceptable salt thereof.

6. The method according to claim 1, wherein the compound of the formula (I) is selected from the group consisting of:

(2R,4S)-4-{[3,5-Bis(trifluoromethyl)benzyl]-[5-(3-hydroxypropoxy)pyrimidin-2-yl]}amino-2-ethyl-6-trifluoromethyl-3,4-dihydro-2H-quinoline-1-carboxylic acid 2-carboxy-2-methylpropyl ester;

(2R,4S)-4- {[3,5-Bis(trifluoromethyl)benzyl]-[5-(2,3-dihydroxypropoxy)pyrimidin-2-yl]}amino-2-ethyl-6-trifluoromethyl-3,4-dihydro-2H-quinoline-1-carboxylic acid 2-carboxy-2-methylpropyl ester;

(2R,4S)-4-{[3,5-Bis(trifluoromethyl)benzyl]-[5-(3-hydroxypropoxy)pyrimidin-2-yl]}amino-2-ethyl-6-trifluoromethyl-3,4-dihydro-2H-quinoline-1-carboxylic acid 2-carboxyethyl ester;

(2R,4S)-4-{[3,5-Bis(trifluoromethyl)benzyl]-[5-(2,3-dihydroxypropoxy)pyrimidin-2-yl]}amino-2-ethyl-6-trifluoromethyl-3,4-dihydro-2H-quinoline-1-carboxylic acid 2-carboxyethyl ester;

(2R,4S)-4-{(3-Cyano-5-trifluoromethylbenzyl)-[5-hydroxyethoxy)pyrimidin-2-yl]}amino-2-ethyl-6-trifluoromethyl-3,4-dihydro-2H-quinoline-1-carboxylic acid 2-carboxy-2-methylpropyl ester;

(2R,4S)-4-{(3-Cyano-5-trifluoromethylbenzyl)-[5-(2-methoxyethoxy)pyrimidin-2-yl ]{amino-2-ethyl-6-trifluoromethyl-3,4-dihydro-2H-quinoline-1-carboxylic acid 2-carboxy-2-methylpropyl ester;

(2R,4S)-4-{[5-(3-Cyanopropoxy)pyrimidin-2-yl]-(3-Cyano-5-trifluoromethylbenzyl) }amino-2-ethyl-6-trifluoromethyl-3,4-dihydro-2H-quinoline- 1-carboxylic acid 2-carboxy-2-methylpropyl ester;

(2R,4S)-4-{(3-Cyano-5-trifluoromethylbenzyl)-[5-(2-hydroxyethoxy)pyrimidin-2-yl]}amino-2-ethyl-6-trifluoromethyl-3,4-dihydro-2H-quinoline-1-carboxylic acid 2-carboxyethyl ester;

(2R,4S)-4-{(3-Cyano-5-trifluoromethylbenzyl)-[5-(2-methoxyethoxy)pyrimidin-2-yl]}amino-2-ethyl-6-trifluoromethyl-3,4-dihydro-2H-quinoline-1-carboxylic acid 2-carboxyethyl ester;

(2R,4S)-4-{[5-(3-Cyanopropoxy)pyrimidin-2-yl]-(3-Cyano-5-trifluoromethylbenzyl)}amino-2-ethyl-6-trifluoromethyl-3,4-dihydro-2H-quinoline-1-carboxylic acid 2-carboxyethyl ester;

(2R,4S)-4-[(3-Cyano-5-trifluoromethylbenzyl)-(5-dimethylaminopyrimidin-2-yl)]amino-2-ethyl-6-trifluoromethyl-3,4-dihydro-2H-quinoline-1-carboxylic acid 2-carboxyethyl ester;

(2R,4 S)-4-([3,5-Bis(trifluoromethyl)benzyl]-{5-[(ethylmethyl)amino]pyrimidin-2-yl})amino-2-ethyl-6-trifluoromethyl-3,4-dihydro-2H-quinoline-1-carboxylic acid 2-carboxyethyl ester;

(2R,4S)-4-{[3,5-Bis(trifluoromethyl)benzyl]-(5-diethyl aminopyrimidin-2-yl)}amino-2-ethyl-6-trifluoromethyl-3,4-dihydro-2H-quinoline-1-carboxylic acid 2-carboxyethyl ester;

(2R,4S)-4-([3,5-Bis(trifluoromethyl)benzyl]-{5-[(ethylmethyl)amino]pyrimidin-2-yl})amino-2-ethyl-6-trifluoromethyl-3,4-dihydro-2H-quinoline-1-carboxylic acid 2-carboxy-2-methylpropyl ester; and (2R,4S)-4-{[3,5-Bis(trifluoromethyl)benzyl]-(5-di ethylaminopyrimidin-2-yl)}amino-2-ethyl-6-trifluoromethyl-3,4-dihydro-2H-quinoline-1-carboxylic acid 2-carboxy-2-methylpropyl ester, or a pharmaceutically acceptable salt thereof.

7. The method according to claim 2, wherein $R^1$ is an ethoxycarbonyl group or a hydroxyethoxycarbonyl group; $R^2$ is an ethyl group; $R^{10}$ is a phenyl group substituted by 1 to 2 substituents selected from cyano group, trifluoromethyl group and methoxy group; $R^7$ is a trifluoromethyl group or a methoxy group.

8. The method according to claim 1, wherein the compound of the formula (I) is (2R,4S)-4-{[3,5-Bis(trifluoromethyl)benzyl]-[5-(4-carboxybutoxy) pyrimidin-2-yl]}amino-2-ethyl-6-trifluoromethyl-3,4-dihydro-2H-quinoline-1-carboxylic acid ethyl ester, or a pharmaceutically acceptable salt thereof.

9. The method according to claim 1, wherein the compound of the formula (I) is (2R,4S)-4-{[3,5-Bis(trifluoromethyl)benzyl]-[5-(3-carboxypropoxy)-pyrimidin-2-yl]}amino-2-ethyl-6-trifluoromethyl-3,4-dihydro-2H-quinoline-1-carboxylic acid ethyl ester, or a pharmaceutically acceptable salt thereof.

10. The method according to claim 1, wherein the arteriosclerosis is atherosclerosis.

11. The method according to claim 1, wherein the dyslipidemia is selected from the group consisting of hyperbetalipoproteinemia, hypoalphalipoproteinemia, hypercholesterolemia, familial-hypercholesterolemia, and hypertriglyceridemia.

* * * * *

UNITED STATES PATENT AND TRADEMARK OFFICE
CERTIFICATE OF CORRECTION

Page 1 of 1

PATENT NO.       : 8,158,640 B2
APPLICATION NO.  : 12/911149
DATED            : April 17, 2012
INVENTOR(S)      : Hitoshi Kubota et al.

It is certified that error appears in the above-identified patent and that said Letters Patent is hereby corrected as shown below:

ON THE TITLE PAGE:

Correct the Related U.S. Application Data, at item (63), to read as follows:
-- Continuation of Application No. 11/597,691, filed on Sep. 27, 2006, now Pat. No. 7,872,126, which is a Continuation-in-Part of PCT/JP2005/006894, filed on Apr. 1, 2005. --.

Correct the Related U.S. Application Data, at item (60), to read as follows:
-- Provisional application No. 60/720,448, filed on Sep. 27, 2005. --.

Insert the following Foreign Application Priority Data as item (30):
-- (30) Apr. 2, 2004 (JP) .................... 2004-109550 --.

IN THE SPECIFICATION:

Column 1, at line 8, change "60/720,447" to -- 60/720,448 --.

Signed and Sealed this
Twenty-eighth Day of August, 2012

David J. Kappos
*Director of the United States Patent and Trademark Office*

UNITED STATES PATENT AND TRADEMARK OFFICE
CERTIFICATE OF CORRECTION

PATENT NO. : 8,158,640 B2  
APPLICATION NO. : 12/911149  
DATED : April 17, 2012  
INVENTOR(S) : Hitoshi Kubota et al.

Page 1 of 1

It is certified that error appears in the above-identified patent and that said Letters Patent is hereby corrected as shown below:

ON THE TITLE PAGE:

Correct the Related U.S. Application Data, at item (63), to read as follows:

-- Continuation of Application No. 11/527,691, filed on Sep. 27, 2006, now Pat. No. 7,872,126, which is a Continuation-in-Part of PCT/JP2005/006894, filed on Apr. 1, 2005. --.

Correct the Related U.S. Application Data, at item (60), to read as follows:

-- Provisional application No. 60/720,448, filed on Sep. 27, 2005. --.

Insert the following Foreign Application Priority Data as item (30):

-- (30) Apr. 2, 2004 (JP) .................... 2004-109550 --.

IN THE SPECIFICATION:

Column 1, at line 8, change "60/720,447" to -- 60/720,448 --.

This certificate supersedes the Certificate of Correction issued August 28, 2012.

Signed and Sealed this  
First Day of January, 2013

David J. Kappos  
*Director of the United States Patent and Trademark Office*